(12) United States Patent
Harrison et al.

(10) Patent No.: US 11,051,793 B2
(45) Date of Patent: Jul. 6, 2021

(54) APPARATUS AND METHODS FOR LOADING SUTURE

(71) Applicant: Anchor Orthopedics XT Inc., Mississauga (CA)

(72) Inventors: Robert Harrison, Milton (CA); Andrew Oldham, Etobicoke (CA); Neil Godara, Milton (CA); Jeffery Arnett, Gilbert, AZ (US)

(73) Assignee: Anchor Orthopedics XT Inc., Mississauga (CA)

( * ) Notice: Subject to any disclaimer, the term of this patent is extended or adjusted under 35 U.S.C. 154(b) by 741 days.

(21) Appl. No.: 15/126,197

(22) PCT Filed: Sep. 17, 2014

(86) PCT No.: PCT/IB2014/064608
§ 371 (c)(1),
(2) Date: Sep. 14, 2016

(87) PCT Pub. No.: WO2015/140606
PCT Pub. Date: Sep. 24, 2015

(65) Prior Publication Data
US 2017/0095235 A1  Apr. 6, 2017

Related U.S. Application Data

(63) Continuation-in-part of application No. PCT/IB2014/059847, filed on Mar. 15, 2014.

(51) Int. Cl.
*A61B 17/00* (2006.01)
*A61B 17/04* (2006.01)
(Continued)

(52) U.S. Cl.
CPC .......... *A61B 17/00* (2013.01); *A61B 17/0469* (2013.01); *A61B 17/0483* (2013.01);
(Continued)

(58) Field of Classification Search
CPC .......... A61B 17/0483; A61B 17/06004; A61B 2017/0053; A61B 17/0491;
(Continued)

(56) References Cited

U.S. PATENT DOCUMENTS 3,901,244 A   8/1975   Schweizer
4,841,888 A   6/1989   Mills et al.
(Continued)

FOREIGN PATENT DOCUMENTS

EP   0174843 B1   12/1991
EP   1839585 B1   10/2007
(Continued)

OTHER PUBLICATIONS

Related European Application, Supplementary European Search Report, dated Sep. 30, 2016.
(Continued)

*Primary Examiner* — Majid Jamialahmadi
(74) *Attorney, Agent, or Firm* — Vincent Man; Samuel Tekie; Glenn Arnold

(57) ABSTRACT

Various embodiments of a cartridge are disclosed, for loading a suture onto a suturing instrument and, in some embodiments, for loading a pre-tied knot formed from the suture onto the suturing instrument. The suturing instrument is typically of the type having a suture passing member defining a suture receiving passage therein. The cartridge may be operable to load the suture and/or the knot onto the suturing instrument at a point of use. In some embodiments, the cartridge defines a path for insertion thereto and withdrawal therefrom of the suturing instrument. The cartridge further comprises a seat for releasably holding a portion of a suture and a mechanism for transferring the suture from seat to the suturing instrument, various features of which are described herein.

15 Claims, 66 Drawing Sheets

(51) Int. Cl.
  *A61B 17/06* (2006.01)
  *A61B 17/062* (2006.01)
  *A61B 90/00* (2016.01)
  *A61M 25/01* (2006.01)

(52) U.S. Cl.
  CPC .......... *A61B 17/0491* (2013.01); *A61B 17/06* (2013.01); *A61B 17/06004* (2013.01); *A61B 17/0625* (2013.01); *A61B 90/39* (2016.02); *A61M 25/0108* (2013.01); *A61B 17/0482* (2013.01); *A61B 2017/0053* (2013.01); *A61B 2017/0409* (2013.01); *A61B 2017/0419* (2013.01); *A61B 2017/0474* (2013.01); *A61B 2017/0477* (2013.01); *A61B 2017/06009* (2013.01); *A61B 2017/06052* (2013.01); *A61B 2090/3966* (2016.02)

(58) Field of Classification Search
  CPC . A61B 17/0482; A61B 17/06; A61B 17/0469; A61B 17/062
  See application file for complete search history.

(56) References Cited

U.S. PATENT DOCUMENTS

| | | | |
|---|---|---|---|
| 5,478,345 | A | 12/1995 | Stone et al. |
| 5,733,293 | A | 3/1998 | Scirica et al. |
| 5,814,069 | A | 9/1998 | Schulze et al. |
| 6,533,796 | B1 | 3/2003 | Sauer et al. |
| 6,638,283 | B2 | 10/2003 | Thal |
| 8,821,520 | B2 | 9/2014 | Schwemberger et al. |
| 9,370,354 | B1 * | 6/2016 | Martin .................. A61B 17/06 |
| 2004/0092967 | A1 | 5/2004 | Sancoff et al. |
| 2004/0193217 | A1 | 9/2004 | Lubbers et al. |
| 2007/0162052 | A1 | 7/2007 | Hashimoto et al. |
| 2007/0203508 | A1 | 8/2007 | White et al. |
| 2007/0213745 | A1 | 9/2007 | Takemoto et al. |
| 2008/0275474 | A1 | 11/2008 | Martin et al. |
| 2010/0268274 | A1 | 10/2010 | Williams |
| 2013/0023905 | A1 | 1/2013 | Kubalak |

FOREIGN PATENT DOCUMENTS

| | | |
|---|---|---|
| JP | S61122852 A1 | 6/1986 |
| JP | 2000116659 A | 4/2000 |
| JP | 2010525894 A | 7/2010 |
| JP | 2010525895 A | 7/2010 |
| JP | 2012523914 A | 10/2012 |
| WO | 97/22300 A1 | 6/1997 |
| WO | 0230294 A1 | 4/2002 |
| WO | 2008137537 A2 | 11/2008 |
| WO | 2013024466 | 2/2013 |
| WO | 2013024466 A2 | 2/2013 |
| WO | 2013142487 A1 | 9/2013 |

OTHER PUBLICATIONS

Related European Application, European Search Opinion, dated Oct. 12, 2016.
Related European Application, Communication pursuant to Art 94(3) EPC, dated Oct. 19, 2018.
Related Application, Patent Corporation Treaty, International Search Report for PCT Application No. PCT/IB2014/059847, dated Aug. 21, 2014.
Related Application, Patent Corporation Treaty, International Preliminary Report on Patentability, PCT Application No. PCT/IB2014/059847, dated Sep. 15, 2015.
Related Application, Patent Corporation Treaty, Written Opinion for PCT Application No. PCT/IB2014/059847, dated Aug. 21, 2014.
Related Canadian Application, Examiner Requisition, dated Jun. 18, 2019.
Related Japanese Application, Office Action, dated Dec. 27, 2017.
Related Japanese Application, Office Action, dated Aug. 24, 2018.
Corresponding European Application, Supplementary European Search Report, dated Oct. 18, 2017.
Corresponding European Application, European Search Opinion, dated Oct. 18, 2017.
Corresponding European Application, Communication pursuant to Art 94(3) EPC, dated Jul. 27, 2018.
Corresponding European Application, Communication pursuant to Art 94(3) EPC, dated Mar. 7, 2019.
Corresponding European Application, Communication pursuant to Art 94(3) EPC, dated Feb. 14, 2020.
Corresponding Japanese Application, Office Action, dated Jun. 29, 2018.
Corresponding Japanese Application, Office Action, dated Jun. 21, 2019.
Related US Application, Office Action, dated Dec. 14, 2018.
Related Japanese Application, Office Action, dated Oct. 23, 2020.
Corresponding Canadian Application, Office Action, dated Sep. 8, 2020.
Corresponding Canadian Application, Office Action, dated Feb. 8, 2021.
Corresponding European Application, Summons to attend oral proceedings, dated Nov. 16, 2020.
Related Canadian Application, Office Action, dated Jul. 7, 2020.

* cited by examiner

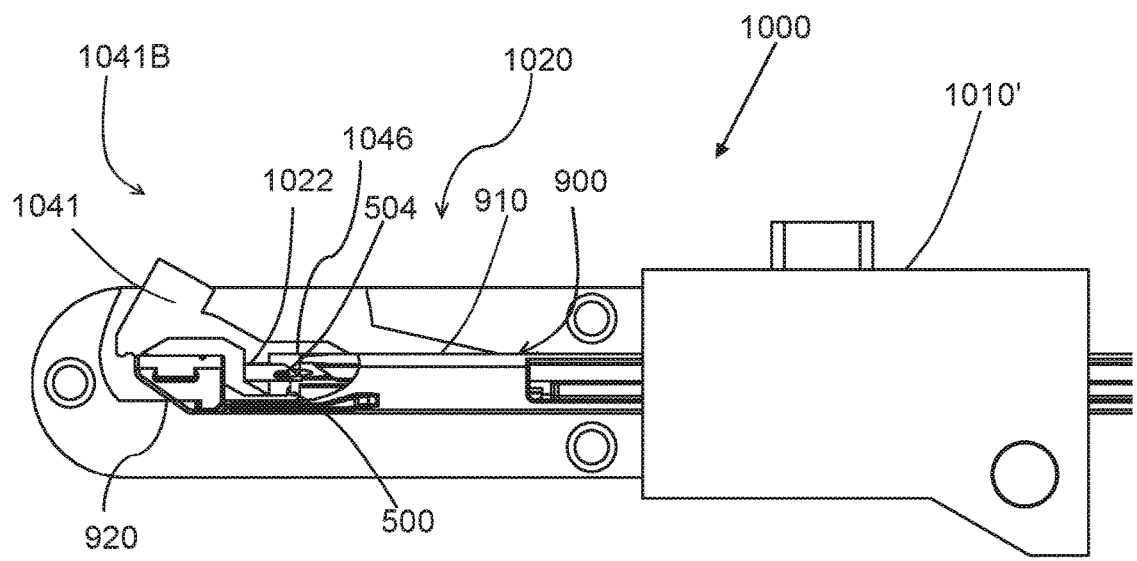
FIG. 4C(ii)
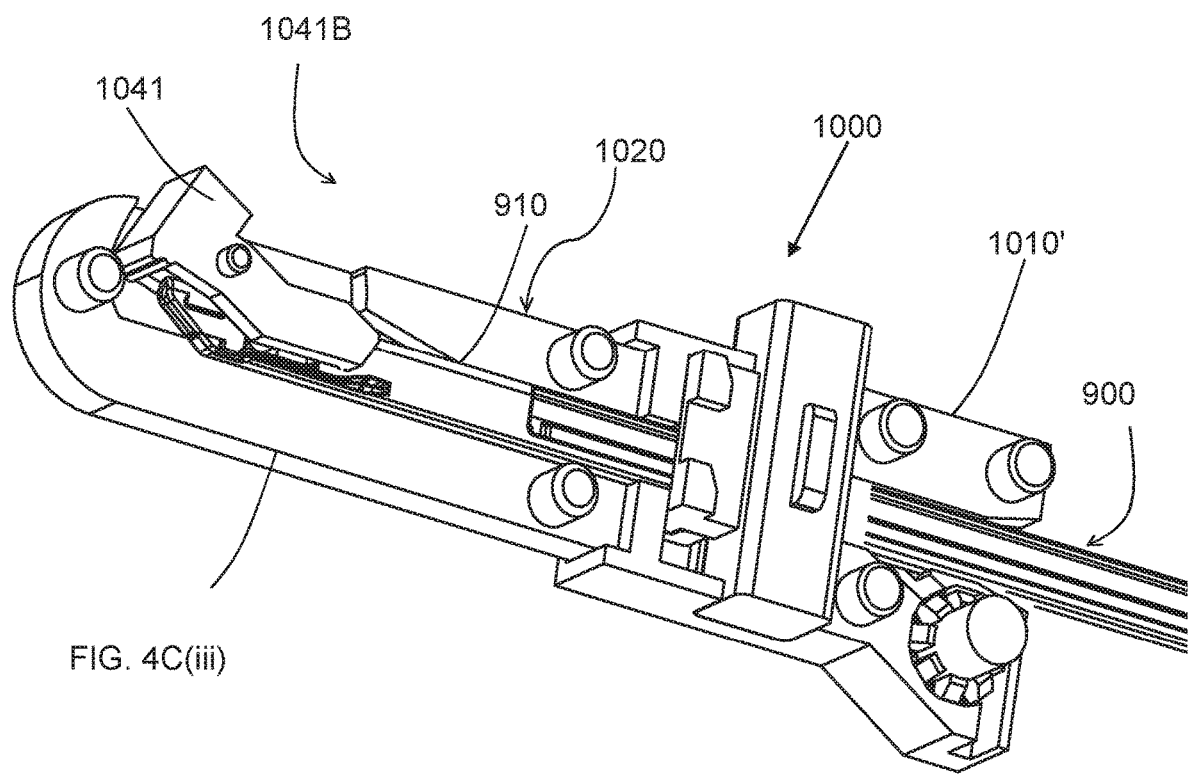
FIG. 4C(iii)

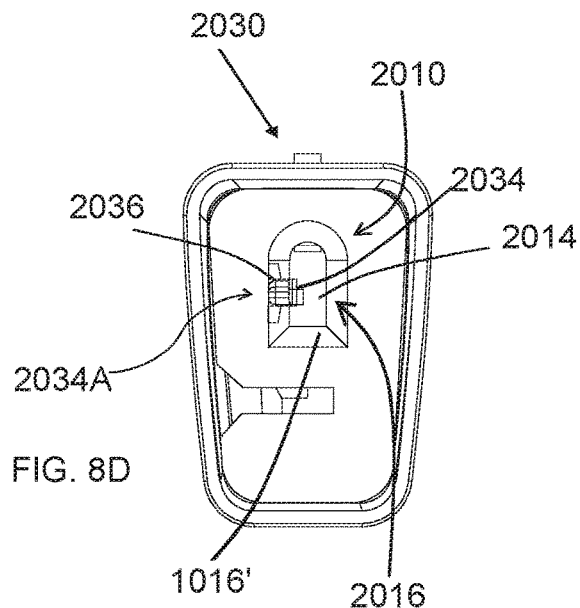
FIG. 8D
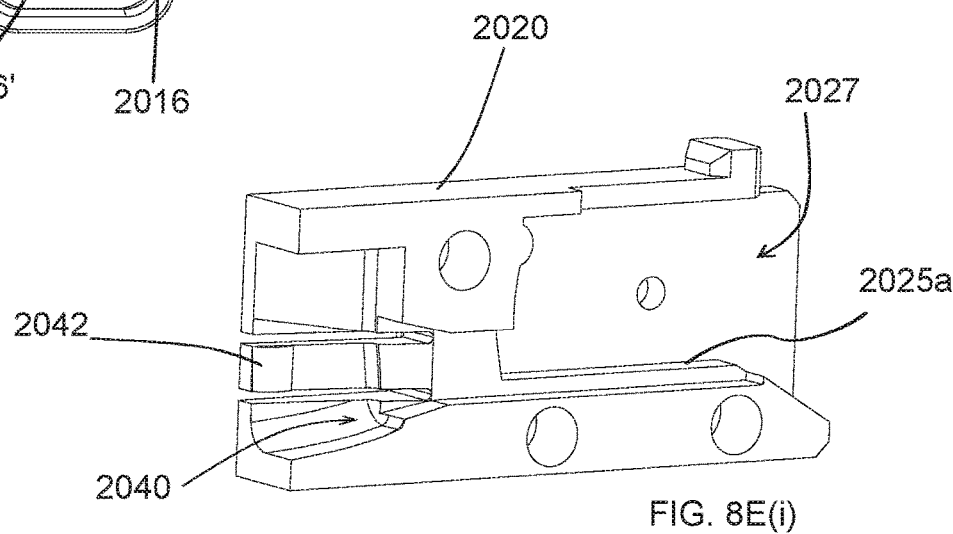
FIG. 8E(i)
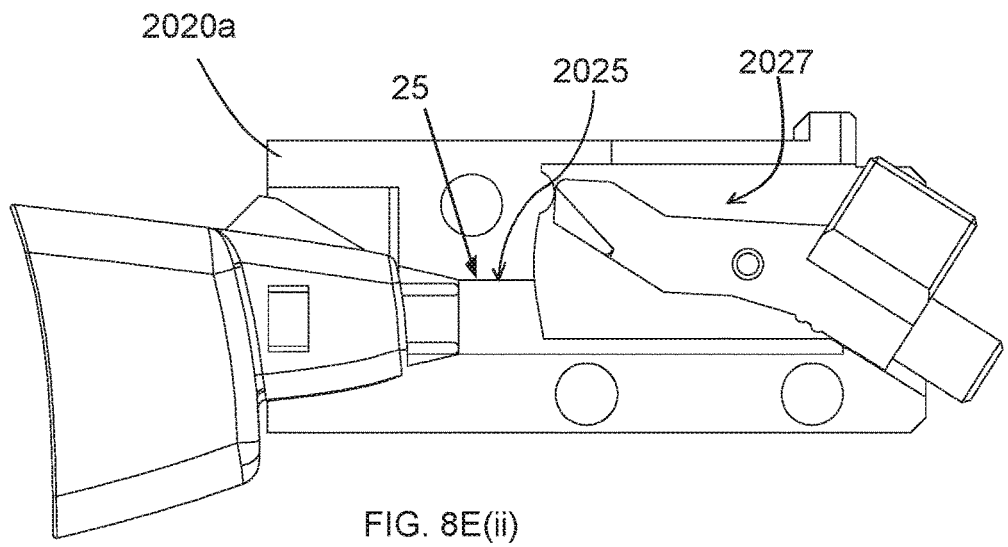
FIG. 8E(ii)

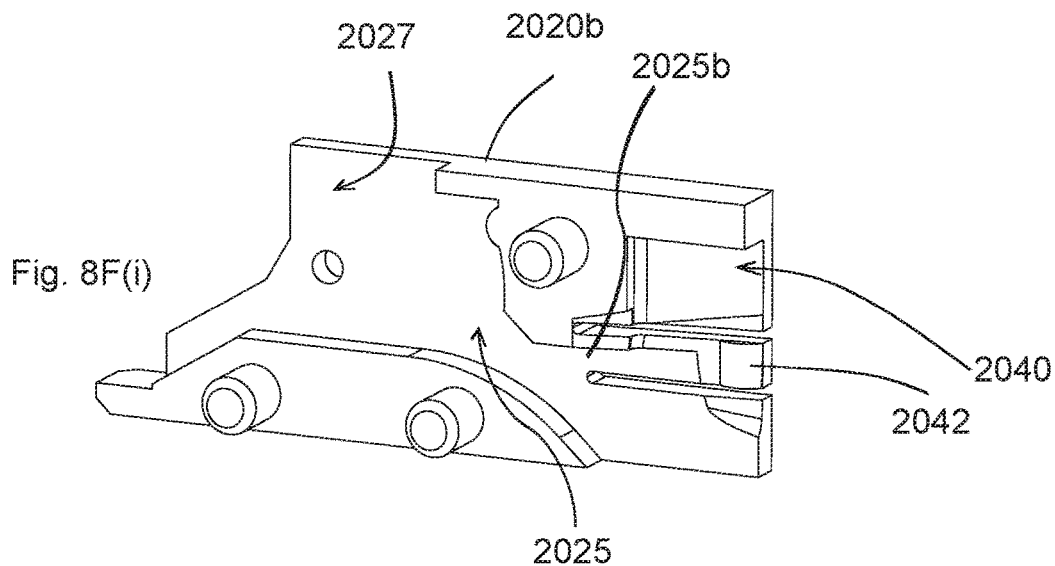
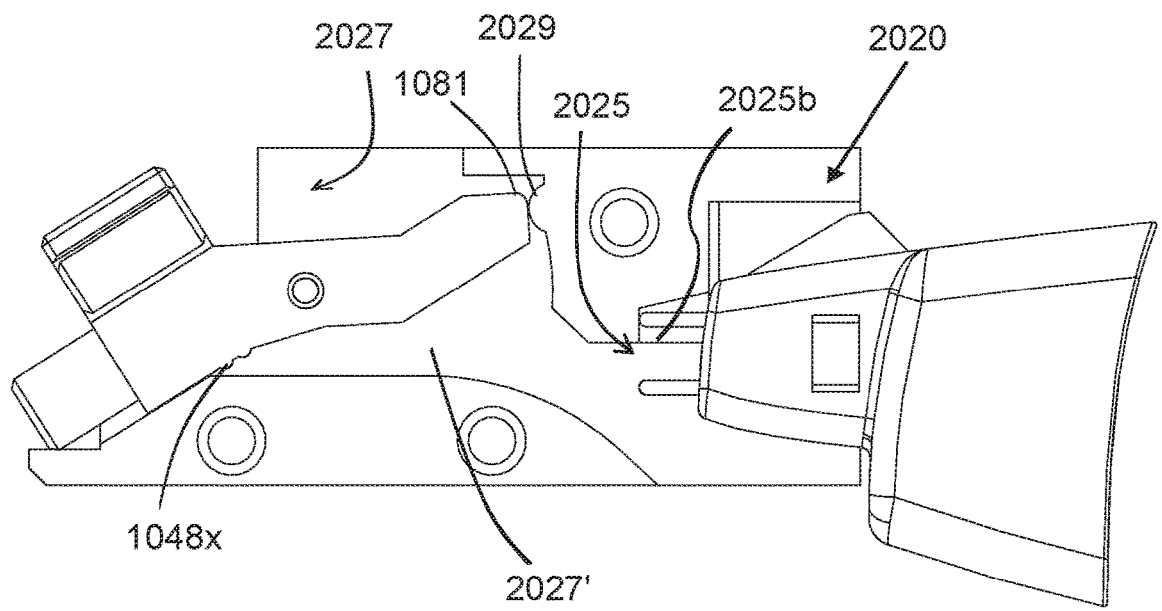
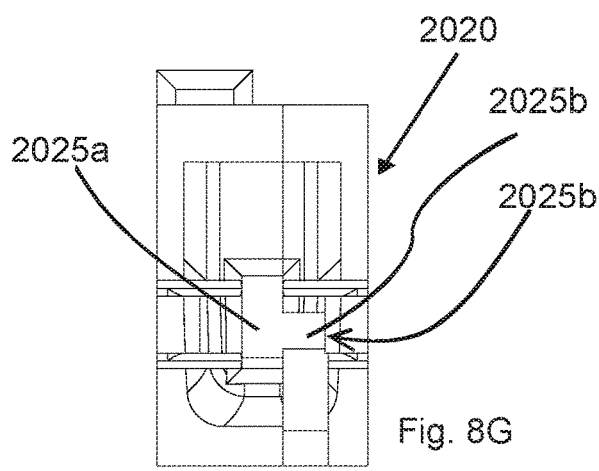

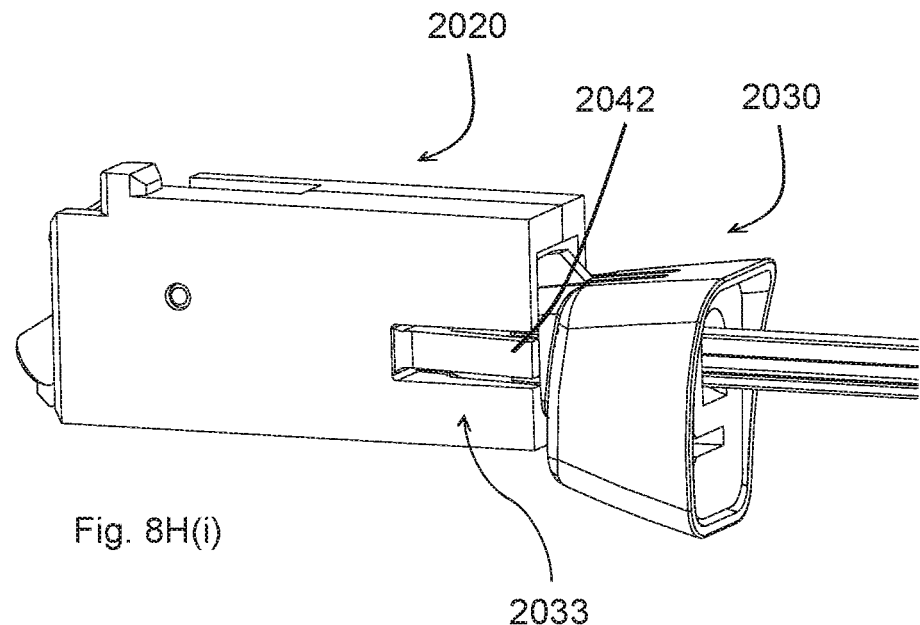
Fig. 8H(i)
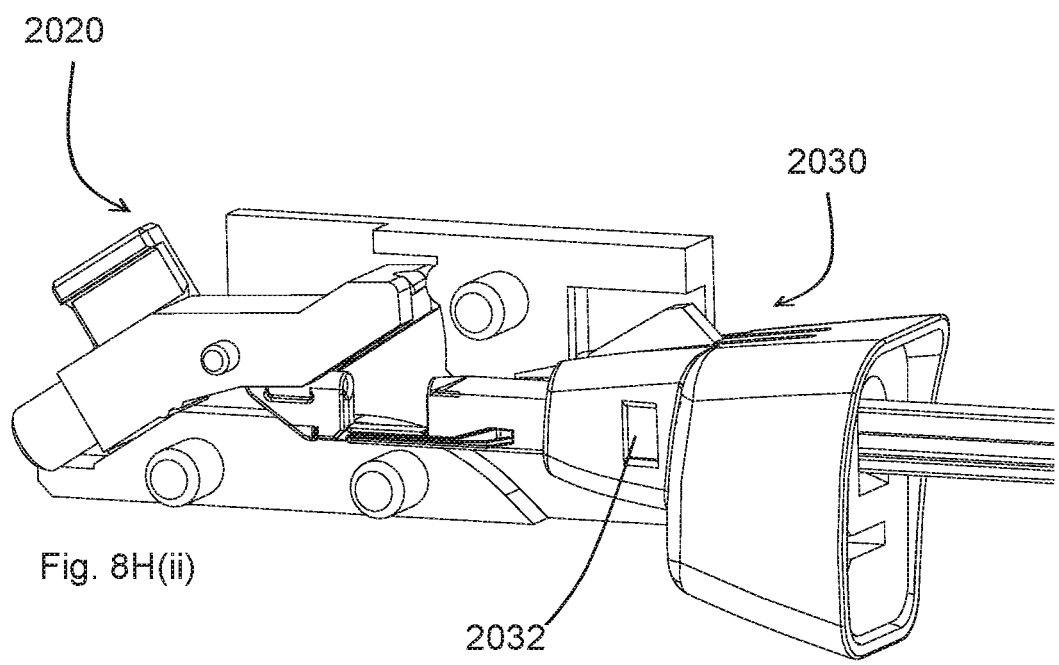
Fig. 8H(ii)

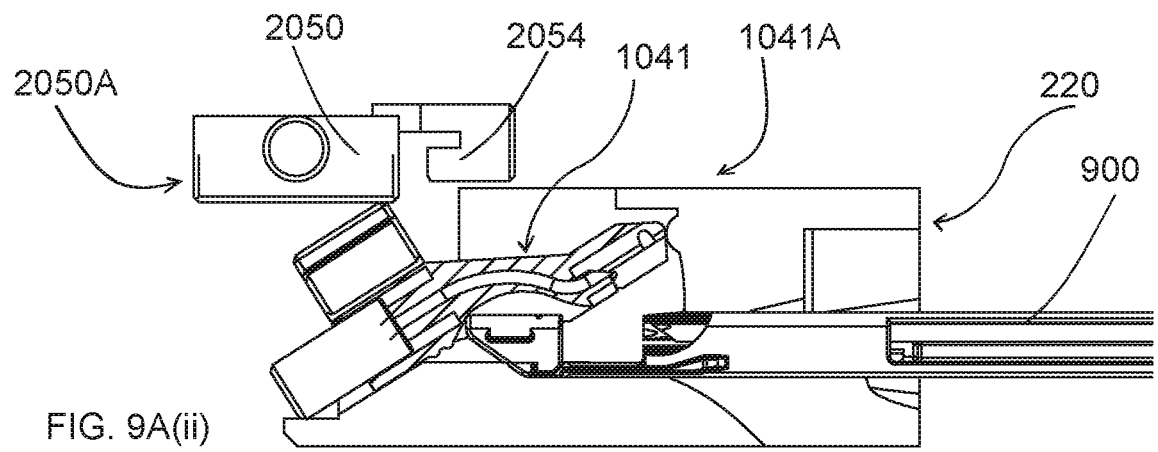
FIG. 9A(ii)
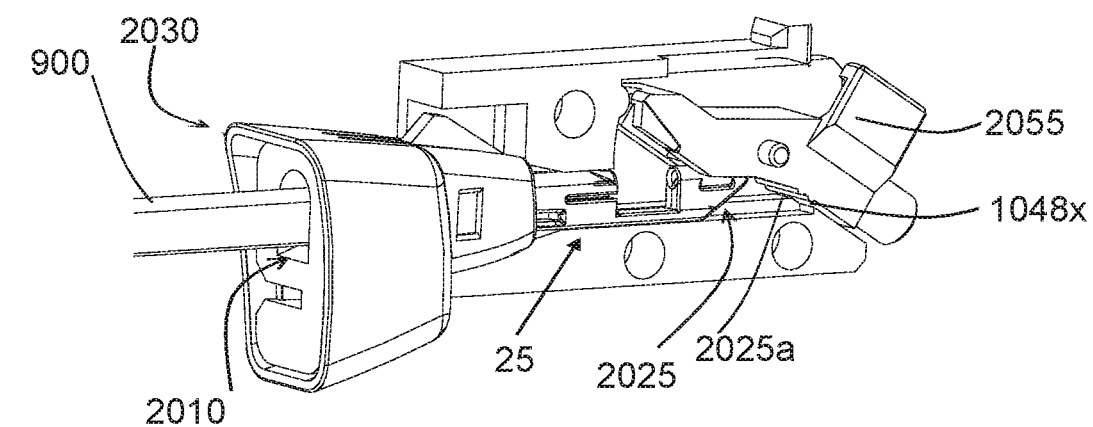
Fig. 9A(iii)

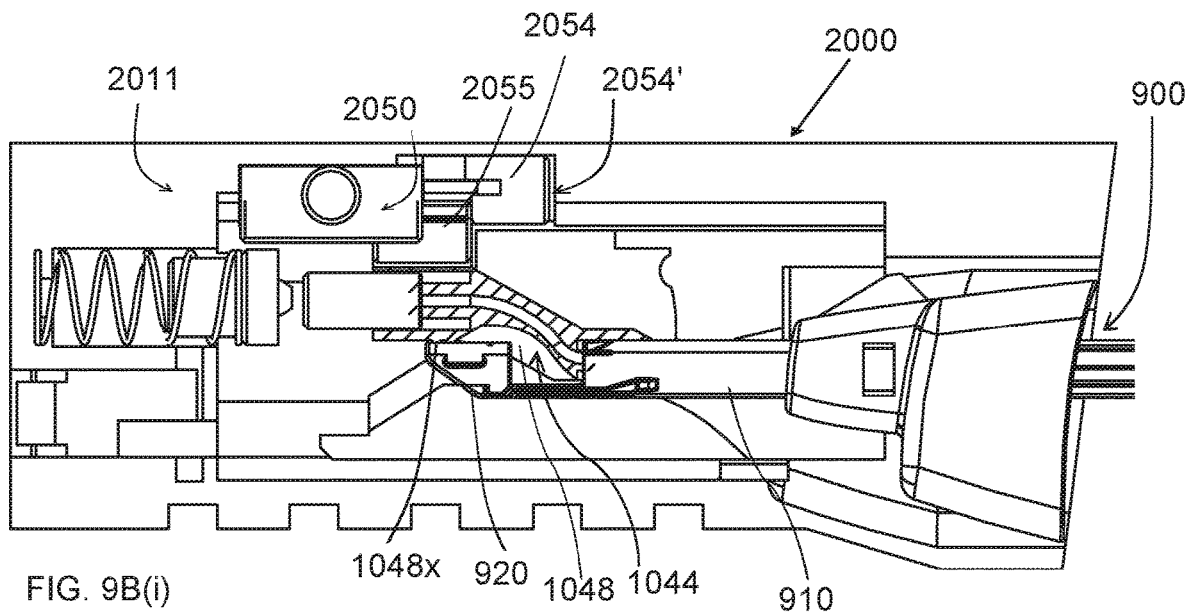
FIG. 9B(i)
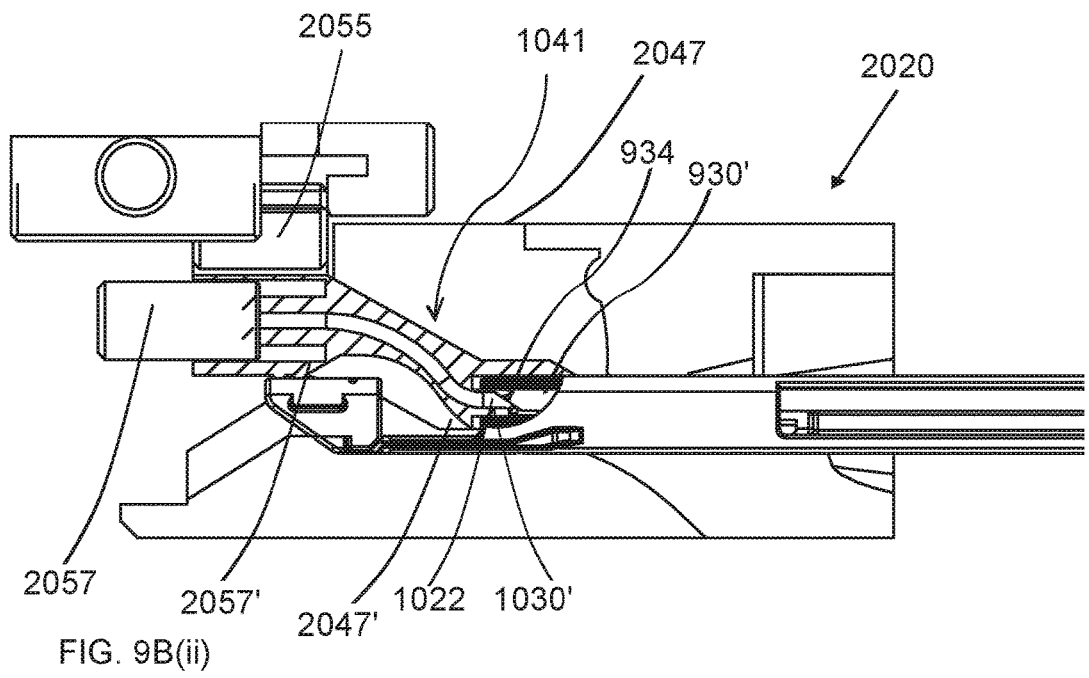
FIG. 9B(ii)

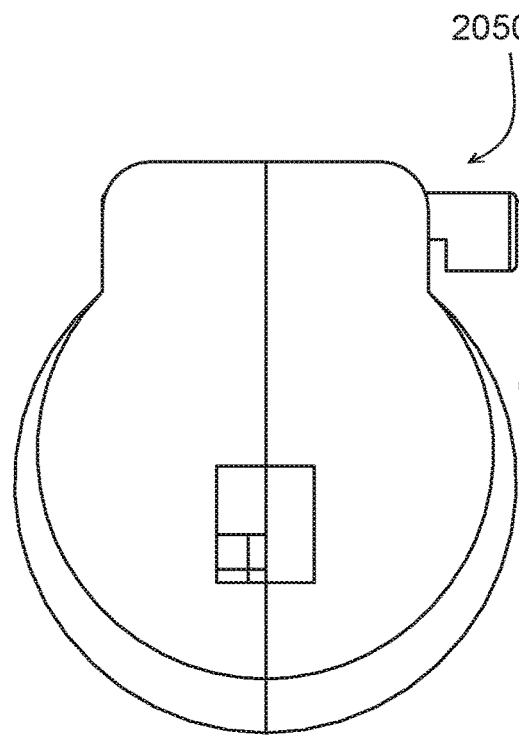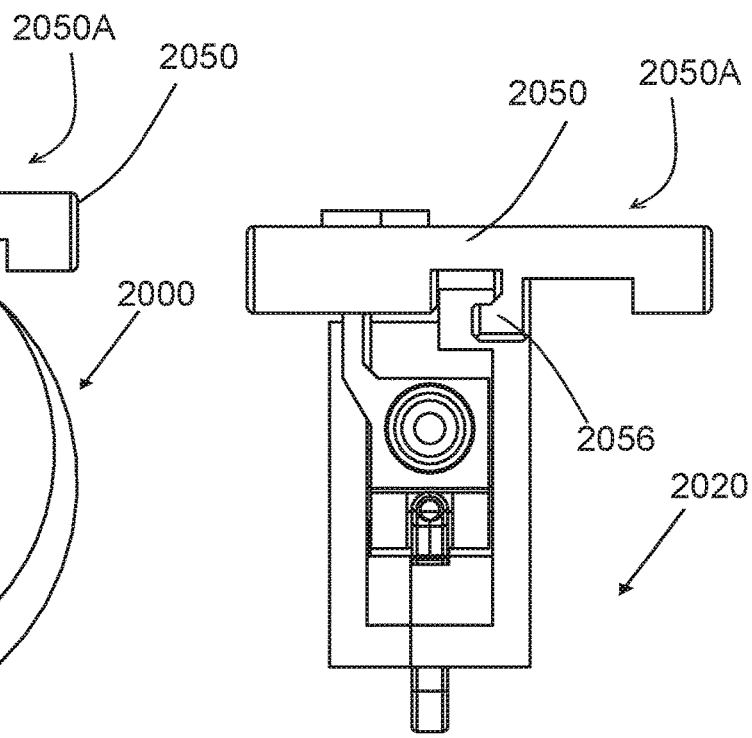
FIG. 9C(i)    FIG. 9C(ii)
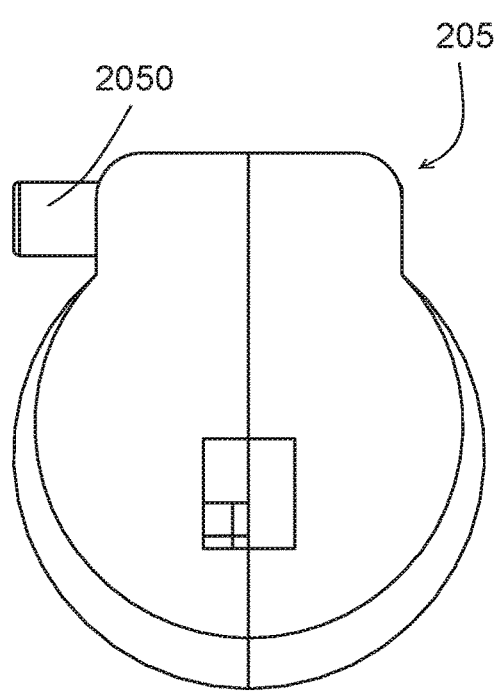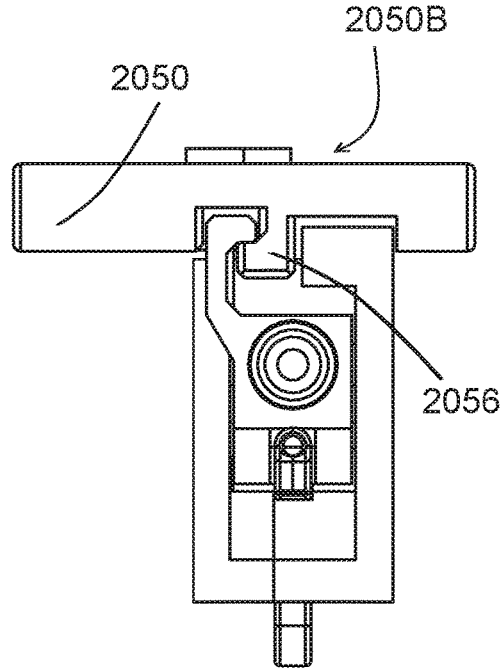
FIG. 9D(i)    FIG. 9D(ii)

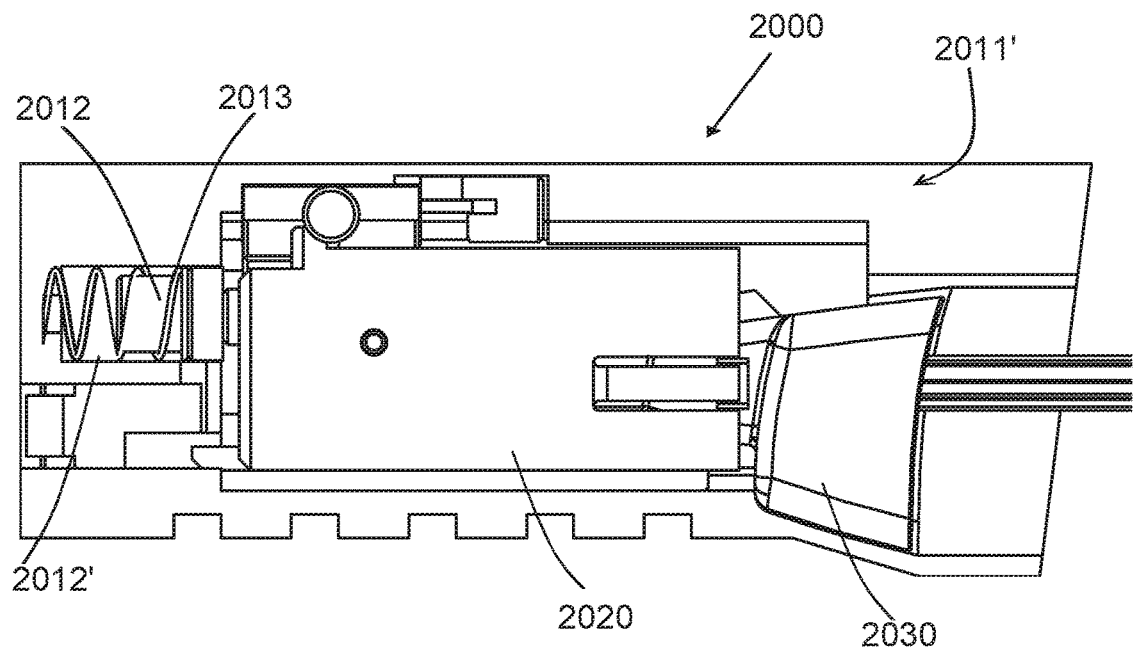
FIG. 9E(i)
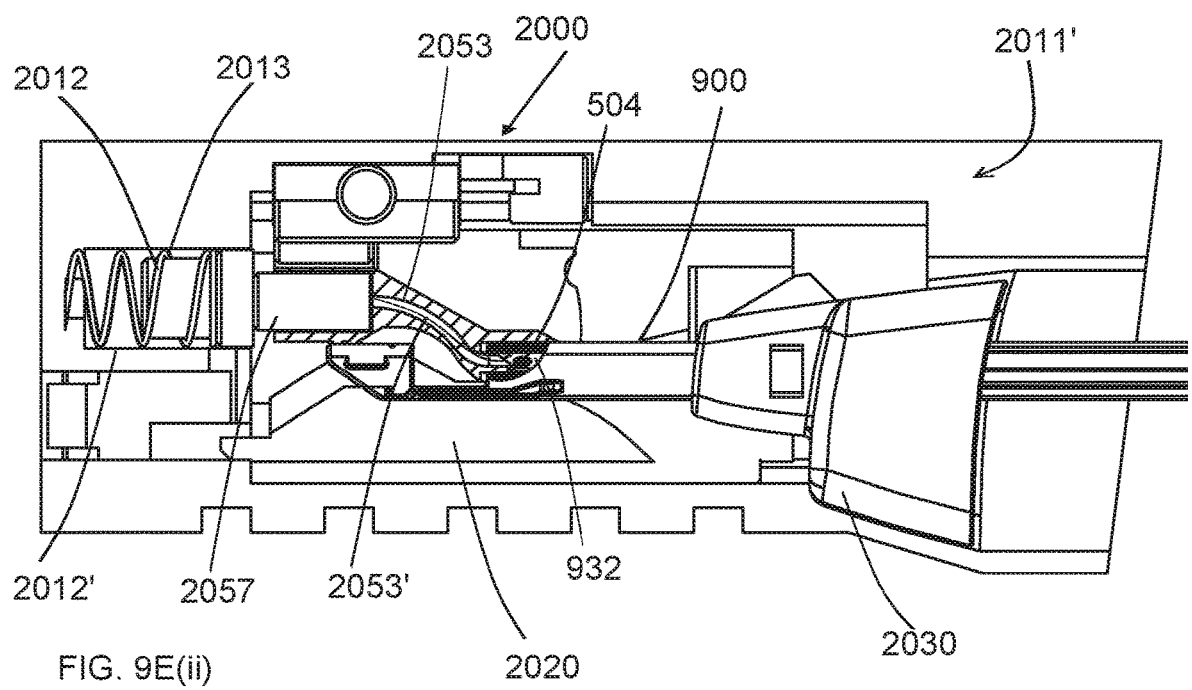
FIG. 9E(ii)

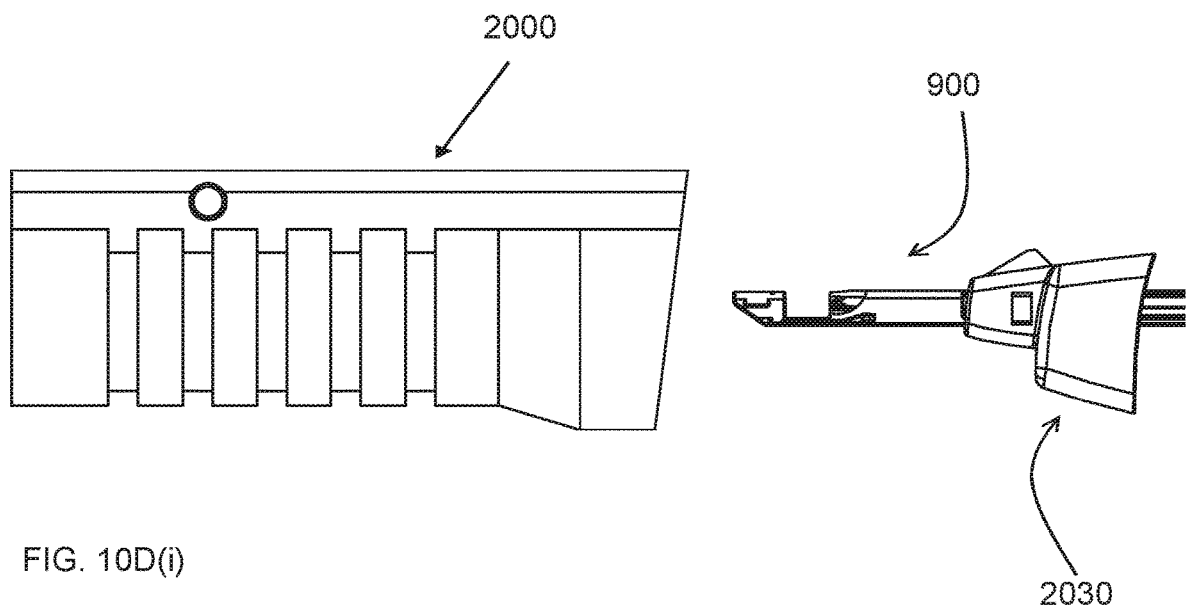
FIG. 10D(i)
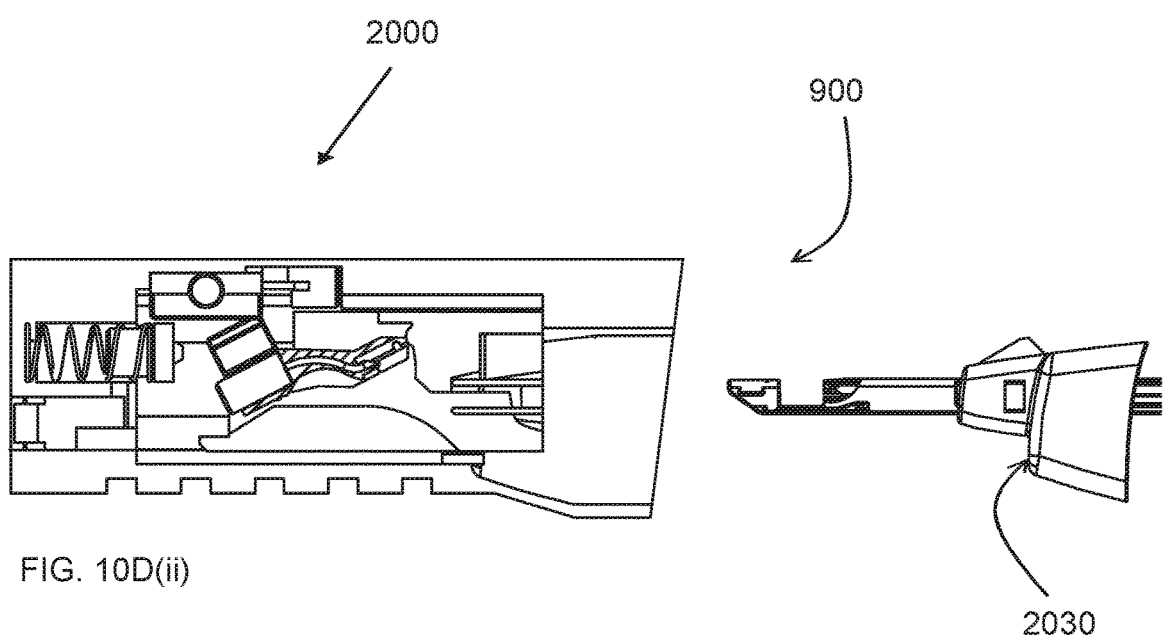
FIG. 10D(ii)

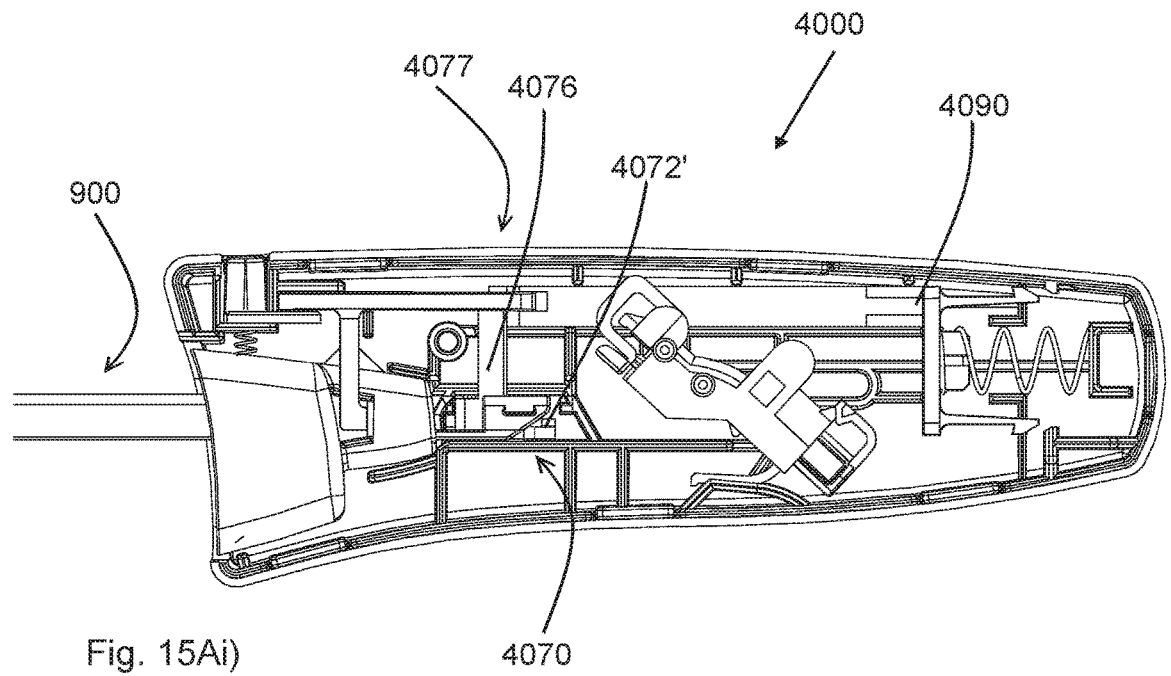
Fig. 15Ai)
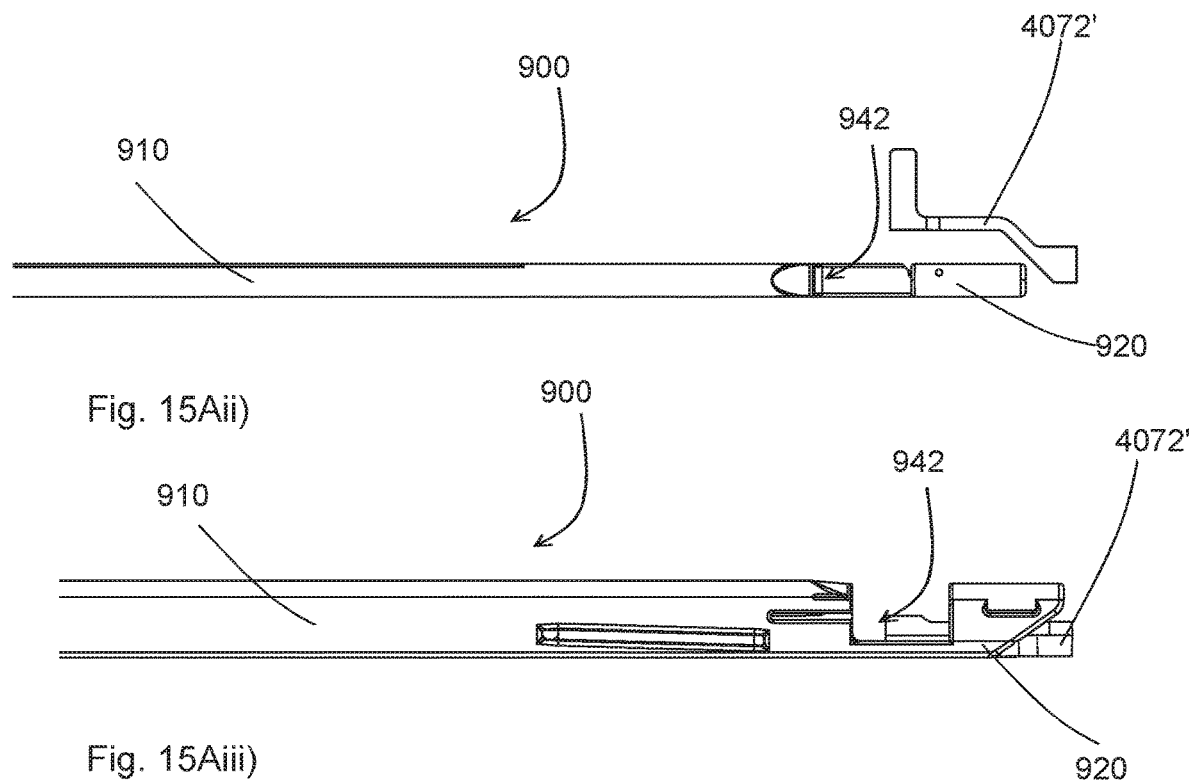
Fig. 15Aii)
Fig. 15Aiii)

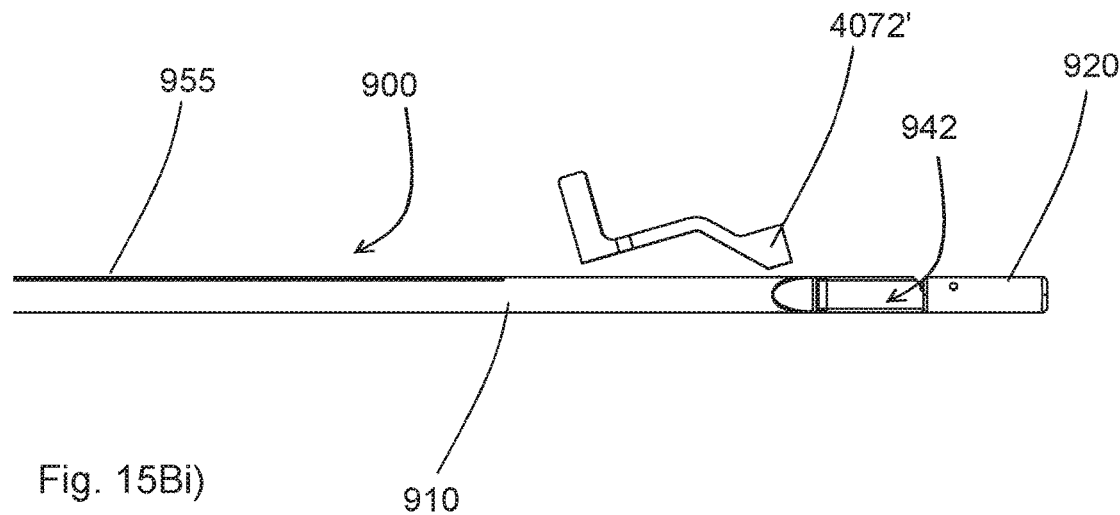
Fig. 15Bi)
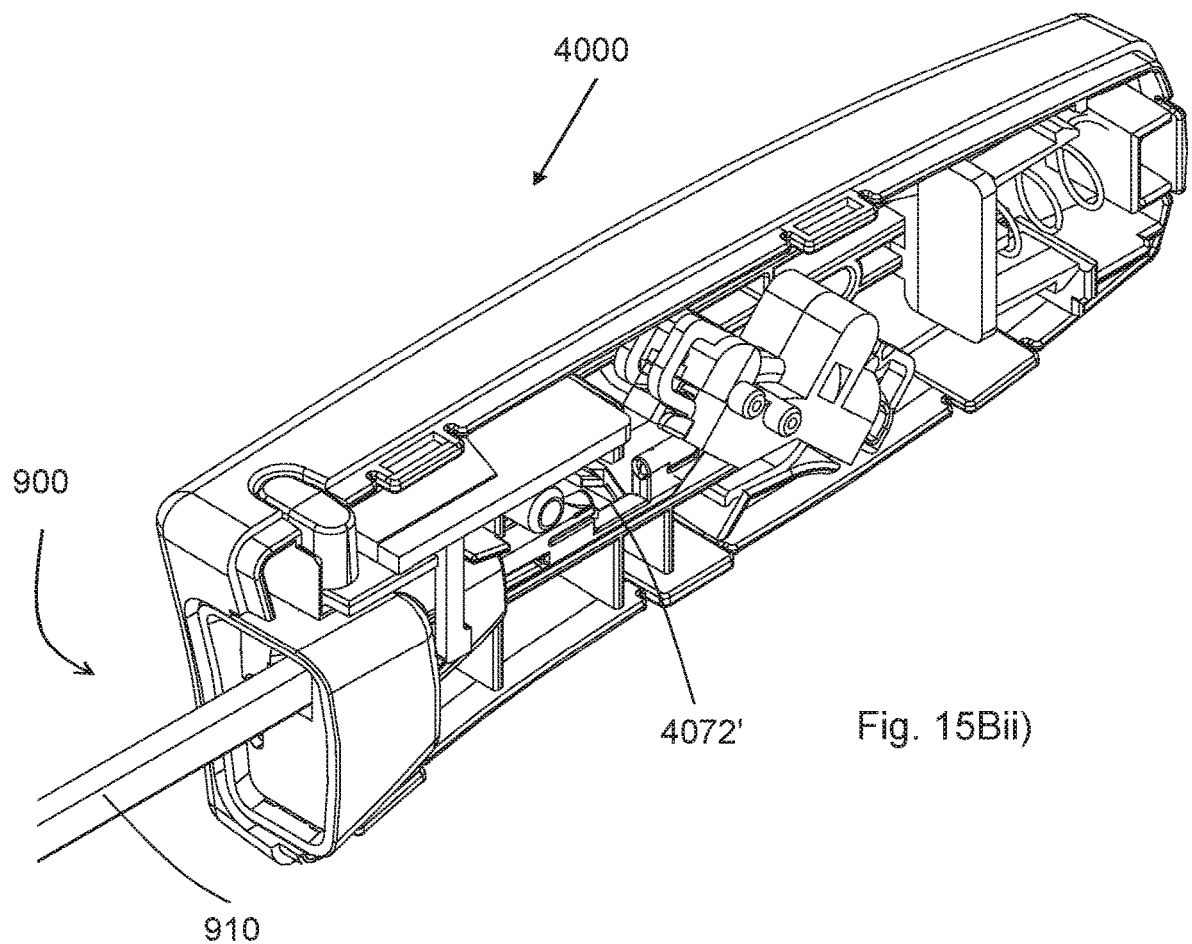
Fig. 15Bii)

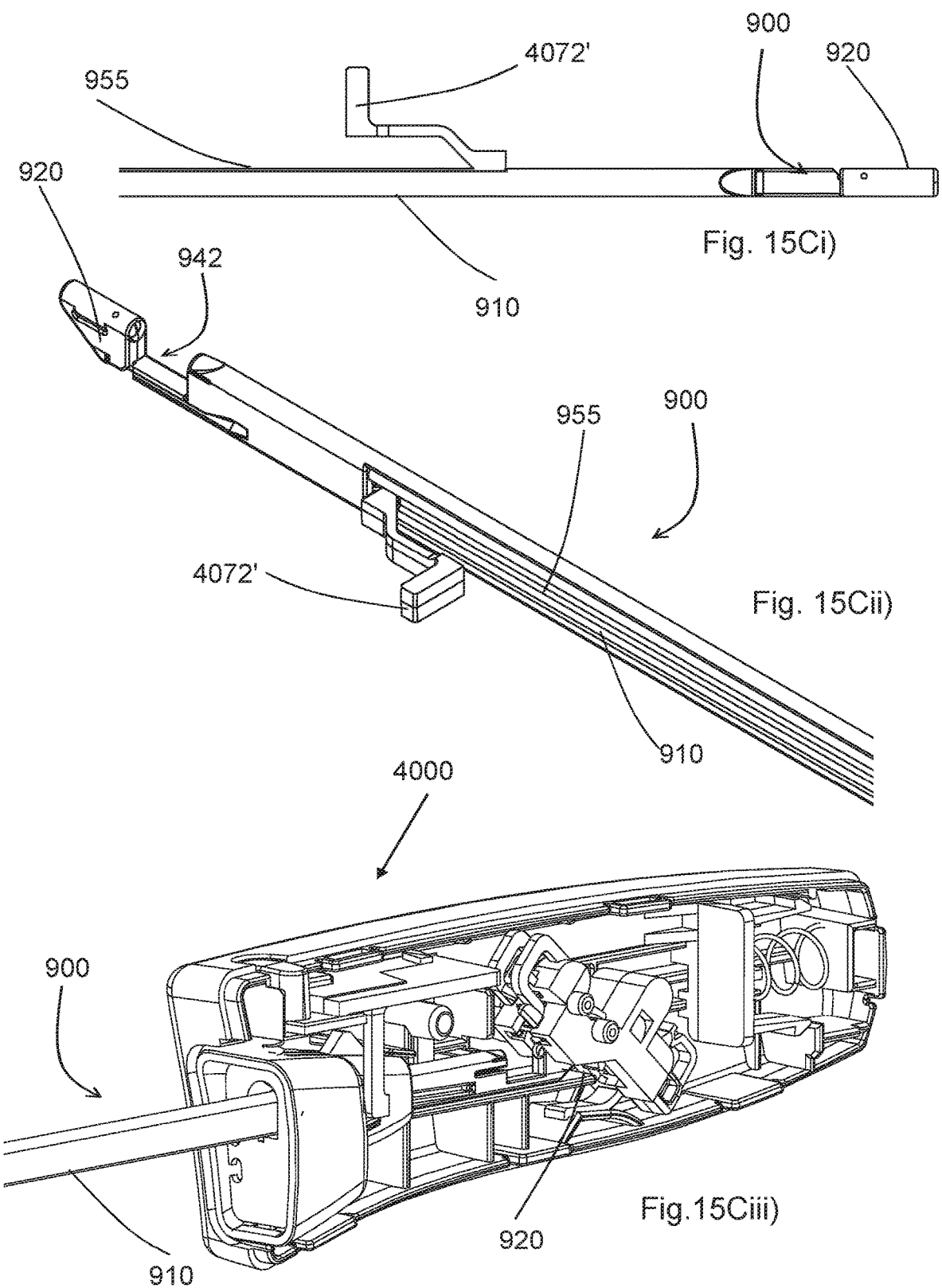

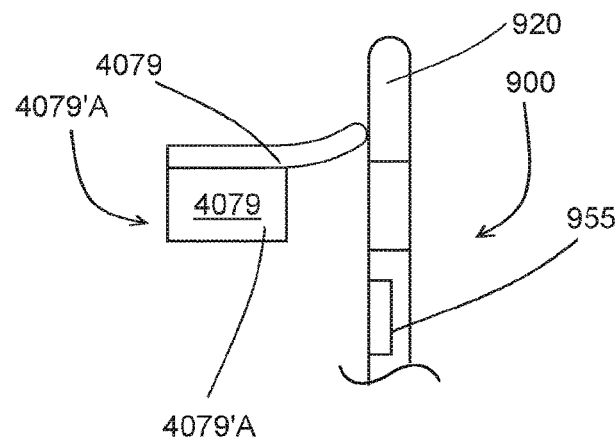
Fig.17A
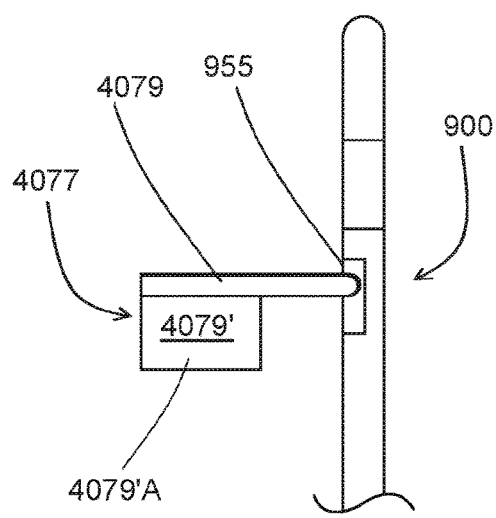
Fig.17B(ii)
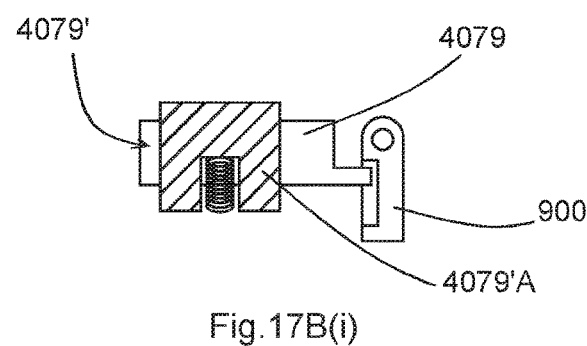
Fig.17B(i)
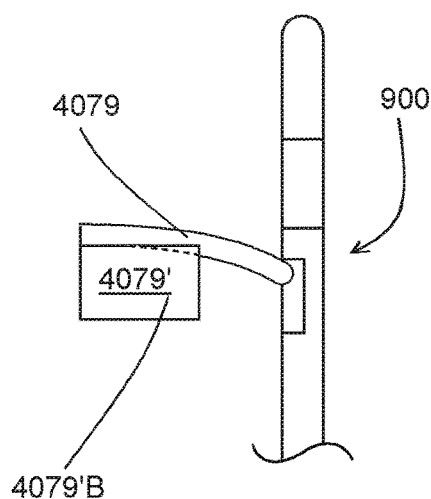
Fig.17C(ii)
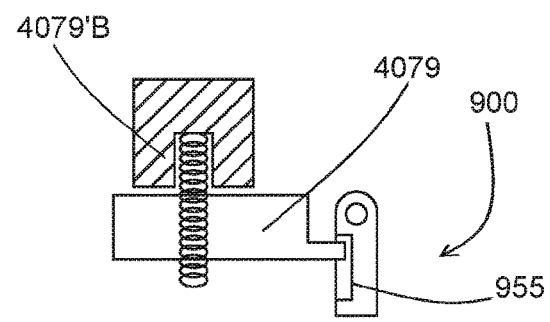
Fig.17C(i)

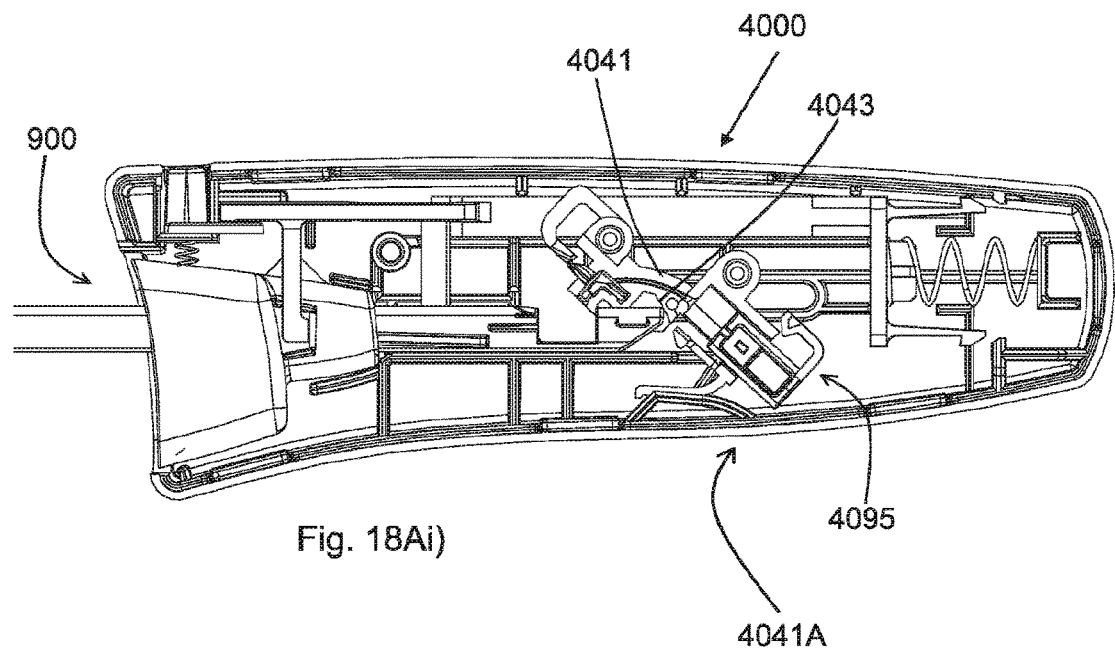
Fig. 18Ai)
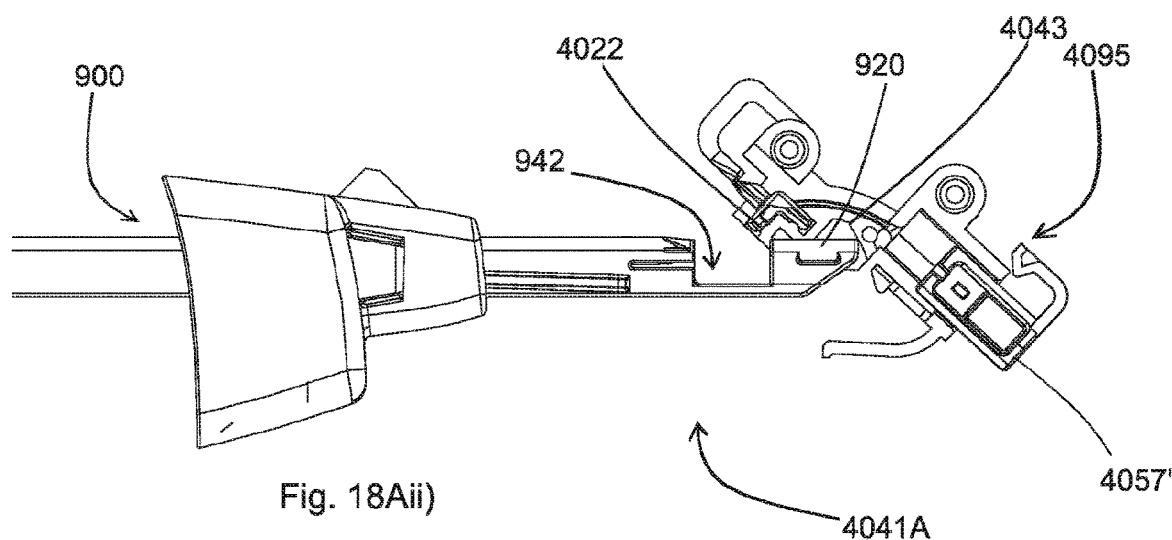
Fig. 18Aii)

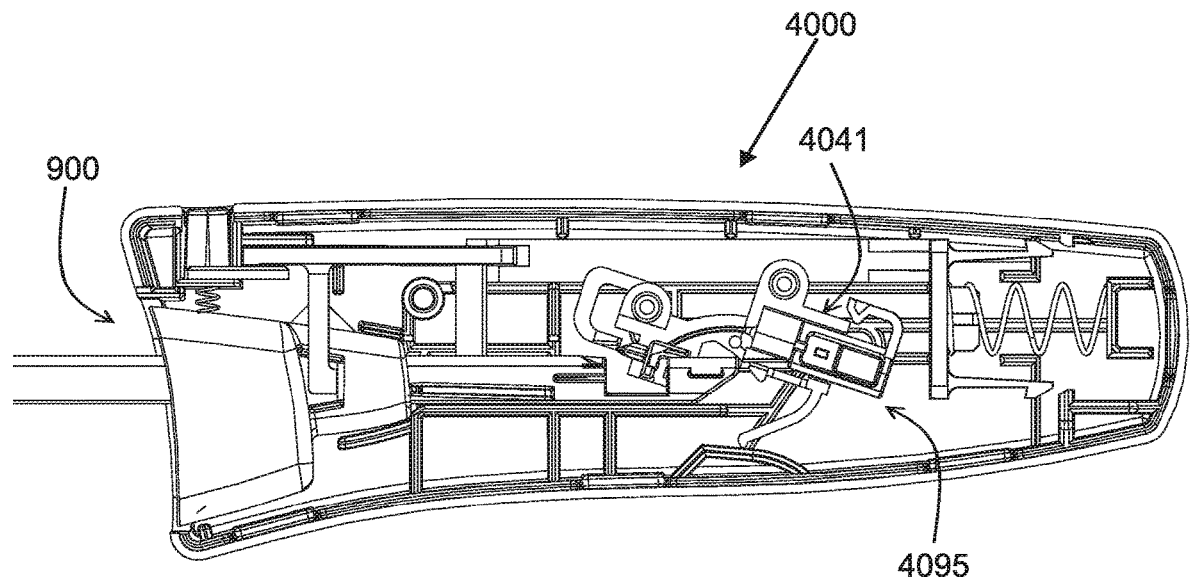
Fig. 18Bi)
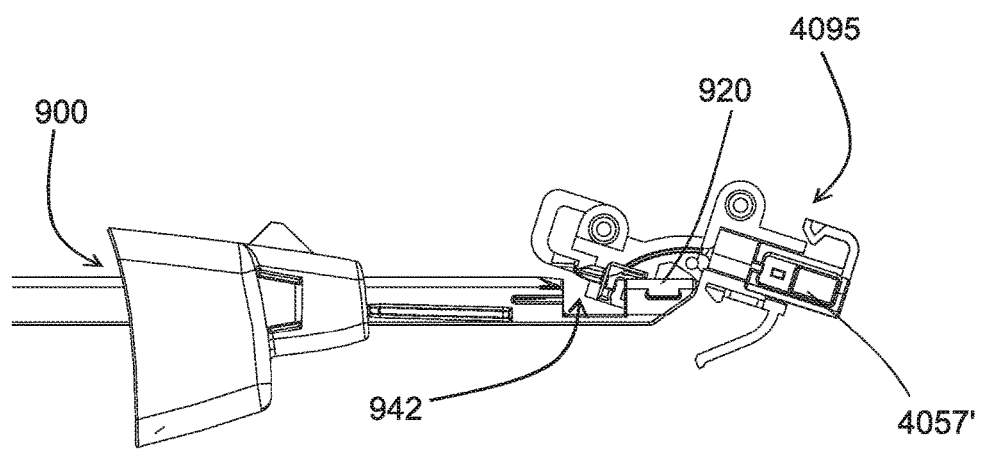
Fig. 18Bii)

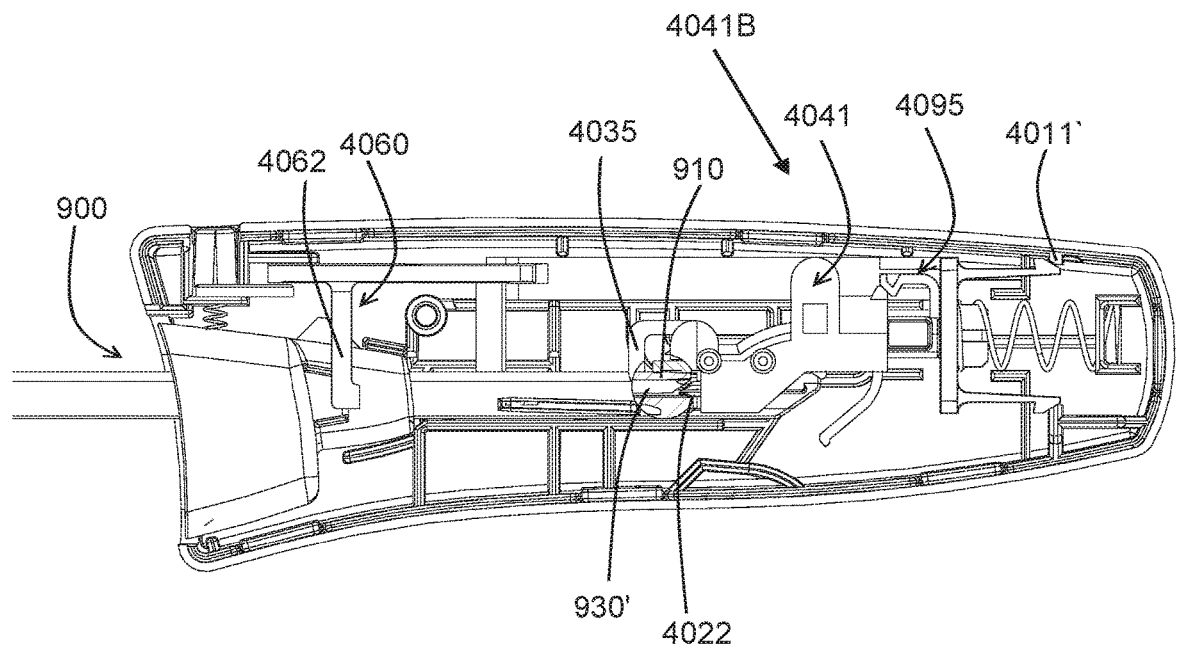
Fig. 18C(i)
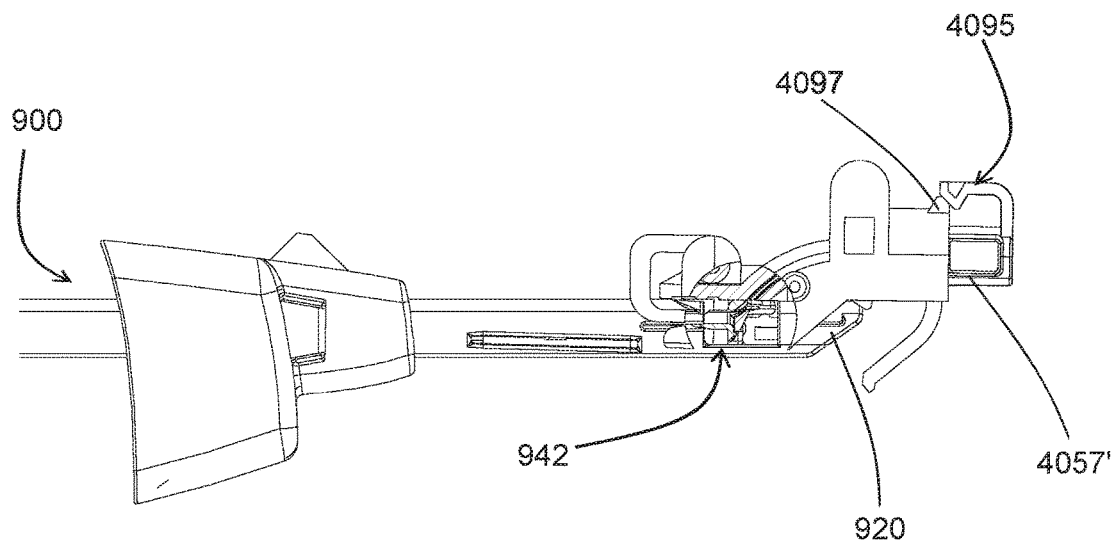
Fig. 18C(ii)

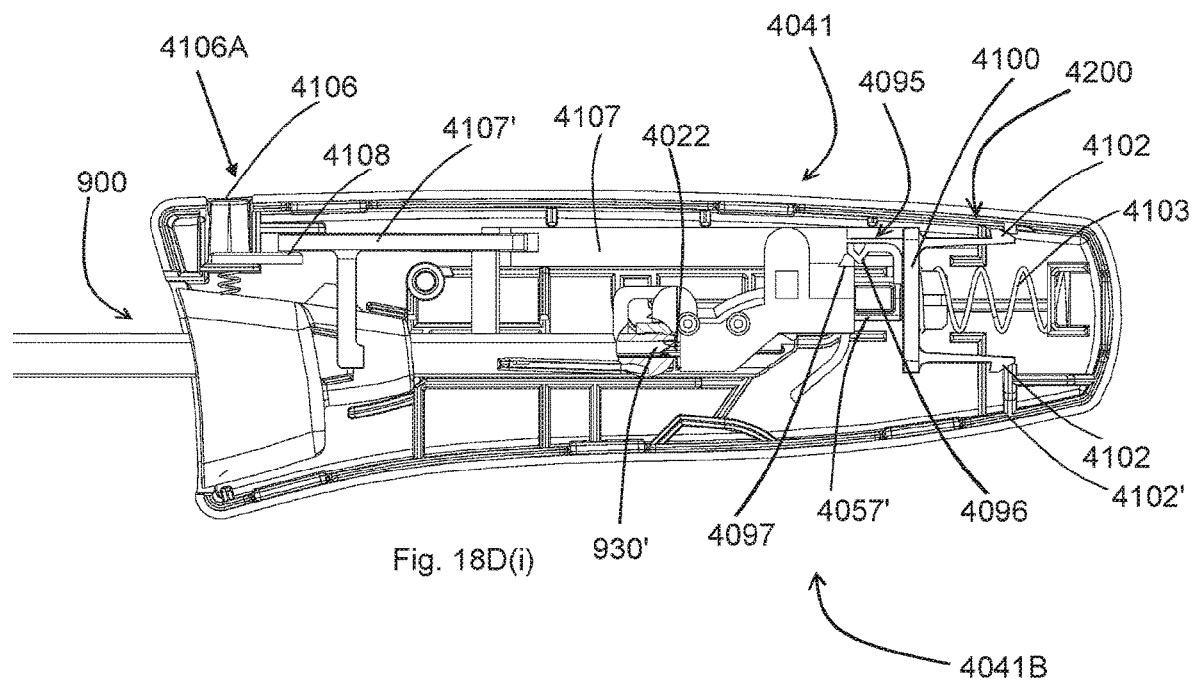
Fig. 18D(i)
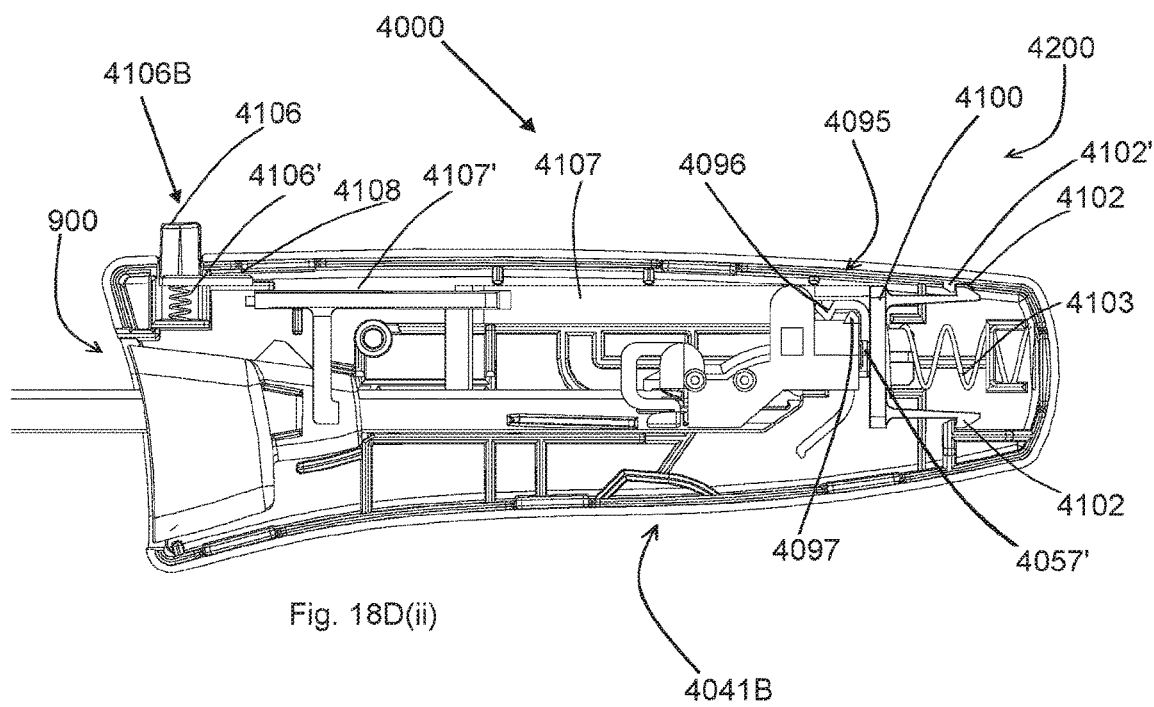
Fig. 18D(ii)

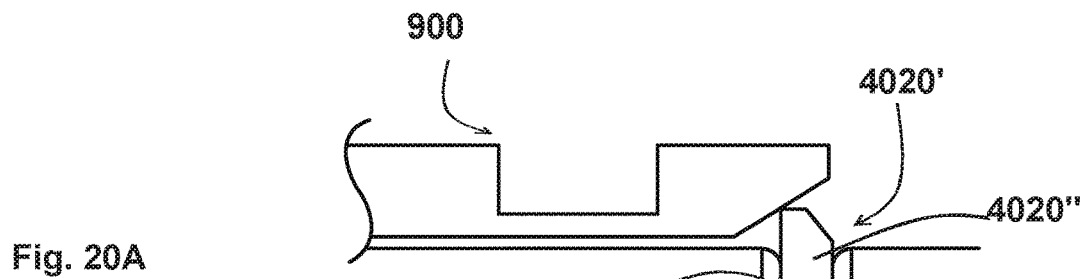
Fig. 20A
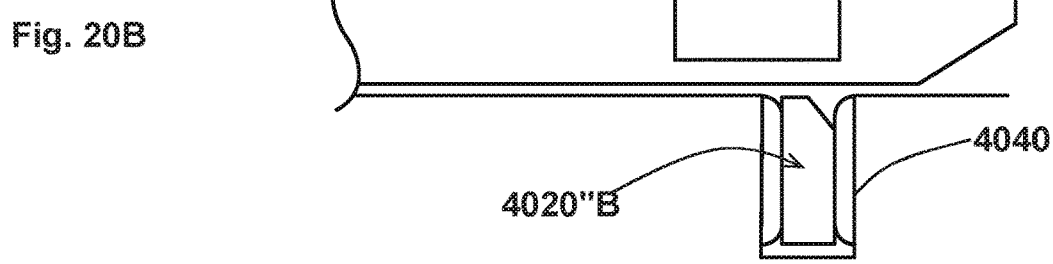
Fig. 20B
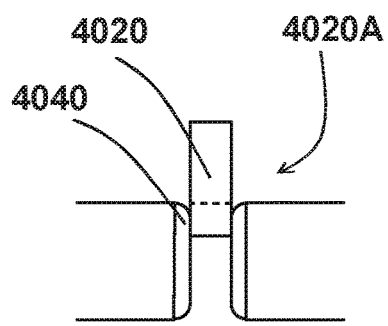
Fig. 21A(i)
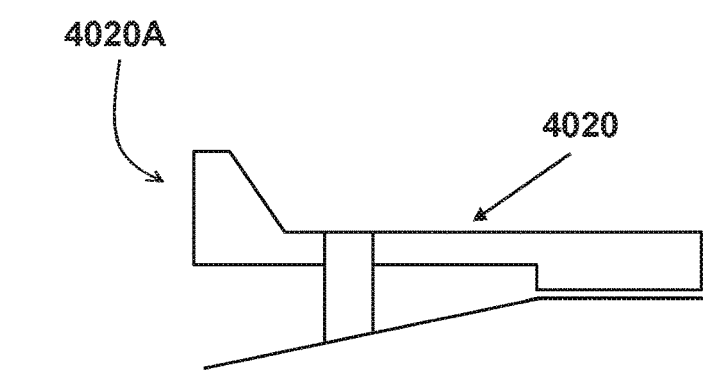
Fig. 21A(ii)
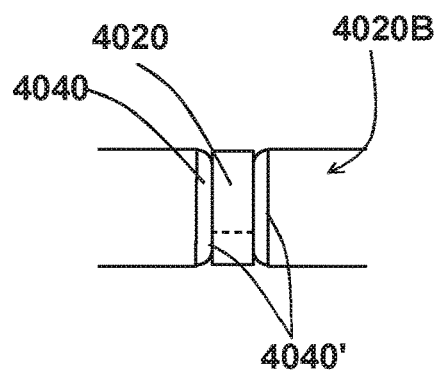
Fig. 21B(i)
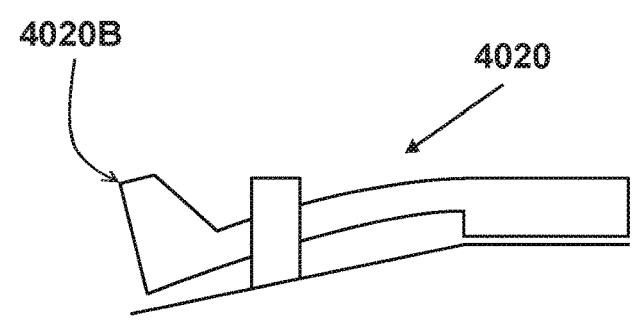
Fig. 21B(ii)

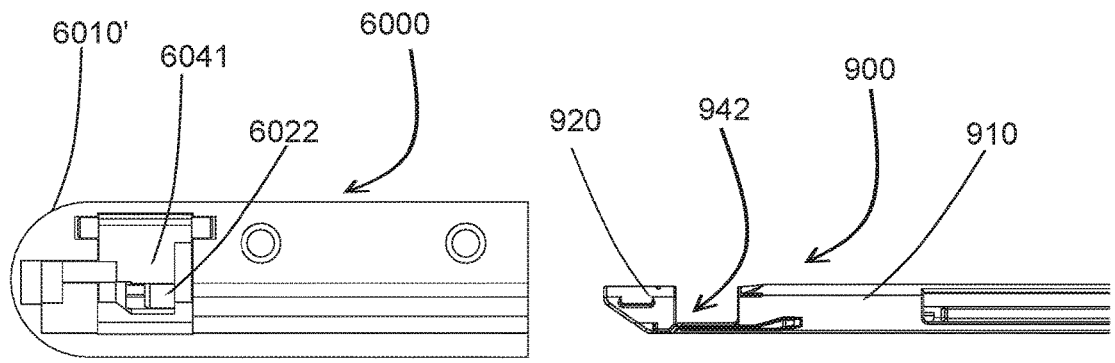
Fig. 23A
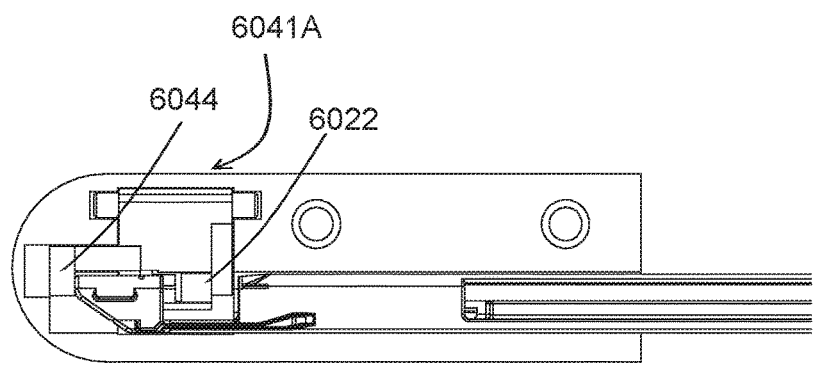 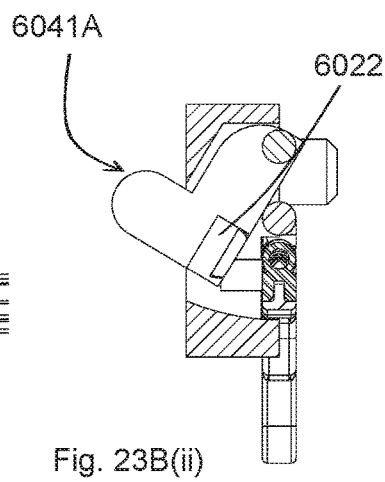
Fig. 23B(i)　　　　　　　　Fig. 23B(ii)
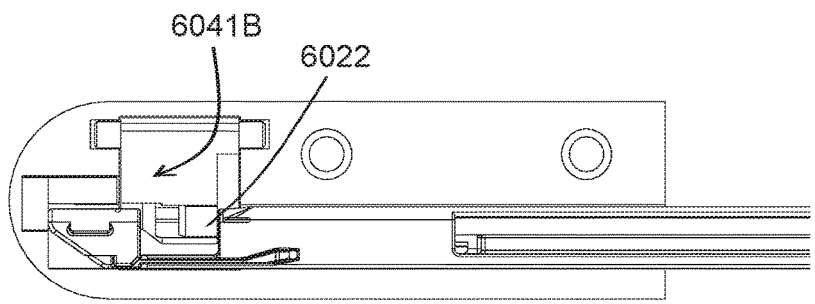 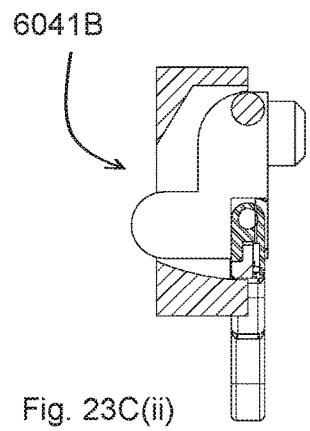
Fig. 23C(i)　　　　　　　　Fig. 23C(ii)

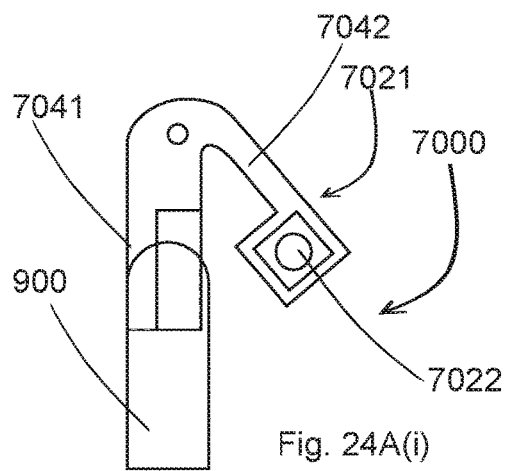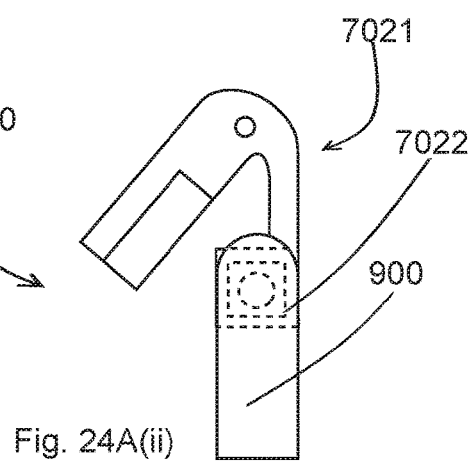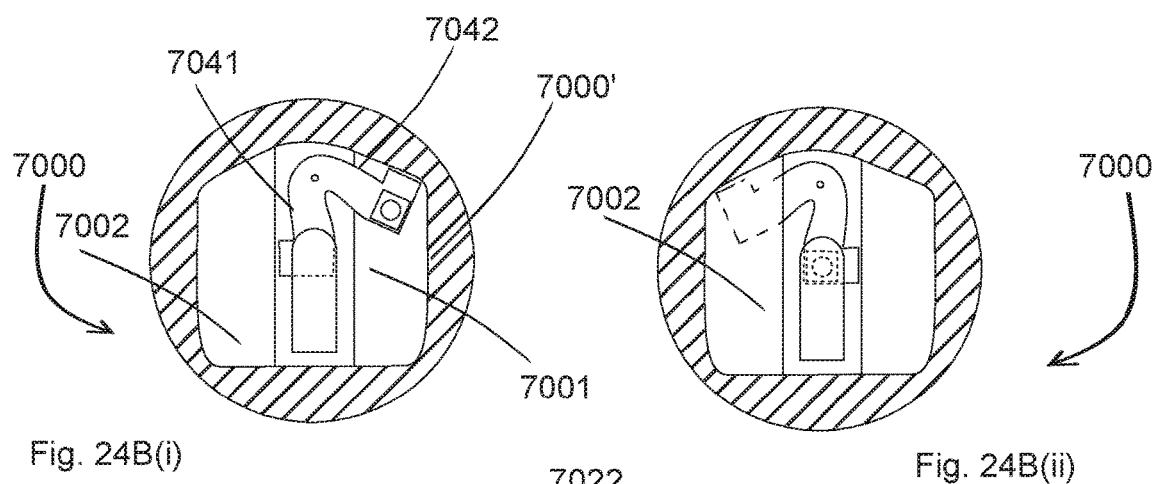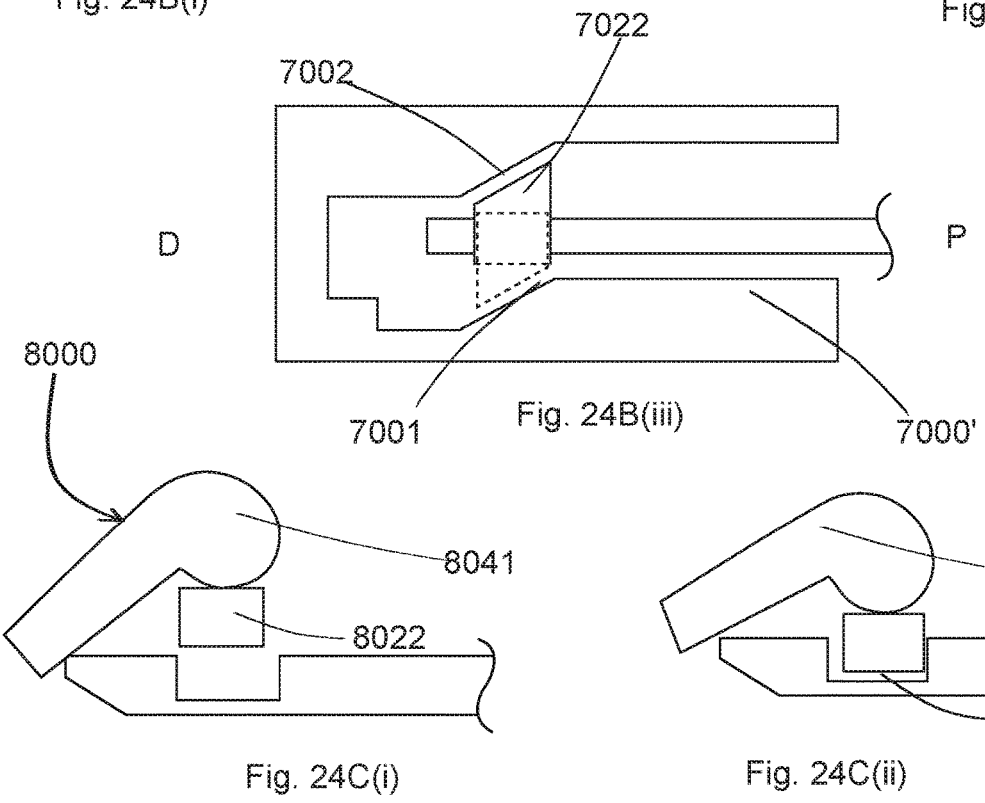

APPARATUS AND METHODS FOR LOADING SUTURE

TECHNICAL FIELD

The disclosure relates to an apparatus for loading suture onto a medical device, more specifically, to cartridge for loading suture onto a surgical suturing instrument.

SUMMARY OF THE DISCLOSURE

Various embodiments of a cartridge are disclosed, for loading a suture onto a suturing instrument and, in some embodiments, for loading a pre-tied knot formed from the suture onto the suturing instrument. The suturing instrument is typically of the type having a suture passing member defining a suture receiving passage therein. The cartridge may be operable to load the suture and/or the knot onto the suturing instrument at a point of use. In some embodiments, the cartridge defines a path for insertion thereto and withdrawal therefrom of the suturing instrument. The cartridge further comprises a seat for releasably holding a portion of a suture and a mechanism for transferring the suture from seat to the suturing instrument, various features of which are described herein.

In one broad aspect, embodiments of the present invention provide a cartridge for loading a suture onto a suturing instrument, the cartridge defining a path for insertion thereto and withdrawal therefrom of the suturing instrument, the cartridge comprising: a seat for releasably holding a portion of a suture; and a translation mechanism for moving the seat out of a path of a suturing instrument inserted into the cartridge to allow for withdrawal of the suturing instrument from the cartridge.

In another broad aspect, embodiments of the present invention provide a cartridge for loading a suture onto a suturing instrument, the cartridge comprising: a seat for releasably holding a portion of a suture; and an alignment feature for facilitating alignment of the seat with a suturing instrument to permit transfer of the suture portion from the seat onto the suturing instrument.

In still an additional broad aspect, embodiments of the present invention provide A cartridge for loading suture onto a suturing instrument, the cartridge comprising: a seat for holding a portion of the suture; and an instrument retention mechanism configured to allow advancement of a suturing instrument into the cartridge and to prevent premature retraction therefrom.

In a further broad aspect embodiments of the present invention comprise a cartridge for loading a suture onto a suturing instrument, the cartridge comprising: a seat for releasably holding a portion of a suture to enable transfer of the suture onto the suturing instrument; and an indicator for indicating transfer of the suture portion onto the suturing instrument.

In still an additional embodiment, a cartridge is provided for loading suture onto a suturing instrument, the cartridge comprising: a seat for holding a portion of a suture; and an obstructing feature having a closed configuration and an open configuration, the obstructing feature being configured to be initially in the closed configuration for preventing advancement of an inverted suturing instrument into the cartridge, and to be moveable into the open configuration upon insertion of the suturing instrument into the cartridge in a nominal orientation.

In still another broad aspect, embodiments of the present invention provide a cartridge for loading suture onto a suturing instrument, the cartridge comprising: a seat for releasably holding a portion of the suture; an alignment feature for aligning the seat with a portion of the suturing instrument; a suture insertion mechanism that is actuatable to insert the suture portion from the seat onto the suturing instrument; and a delay interlock to prevent actuation of the suture insertion mechanism prior to alignment of the seat with the portion of the suturing instrument.

In still another broad aspect, embodiments of the present invention provide a cartridge for In still a further broad aspect, embodiments of the present invention provide a cartridge for loading a pre-tied knot onto a suturing instrument, the cartridge comprising: a cartridge housing; a knot slider for carrying a pre-tied knot thereabout; and a knot slider release mechanism for detachably coupling the knot slider to the cartridge housing.

In an additional broad aspect, embodiments of the present invention provide a cartridge for a cartridge for loading suture onto a suturing instrument comprising a suture passing member, the cartridge comprising a seat for holding an end of the suture, the seat being structured and configured to allow a suture passing member to be advanced over the suture end to capture the suture end.

Furthermore, as an additional broad aspect of the present invention, embodiments of a kit are provided, the kit generally including at least one cartridge as described hereinbelow, along with at least one suturing instrument, the cartridge being operable in cooperation with the suturing instrument to load suture from the cartridge onto the instrument.

BRIEF DESCRIPTION OF THE DRAWINGS

In order that the invention may be readily understood, embodiments of the invention are illustrated by way of examples in the accompanying drawings, in which:

FIGS. 8A-8H(ii) illustrate views of a cartridge in accordance with an alternate embodiment of the present invention;

FIGS. 10A-10D(ii) illustrate views of a cartridge and a method of using the same in accordance with an alternate embodiment of the present invention;

FIG. 15A(i)-15C(iii) illustrate a cartridge comprising an instrument retention mechanism in accordance with an embodiment of the present invention;

FIGS. 17A-17C(ii) illustrate a still further alternative for an instrument retention mechanism for a cartridge in accordance with an embodiment of the present invention;

FIGS. 20A-20B illustrate an alternate embodiment of an interlock for preventing upside-down (reverse-oriented) insertion of the suturing instrument, in accordance with an embodiment of the present invention;

FIG. 21Ai)-21Bii) illustrate an alternate embodiment of an interlock for preventing upside-down (reverse-oriented) insertion of the suturing instrument, in accordance with an embodiment of the present invention;

FIGS. 23A-23G illustrate various views of an alternate embodiment of a cartridge for facilitating capture of a suture portion by a suture passing member, in accordance with an embodiment of the present invention; and FIG. 24Ai)-24Cii) illustrate various alternative of a cartridge in accordance with alternative embodiments of the present invention.

DETAILED DESCRIPTION

Figure 1A:
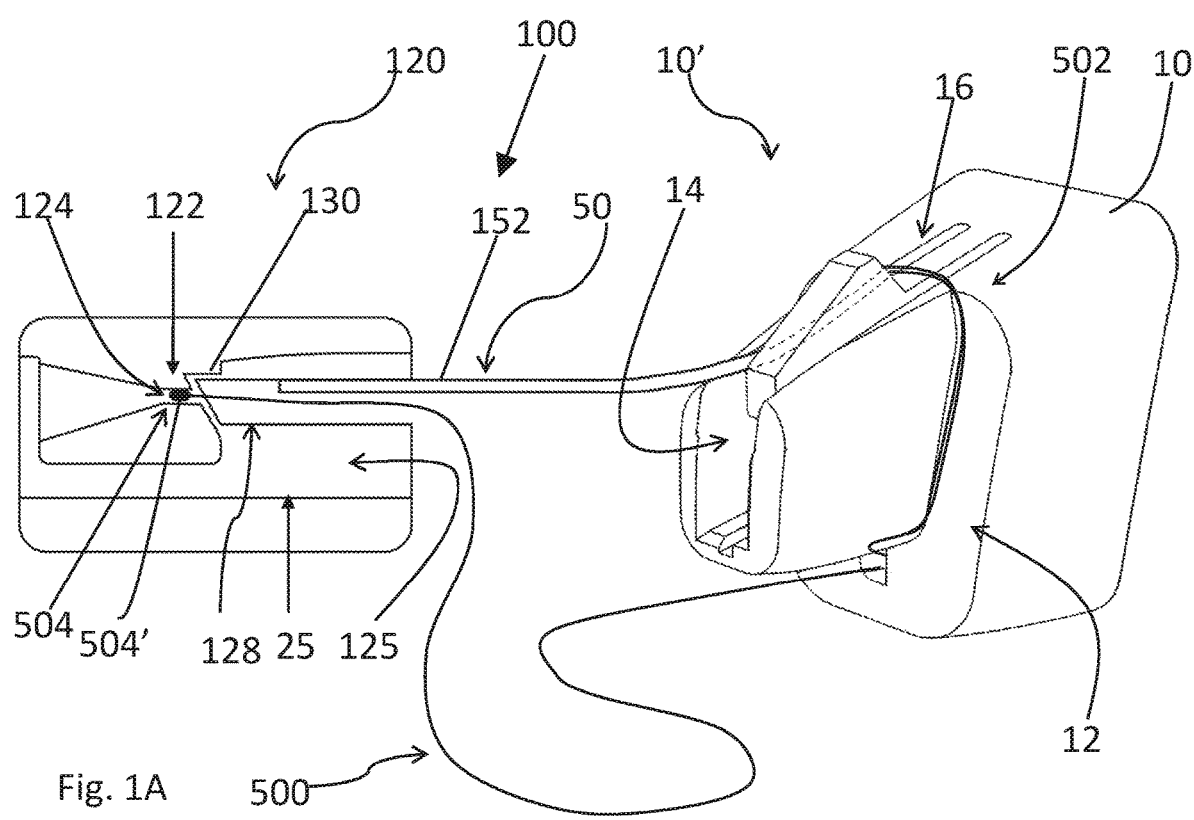
FIG. 1A illustrates a left side perspective view of a cartridge, in accordance with an embodiment of the present invention.

In certain medical interventional procedures, a suturing instrument may be used by physicians to pass suture through a region of tissue having a cut or a defect in order to approximate the tissue to repair the defect. In some such procedures, there may be a need to load suture onto the surgical suturing instrument at the point of use. However, it may be difficult to load the suture using conventional loading mechanisms as they may require the user to perform several steps, may require user dexterity, concentration and a specific order of operation which if done out of order could result in a failure of the device and may be time consuming. Thus, there is a need in the art to provide a cartridge for loading suture onto a suturing instrument at the point of use that provides ease of use and which allows the suture to be loaded in an efficient manner.

The present inventors have discovered, and reduced to practice, several embodiments of a novel apparatus and method that facilitates loading of suture onto a suturing instrument at the point of use. In general, in accordance with embodiments of the present invention, a cartridge is provided that permits loading of a suture onto a suturing instrument upon axial or linear movement of the suturing instrument at least partially through the cartridge. The cartridge may additionally comprise one or more features that facilitate alignment and transferring of the suture onto the instrument.

More specifically, some embodiments of the present invention provide a suture cartridge that is usable for loading suture onto a medical device such as a surgical suturing instrument at the point of use in a situation where suture is to be supplied separate from the device. In some such embodiments of the present invention, a cartridge is provided that allows the physician to load the suture onto a surgical suturing instrument prior to a surgical procedure using an axial or front end loading mechanism. The cartridge defines a seat for holding a portion of the suture and defines an opening extending longitudinally through at least a portion of the cartridge, which allows a portion of the surgical suturing instrument to be received axially therethrough for aligning a portion of the suture held therein with the surgical suturing instrument. This allows direct transfer of the portion of the suture held within the seat from the cartridge onto the surgical suturing instrument, allowing it to be independently transferred to enable the surgical suturing instrument to suture therewith.

In some embodiments of the present invention, the cartridge may additionally comprise one or more features that facilitate transferring or loading the suture onto the device.

In some embodiments, the cartridge additionally provides one or more of: a means to mount a pre-tied knot onto the surgical instrument, a restraint to secure a position of the suturing instrument upon insertion into the cartridge, and an alignment feature to align the suture with the suturing instrument, such as a moveable seat. In some such embodiments, a cartridge is provided that is usable with a suturing instrument that defines a tissue receiving gap, where the cartridge is configured to position the seat within the tissue receiving gap to facilitate alignment of the portion of the suture held within the seat with a suture passing member of the suturing instrument.

Certain embodiments of the present invention thereby provide a suture cartridge for loading suture onto a suturing instrument, for example at a point of use, by efficiently aligning the suture with the suturing instrument. In some embodiments, the cartridge additionally provides one or more of a means to load a pre-tied knot onto a suturing instrument and a means for transferring the suture onto the suturing instrument.

Furthermore, several novel embodiments of methods for loading a suture onto a suturing instrument are described hereinbelow. In addition, methods of suturing tissue of an intervertebral disc including a cartridge for loading the suture onto a suturing instrument, are described as well.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

EXAMPLE 1A

In accordance with an embodiment of the present invention a suture carrying cartridge is provided for loading a surgical suturing instrument such as a suture passer at the point of use (where the suturing instrument requires a pre-tied knot and comprises a suture passing member, and where loading involves loading the suture onto the suture passing member and loading the pre-tied knot onto the surgical suturing instrument). The suture carrying cartridge (having a pre-tied knot secured thereto) is coupled to the suture passer and allows coupling of the suture to the suture passing member by allowing the suture to be moved so that it is aligned with the suture passing member.

Figure 1B:
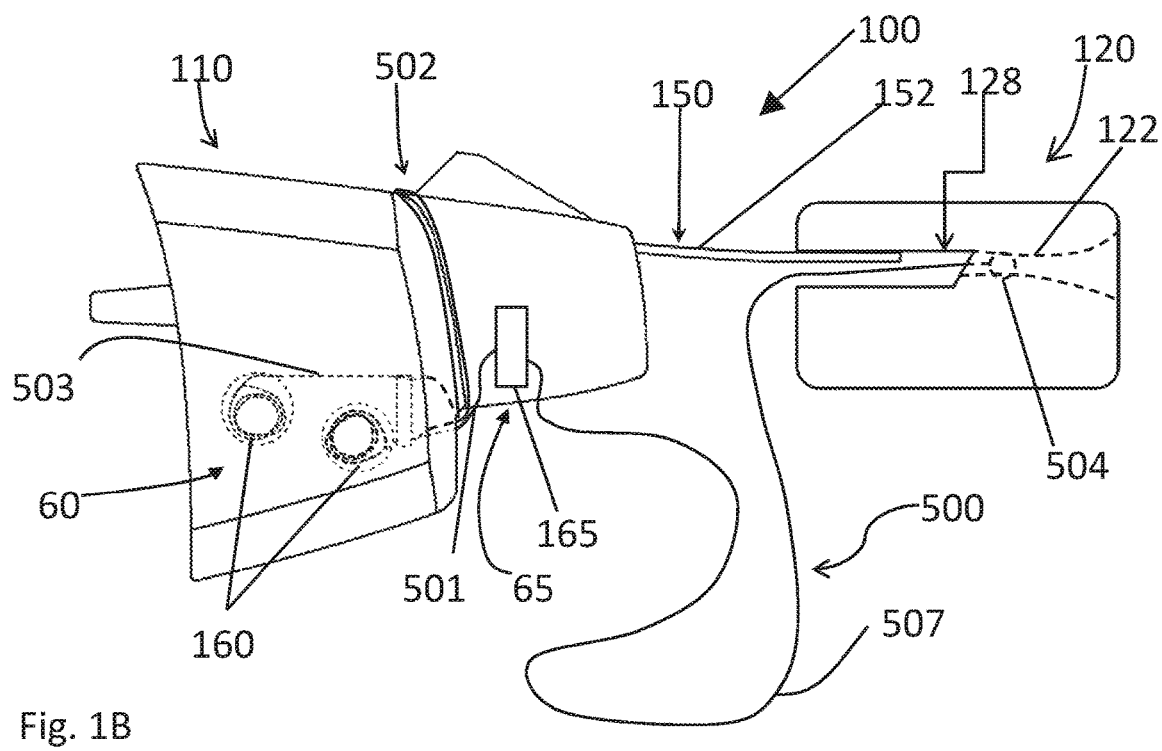
FIG. 1B illustrates a right side view of a cartridge in accordance with an embodiment of the present invention.

FIG. 1A further illustrates a cartridge 100 in accordance with an embodiment of the present invention. The cartridge 100 is provided for loading a length of suture 500 onto a surgical suturing instrument including loading a pre-tied knot 502 comprising suture loops (which in some embodiments is formed from and/or attached to the suture 500) onto the suturing instrument. In exemplary embodiment shown, the suture 500 may define an end portion 504 (of the suture (or suture end) 504, such as a knot 504'), for loading onto the surgical suturing instrument 900. As shown in FIG. 1B, the suture 500 emanating from the pre-tied knot 502 terminates in two strands of suture: a service loop 501 terminating in tug loop 507 that is connected to the suture end 504, and a locker 503. In some embodiments the surgical suturing instrument is of the type defining a suture passing member defining a suture receiving passage therein for receiving the end portion 504 of the suture 500 from the cartridge 100.

Figure 1C:
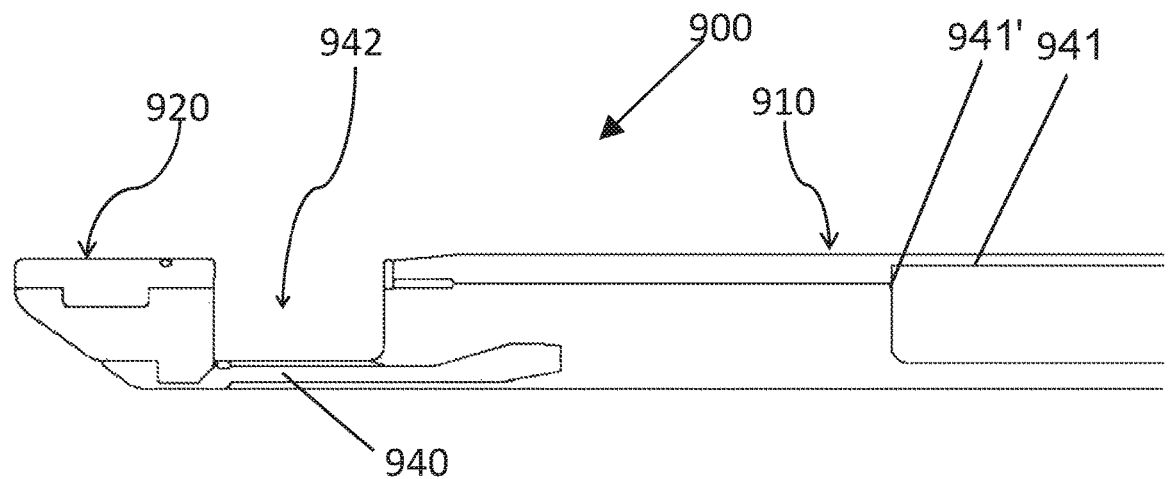
FIG. 1C illustrates a left side view of a portion of a surgical suturing instrument for use with a cartridge in accordance with an embodiment of a the present invention.
Figure 1D:
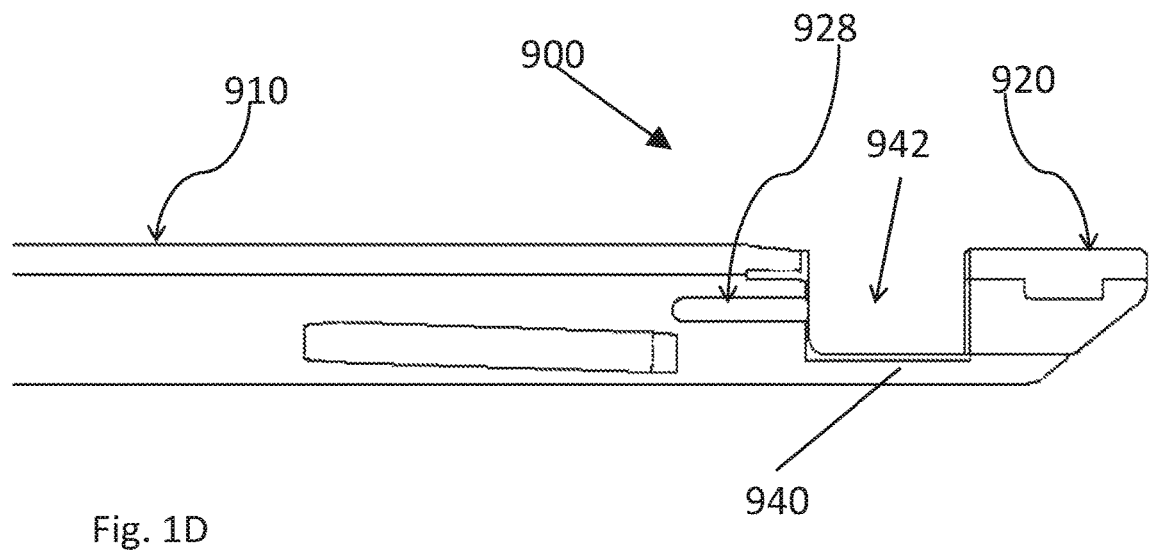
FIG. 1D illustrates a right side view of a portion of surgical suturing instrument for use with a cartridge in accordance with an embodiment of the present invention.

In one example as illustrated in FIGS. 1C and 1D the surgical suturing Instrument or suturing instrument 900 is of the type having an Instrument proximal portion (or shaft) 910 and an Instrument distal portion 920 coupled thereto via a neck portion 940 and defining a tissue receiving gap 942 there-between. The instrument distal portion 920 may alternatively be referred to as the distal end or distal tip 920. As shown in the cross-sectional view of FIG. 1E, the suturing instrument 900 comprises a suture passing member 930 such as a hollow needle 930' housed within the instrument proximal portion 910, the suture passing member 930 defining a suture receiving passage 932 for receiving the end portion 504 of the suture. In some embodiments, the suture passing member 930 is reciprocally movable for example, between the device proximal portion 910 and the device distal portion 920. In some embodiments movement of the suture passing member 930 may assist in transferring the suture end portion 504 from the cartridge 100 to the suturing instrument 900. In a particular example the suturing instrument 900 is of the type shown and described in the PCT application: PCT/IB2012/054204, which is incorporated herein by reference in its entirety.

Referring again to the exemplary embodiment shown in FIG. 1A, a cartridge 100 is shown for loading suture 500 onto the surgical suturing instrument 900. In accordance with a general embodiment of the present invention, the cartridge 100 comprises a housing 10' defining a chamber 10 for receiving the surgical suturing instrument 900. The cartridge further comprises a base 120 coupled to the chamber 10.

In the specific example shown in FIG. 1A, the chamber 10 comprises a means for securing or mounting the pre-tied knot 502 about the chamber 10. In the illustrated embodiment, the means for securing the pre-tied knot 502 comprises a mount 12 for holding the pre-tied knot 502 about the chamber 10. More specifically, the mount 12 may form a part of the housing 10'. Additionally, the chamber 10 defines a channel to allow a portion of the suturing instrument 900 to be received through the pre-tied knot 502 to enable the pre-tied knot 502 to be deployed thereon.

In the exemplary embodiment shown in FIG. 1A, the base 120 defines a seat 122 for releasably holding a portion of a suture 500, such as an end 504 of the suture 500. In the specific example shown, the seat 122 defines a seat channel (recess or passage) 124 for retaining the suture end 504. More specifically, the cartridge 100 specifies a seat 122 for 'directly holding' the end 504 of the suture 500 such the suture 500 by itself is held directly by the seat 122.

In accordance with a broad embodiment of the present invention, the cartridge 100 is structured to allow the seat 122 to be brought into alignment with and in some examples adjacent the suture receiving passage 932 of the suture passing member 930. In some embodiments, as will be discussed herein below with respect FIG. 1F, the seat 122 is moveable (along with the base 120) relative to the chamber 10 and housing 10' to bring the suture end 504 into alignment with the suture receiving passage 932.

Figure 1E:
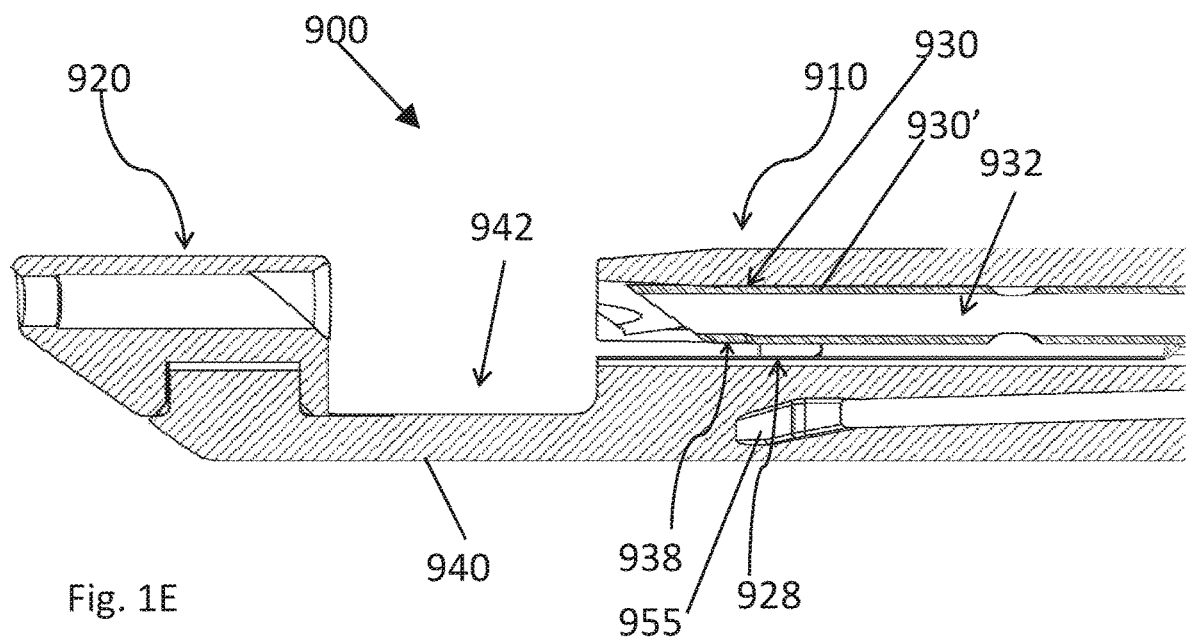
FIG. 1E illustrates a cross-sectional view of a portion of the surgical suturing for use with a cartridge in accordance with an embodiment of the present invention.
Figure 1F:
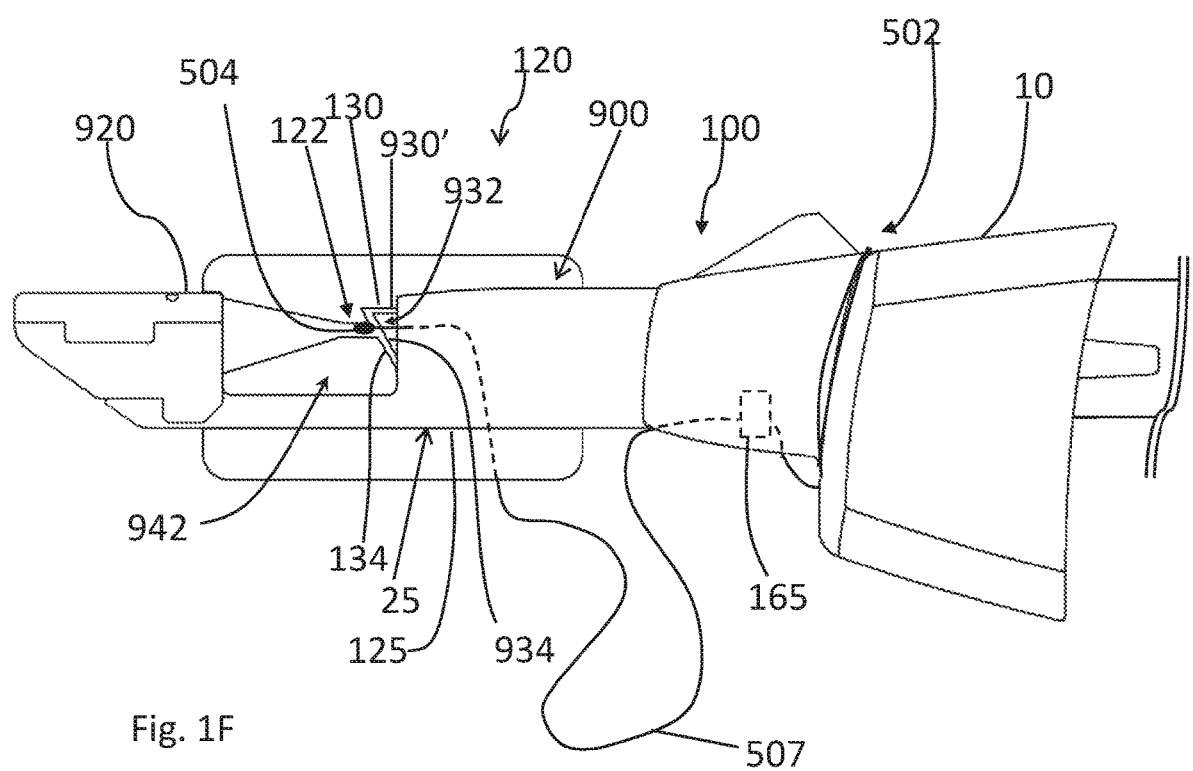
FIG. 1F illustrates a left side view of a cartridge mounted onto a surgical suturing instrument in accordance with an embodiment of the present invention.

In some embodiments of the present invention as shown in FIG. 1A, the cartridge 100 includes an alignment feature that restrains or fixes/locks the position of the suturing instrument 900 relative to the cartridge to help align the seat 122 with suture receiving passage 932 of the of the suture passing member 930 such as a needle 930'. More specifically, the cartridge base 120 comprises a restraint 25 (means for restraining) for positioning a portion of the suturing instrument 900 received through the chamber 10 relative to the seat 122 for aligning the seat 122 with a suture receiving passage 932 of the suture passing member 930. In some embodiments, the restraint may function as a means for locking or snapping the cartridge 100 onto the suturing instrument, such as a locking feature. In the embodiment illustrated in FIG. 1A, the restraint 25 comprises a recess that functions as a locking recess 125 for receiving a portion of the surgical suturing instrument 900. As shown in FIG. 1F, the locking recess 125 receives the suturing instrument 900 and allows the base 120 of the cartridge 100 to be latched onto the suturing instrument 900. In other words, the locking recess 125 within the base 120 receives a portion of the surgical suturing instrument 900 (neck portion 940 and sections of the proximal and distal portions 910, 920) such that the base 120 press-fits around the portion of the suturing instrument 900, to lock the position of the surgical suturing instrument 900 relative to the base 120.

As shown in FIG. 1A, the cartridge 100 additionally comprises an alignment feature in the form of an alignment recess 130 located adjacent the seat 122. In a specific example, as shown in FIG. 1F, the alignment recess 130 is sized to allow the suture passing member 930 to be advanced therein to allow the suture receiving passage 932 to be aligned with the seat 122. As shown in FIG. 1F, the alignment recess 130 additionally comprises a bevel face 134 that matches the bevel face 934 of the needle 930' to further assist in aligning the needle 930' with the seat 122. Thus in the exemplary embodiment, the alignment recess 130 receives a portion of the suture passing member 930 such as needle 930' when it is advanced distally to allow the suture receiving passage 932 to be placed in line with the suture end 504 held within the seat 122. This permits suture 500 to be loaded onto the suturing instrument 900, for example by allowing the tug loop 507 (that is connected to the end portion 504 of the suture 500) to be pulled to transfer the suture end 504 from the cartridge 100 into the suture receiving passage 932. The alignment recess 130 allows the seat 122 to be brought adjacent and in communication with the suture receiving passage 932 to allow the suture end 504 to be transferred into the lumen of the suture passing member 930.

The cartridge may additionally comprise features to assist in routing of the suture 500 to facilitate manipulation of the suture 500 in order to transfer the suture 500 from the cartridge 100 to the surgical suturing instrument 900. With reference now to FIGS. 1B and 1E, in some embodiments the base 120 of the cartridge 100 further defines a base channel or base slot 128 in communication with the seat 122 for routing the suture 500 to facilitate manipulation of the suture 500 in order to load the suture 500 onto/within the suture passing member 930. In some embodiments, once the cartridge 100 is loaded onto the suturing instrument 900, the base slot 128 may be aligned with a longitudinal opening 928 within the suturing instrument 900 (for example, within the instrument proximal portion 910). In some embodiments, the suture passing member 930 may also comprise a slit 938 that can line up with the base slot 128 so that it is in communication with the base slot 128. This facilitates loading of the suture 500 into the suture receiving passage 932 by allowing room for suture 500 to exit the cartridge 100, so that it may be manipulated, for example by tugging on the suture 500 to allow it to be transferred from the seat 122 to within the suture passing member 930.

In some embodiments, the cartridge 100 may comprise a base 120 that is formed integrally with the chamber 10 or housing 10'. In other embodiments, the base 120 may be detachably coupled to the housing 10' via a detachable coupling 50, as shown in FIG. 1A. This may allow the base 120 to be decoupled to from the housing 10' after suture end 504 is loaded into a suturing instrument using the cartridge 100. The housing 10' may then be advanced or slid proximally to position the housing 10' and pre-tied knot 502 thereon along the instrument proximal portion, to permit deployment of the pre-tied knot 502 after the suturing instrument is used to apply suture to a region of tissue (such as an inter-vertebral disc) to help secure the suture 500 within the region of tissue.

In some such embodiments, with reference now to FIGS. 1A and 1B, the base 120 is indirectly coupled to the housing 10' through a flexible coupling 150 such as a flexible tube or tether 152. In some examples, a first end of the flexible tube 152 may be affixed permanently to one of the base 120 and the housing 10', whereas the a second end of the flexible tube 152 may be removably attached to the other of the base 120 and the housing 10'. In the example shown, one end of the flexible tube 152 is permanently secured to the base 120 within the base slot 128 and the second end of the flexible tube 152 is received within a groove 16 within the housing 10' to be removably attached thereto. Alternatively, both ends of the flexible tube 152 could be permanently affixed to each of the base 120 and the housing 10' and the flexible tube 152 may be designed with break lines to allow separation of the flexible tube 152 into two parts under application of force, allowing detachment of the base 120 from the housing 10'. In another example, the flexible coupling 150 may comprise a flexible or soft hinge. Alternatively, the base 120 may be directly coupled to the housing 10'.

In some embodiments, the cartridge 100 may additionally comprise a means to store the length of suture 500 such as suture storage 60, shown in FIG. 1B. The suture storage 60 may comprise one or more spools 160 held within the cartridge 100 to store the length of suture 500. More specifically, the one or more spools 160 may be held within the housing 10' to store the service loop 501 and the locker 503 of the suture 500. The one or more spools 160 may help prevent entanglement of the suture 500 during loading of the suturing instrument 900 and/or during use of the suturing instrument 900. Alternatively, the suture 500 may be held within suture payout tubes.

EXAMPLE 1B

Referring again to FIG. 1B, in some embodiments the cartridge 100 comprises a suture retaining component 65 such as a suture retaining pin 165 for retaining a portion of the suture 500 to allow the tug loop 507 of the suture 500 to be pulled (to transfer the suture end 504 within the suture receiving passage 932 of the suture passing member 930) while minimizing or preventing force from being applied to the service loop 501. This may help prevent the service loop 501 from being pulled out prematurely from the suture storage 60. In the illustrated embodiment, the suture retention pin 165 is releasable which allows the housing 10' (and thus chamber 10) to be advanced independently from the base 120 proximally along the proximal portion 910 of the surgical suturing instrument 900 in order to place the housing 10' in a position for deployment of the pre-tied knot 502 carried thereon.

EXAMPLE 2

Figure 2A:
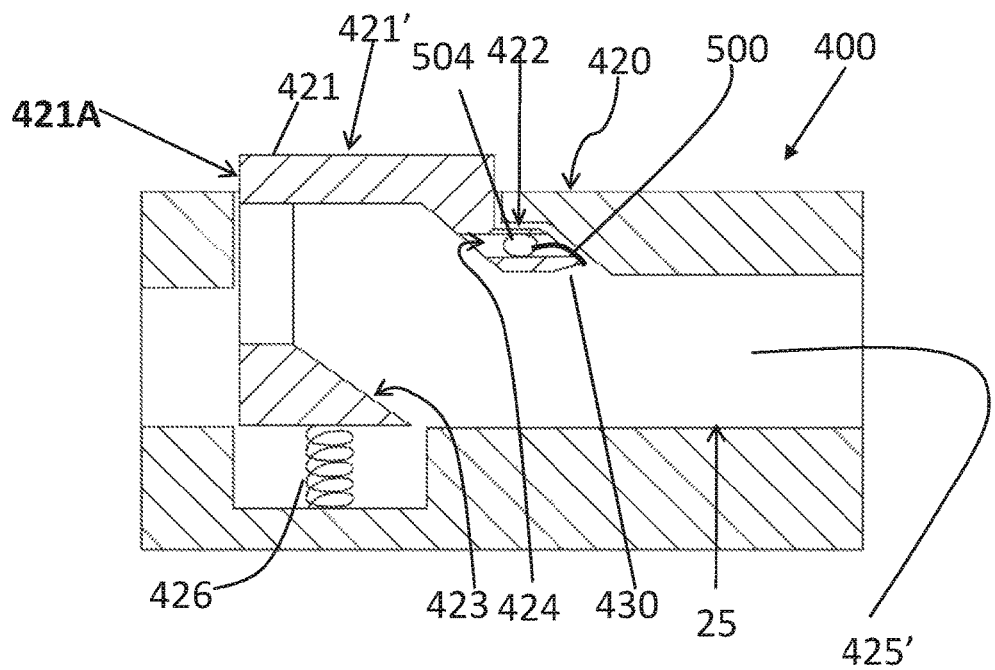
FIG. 2A illustrates a cross-sectional view of a cartridge, in accordance with an alternate embodiment of the present invention.
Figure 2B:
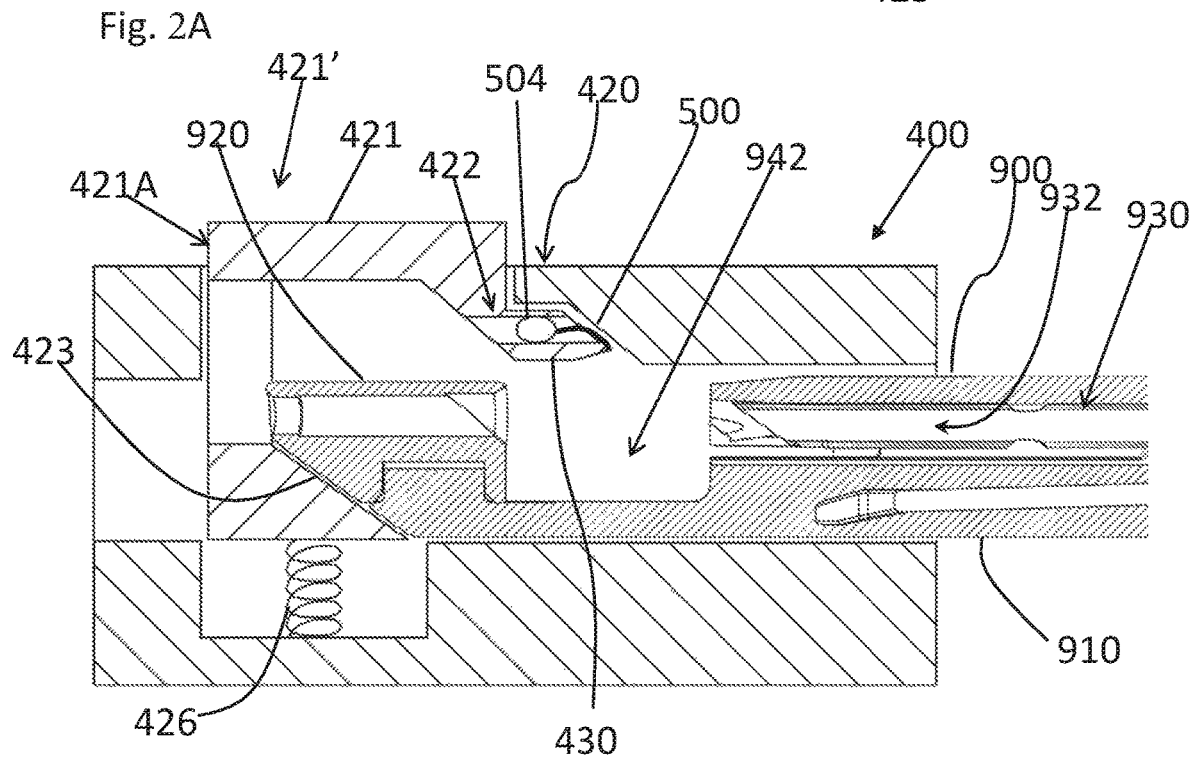
FIG. 2B illustrates a cross-sectional view of a cartridge with a surgical suturing instrument partially advanced therein, in accordance with an embodiment of the present invention.
Figure 2C:
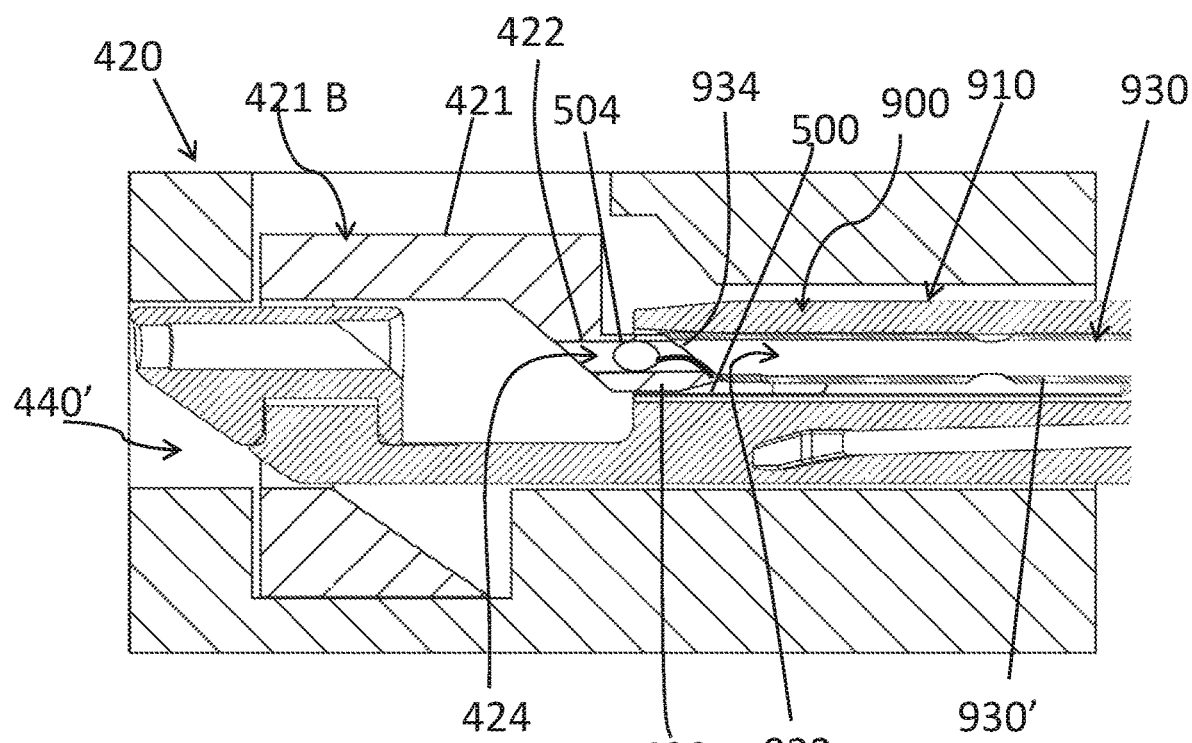
FIG. 2C illustrates a cross-sectional view of a cartridge with a surgical suturing instrument advanced therein, in accordance with an embodiment of the present invention.

In an alternate embodiment of the present invention, as shown in FIGS. 2A-2C, a cartridge 400 is disclosed. Similar to cartridge 300, cartridge 400 provides a seat 422 that is moveable relative to the chamber 10 (housing 10'). Additionally, cartridge 400 incorporates a seat 422 that is automatically moveable.

With reference now to FIG. 2A, a cartridge 400 is disclosed comprising a cartridge base 420 that is coupled to a housing, for example a housing 10' of the type discussed previously herein above. In one example, the base 420 may be detachably coupled to the housing 10' (chamber 10). Base 420 comprises a magazine 421 which defines the seat 422 for releasably holding or retaining the suture end 504. More specifically, the magazine 421 comprises a projection 430 which defines the seat 422. In a specific example the seat 422 comprises a seat channel 424 and the suture end 504 is press-fit within the seat channel.

In the embodiment shown in FIGS. 2A-2C, the cartridge 400 comprises an alignment feature in the form of a restraint 25 comprising an instrument receiving recess or locking recess 425' that allows the suturing instrument 900 to be positioned within the base 420 to allow the seat 422 to be aligned with the suture receiving passage 932. Additionally the alignment comprises a moveable seat 422. The magazine 421 is mounted onto a spring 426 forming a spring biased interlock 421' which is automatically moveable upon advancement of the surgical suturing instrument 900 within an instrument receiving recess 425' of the base 420. Movement of the interlock 421' translates into a movement of the projection 430 defining the seat 422. Thus the seat 422 is moveable upon advancement of the suturing instrument 900 to bring the suture into alignment with the suture receiving passage 932. Thus in some embodiments of the present invention, the magazine 421 comprises a spring biased translation mechanism.

Figure 4A:
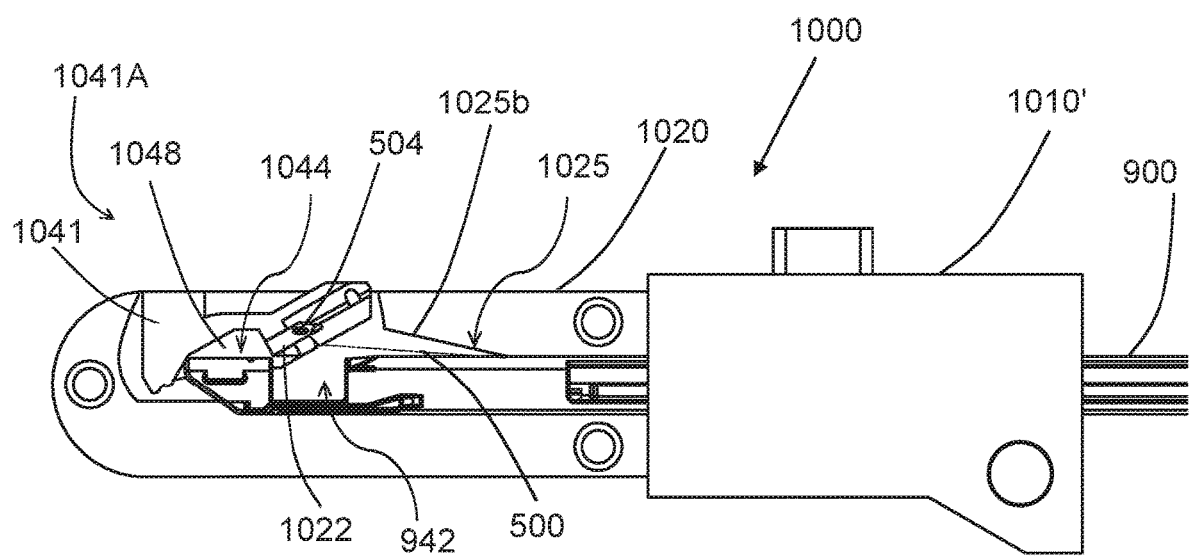
FIGS. 4A-4D illustrate views of a cartridge and a method of using the same in accordance with an embodiment of the present invention.
Figure 4B:
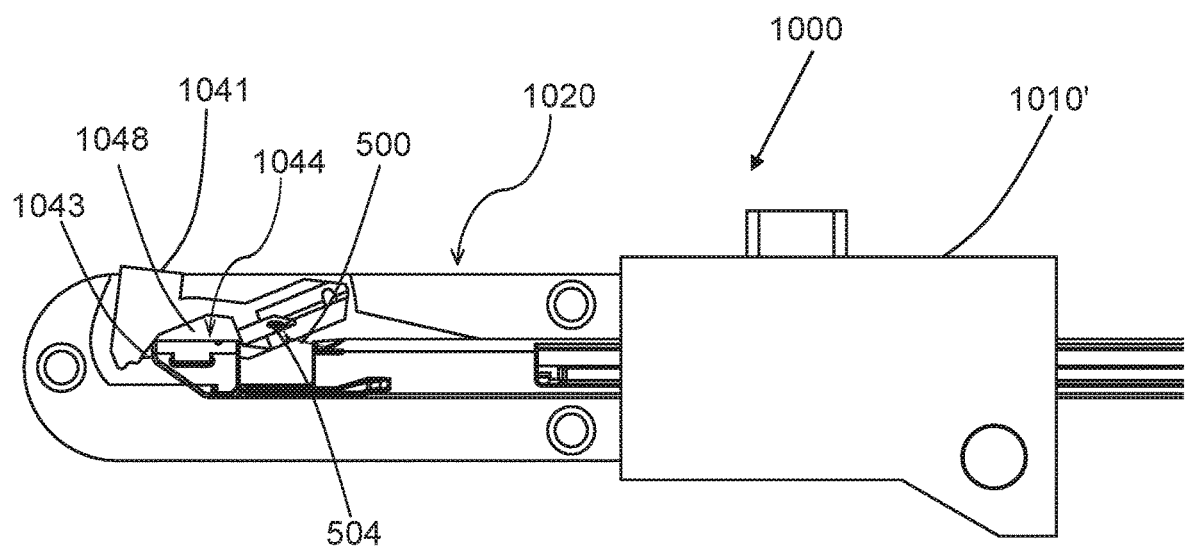

More specifically, referring now to FIG. 4B, the spring biased interlock 421' is shown in its initial position 421A. As shown in FIG. 2C, the interlock 421' is moveable from its first or initial position 421A into its second position 421B upon advancement of the suturing instrument 900 within the instrument receiving recess 425'. Movement or depression of the interlock 421' into its second position 421B allows the seat 422 to be brought into alignment with the suture passing member 930 and the suture receiving passage 932. More specifically, the interlock 421' comprises a ramp 423 (shown in FIGS. 2A, 2B) that is engaged by the distal tip 920 of the instrument 900 as the suturing instrument 900 is advanced to automatically move the interlock 421'. For example ramp 423 is engaged by a tapered surface of the distal tip 920. As a result seat 422 (defined by projection 430) is automatically moveable and travels downwards into the tissue receiving gap 942 to bring the seat 422 (and thus the suture end 504 it retains) into alignment with the suture receiving passage 932 of the surgical suturing instrument 900. In other words, the (magazine 421) and thus seat 422 is automatically moveable upon relative movement between the cartridge base 420 and the surgical suturing instrument 900

In some embodiments, an additional alignment feature is provided to further aid in aligning the seat 422 with the suture receiving passage 932. As mention previously, cartridge base 420 comprises a projection 430 that defines the seat 422. The projection 430 extends into the instrument receiving recess 425' and defines an alignment feature. The projection 430 is capable of abutting against/mating with the suture passing member 930 such as needle 930' when brought into engagement therewith. In the present embodiment illustrated in FIG. 2C, as the surgical suturing instrument 900 is advanced, the magazine 421 moves downwards into the tissue receiving gap. Magazine 421, and thus projection 430 and the seat 422 it defines, all move proximally with respect to the suturing instrument 900, so that the projection 430 abuts against the needle 930' to align the seat 422 with the suture receiving passage 932. More specifically, the projection 930 abuts against the needle 930' to co-operatively engage with and align the needle 930' to bring the seat 422 into alignment with the suture receiving passage 932. The seat 422 is brought into communication with the suture receiving passage 932. In the specific example shown in FIGS. 2B-2C, the projection 430 defines a bevel face 434 for engaging with a bevel face 934 of the needle 930' for docking the needle 930' to align the needle 930' with the seat 222 to permit transfer of the suture end 504 from the seat 222 into the suture receiving passage 932 of the needle 930' for example by pulling on the tug loop 507. Alternatively, in some embodiments, the suture end 504 may be transferred automatically from the seat 422 into the suture receiving passage 932 for example using a plunger.

In one particular embodiment, the cartridge 400 may comprise a mechanism to permit automatic decoupling of the cartridge base from the suturing instrument 900 and/or the housing 10'. In the illustrated embodiment, once the suturing instrument 900 is withdrawn from the cartridge base 420, the spring biased interlock 421' is capable of automatically returning from its second position 421B (shown in FIG. 2C) to its original position 421A (shown in FIG. 2A) to permit de-coupling of the base 420 from the suturing instrument 900 and/or housing 10' (chamber 10).

EXAMPLE 3

In an alternate embodiment of the present invention, as shown in FIGS. 3A-3I, a cartridge 1000 is disclosed for loading suture onto a surgical suturing instrument, for example a suturing instrument 900 as discussed previously herein above with reference to FIG. 1E. The cartridge 1000 carries suture therein and functions to align the suture with the suturing instrument 900 upon insertion and axial advancement of the suturing instrument 900 within the cartridge 1000, in order to allow transfer of suture onto the surgical suturing instrument 900. In some such embodiments, the cartridge 1000 additionally functions to transfer the suture onto the suturing instrument 900.

Figure 3A:
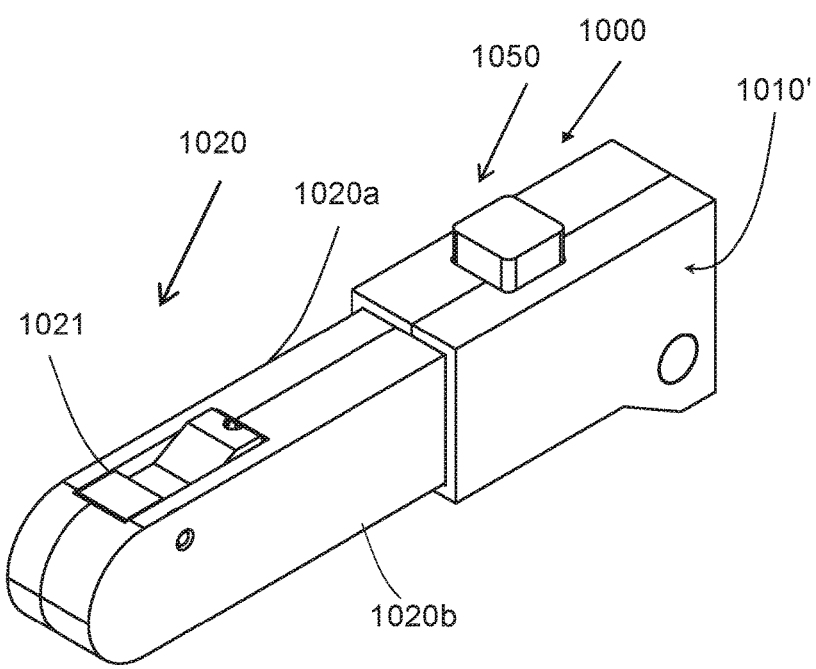
FIGS. 3A-3O illustrate views of a cartridge in accordance with an alternate embodiment of the present invention.
Figure 3C:
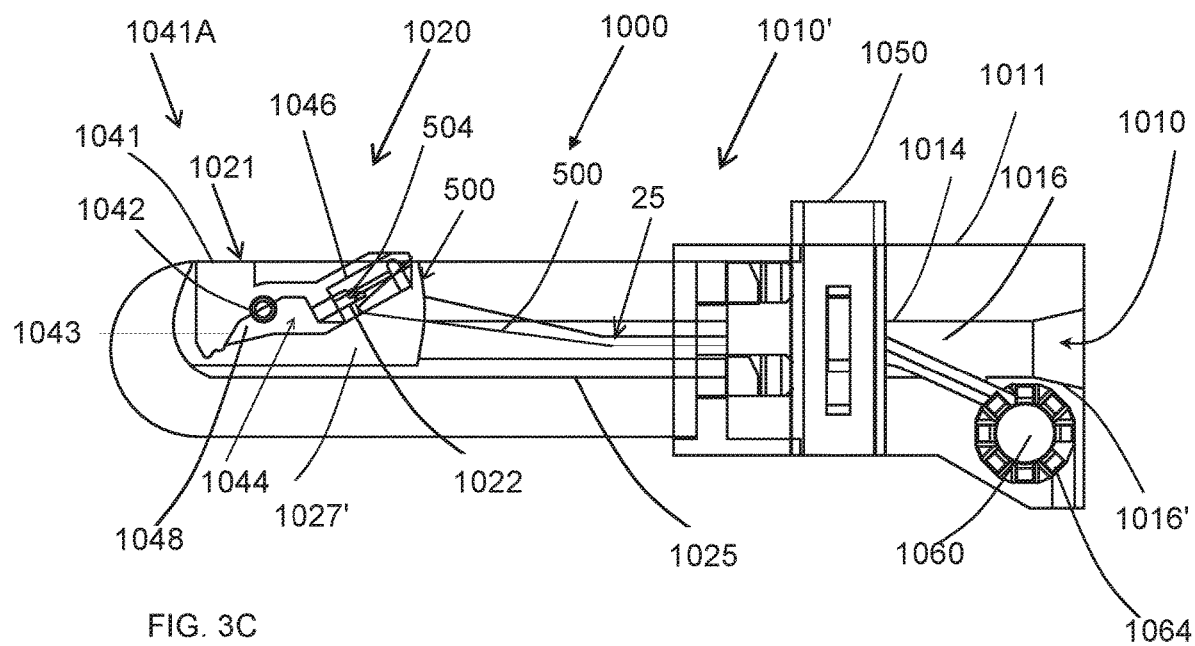
Figure 3G:
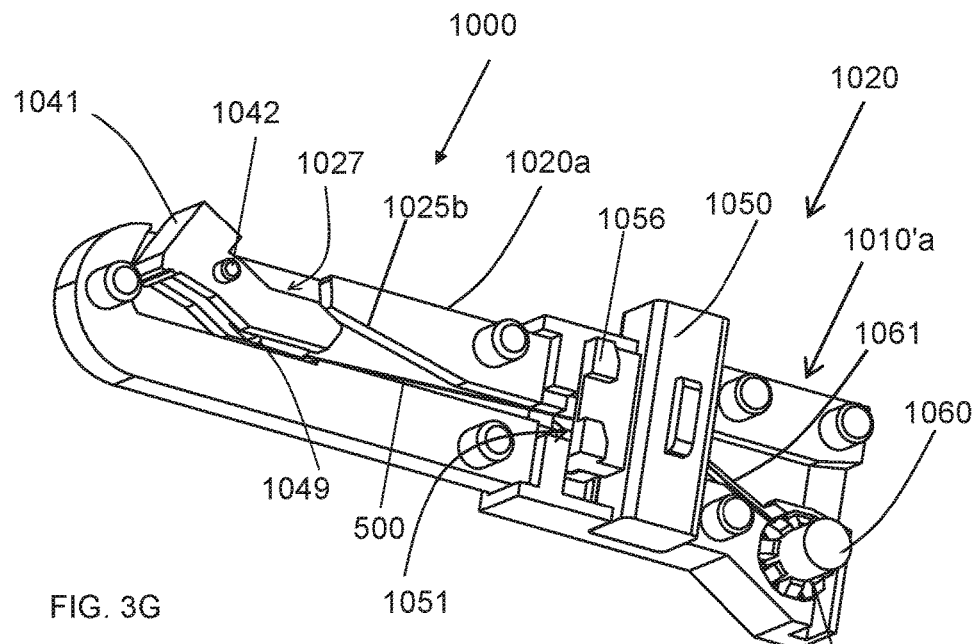
Figure 3B:
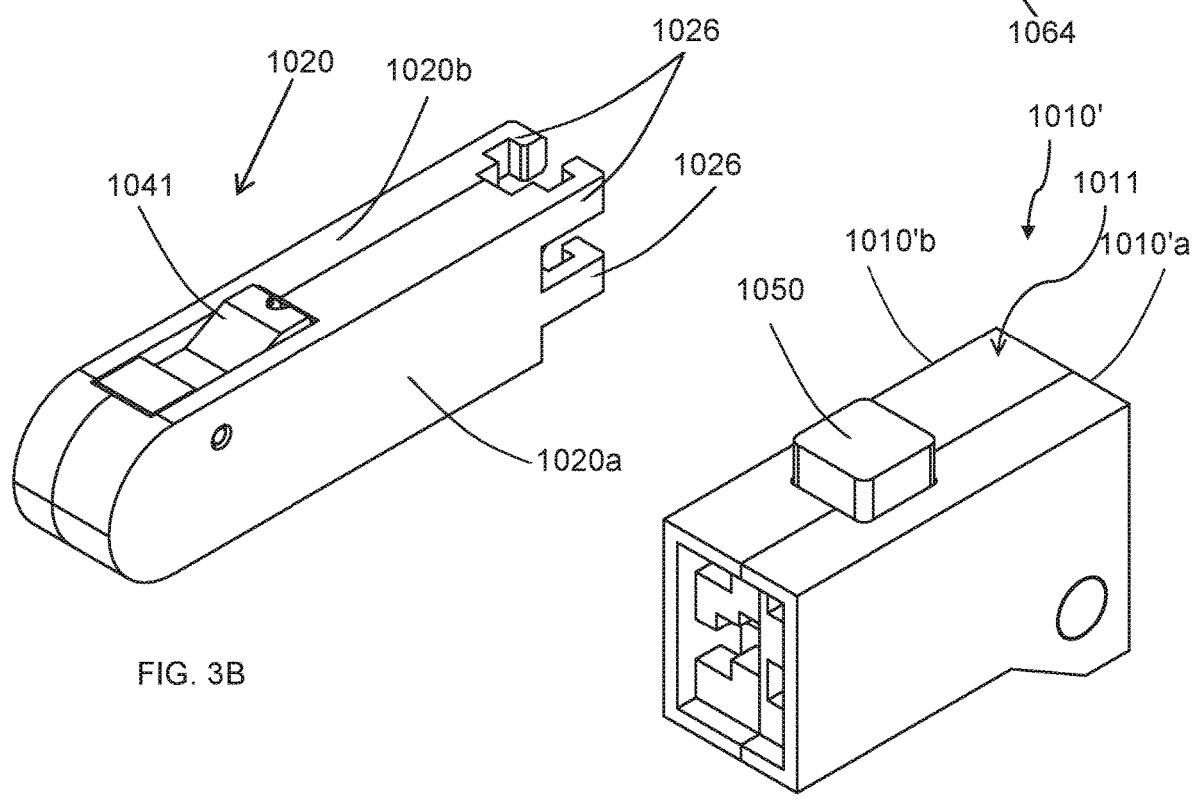

In the specific example shown in FIGS. 3A and 3B, a cartridge 1000 is provided that is functional to carry suture for loading onto a surgical suturing instrument 900. The cartridge comprises a housing 1010' that defines a chamber for axially receiving the surgical suturing instrument 900. Additionally, the chamber 1010 includes a recess or channel that is a part of the chamber 1010 that receives the suturing instrument 900. As such in some embodiments, as discussed herein the channel may be referred to as a channel or a recess. In the particular example discussed herein the chamber 1010 defines a channel for receiving the suturing instrument. The cartridge further comprises a base 1020 that is detachably coupled to the housing 1010' that defines a seat for releasably holding the suture therein and enables alignment of the suture with the suture passing member 930 of the suturing instrument 900. The housing 1010' additionally comprises a means to secure a portion of the suture thereto and is detachable from the base 1020 to function as a suture transferring component to transfer suture from the cartridge onto the suturing instrument 900. Thus, in some embodiments, as shown in FIG. 3B the base 1020 and the housing 1010' comprise separate components of the cartridge 1000 that are coupled to one another to assist in loading suture and may be detachable therefrom to assist in transferring suture. In other embodiments, the housing 1010' may be integrally formed with the base 1020. In some examples the base 1020 may be formed from two halves 1020a and 1020b, and the housing similarly may also be formed from two halves 1010'a and 1010'b. The housing 1010' and the base 1020 collectively provide alignment features to assist in alignment of the suture upon loading of the cartridge 1000 onto the suturing instrument 900 to facilitate transfer of suture from the cartridge 1000 onto the suturing instrument 900 using the suture transferring component. The detailed mechanism and operation of the base 1020 and the housing 1010' in aligning and transferring the suture are described further herein below.

With reference now to FIG. 3C, in some embodiments the housing 1010' of the cartridge defines a chamber 1010 that comprises a channel 1014 for receiving the suturing instrument there-through. In some examples, the channel 1014 comprises a proximal opening 1016 that narrows towards the interior of the cartridge housing 1010' as defined by a beveled interior edge 1016'. The beveled interior edge 1016' functions as a lead in to guide the suturing instrument 900 into the channel 1014. The channel 1014 extends longitudinally through the housing 1010' and is in communication with a recess 1025 that defines an instrument receiving recess or locking recess] formed within the base 1020. In some embodiments the channel 1014 may be formed continuously with the recess 1025 within the cartridge base 1020. The channel 1014 defines an opening through which the suturing instrument 900 may be advanced though the housing 1010' into the base 1020. The channel 1014 and the recess 1025 each function as a restraint 25 to constrain or restrict the lateral and transverse movement of the suturing instrument 900 within the cartridge 1000 while allowing the suturing instrument 900 to be advanced linearly or axially therein in sliding engagement to maintain the position of the suturing instrument 900 along the longitudinal axis as it is advanced. As such the restraint 25 constraints or limits the movement of the suturing instrument 900 in the transverse and lateral directions as well along a longitudinal path defined thereby. Thus the restraint 25 facilitates alignment of the suturing instrument 900 with a portion of the suture 500 that is held within a seat 1022 defined by the base 1020, More specifically, the channel 1014 and the recess 1025 allow the suturing instrument 900 to be advanced therein in sliding engagement therein and additionally function to restrain the suturing instrument 900 in a linear path as it is advanced along the cartridge 1000 to allow the seat 1022 to be aligned with the suture receiving passage 932 of the suture passing member.

Therefore, the cartridge 1000 comprises an alignment feature in the form of a restraint 25 that comprises an instrument receiving recess defined by channel 1014 and recess 1025, which allow the suturing instrument 900 to be positioned within the base 1020 to allow the seat 1022 holding a portion of the suture to be aligned with the suture passing member 930 of the suturing instrument 900.

Figure 3D:
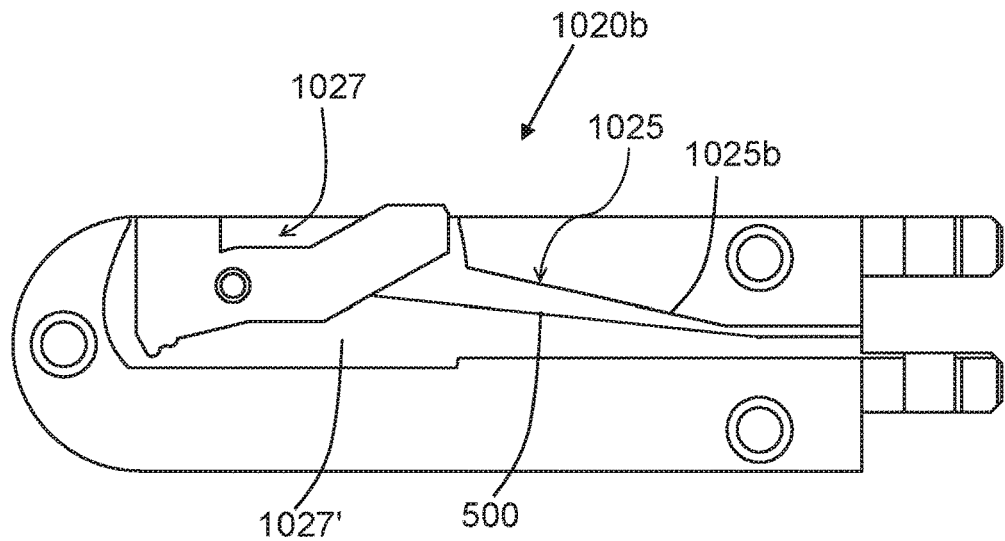
Figure 3E:
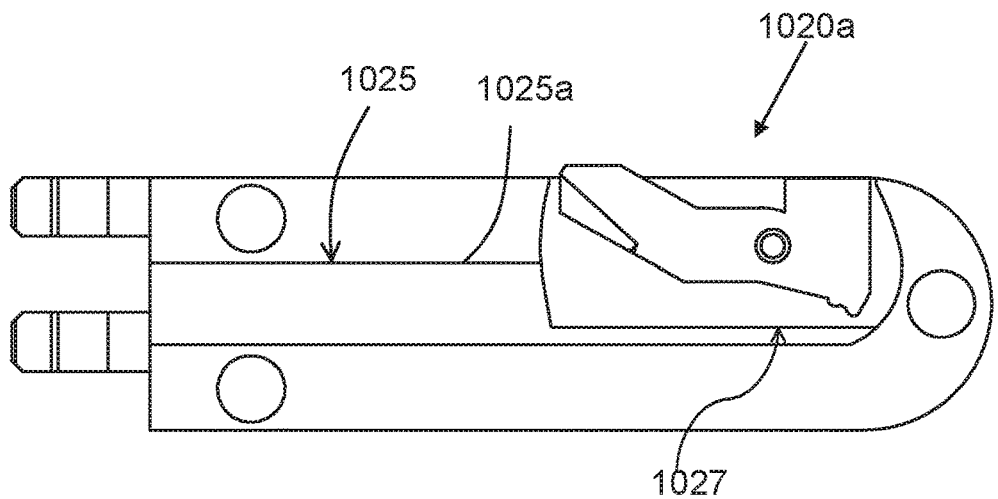
Figure 3F:
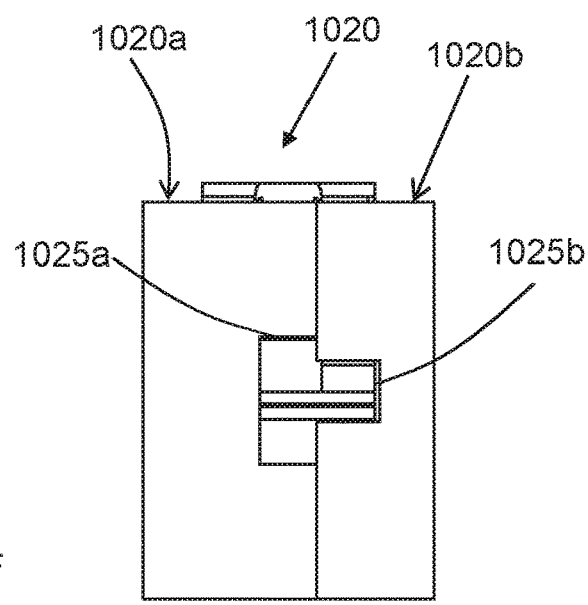
Figure 3H:
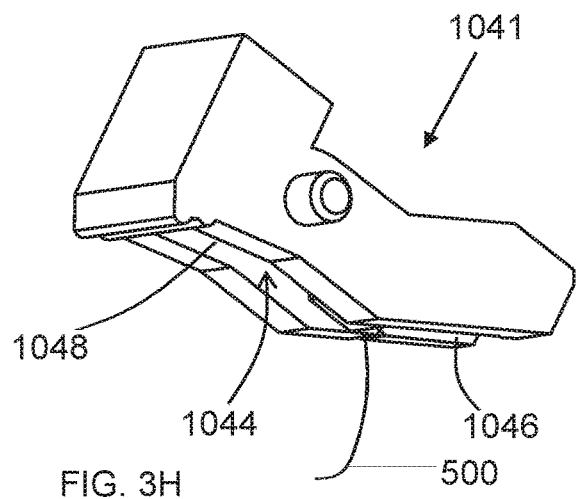
Figure 3I:
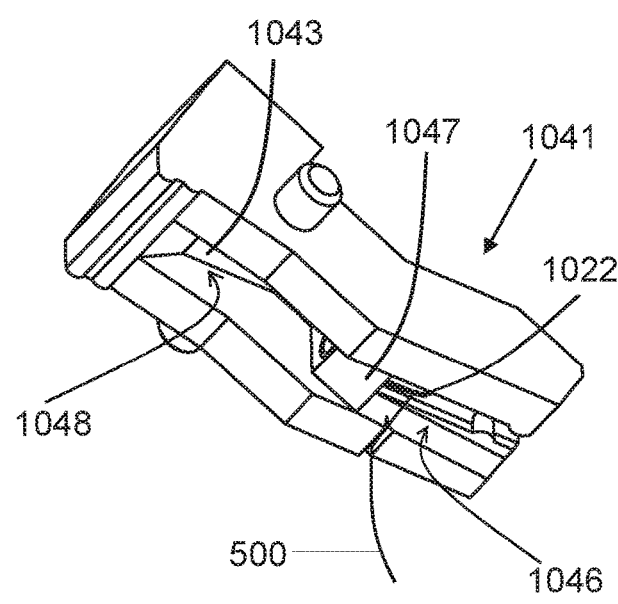

Furthermore, in some embodiments as shown in FIGS. 3C, 3D and 3E, the recess 1025 within the base is formed from two grooves, an instrument receiving groove 1025*a* defining an instrument receiving recess and a suture receiving groove 1025*b* defining a suture receiving recess, as shown in FIG. 3F. The instrument and suture receiving grooves 1025*a* and 1025*b* respectively are formed within the opposing halves 1020*a* and 1020*b* of the base 1020 (also illustrated in FIG. 3B). With reference again to FIG. 3D, the instrument receiving groove 1025*a* provides a track which functions as a restraint 25 to allow the suturing instrument 900 to be advanced therein, whereas suture groove 1025*b* provides a track to guide the portion of the suture held within the seat into the suture passing member 930 of the suturing instrument 900 by maintaining/routing the suture 500 therein such that it is adjacent and in line with the shaft or proximal portion 910 of the suturing instrument 900 that is receivable within the instrument receiving groove 1025*a* as further illustrated in FIG. 3E. More specifically, the suture receiving groove 1025*b* allows the suture to be routed such that when the suturing instrument is received within the instrument receiving recess 1025*b*, the suture 500 is held adjacent the groove 928 within the shaft or the instrument proximal portion 910 as well groove 938 within suture passing member 930 such as needle 930' (shown in FIG. 1E). Furthermore, the groove 1025*b* provides room for routing the suture without excess tension being placed in the suture by providing a wider opening into a rocker recess 1027 as shown by FIGS. 3D and 4A. As such the groove 1025*b* accommodates as it enters a rocker recess 1027 in both a final position 1041B as well as an initial position 1041A of a rocker 1041 (Discussed further herein below). As such the suture receiving groove 1025*b* enables the suture 500 to be maintained out of the way of the advancing suturing instrument 900 during use of the cartridge 1000. Additionally recess groove 1025*b* is in line with grooves 928, 938 within the suturing instrument 900 to further facilitate transfer of suture from the seat 1022 within the base 1020 into the needle 930'. In the illustrated embodiment, both the instrument receiving groove and the suture receiving groove exit into the rocker recess 1027.

With reference now to FIG. 3C in some embodiments of the present invention the cartridge 1000 additionally provides an alignment feature comprising a moveable seat 1022. In some such embodiments, the cartridge 1000 comprises a magazine 1021 that is defined by the base 1020 that functions to align the suture with a portion of the surgical suturing instrument 900 that is receivable within the cartridge 1000. The magazine 1021 defines the seat 1022 for releasably holding or retaining a portion of the suture 500. More specifically, the seat 1022 is configured to hold an end portion 504 of the suture 500 as shown. The magazine 1021 is moveable with respect to the cartridge 1000 and as such defines a moveable seat 1022 for aligning the suture end 504 held therein with a portion of the surgical suturing instrument 900 that is received within the cartridge 1000. More particularly, as shown in FIG. 3C, the seat 1022 is moveable with respect to the base 1020. (Alternatively, in some embodiments the seat 1022 may be moveable relative to the chamber 1010 defined by housing 1010', for example in embodiments where the base 1020 may be formed integrally with the housing 1010' forming a unitary cartridge 1000).

Figure 4C:
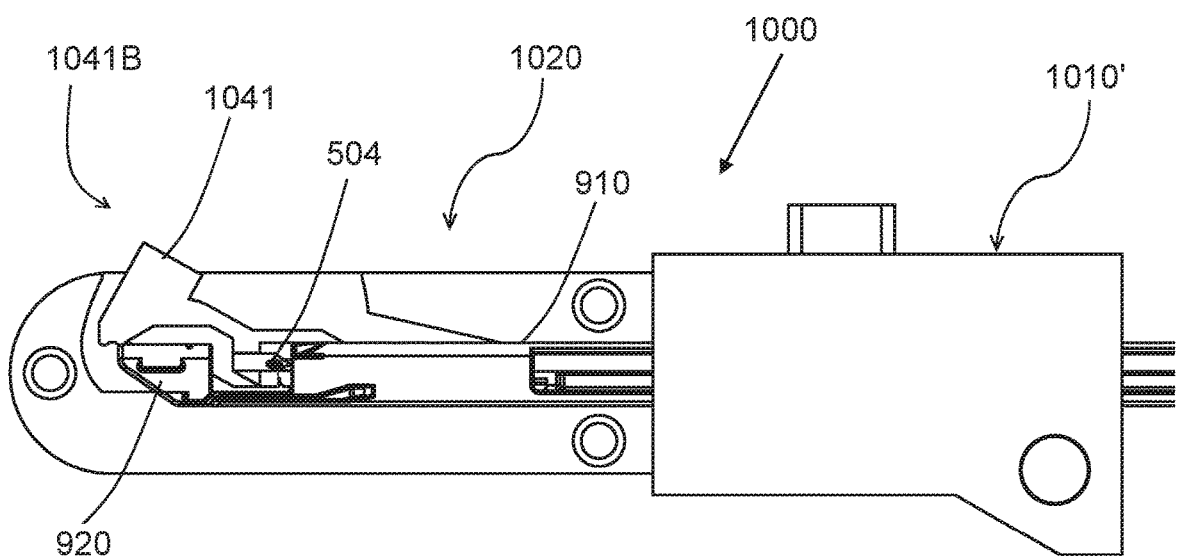

In some embodiments of the present invention, particularly with reference to FIG. 3C, the seat 1022 is automatically moveable upon insertion of the suturing instrument 900 within the cartridge 1000. In the particular example shown, the magazine 1021 comprises a rocker 1041 that is rotatable about a pivot 1042, and the base 1020 defines a rocker recess 1027 for enabling pivotal movement of the rocker 1041 therein. In the illustrated embodiment, the pivot 1042 is formed by laterally extending pins 1043 of the rocker 1041 (also illustrated in 3G) that are held within pivot support openings 1023 of the base 1020 and are moveable freely therein. The rocker 1041 is moveable about the pivot 1042 from its initial position 1041A (as shown in FIG. 3C) to its second position (as shown in FIG. 4C(i)) in order to align the seat 1022 and the suture end 504 held therein with the path of an advancing suturing instrument 900 that is inserted within the cartridge 1000.

In some embodiments, the rocker 1041 is held in its initial position 1041A within the rocker recess 1027 through frictional engagement. For example the rocker 1041 may be kept in its initial position 1041A by an engagement feature such as a raised tab or detent [not shown] that is formed within the base 1020 and may extend or juts into the rocker recess 1027. The tab may be engageable with a portion of the rocker 1041 to maintain the rocker in its initial position 1041A during shipment and prior to use. In other embodiments the rocker 1041 may be held in its initial position 1041A through frictional engagement via a spring based mechanism. The frictional force may be sufficient to keep the rocker 1041 in its initial position 1041A when the cartridge is empty, but may be overcome upon contact with the suturing instrument 900. Thus the rocker 1041 may be released from engagement with the base 1020 upon advancement of the suturing instrument 900 within the cartridge 1000 allowing the rocker 1041 to move into its second position 1041B to align the portion of the suture held therein with a portion of the suturing instrument 900. In its second position 1041B, the rocker 1041 moves into a cavity defined by the rocker recess 1027. More specifically, as defined herein the rocker 1041 is moveable into a rocker cavity 1027' of the rocker recess 1027 to align the seat 1022 with the suturing instrument 900. The rocker cavity 1027' is defined as a portion of the rocker recess 1027 that corresponds to a tissue receiving gap 942 of the suturing instrument 900, upon loading of the cartridge 1000 onto the suturing instrument 900 [FIG. 3C].

In some embodiments, the cartridge may comprise additional features that assist in aligning the seat 1022 with a portion of the suturing instrument 900 as the suture passing member 930 held within the shaft or instrument proximal portion or shaft 910. In one such example, referring again to FIG. 3C, the rocker 1041 additionally defines an instrument receiving or locking recess defined by a groove 1044 that is designed for receiving the suturing instrument 900 as it is advanced distally. The groove 1044 functions as a restrain to position the suturing instrument 900 in a desired position relative to the seat 1022 to assist in aligning the seat 1022 with a suture passing instrument 900. The groove 1044 enables the rocker 1041 to pivot down into its second position 1041B while allowing the suturing instrument 900 to be advanced into the cartridge 1000 to permit loading the suture into the suturing instrument 900. [The operation of the groove 1044 is discussed further herein below with reference to FIGS. 4A-4D that illustrate the operation of the device]. As further shown in FIGS. 3H and 3I, the groove 1044 comprises a groove proximal portion 1046 for receiving the instrument proximal portion or shaft 910 of the suturing instrument 900, and additionally comprises a groove distal portion 1048 for receiving the instrument distal portion or tip 920.

Additionally, the rocker 1041 comprises a median 1047 that is defined by the groove 1044. The groove proximal and distal portions 1048, 1048 are separated by the median 1047 functions to hold or define the seat 1022 to enable the seat to be brought down into the tissue receiving gap 942. The median 1047 functions as an alignment feature by holding and aligning the seat 1022 with the suture passing member such as needle 930' of the suturing instrument 900. As such median 1047 functions to holding the seat to enable the seat 1022 to be brought down into the cavity 1027' corresponding to the tissue receiving gap upon reception to the suturing instrument within the cartridge.

Still furthermore the groove 1044 defines an additional alignment feature in the form of an interior bevel face 1043 that is defined by the groove distal portion 1048 of the rocker 1041, along a distal end thereof. The bevel 1043 enables the distal portion 920 of the suturing instrument to pivot the rocker 1041 from its initial position 1041A into its aligned position or second position 1041B to enable alignment of the seat 1022 and the suture held therein with the suture passing member 930 of the suturing instrument.

Figure 3J:
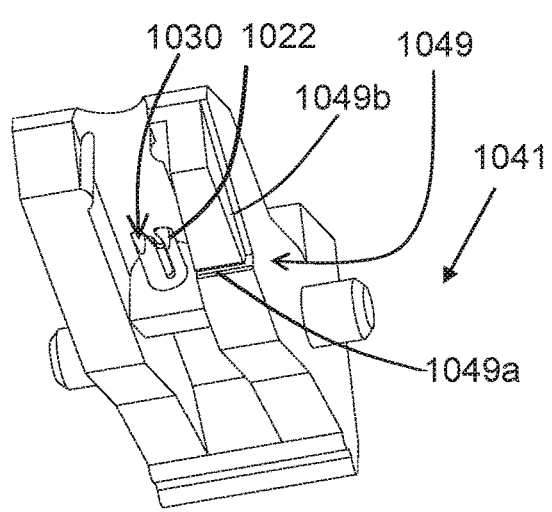

In some embodiments, the rocker 1041 additionally defines another alignment feature in the form of a slot 1049 (as shown in FIGS. 3J) and 3L within the groove 1044 to assist in alignment and transfer of the suture end 504 into the suture passing member 930. The slot 1049 comprises a slit or channel 1049a that is formed within a wall 1044' of the rocker 1044 and extends transversally along the base of the wall 1044' to route the suture there-through upon exiting the seat 1022. The slit or channel 1049a functions to retain the suture 500 therein as it exits the seat 1022 within the rocker 1041 to aid in routing the suture 500 within the suture receiving groove 1025b (FIG. 3D) of the base 1020 and to align the suture with the suture receiving slot 928 in the shaft. The slit or channel 1049 exists into a cut-out portion defined within the exterior wall of the rocker 1041. The cutout defines a side slot 1049b defining a space enabling the suture 500 to be routed there-through to be guided into the suture receiving groove 1025b of the base 1020. The slit or groove 1049a is in communication with the rocker side slot 1049b to hold the suture to the side within the suture receiving groove 1025b of the base. This allows the suture to be held to the side of the suturing instrument 900 during advancement of the suturing instrument within the cartridge base 1020.

Figure 3K:
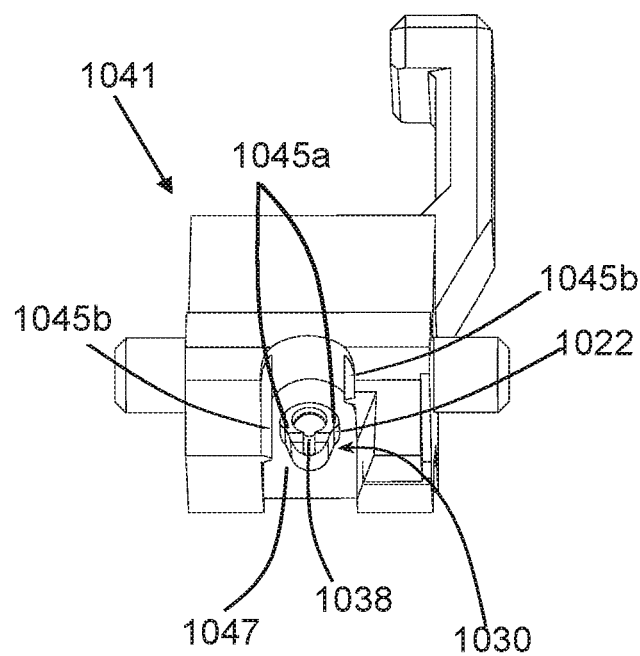
Figure 3M:
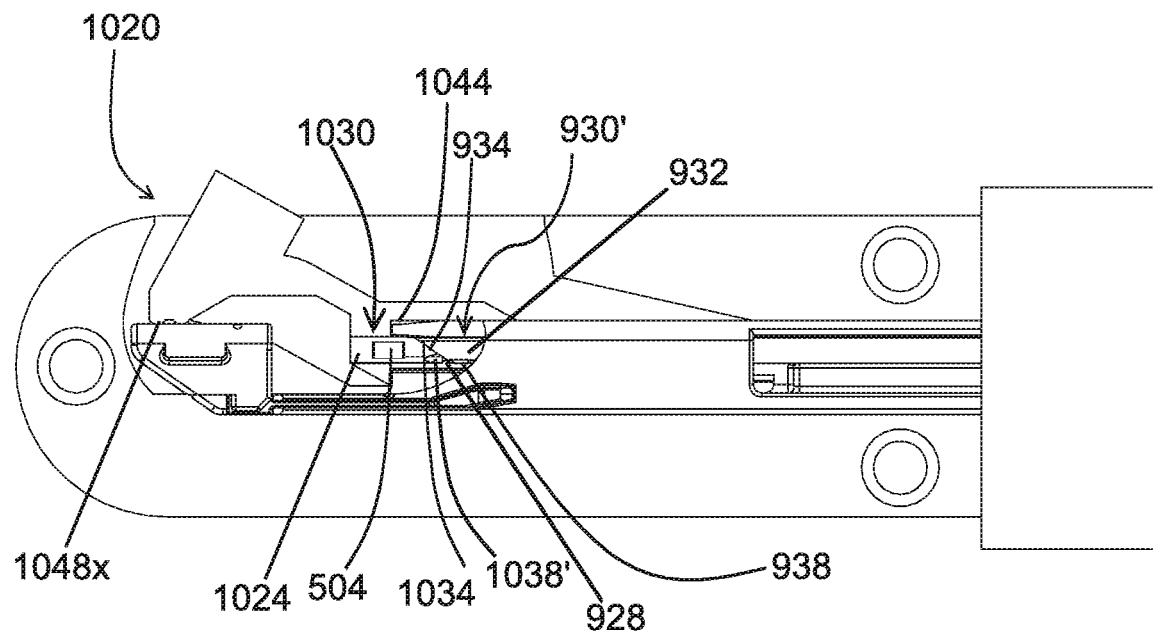
Figure 4D:
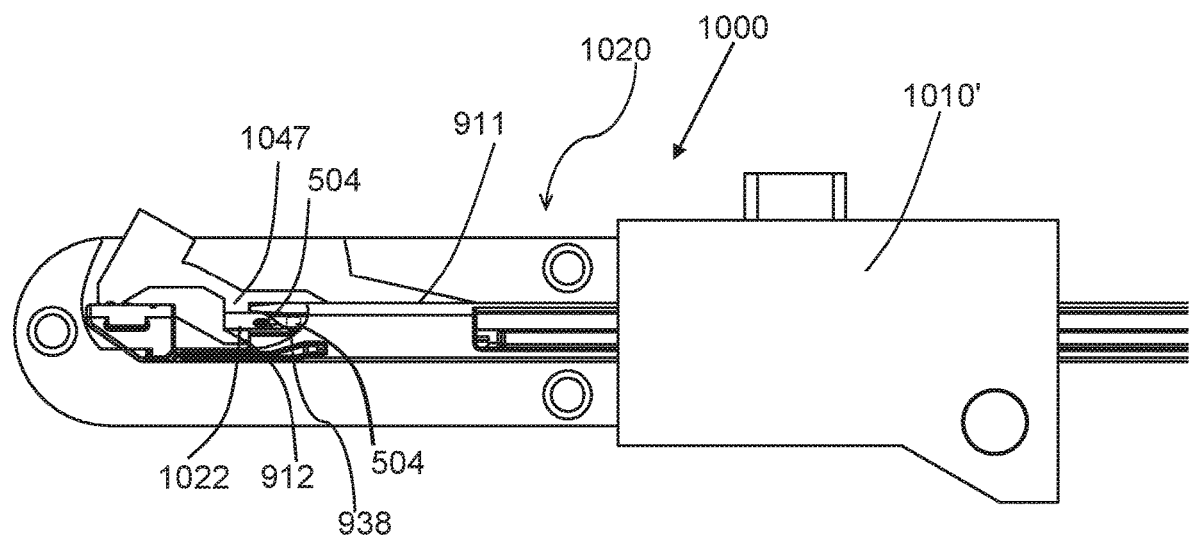

In one specific example, as shown in FIGS. 3J and 3K, the seat 1022 is defined by a projection 1030 that is housed within the magazine 1021, specifically within the rocker 1044. In one specific embodiment, the median 1047 comprises an axially extending channel or opening therein for receiving and retaining a projection 1030 that defines the seat 1022. In some embodiments, the projection may be press-fit within the channel or opening. In other embodiments it may be coupled to the median using an adhesive. In other embodiments the projection 1030 defining the seat 1022 may be formed in one piece as part of the rocker. The projection 1030 defines a hollow interior forming a seat channel 1024 and the suture end 504 is press-fit within the seat channel 1024 to be held therein. As such the projection 1030 forms an alignment feature to further aid in aligning the seat 1022 with the suture receiving passage 932 of the suture passing member 930 such as the needle 930' within the shaft 910. As shown in FIGS. 3M and 4D, the projection 1030 extends into the instrument receiving recess defined by the groove 1044. More specifically, the projection 1030 is capable of abutting against/mating with the suture passing member 930 (such as needle 930') when brought into engagement therewith. In one specific example, the projection 1030 defines a bevel face 1034 for engaging with a bevel face 934 of the needle 930' for docking the needle 930' to align the seat 1022 with the needle 930' with to permit transfer of the suture end 504 from the seat 1022 into a suture receiving passage 932 of the needle 930'. In one specific example, the projection 1030 is receivable into the instrument proximal portion or shaft 910 to facilitate alignment of the seat 1022 with the needle 930'.

In some such embodiments, as shown in FIG. 3K, the rocker 1041 comprises additional alignment features to assist in alignment of the seat 1022. In one such example the projection 1030 comprises interference features in the form of raised bumps 1045a on the exterior of the projection 1030 that are configured to frictionally engage the interior of the instrument proximal portion or shaft 910 with the needle 930' as the projection 1030 is received within the shaft 910. In additional embodiments, the rocker 1041 also, as shown in FIGS. 3K and 3M, the cartridge 1000 defines a suture groove or slot to allow the suture to exit the seat 1022. In some such embodiments, the rocker 1041 defines a suture slot that is in communication with the seat 1022 for allowing the suture to exit the seat 1022. In the specific example shown the comprises additional raised bumps 1045*b* along the interior of the proximal groove portion 1046 for frictionally engaging the exterior of the instrument proximal portion or shaft 910 once it is received within the proximal groove portion 1046 in order to align the seat 1022 with the needle 930'. This may be referred to as the needle-in configuration of cartridge 1000 as the needle 930' remains inside the shaft 910 during loading of the suturing instrument 900.

In some embodiments projection 1030 defines a suture slot 1038 therein allowing the suture 500 to exit therefrom to enable alignment of the suture end 504 with the suture receiving passage 932 within the needle 930'. More specifically, the suture slot 1038 enables the suture to be to be routed through it upon exiting the seat 1022, such that suture is aligned with the needle slot 928 and shaft slot 938. This facilitates transfer of the suture end into the suture receiving passage 932 of the needle 930 using a suture transferring component of the cartridge 1000. Once the suture exits the suture slot 1038, it is routed though the slot 1049 of the rocker 1041 to enable suture be held to the side of the rocker such that it is off to the side of the path of the suturing instrument 900 as it is advanced into the cartridge 1000.

Figure 3L:
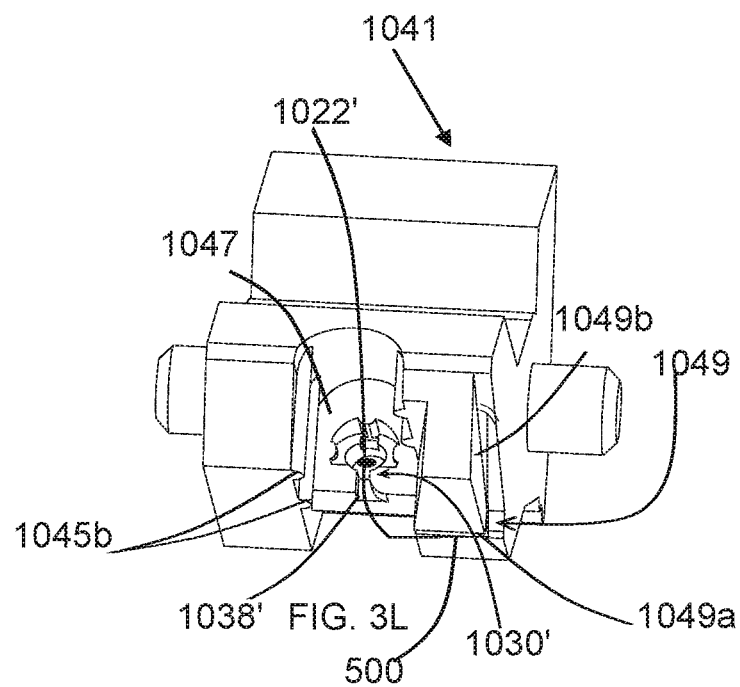
Figure 3N:
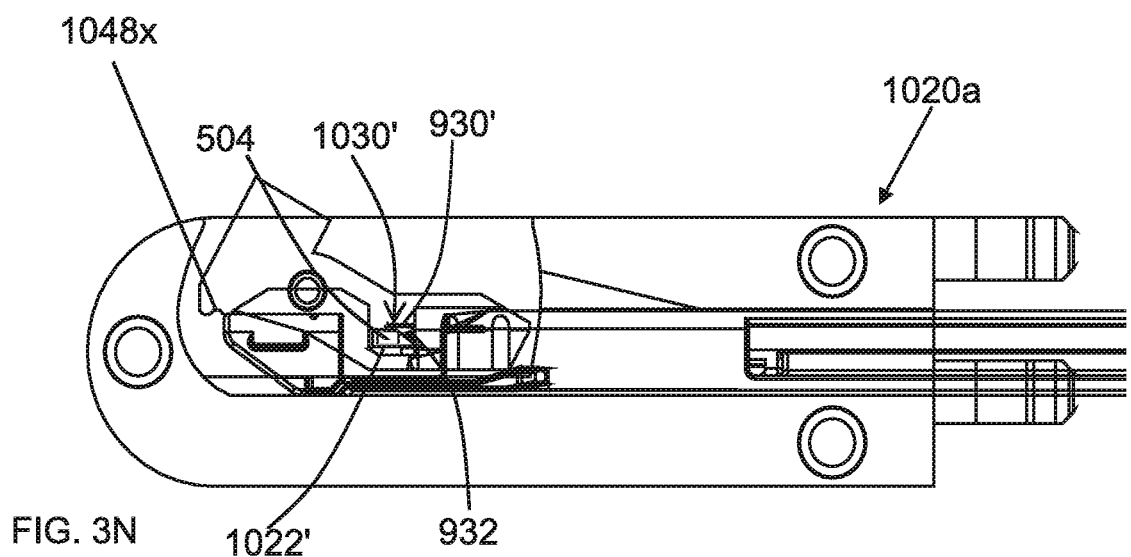

In an alternate embodiment of the present invention, as shown in FIGS. 3L and 3N, the magazine, for example the rocker 1041, comprises an alignment recess 1030' that is located adjacent the seat, for holding the suture therein. In some such embodiments, the rocker 1041 defines an opening/space or such as a seat recess or seat channel that forms the seat 1022' for holding the suture end 504 in frictional engagement therein. The alignment recess 1030' is positioned adjacent the seat 1022' and is in line with the suture passing member 930. The alignment recess 1030' and is configured for receiving the suture passing member 930 (such as needle 930') therein, to allow suture end 504 to be transferred from the seat 1022' to the suture receiving passage 932 of the suture passing member 930. The present configuration of the cartridge 1000 may be referred to as the needle-out configuration as the needle 930' is maintained in a partially extended position during loading of the cartridge 1000 onto the suturing instrument 900, as shown in FIG. 3N. In other words a distal portion of the needle 930 extends distally outside the shaft 910 of the suturing instrument at the time of loading the cartridge 1000 onto the suturing instrument. For example, the suture passing member 930 such as the needle 930' can be held in a partially extended position to allow the needle 930' to be receiving within the alignment recess 1030' for loading of suture therein. In some embodiments, a needle lock is provided that is mounted along the instrument proximal portion or shaft 910 of the suturing instrument 900 and is engageable with an aperture 935 within the needle 930' in its locking position to maintain the needle 930' in the partially extended position during loading of the cartridge 1000 onto the suturing instrument 900. The needle lock may be disengaged thereafter to allow the needle 930' to be retracted to its nominal position prior to use of the suturing instrument 900.

Figure 3O:
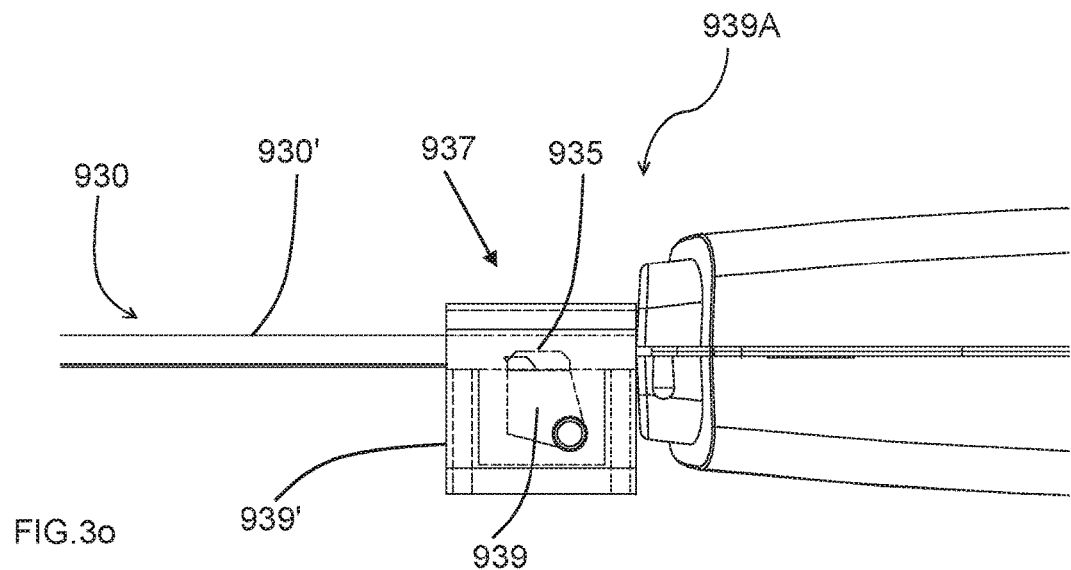

In one specific example, as shown in FIG. 3*o*, the needle lock comprises a cam lock 937 comprising a cam 939 within a cam housing 939'. In its locked position 937A as shown, the cam is engaged with the aperture 935 of the needle 930' preventing the needle 930' from retracting into the instrument proximal portion or shaft 910. As such the cam 939 allows the needle 930' to remain in its partially extended position to allow the needle 930' to be received within the alignment recess 1030' of the cartridge 1000 facilitating alignment and transfer of suture end form the seat 1022' into the needle 930'. The cam 939 may then be disengaged from the needle aperture 935 thereafter moving the cam lock 937 into its unlocked position which the needle 930' to retract back into the shaft or instrument proximal portion 910. In some examples, a component of the cartridge 1000, for example a component of the cartridge housing 1010' may moveable proximally along the instrument proximal portion of shaft 910 to disengage the cam lock moving it into its unlocked position to allow the needle to move into its unactuated/nominal position.

In some such embodiments, as shown in FIG. 3L, the rocker 1041 comprises additional alignment features to assist in alignment of the seat 1022'. In one such example, the alignment recess 1030' adjacent the seat 1022' comprises interference features for frictionally engaging an exterior of the needle 930' of the suturing instrument 900 upon advancement of the needle 930' into the alignment recess 1030'. More specifically, the cartridge 1000 comprises interference features in the form of raised bumps 1045*a* on the inner surface of the wall defining the alignment recess 1030'. The raised bumps 1045*a* extend proximally along the inner surface of the wall of the alignment recess 1030' and are configured to frictionally engage the exterior of the needle 930' as the needle 930' is received within the alignment recess 1030'. As outlined previously herein above for the embodiment illustrated in FIG. 3*k*, the rocker 1041 shown in FIG. 3L, also comprises additional raised bumps 1045*b* along the interior of the proximal groove portion 1046 for frictionally engaging the exterior of the instrument proximal portion or shaft 910 once it is received within the proximal groove portion 1046 in order to align the seat 1022 with the needle 930'. This may be referred to as the needle-out configuration of the cartridge 1000 as the needle 930' remains partially extended outside the distal end of the shaft 910, during loading of the cartridge 1000 onto the suturing instrument 900.

In some embodiments, as shown in FIG. 3L, the cartridge 1000 defines a suture groove or slot to allow the suture to exit the seat 1022. In some such embodiments, the rocker 1041 defines a suture slot that is in communication with the seat 1022 for allowing the suture to exit the seat 1022. In the specific example shown in FIG. 3L, the alignment recess 1030' defines a suture slot 1038' therein allowing the suture 500 to exit therefrom to enable alignment of the suture end 504 with the suture receiving passage 932 within the needle 930'. More specifically, the suture slot 1038' enables the suture to be to be routed through it upon exiting the seat 1022, such that suture is aligned with the needle slot 928 and shaft slot 938. This facilitates transfer of the suture end into the suture receiving passage 932 of the needle 930 using a suture transferring component of the cartridge 1000. Once the suture exits the suture slot 1038', it is routed though the slot 1049 of the rocker 1041 to enable suture be held to the side of the rocker such that it is off to the side of the path of the suturing instrument 900 as it is advanced into the cartridge 1000.

In some embodiments of the present invention, the rocker 1041 additionally comprises interference tabs 1048*x* (as shown in 9M) for engagement with the suturing instrument 900 which allow the rocker 1041 to over-rotate to ensure alignment of the rocker 1041 with the instrument proximal portion or shaft 910 of the suturing instrument 900 to allow advancement of the rocker 1041 along the shaft 910. In other words the interference tabs 1048*x* may allow the rocker 1041 to rotate sufficiently to enable the seat 1022 to be positioned adjacent the suturing instrument 900 by ensuring that the shaft 910 is received within the rocker groove proximal portion 1046. For example where the seat 1022 is defined by the projection 1030, the interference tabs allow the rocker 1041 to rotate sufficiently to enable the projection 1030 to be received within the instrument shaft 910. Whereas, where the seat 1022 is positioned adjacent an alignment recess (as discussed earlier with reference to FIG. 3N, the interference tabs allow the rocker 1041 to rotate sufficiently such that the alignment recess and the seat 1022 adjacent to it are both aligned with the needle 930'.

As outlined previously herein, with reference to FIG. 3A-3C some embodiments of the present invention define base 1020 that is detachably coupled to the housing 1010' enabling the base 1020 and the housing 1010' to operate as a single unit upon loading of the cartridge 1000 onto the suturing instrument 900 where both the base 1020 and the housing 1010' provide features to assist in alignment of a portion of the suture 500 such as a suture end 504 with the suture passing member 930. In some such embodiments, the housing 1010' additionally comprises a means to frictionally engage a portion of the suture and is detachable from the base 1020 after alignment of the suture portion with the suture passing member 930 to transfer the suture portion into the suture passing member. In one such example as described further herein below the means to frictionally engage a portion of the suture comprises a suture lock.

As such, the cartridge housing 1010' defines a suture transferring component 1011 to transfer of the suture end into the suture passing member 930. In one embodiment as shown and described herein the suture transferring component 1011 is operable to pull the portion of the suture that is held in frictional engagement in order to transfer the suture portion such as suture end 504 held within the seat 1022, onto the suturing instrument 900. As such the cartridge 1000 comprises a suture transferring component 1011 that forms or defines a pull mechanism as described further in the method outlined herein below. The pull mechanism is defined as the mechanism of the cartridge that enables a pulling force to be exerted or applied to the suture portion such as the suture end to transfer the suture portion from the seat into the suturing instrument. In some embodiments the housing 1010' may additionally comprise suture loops that form a partially pre-tied knot that are mounted about the housing 1010'. Additionally in some embodiments the housing 1010' may provide a means to house excess suture. In one example, the excess suture may be provided on spools that are carried by housing 1010'.

Figure 5A:
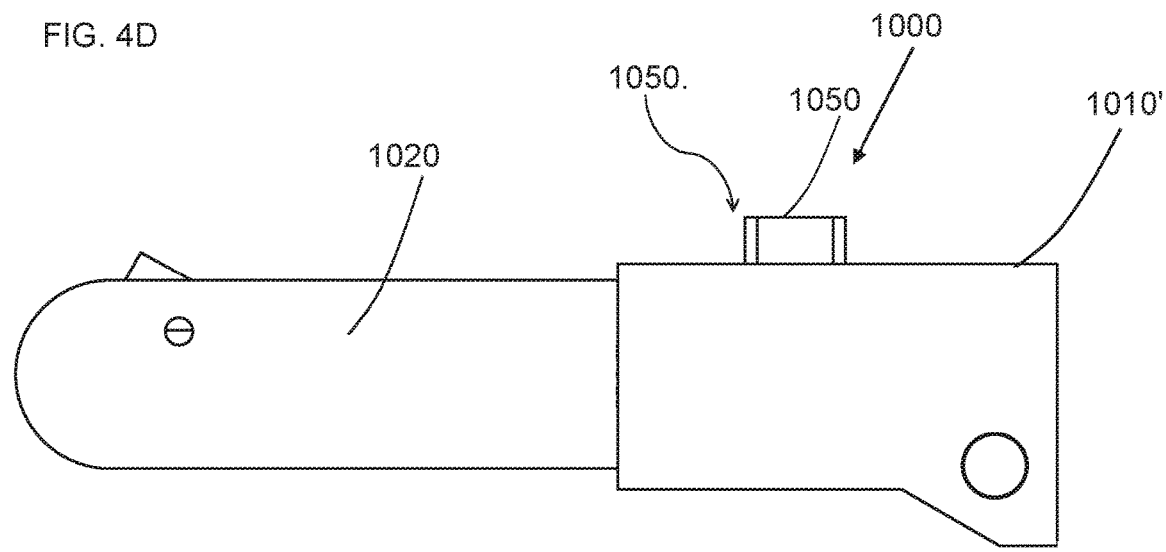
FIGS. 5A-5C illustrate views of an interlock mechanism of a cartridge in accordance with an embodiment of the present invention.
Figure 5B:
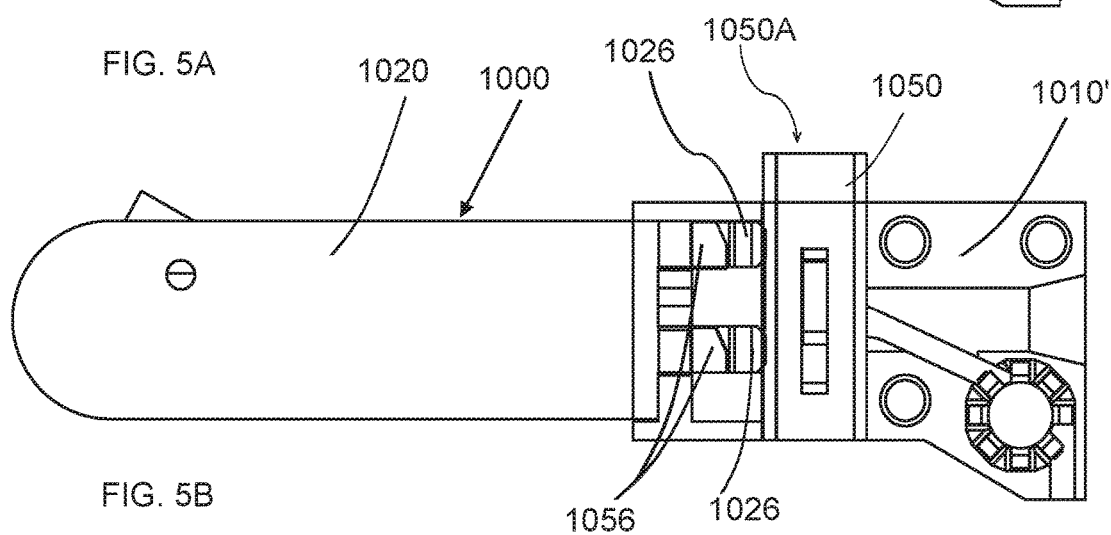
Figure 5C:
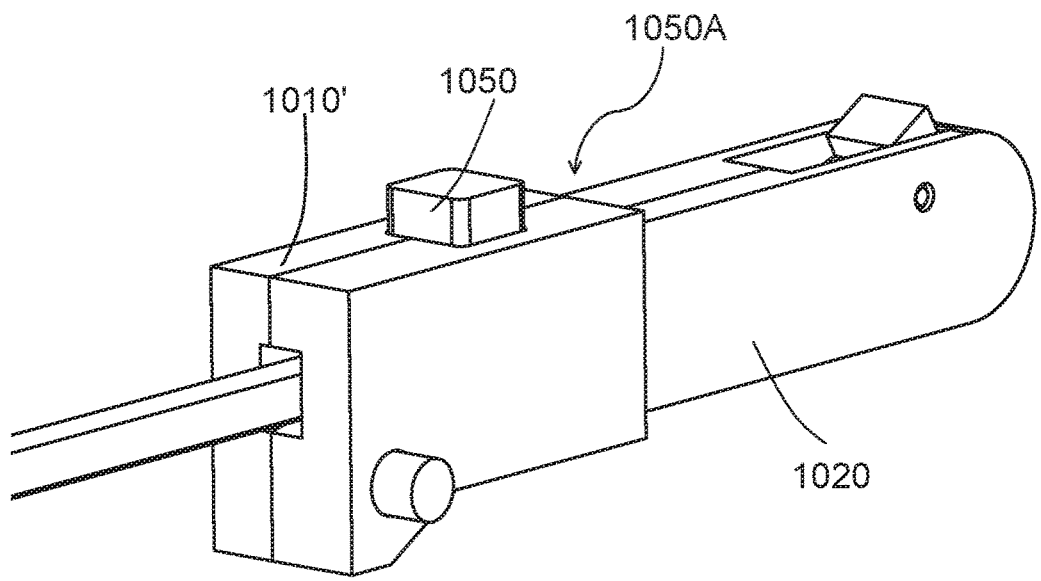

In some embodiments of the present invention as shown in FIGS. 3B, 3C and 3G, the cartridge base 1020 is detachably coupled to the cartridge housing 1010' via an interlock. In the specific example shown, the cartridge housing 1010' defining the suture transferring component 1011, comprises an interlock 1050. The interlock 1050 secures the base 1020 to the housing 1010' (and thus the suture transferring component) allowing the cartridge 1000 to operate a single functional unit upon loading of the cartridge 1000 onto the suturing instrument 900, until the seat 1022 is aligned with the suturing passing member 930. The interlock 1050 may then be disengaged to allow the housing 1010' that defines the suture transferring component 1011 to translate independently along the suturing instrument 900 to transfer the suture end 504 from the seat 1022 into the suture passing member 930 of the suturing instrument 900. FIGS. 5A-5C, illustrate the interlock 1050 in its initial locked position 1050A, with the interlock arms 1056 of the interlock 1050 being axially aligned with the locking arms 1026 of the base.

The interlock arms 1056 prevent movement of the housing 1010' with respect to the base 1020 to form a cartridge unit 1000 by blocking longitudinal movement of the locking arms 1026 of the base 1020 (and as such block the longitudinal movement of the base 1020). The function of the interlock 1050 is described further herein below with respect to FIGS. 5A-6B. The interlock 1050 is moveable into its unlocked position 1050B to allow the housing 1010' to be disengaged from the base 1020. In some embodiments, the interlock 1050 comprises a manual interlock that is moveable into the unlocked position 1050B to manually disengage the housing 1010' (and thus the suture transferring component 1011 defined thereby) from the base 1020 upon alignment of the seat 1022 with the suture passing member 930.

Still furthermore, suture transferring component defined by the housing 1010' comprises a means to hold a portion of the suture 500 in frictional engagement with the housing 1010' to allow the housing 1010' to move the suture 500 therewith to enable the housing 1010' to transfer the suture end 504 held within the seat 1022 of the base to the suture passing member 930. In the embodiment shown in FIGS. 3C and 3G, a portion of the suture is held in frictional engagement with a suture lock 1060 to secure the suture 500 thereto to enable the housing to pull the suture end 504 by applying tension to the suture (for example a segment of suture held in frictional engagement within the housing, for example via a suture lock) from the seat 1022 into the suture passing member 930.

Figure 7A:
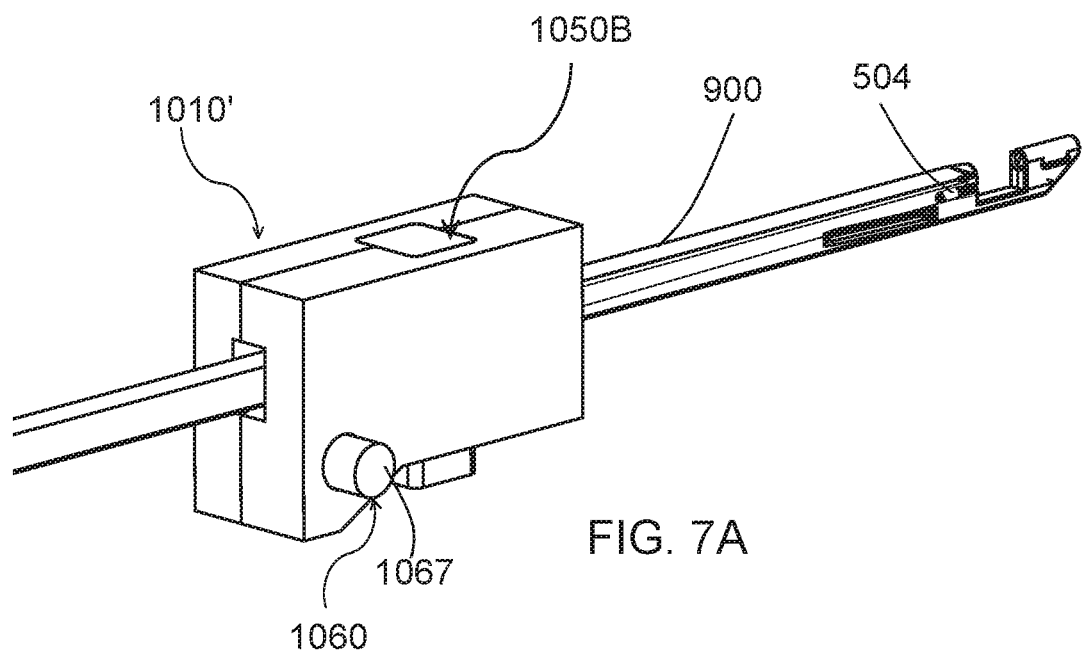
FIGS. 7A-7F illustrate views of a suture lock mechanism of a cartridge in accordance with an embodiment of the present invention.
Figure 7C:
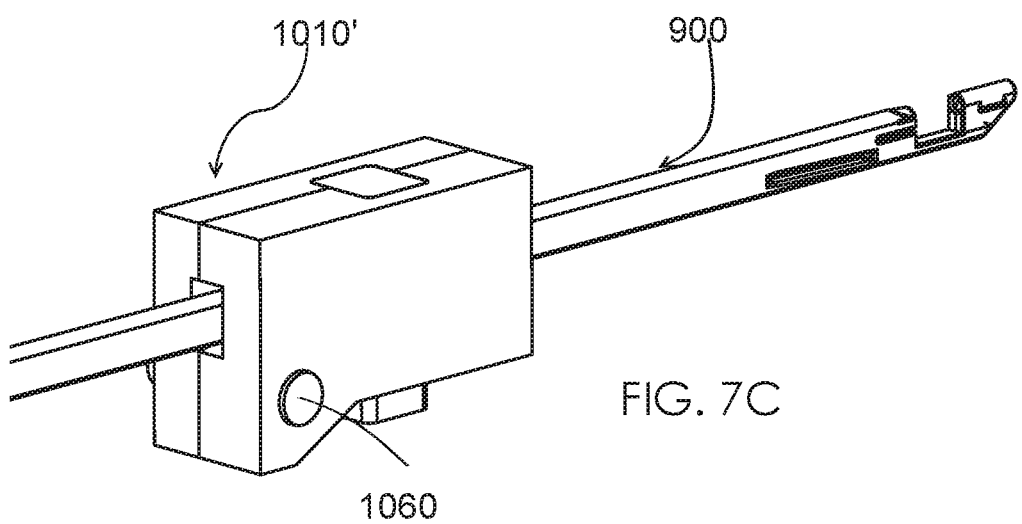
Figure 7B:
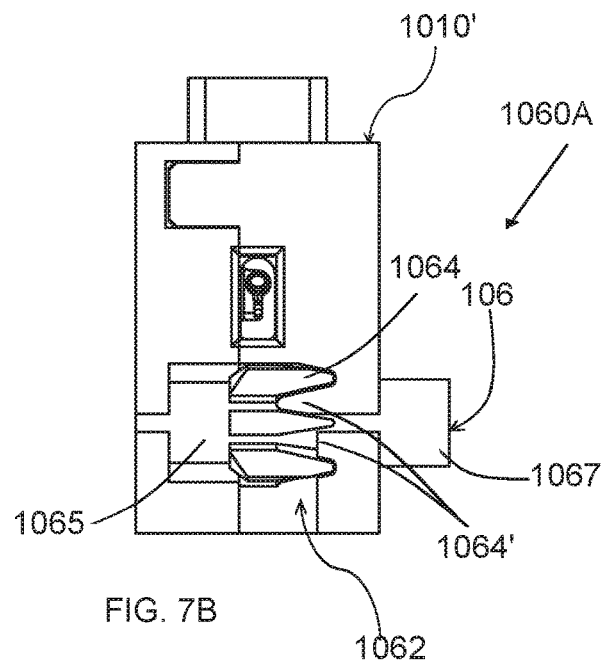
Figure 7D:
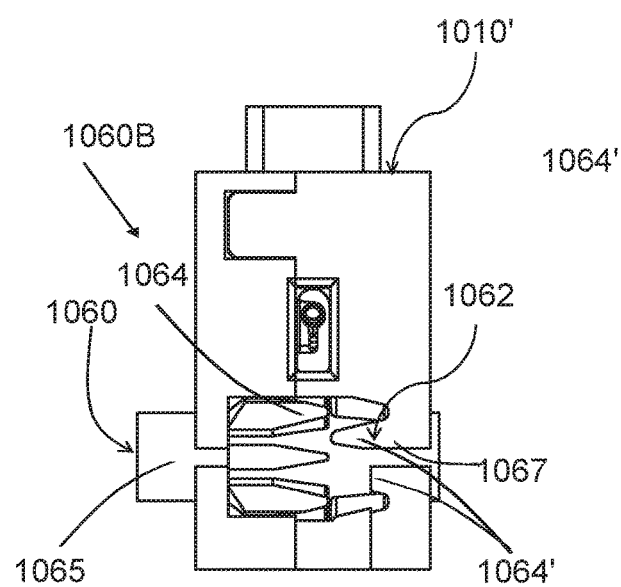
Figure 7E:
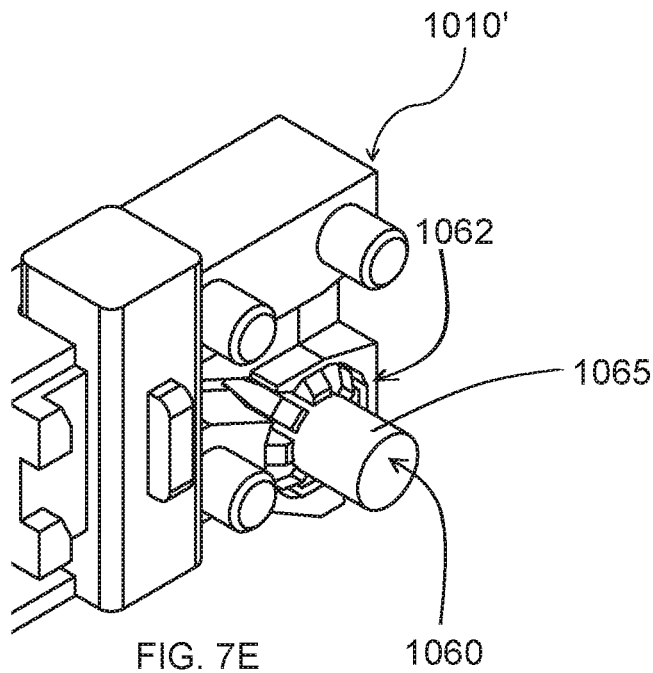

More specifically, in the embodiment shown, the suture 500 is held within the cartridge 1000 such that the suture 500 is routed from the suture end 504 within the seat 1022 upon exiting the seat slot 1038 such that it enters the slot 1049 of the rocker to be routed there-through. More specifically, in some examples the suture passed through and pinched within the slit or channel 1049 such that it is held therein in a force fit engagement. The suture 500 then enters the side slot 1049b on the exterior face of the rocker 1041 [FIGS. 3J and 3L]. The suture 500 exits the rocker 1041 into the rocker recess 1027 and is routed through the recess groove 1025b within the base 1020 which allows the suture 500 to be maintained within recess groove 1025b adjacent and out of the way of the path of the suturing instrument 900 to be inserted through the recess groove 1025a [FIG. 3D]. The suture is then routed through an opening 1051 within the interlock and guided into a suture channel 1061 to engage with the suture lock 1060 In one particular embodiment, as shown in FIGS. 7A-7E the suture lock 1060 comprises projections or teeth 1064 defining contours or ridges and valleys that are configured to engage corresponding features in the form or projections or teeth 1064 within a suture lock engaging component 1062 of the housing 1010'. The suture 500 is routed through the suture lock engaging component 1062 of the housing 1010' and the suture lock 1060 is press fit to engage with the suture lock engaging component 1062 pressing the suture between the two, and as such coupling the suture to the housing 1010'. FIGS. 7B and 7E show the lock in its initial locked configuration 1060A. The lock 1060 remains in its locked configuration until the suture portion such as the end of the suture has been loaded into the suturing instrument 900. It is moveable thereafter into its second of unlocked configuration as shown in FIGS. 7C and 7D and additionally in FIG. 7F to allow the suture 500 to be disengaged from the housing 1010'.

In some embodiments, as described herein above in example 3, the movement of the suturing instrument 900 may be a relative movement with respect to the cartridge 1000. In other words the user may move the cartridge 1000 axially over the suturing instrument 900 in a proximal direction while the suturing instrument is held by the user in order to create a relative advancement of the suturing instrument 900 with respect to the cartridge 1000 in order to load the suture onto the suturing instrument 900. This may be refer to as loading of suture using pumping action. As such, the mechanism of loading of the suture may remain as described above but the movement may be created either by the proximal movement of the cartridge over the suturing instrument or the distal movement of the suturing instrument within the cartridge.

In some embodiments of the present invention as described herein, the cartridge is configured to align and transfer the suture upon a single linear motion of the cartridge with respect to the suturing instrument. In some such embodiments, the interlock 1050 may be automatically disengaged upon alignment of the suture end within the seat with the suture passing member to enable automatic transfer of the suture end 504 into the suture passing member as the housing 1010' is continued to be pulled proximally. Additionally the suture lock 1060 may be automatically disengaged thereafter upon transfer of the suture end from the seat 1022 into the suture passing member 930, which would allow the suturing instrument to be able to pass the suture in order to suture therewith. In some such embodiments, the cartridge is loaded onto the suturing instrument 900 with a single linear movement. In some such embodiments a single pumping action is used involving a single linear relative movement of the cartridge onto the suturing instrument and removal of the base 1020 [for example via a linear movement in the opposing direction to the loading direction] thereafter leaving the housing coupled to the suturing instrument for example to mount a pre-tied knot held therein onto the suturing instrument.

EXAMPLE 4

Figure 8A:
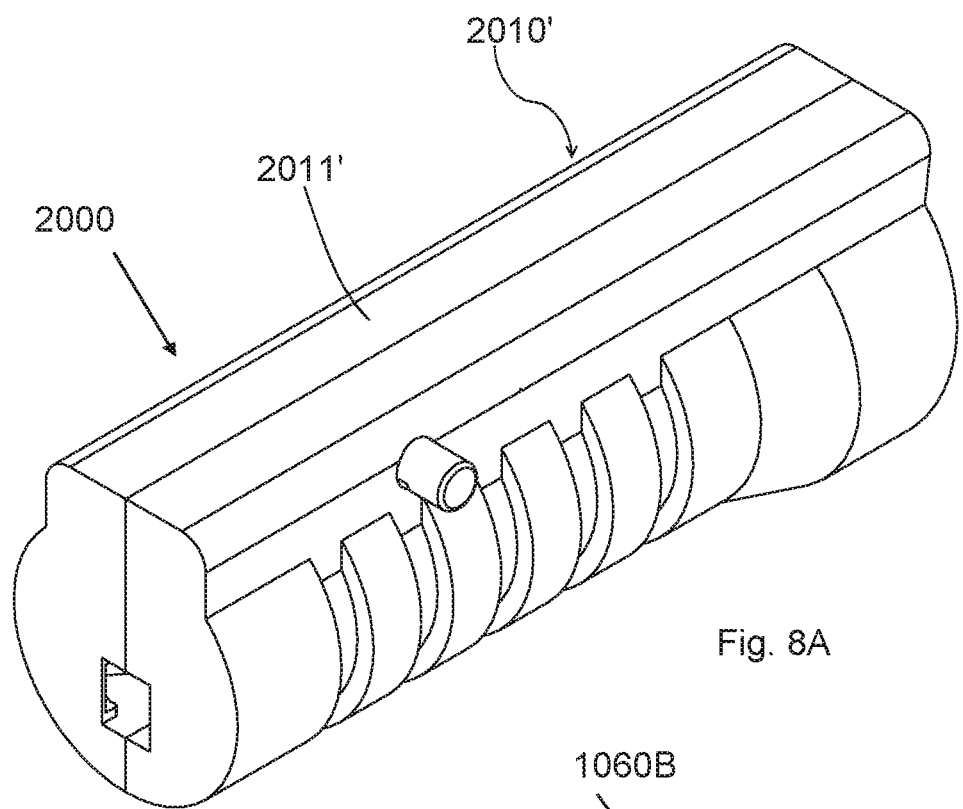
Figure 8B:
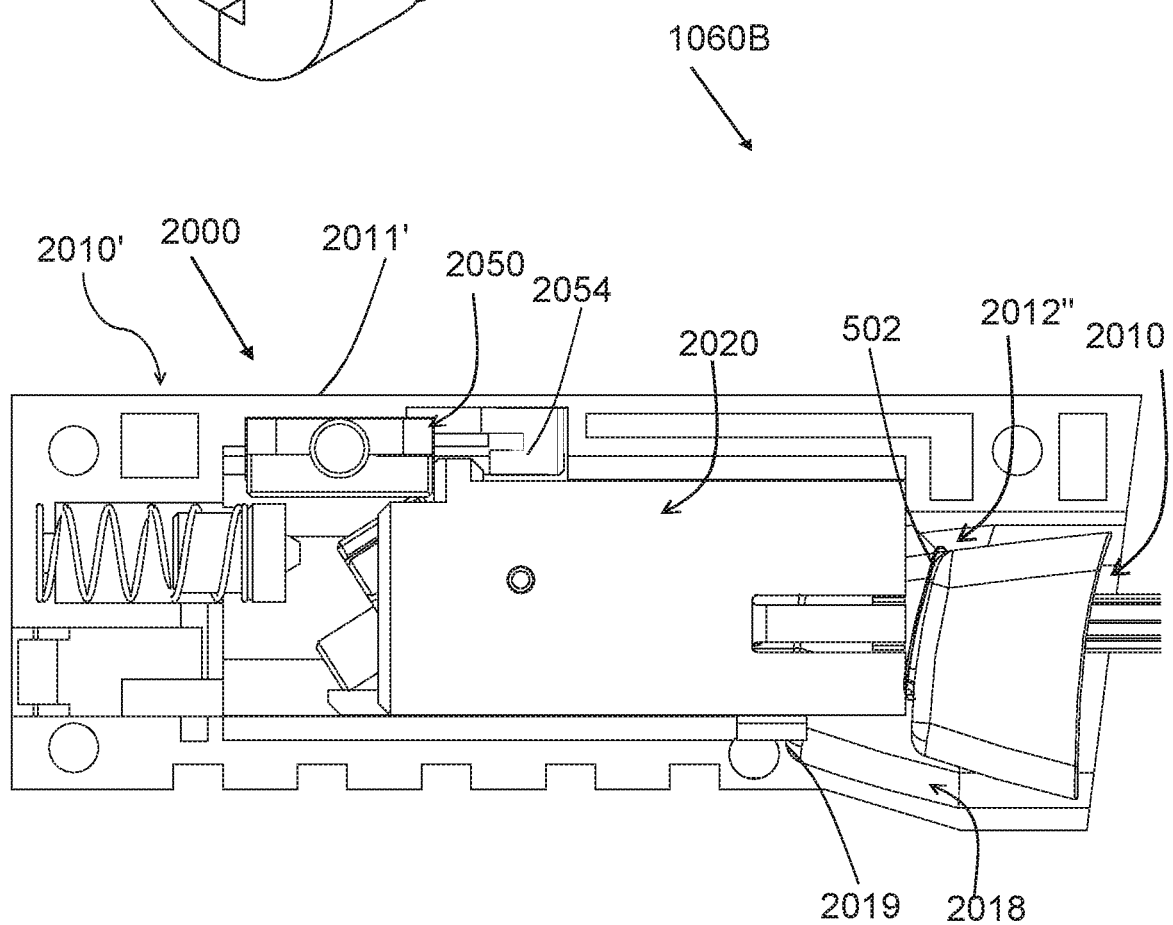
Figure 8C:
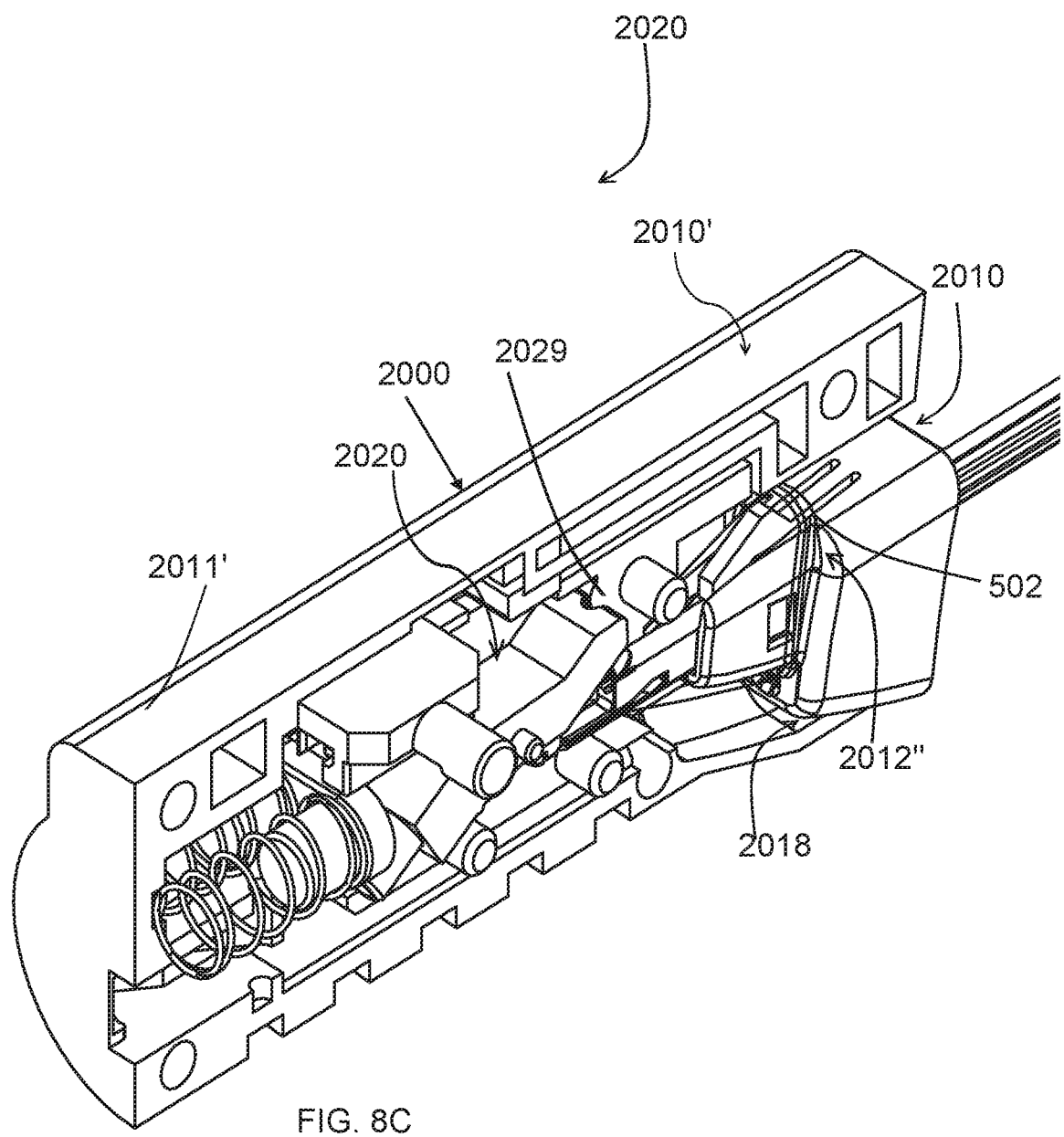

In an alternate embodiment of the present invention, as shown in FIGS. 8A-8C, a cartridge 2000 is disclosed for loading suture onto a surgical suturing instrument, for example a suturing instrument 900 as discussed previously herein above with reference to FIGS. 1D and 1E. Similar to embodiments described previously herein above, the cartridge 2000 carries suture therein and allows suture to be loaded onto a surgical suturing instrument 900 for example, at the point of use. The cartridge 2000 functions to align the suture with the suturing instrument 900 upon insertion and relative axial advancement of the suturing instrument 900 within the cartridge 2000, and additionally functions to transfer of the suture onto the surgical suturing instrument 900. In some such embodiments, either the suturing instrument 900 may be advanced distally into the cartridge 2000 or the cartridge 2000 may be pulled proximally over the suturing instrument. As described herein either of these techniques may be utilized to provide the functionally described herein for creating relative axial movement between the cartridge 2000 and the suturing instrument 900 for loading the suture onto the suturing instrument 900. This is also applicable to embodiments described herein above in example 3. In some such embodiments, the cartridge 2000 additionally provides a pre-tied knot therein and enables the pre-tied knot to be loaded onto the suturing instrument 900. In some embodiments, the pre-tied knot may comprise loops that substantially form a pre-tied knot. In other words a pre-tied knot may comprise a partially pre-tied knot. In some such embodiments, the partially pre-tied knot is configured to be deployed from the suturing instrument after suturing to form a knot to secure the suture.

With reference now to FIGS. 8B and 8C, the cartridge 2000 comprises a housing 2010' that defines a chamber 2010 for axially receiving the surgical suturing instrument 900. The cartridge 2000 further comprises a base 2020 that is detachably coupled to the housing 2010', the base 2020 defining a seat 2022 for releasably holding the suture therein [As shown in FIG. 8E(ii)]. The base 2020 enables alignment of the suture held therein with the suture passing member 930 of the suturing instrument 900. The housing 2010' additionally comprises a suture transferring component to transfer suture from the base 2020 onto the surgical suturing instrument 900. Thus, in some embodiments, as shown in FIG. 8B the base 2020 and the housing 2010' comprise separate components of the cartridge 2000 that are coupled to one another to assist in loading suture and may be detachable therefrom to assist in transferring suture. The housing 2010' additionally comprises a chamber 2010 therein and a means for securing or mounting a pre-tied knot 502 about the chamber 2010, to enable the pre-tied knot to be mounted onto the suturing instrument 900. The housing 2010' and the base 2020 collectively provide alignment features to assist in alignment of the suture upon loading of the cartridge 2000 onto the suturing instrument 900 to facilitate transfer of suture from the cartridge 1000 onto the suturing instrument 900 using the suture transferring component. In some embodiments the housing 2010' comprises a knot slider 2030 that defines the chamber 2010, the knot slider 2030 includes suture loops coupled thereto, the suture loops are configured to form a knot upon deployment thereof from the knot slider 2030, wherein the suturing instrument 900 is receivable within the chamber 2010 for mounting the suture loops onto the suturing instrument.

In some such embodiments, a suturing system is provided that comprises a suturing instrument 900 comprising a suture passing member 930; and a cartridge (such as cartridge 2000) for releasably holding an end of a suture and defining a chamber 2010 for coupling a partially pre-tied knot thereabout, the chamber 2010 is configured to receive the suturing instrument 900 therethrough. The cartridge 2000 is configured to transfer the suture end 504 into to the suture passing member 930 and to transfer the partially pre-tied knot (for example 502) onto the suturing instrument. In some such examples the suture passing member 930 is configured to pass the suture end 504 from a proximal side of a tissue to a distal side of the tissue in a first actuation of the suture passing member.

In an additional embodiment, a cartridge (such as cartridge 2000) is provided for loading suture onto a suturing instrument 900 to enable the suturing instrument to form a pre-tied knot, the cartridge comprises: a chamber 2010 for receiving a suturing instrument 900, the chamber 2010 supporting loops of suture coupled thereto (such as loop 502 shown in FIG. 8B) for transferring onto the suturing instrument 900 upon advancement of the suturing instrument into the chamber 2010, the loops 502' of suture being configured to form a pre-tied knot upon deployment from the suturing instrument; and a seat 1022 for releasably holding a portion of the suture to enable transfer of the suture portion 504 onto the suturing instrument, the suture portion comprising an end of the suture configured to define a post of the pre-tied knot upon deployment of the loops from the suturing instrument.

In one particular embodiment, the cartridge housing 2010' is detachably coupled to the base 2020 and defines a chamber 2010 for receiving the surgical suturing instrument 900 there-through. In some such embodiments, the chamber 2010 additionally comprises a means for storing a pre-tied knot about the chamber. In some embodiments, the housing 2010' additionally comprises a knot slider 2030 defining the chamber 2010 having a pre-tied knot mounted thereon wherein the surgical suturing instrument is receivable within the chamber 2010 to mount the pre-tied knot onto the surgical suturing instrument 900. In one particular example, the cartridge housing 2010' comprises an outer housing sleeve 2011' that defines a hollow interior for holding the knot slider 2030 therein. The knot slider 2030 is detachably coupled to the housing sleeve 2011' and forms a part of the housing 2010'. In a particular example as shown in FIG. 8B, the knot slider 2030 is detachably coupled to the housing 2010' via the base 2020 for holding a pre-tied knot about the chamber 2010.

Additionally, the chamber 2010 includes a recess or channel 2014 that is a part of the chamber that receives the suturing instrument. In the particular example discussed herein the chamber 2010 defines a channel 2014 as shown in FIG. 8D which illustrates a rear view of the knot slider 2030 to allow a portion the suturing instrument 900 to be received there-through As such the channel 2014 defines an instrument receiving recess for receiving the suturing instrument 900 that additionally functions as a restraint for maintaining the position of the suturing instrument 900 as it is advanced through the cartridge 2000. Similar to Example 3 described previously herein above, in some examples, the channel 2014 comprises a proximal opening 2016 that narrows towards the interior of the knot slider 2030 as defined by a beveled interior edge 2016'. The beveled interior edge 2016' functions as a lead in to guide the suturing instrument 900 into the channel 2014.

The channel 2014 extends longitudinally through the knot slider 2030 of the housing 2010' and is in communication with a base recess 2025 within the base 2020. As shown in FIGS. 8A-8C, the base 2020 is detachably coupled to the housing 2010'. More specifically, the base 2020 is held within the housing sleeve 2011'. In some examples the channel 2014 may be formed continuously with the base recess 2025 within the cartridge base 2020. One example of this discussed further herein below. The channel 1014 and the base recess 1025 both function as a restraint 25 (FIG. 8E (i)), to constrain or restrict the lateral and transverse movement of the suturing instrument 900 within the cartridge 2000 while allowing the suturing instrument 900 to be advanced linearly or axially therein in sliding engagement to maintain the position of the suturing instrument 900 along the longitudinal axis as it is advanced. As such the restraint 25 constraints or limits the movement of the suturing instrument 900 in the transverse and lateral directions as well along a longitudinal path defined thereby. Thus the restraint 25 facilitates alignment of the suturing instrument 900 with a portion of the suture 500 that is held within a seat 1022 defined by the base 2020. More specifically, the channel 1014 and the recess 1025 allow the suturing instrument 900 to be advanced therein in sliding engagement therein and additionally function to restrain the suturing instrument 900 in a linear path as it is advanced along the cartridge 2000 to allow the seat 1022 to be aligned with the suture receiving passage 932 of the suture passing member 930.

Furthermore, similar to embodiments discussed previously with respect to Example 3 herein above, the recess 2025 within the base is formed from two grooves, an instrument receiving groove 2025a defining an instrument receiving recess as shown in FIG. 8E(i) and FIG. 8E(ii) and a suture receiving groove 1025b defining a suture receiving recess, as shown in FIG. 8F(i) and FIG. 8F(ii). The instrument and suture receiving grooves 2025a and 2025b respectively are formed within the opposing halves 2020a and 2020b of the base 2020 (as illustrated in FIG. 8E(i)-FIG. 8F(ii)).

With reference again to FIG. 8E(i),(ii) the instrument receiving groove 2025a defines an instrument receiving recess by providing a track which functions as a restraint 25 to allow the suturing instrument 900 to be advanced therein, whereas suture groove 2025b (FIG. 8F(i)) provides a track to guide the portion of the suture held within the seat into the suture passing member 930 of the suturing instrument 900 by maintaining/routing the suture 500 therein such that it is adjacent and in line with the shaft or proximal portion 910 of the suturing instrument 900 that is receivable within the instrument receiving groove 2025a as further illustrated in FIGS. 8F(ii) and 8G. More specifically, the suture receiving groove 2025b allows the suture to be routed such that when the suturing instrument is received within the instrument receiving recess 2025b, the suture 500 is held adjacent the groove 928 within the shaft or the instrument proximal portion 910 as well groove 938 within suture passing member 930 such as needle 930' (shown in FIG. 1E). Furthermore, the groove 2025b provides room for routing the suture without excess tension being placed in the suture by providing a wider opening into a rocker recess 2027 as shown by FIG. 8F(ii). As such the groove 2025b accommodates the suture as it enters a rocker recess 2027 in both a final position 1041B as well as an initial position 1041A of a rocker 1041 (Discussed further herein below). As such the suture receiving groove 2025b enables the suture 500 to be maintained out of the way of the advancing suturing instrument 900 during use of the cartridge 2000. Additionally recess groove 2025b is in line with grooves 928, 938 within the suturing instrument 900 to further facilitate transfer of suture from a seat 2022 for example within the rocker 1041 within the base 2020 into the needle 930'. In the illustrated embodiment, both the instrument receiving groove and the suture receiving groove exit into the rocker recess 2027.

In some embodiments as provided herein the cartridge 2000 additionally provides a pre-tied knot and a means to load the pre-tied knot onto the suturing instrument 900. In some such embodiments, the cartridge defines a chamber 2010 and a means to mount or retain a pre-tied knot about the chamber 2010. In one such example as discussed herein a knot slider 2030 is provided with reference to FIG. 8C that enables a pre-tied knot to be mounted thereon so that it is held about and surrounds or circumscribes the chamber 2010. This enables the suturing instrument 900 to be received through a channel 2014 within the chamber 2010 such that is passes through the pre-tied knot to allow the pre-tied knot to be mounted thereon. In one specific example the knot slider forms a mount 2012" for holding the pre-tied knot 502 about the chamber 2010, as shown in FIGS. 8B and 8C. The pre-tied knot 502 may be of the type as previously illustrated herein in FIG. 1A. In some embodiments, the knot slider 2030 forms an instrument mounted component of the cartridge 2000.

Additionally some embodiments of the present invention provide a means to hold the knot slider 2030 within the cartridge 2000 to permit the knot slider 2030 to be held therein until a suturing instrument 900 is inserted within the cartridge 2000 to enable the knot slider 2030 to be detached from the rest of the cartridge 2000 to be coupled to the suturing instrument 900 thereafter. In some such embodiments, the knot slider 2030 is held within a knot slider recess 2018 (FIG. 8B and FIG. 8C) within the outer sleeve 2011' and is detachably coupled thereto via the base 2020. In one particular example, the knot slider 2030 is detachably coupled to the base 2020 via a knot slider release interlock 2033 that for example comprises a snap fit arrangement as shown in FIG. 8H(i) As additionally illustrated in FIGS. 8E(i), 8F(i), the base comprises snap arms 2042 that are receivable within and engageable with grooves formed within the knot slider 2030 that may be referred to as snap grooves 2032 to couple knot slider 2030 therein, forming the knot slider release interlock 2033. In order to facilitate coupling between the knot slider 2030 and the base 2020, the base 2020 additionally comprises a knot slider s 2040 therein that is configured for receiving a portion of the knot slider 2030 therein.

In the illustrated embodiment, the knot slider 2030 is detachable from the base to enable loading of the knot slider 2030 and thus the pre-tied knot 502 onto the suturing instrument 900 upon disengagement of the knot slider release interlock 2033. In one specific embodiment, the knot slider 2030 is detachable from the base 2020 upon relative movement of base 2020 with respect to the housing 2010'. In one such example, the knot slider 2030 is moveable distally along the knot slider recess 2018 within the housing sleeve 2011' upon distal movement of the base 2020 within the housing sleeve 2011'. However, the wall 2019' of the housing sleeve 1011' adjacent the tapered inner wall 2019 [FIG. 8B] of the knot slider recess 2018 functions as a stop to prevent further distal movement of the knot slider 2030 to disengage snap arms 2042 of the base 2020 from the snap grooves of the knot slider 2030, and as such disengages the knot slider release interlock 2033.

Figure 9A:
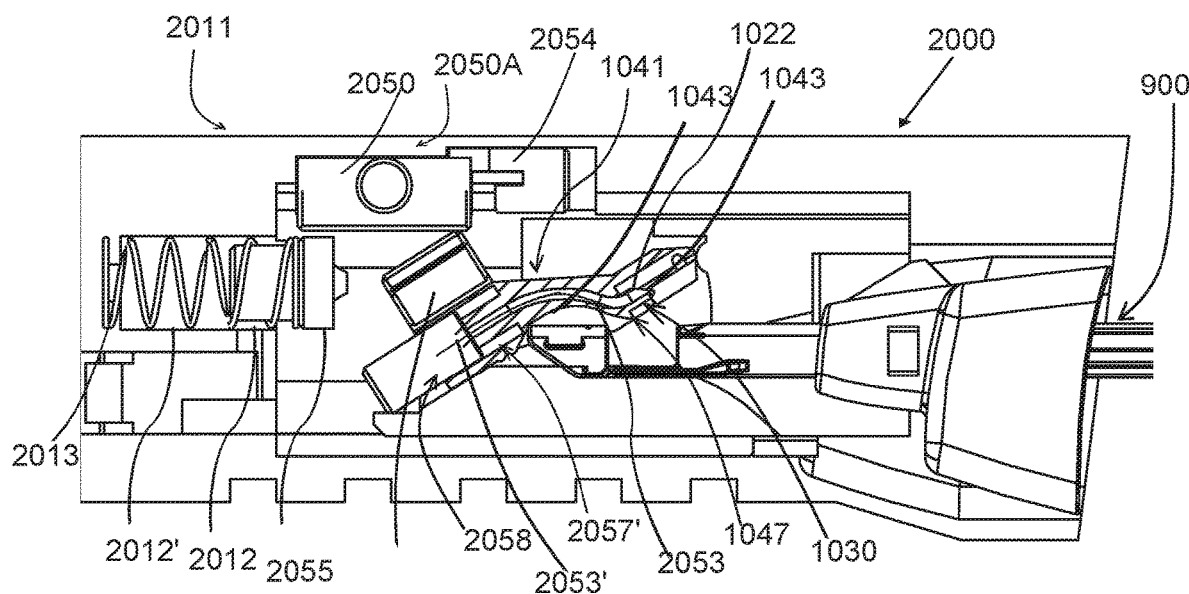
FIG. 9A(i)-9F illustrate views of a cartridge and a method of using the same in accordance with an alternate embodiment of the present invention.

In some embodiments of the present invention, the cartridge 2000 defines a moveable seat 1022 as previously described herein above with reference to FIG. 3C, the seat 1022 is automatically moveable upon insertion of the suturing instrument 900 within the cartridge 2000. In the particular example shown, the cartridge 2000 comprises a magazine 1021 comprising a rocker 1041 that is rotatable about a pivot, and the base 2020 defines a rocker recess 2027 for enabling pivotal movement of the rocker 1041 therein. Similar to the embodiments illustrated in FIGS. 3C and 4C(i), the rocker 1041 is moveable about the pivot 1042 from its initial position 1041A (as shown in FIG. 9A(i),(ii)) to its second position 1041B (as shown in FIG. 9B(i),(ii)) in order to align the seat 1022 and the suture end 504 held therein with the path of an advancing suturing instrument 900 that is inserted within the cartridge 2000. As outlined previously in example 3, as defined herein the rocker 1041 is moveable within the rocker recess 2027. The rocker 1041 is moveable from its first position 1041A into a rocker cavity 2027' its second position 1041B, as shown in FIG. 9B(ii). The rocker cavity 2027' is defined as a portion of the rocker recess 2027 that corresponds to the tissue receiving gap 942 of the suturing instrument 900 once suturing instrument 900 is positioned within the base 2020 of the cartridge 2000 upon loading of the cartridge 2000 onto the suturing instrument.

In some embodiments, the rocker 1041 is held in its initial position 1041A within the rocker recess 2027 through frictional engagement. For example the rocker 1041 may be kept in its initial position 1041A by an engagement feature such as a raised tab or detent 2029 as shown in FIGS. 8C and 8F(i), that frictionally engages the rocker 1041. The tab or detent 2029 is formed within the base 2020 and may extend or jut into the rocker recess 2027. The tab 2029 is engageable with a portion of the rocker 1041 (for example a nose portion 1081) of the rocker 1041 as shown in FIG. 8F(ii), to maintain the rocker in its initial position 1041A during shipment and prior to use.

In some embodiments, for example as provided in Example 4, the cartridge 2000 may comprise additional features that assist in aligning the seat 1022 with a portion of the suturing instrument 900 as the suture passing member 930 held within the shaft or instrument proximal portion or shaft 910. In one such example, with reference earlier to FIG. 3C, the rocker 1041 additionally defines an instrument receiving or locking recess defined by a groove 1044 that is designed for receiving the suturing instrument 900 as it is advanced distally. The groove 1044 functions as a restrain to position the suturing instrument 900 in a desired position relative to the seat 1022 to assist in aligning the seat 1022 with a suture passing instrument 900. As shown and discussed previously with reference to FIGS. 3H and 3I, the groove 1044 comprises a groove proximal portion 1046 for receiving the instrument proximal portion or shaft 910 of the suturing instrument 900, and additionally comprises a groove distal portion 1048 for receiving the instrument distal portion or tip 920.

As discussed earlier with respect to Example 3, the rocker 1041 of Example 4 additionally comprises a median 1047 (FIG. 9A(i) that is defined by the groove 1044 that functions as an alignment feature by holding and aligning the seat 1022 with the suture passing member such as needle 930' of the suturing instrument 900.

Still furthermore, the groove 1044 defines an additional alignment feature in the form of an interior bevel face 1043 (FIG. 9A (i)) within the distal groove portion 1048 to enables the distal portion 920 of the suturing instrument to pivot the rocker 1041 from its initial position 1041A into its aligned position or second position 1041B to enable alignment of the seat 1022 and the suture held therein with the suture passing member 930 of the suturing instrument.

In some embodiments, in cartridge 2000, the rocker 1041 additionally defines another alignment feature in the form of a rocker slot 1049 (as shown earlier in FIGS. 3J, 3L) within the groove 1044 to assist in alignment and transfer of the suture end 504 into the suture passing member 930. The slot 1049 comprises a slit or channel 1049a (also shown in FIG. 9A(i)) that exit into a side slot 1049b within the rocker 1041, to aid in routing the suture 500 within the suture receiving groove 2025b (FIG. 8F(ii)) of the base 2020 to assist in aligning the suture with the suture receiving slot 928 in the shaft. This allows the suture to be held to the side of the suturing instrument 900 out of the way of the path of the advancing suturing instrument during advancement of the suturing instrument within the cartridge base 2020. As such the rocker 1041 defines a rocker slot 1049 for routing the suture 500 there-through to enable the suture 500 to be kept out of the way of a path of the suturing instrument 900 upon advancement of the suturing instrument 900 therein. For example when a portion of the instrument proximal portion 910 is received within the groove proximal portion 1046 of the rocker groove 1044.

In one specific example, as shown in FIGS. 3J and 3K, the seat 1022 is defined by a projection 1030 that is housed within the magazine 1021, specifically within the rocker 1041. As shown in FIGS. 3M and 4D, the projection 1030 extends into the instrument receiving recess defined by the groove 1044 (specifically, the groove proximal portion 1046). More specifically, the median functions to hold the projection 1030 within the groove proximal portion 1046 of the rocker. In some embodiments the projection 1030 defining the seat 1022 may be formed in one piece as part of the rocker. The projection 1030 additionally defines a bevel face 1034 for engaging with a bevel face 934 of the needle 930' for docking the needle 930' to align the seat 1022 with the needle 930' with to permit transfer of the suture end 504 from the seat 1022 into a suture receiving passage 932 of the needle 930'. In one specific example, the projection 1030 is receivable into the instrument proximal portion or shaft 910 to facilitate alignment of the seat 1022 with the needle 930'.

Alternatively, the rocker may define a seat recess or seat channel and an alignment recess 1030' that is located adjacent the seat 1022. As shown and described further herein with respect to FIGS. 3L and 3N, the alignment recess 1030' is configured for receiving the suture passing member 930 such as needle 930' in its needle out configuration to align the seat with the suture passing member.

In some such embodiments, as shown in FIG. 3K, the rocker 1041 comprises additional alignment features such as interference features in the form of raised bumps 1045*a* on the exterior of the projection 1030 that are configured to frictionally engage the interior of the instrument proximal portion or shaft 910 with the needle 930' as the projection 1030 is received within the shaft 910. The rocker 1041 additionally comprises additional raised bumps 1045*b* along the interior of the proximal groove portion 1046 for frictionally engaging the exterior of the instrument proximal portion or shaft 910 once it is received within the proximal groove portion 1046. The raised bumps 1045*a*, 1045*b* help to align the seat 1022 with the needle 930'.

In some embodiments projection 1030 defines a suture slot 1038 therein allowing the suture 500 to exit therefrom to enable alignment of the suture end 504 with the suture receiving passage 932 within the needle 930'.

In some embodiments of the present invention, the rocker 1041 additionally comprises interference tabs 1048*x* ((as shown in FIG. 9A (iii), and FIG. 9B (i) as discussed earlier with respect to FIG. 3M) for engagement with the suturing instrument 900 which allow the rocker 1041 to over-rotate to ensure alignment of the rocker 1041 with the instrument proximal portion or shaft 910 of the suturing instrument 900 to allow advancement of the rocker 1041 along the shaft 910. In other words the interference tabs 1048*x* may allow the rocker 1041 to rotate sufficiently to enable the seat 1022 to be positioned adjacent the suturing instrument 900 by ensuring that the shaft 910 is received within the rocker groove proximal portion 1046. For example where the seat 1022 is defined by the projection 1030, the interference tabs allow the rocker 1041 to rotate sufficiently to enable the projection 1030 to be received within the instrument shaft 910. Whereas, where the seat 1022 is positioned adjacent an alignment recess (as discussed earlier with reference to FIG. 3N, the interference tabs allow the rocker 1041 to rotate sufficiently such that the alignment recess and the seat 1022 adjacent to it are both aligned with the needle 930'.

As outlined previously herein, with reference to FIG. 8A-8C some embodiments of the present invention provide a housing sleeve 2011' that is detachably coupled to the base 2020 and remains coupled to the base 2020 to operate as a single unit upon loading of the cartridge 2000 onto the suturing instrument 900. The housing sleeve 2011' remains coupled to the base 2020 until the seat 1022 is aligned with the suture passing member 930 of the suturing instrument 900. The cartridge sleeve 2011' is detachable from the base 2020 thereafter to transfer suture from base 2020 into the suturing instrument 900. As such, the cartridge housing 2010' defines a suture transferring component 2011.

In some embodiments of the present invention as shown in FIG. 8B, the cartridge base 2020 is detachably coupled to the suture transferring component 2011 of the housing 2010' via an interlock 2050. The interlock 2050 secures the base 2020 to the housing 2010' in its initial position 2050A may then be disengaged to move into its second position 2050B [shown later in FIGS. 9D[i],[ii]) to allow the housing sleeve 2011' that comprises the suture transferring component 2011 to translate independently relative to the base 2020 to transfer the suture end 504 from the seat 1022 into the suture passing member 930 of the suturing instrument 900. FIGS. 9B [i],[ii] and 9C[i],[ii], illustrate the interlock 2050 in its initial locked position 2050A, with an interlock arm 2056 being axially aligned with and being position distal to the base 2020 preventing longitudinal movement of the base 2020 with respect to the housing 2010'. The interlock 2050 is moveable to its unlocked position 2050B (as shown in FIGS. 9D[i],[ii]) to disengage the transferring component from the base to enable relative movement there-between upon alignment of the seat with a suture passing member of the suturing instrument. The function of the interlock 2050 is described further herein below with respect to FIGS. 9C[i]-9D[ii]. In some embodiments, the interlock 2050 comprises a manual interlock that is moveable into the unlocked position 2050B to manually disengage the suture transferring component 2011 from the base 2020 upon alignment of the seat 1022 with the suture passing member 930.

In some embodiments, the interlock 2050 comprises an automatic interlock (FIG. 9A[i]) that functions to automatically disengage the suture transferring component 2011 from the base 2020 upon alignment of the seat 1022 with the suture passing member 930. In some such embodiments, the operation of the interlock 2050 is partially automatic wherein the interlock 2050 comprises an interlock tab 2054 (as shown in FIG. 9A[i]), that is automatically disengaged upon alignment of the seat 1022 with the suture passing member 930 to enable the interlock 2050 to be moved manually into its unlocked position 2050B (FIG. 9E[i]). This enables the base 2020 to be disengaged from the suture transferring component 2011. More specifically, the rocker 1041 comprises a rocker bar 2055 that is moveable upon alignment of the seat 1022 to disengage the interlock tab 2054. This is discussed further herein below with reference to FIGS. 9A[i]-9B[ii].

In some embodiments, as shown in FIG. 9A[i], the suture transferring component 2011 comprises a push rod 2058, wherein the suture transferring component 2011 is moveable with respect to the base 2020 to enable movement of the base 2020 therein to engage a push rod 2058 to push the suture end 504 held within the seat 1022 to transfer it to the surgical suturing instrument 900. In some such embodiments the push rod 2058 comprises a push rod hub 2057 that is configured to translate within push rod cavity 2057'. In some such embodiments, the suture transferring component 2011 comprises a sleeve push hub 2012 to push the push rod hub 2057 once in engagement therewith. In some embodiments the push sleeve hub 2012 is moveable within a sleeve cavity 2012' and is biased towards the base 2020. In one specific example the push sleeve hub 2012 is biased via a spring mechanism. In a specific instance of this example, the spring mechanism comprises two springs 2013. The push sleeve hub 2012 is configured to push the push rod hub 2057 upon translation of the suture transferring component 2011 with respect to the base 2020. As such the suture transferring component 2011 comprises a hub, such as sleeve push hub 2012 that is biased towards the base 2020 to push the push rod 2058 upon engagement with the push rod 2058 upon translation of the base 2020 within the housing sleeve 2011'. In one example, the sleeve push hub 2012 is biased via a spring mechanism.

In one specific example, the push rod 2058 comprises a longitudinally extending wire 2053' coupled to the push rod hub 2057 that is translatable within a wire channel 2053 in communication with the seat 1022 for receiving the wire 2053' therein to push the suture end 504 held within the seat 1022 into a suture receiving passage 932 of the suturing instrument 900. As such the cartridge 2000 comprises a suture transferring component 2011 defines a push mechanism as described herein above. The push mechanism is defined as the mechanism of the cartridge that enables a pushing force to be applied to the suture portion such as the suture end to transfer from the seat into the suturing instrument. In one such example the push mechanism comprises a push rod 2058 as described above.

In some embodiments, the cartridge 200 is configured to align and transfer the suture end 504 upon a single linear movement of the cartridge 2000 with respect to the suturing instrument 900. As outlined above in some such embodiments surgical suturing instrument 900 comprises a suture passing member 930 defining a suture receiving passage 932 wherein the suture transferring component 2011 that is operable to transfer an end of the suture 500 from the seat 1022 within the base 2020 into the suture receiving passage 932 of the suturing instrument 900.

Figure 11A:
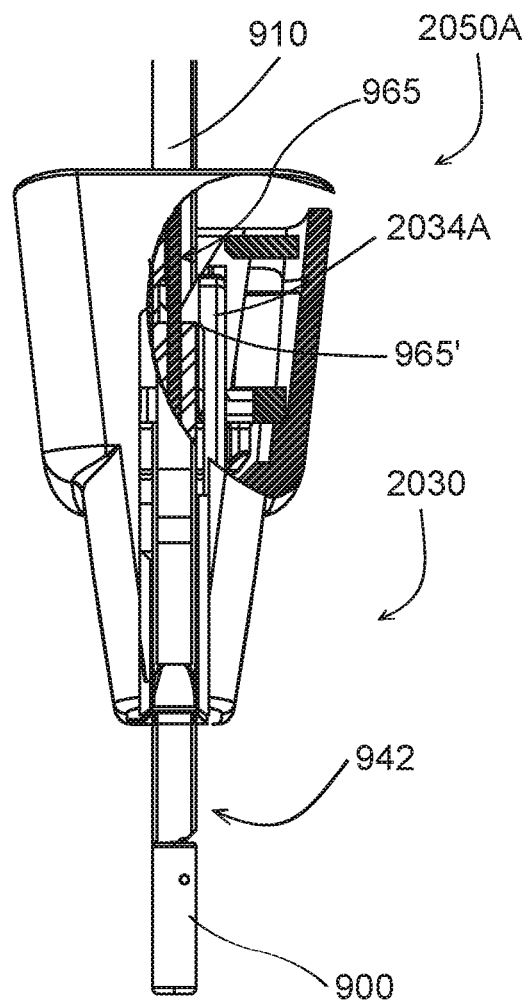
FIGS. 11A-11D illustrate views of a knot slider of a cartridge a method of using the same in accordance with an alternate embodiment of the present invention.

In some embodiments of the present invention, as shown in FIG. 8C, the knot slider 2030 is coupled to the suturing instrument 900. In one such example the knot slider 2030 configured to be slidably engaged with a portion of the surgical suturing instrument to allow the knot slider 2030 to be mounted thereon. In one particular example, the knot slider 2030 is engageable in sliding contact with a portion of the suturing instrument 900 for positioning the knot slider 2030 along the suturing instrument to facilitate deployment of the pre-tied knot 502 from the knot slider 2030. In one specific example, the knot slider 2030 is engageable in sliding contact with the suturing instrument via an arm 2034 that is receivable within an opening/window or groove 965 [FIG. 1C] along the side of the instrument proximal portion 910. The knot slider arm 2034 enables positioning of the suturing instrument along the tissue receiving gap 942 to facilitate deployment of the pre-tied knot from the suturing instrument 900 during use. Furthermore in some embodiments, the knot slider arm 2034 is housed within a slider groove 2036 and comprises an inner position 2034A where it is housed within the slider groove 2036 [FIG. 8D, FIG. 11A]. The knot slider arm 2034 additionally and an outer position 2034B where it extends proximally (at least partially) from the slider groove 2036 [FIG. 11B] to allow the knot slider 2030 to be positioned over the tissue receiving gap 942.

In some embodiments the suture is contained within tubing mounted on the inside the knot slider 2030. The cartridge 2000 stores the suture limbs within the knot slider 2030 for example inside a polytetrafluoroethylene (PTFE) tube that may be coiled and mounted about an internal post 2037 an internal knot slider 2030x that defining a passage 2037' about it once it is press fit inside the external knot slider 2030y as shown in FIG. 11.D The PTFE tube may allow the suture to be released with a constant and small force. In other embodiments, the force of the suture payout may not be constant. In some embodiments, a silicone O-ring provides a dampening effect on the release of the suture to achieve a smoother, more constant force of release and to retain tautness in the Suture throughout the procedure.

In some embodiments, as described herein above in example 3, the movement of the suturing instrument 900 may be a relative movement with respect to the cartridge 2000, with reference now to example 4. In other words the user may move the cartridge 2000 axially over the suturing instrument 900 in a proximal direction while the suturing instrument is held by the user in order to create a relative advancement of the suturing instrument 900 with respect to the cartridge 2000 in order to load the suture onto the suturing instrument 900. This may be referred to as loading of suture using pumping action. As such, the mechanism of loading of the suture may remain as described above but the movement may be created either by the proximal movement of the cartridge over the suturing instrument or the distal movement of the suturing instrument within the cartridge.

In some embodiments of the present invention as described herein, the cartridge is configured to align and transfer the suture upon a single linear motion of the cartridge with respect to the suturing instrument. In some such embodiments, an interlock 2050 may be automatically disengaged upon alignment of the suture end within the seat with the suture passing member to enable automatic transfer of the suture end 504 into the suture passing member (due to advancement of the base and activation/engagement of the push rod) as the housing 1010' is continued to be pulled proximally. Additionally the cartridge enables a pre-tied knot be mounted onto the suturing instrument during the same linear movement of the cartridge. The mechanism provided may be similar to the mechanism described herein above with respect to the knot slider 2030. Thus, embodiments of the present invention may comprise a cartridge that is operable to transfer suture portion such as the suture end 504 from the seat 1022 into the suture passing member 930, which would allow the suturing instrument to be able to pass the suture in order to suture therewith, as well as enable a pre-tied knot to be mounted onto the suturing instrument. In some such embodiments, the cartridge is loaded onto the suturing instrument 900 with a single linear movement. In some such embodiments a single pumping action is used involving a single linear relative movement of the cartridge onto the suturing instrument (to transfer the suture end mount the pre-tied knot) and linear movement the cartridge 2000 [in a direction opposite to the loading direction] thereafter leaving the knot slider 2030 coupled to the suturing instrument 900 for example to mount a pre-tied knot held therein onto the suturing instrument. As such the remainder of the cartridge 2000 other than the knot slider 2030 is removed.

Figure 12A:
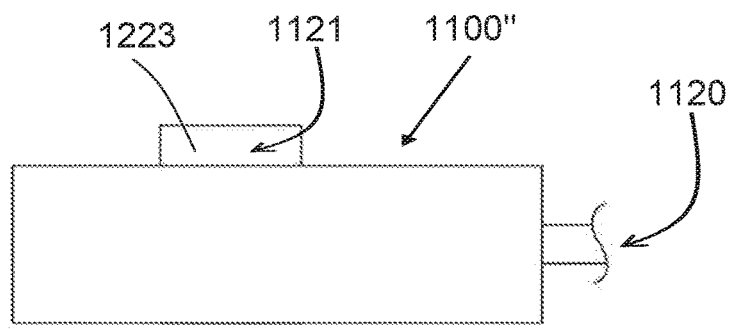
FIGS. 12A-12F illustrate a side loading alignment mechanism of a cartridge and a method of using the same in accordance with an alternate embodiment of the present invention.
Figure 12B:
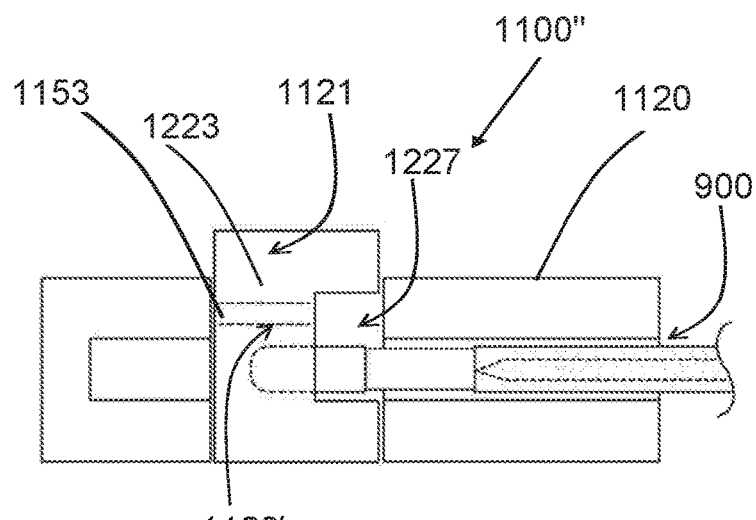
Figure 12C:
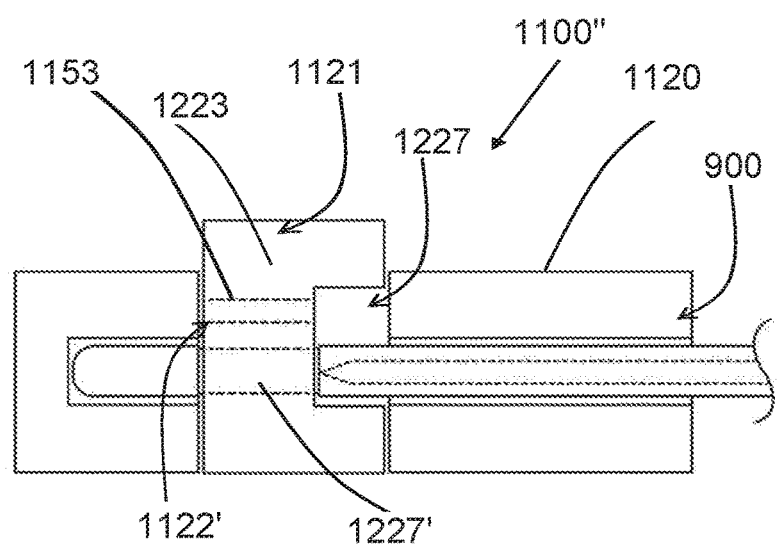
Figure 12D:
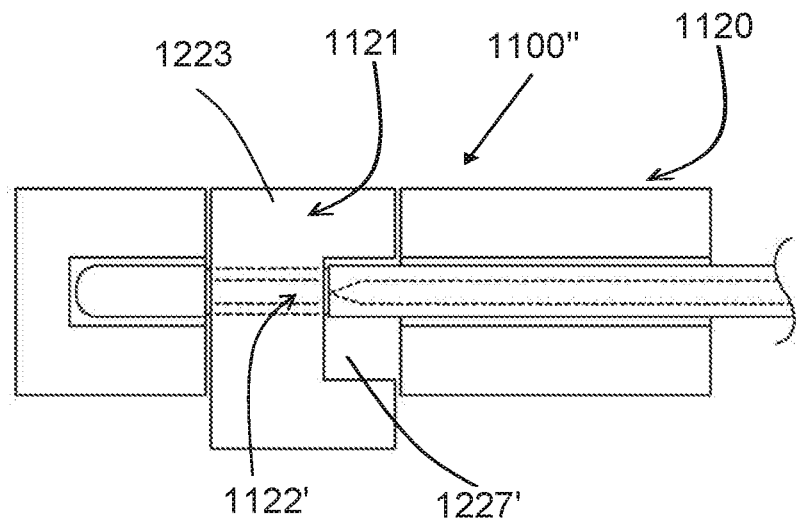
Figure 12E:
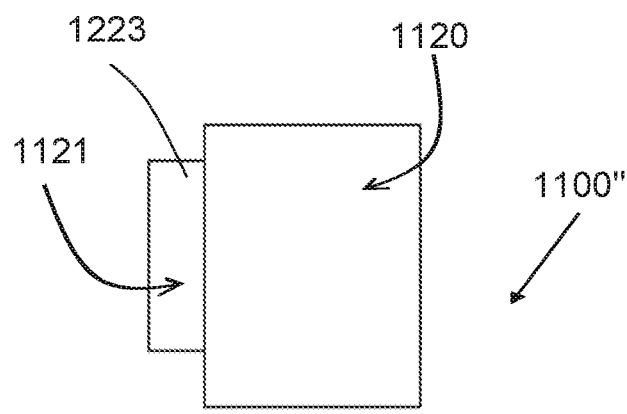
Figure 12F:
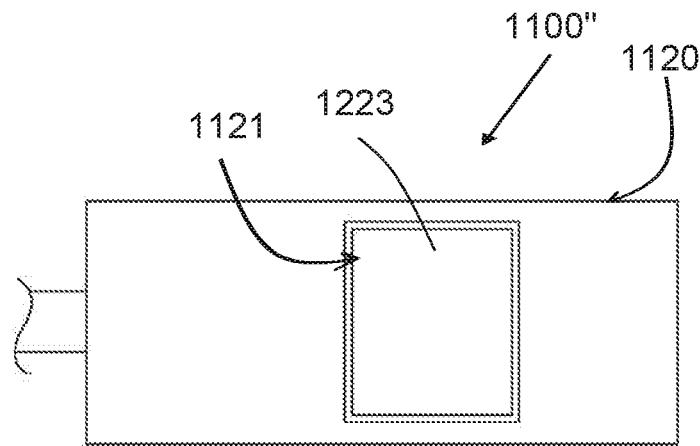

A further example of a side load alignment mechanism 1100" is shown in FIGS. 12A-12F. The 1121 magazine defines a button 1123 shown in its initial position 1121A [FIG. 12A, 12E] comprising a side loading sliding seat 1122' [FIG. 12B]. The base 1120 defines a magazine recess 1127 defining a magazine cavity 1127' and the magazine 1121 is moveable within the magazine recess. Initially, the instrument is advanceable into the base recess 1025 that functions as a restraint to maintain the position of the suturing instrument 900 as it is advanced distally within the base 1120. Upon loading of the cartridge onto the suturing instrument the magazine [FIG. 12C] the cavity 1127' corresponds to the tissue receiving gap 942. In other words, once the suturing instrument 900 is advanced within the base 1120 the tissue receiving gap 942 of the suturing instrument 900 is positioned within the magazine cavity 1127' [As shown in FIG. 12C]. The magazine 1121 is then moveable sideways into the magazine cavity 1127' to align the seat 1122' with respect to the suturing instrument 900. FIG. 12D illustrates a side view of the base 1120 with the button in its depressed or second position 1121A and FIG. 12E illustrates an end view of the same.

Thus as outlined herein above with reference to Examples 3 and 4, in accordance with some embodiments of the present invention, a mechanism is provided for providing both alignment and insertion that may facilitate ease of use by reducing: the number of user steps required, requirements for user dexterity and concentration and in some embodiments additionally facilitates use by providing only one possible order of performing the user steps.

In order to load suture into a surgical suturing instrument or suture passer, in accordance with some embodiments of the present invention as outlined herein below in Examples 3 and 4, two events or functions take place: (1) alignment of the suture portion held within the cartridge with a suture receiving feature within the surgical suturing instrument or the suture passer and (2) insertion of the suture portion into the suture receiving feature within the suturing instrument or suture passer.

EXAMPLE 5

Features of this example as illustrated in FIGS. 13A-13G are similar to those described earlier, for example with respect to Examples 3 and 4. In addition, Example 5 includes various alternatives to features described above and/or additional features not previously mentioned, including but not limited to: movement of the magazine, for example the rocker, alignment of the seat and/or rocker, reversibility-prevention features when suture has not been loaded, coupling of the rocker to the push-rod hub, indicator for indicating loading or transfer of suture onto the suturing instrument, interlock to prevent insertion of the suturing instrument in an incompatible orientation and features related to the knot slider. Each of these features will be presently described in greater detail with reference to the accompanying figures.

Figure 13A:
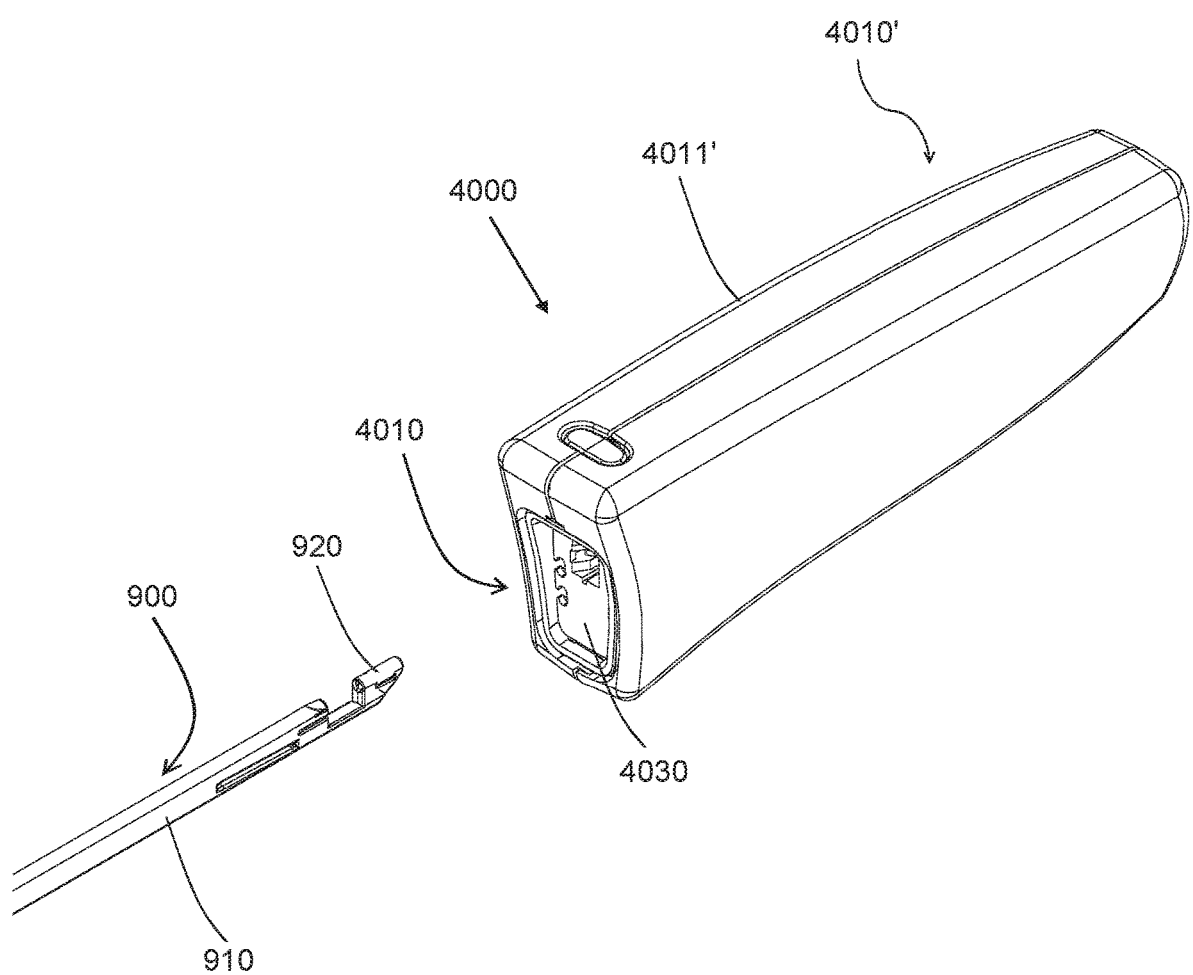
FIGS. 13A-13L illustrate views of a cartridge in accordance with an alternate embodiment of the present invention.

Referring initially to FIG. 13A, a cartridge 4000 is shown that is usable for loading a portion of a suture onto a suturing instrument, such as suturing instrument 900 described previously herein above. Similar to the embodiment discussed in example 4, the cartridge 4000 comprises a housing 4010' that comprises a housing sleeve 4011' and a knot deployment mechanism such as a knot slider 4030, with the housing 4010' defining a chamber 4010 for axially receiving the surgical suturing instrument 900 therein and a means for securing or mounting a pre-tied knot 502 (FIG. 13B) about the chamber 4010. In some embodiments, the knot deployment mechanism or knot slider 4030 is detachably coupled to the cartridge housing sleeve 4011' by a coupling mechanism comprising a knot slider release mechanism 4060 as shown.

Figure 13B:
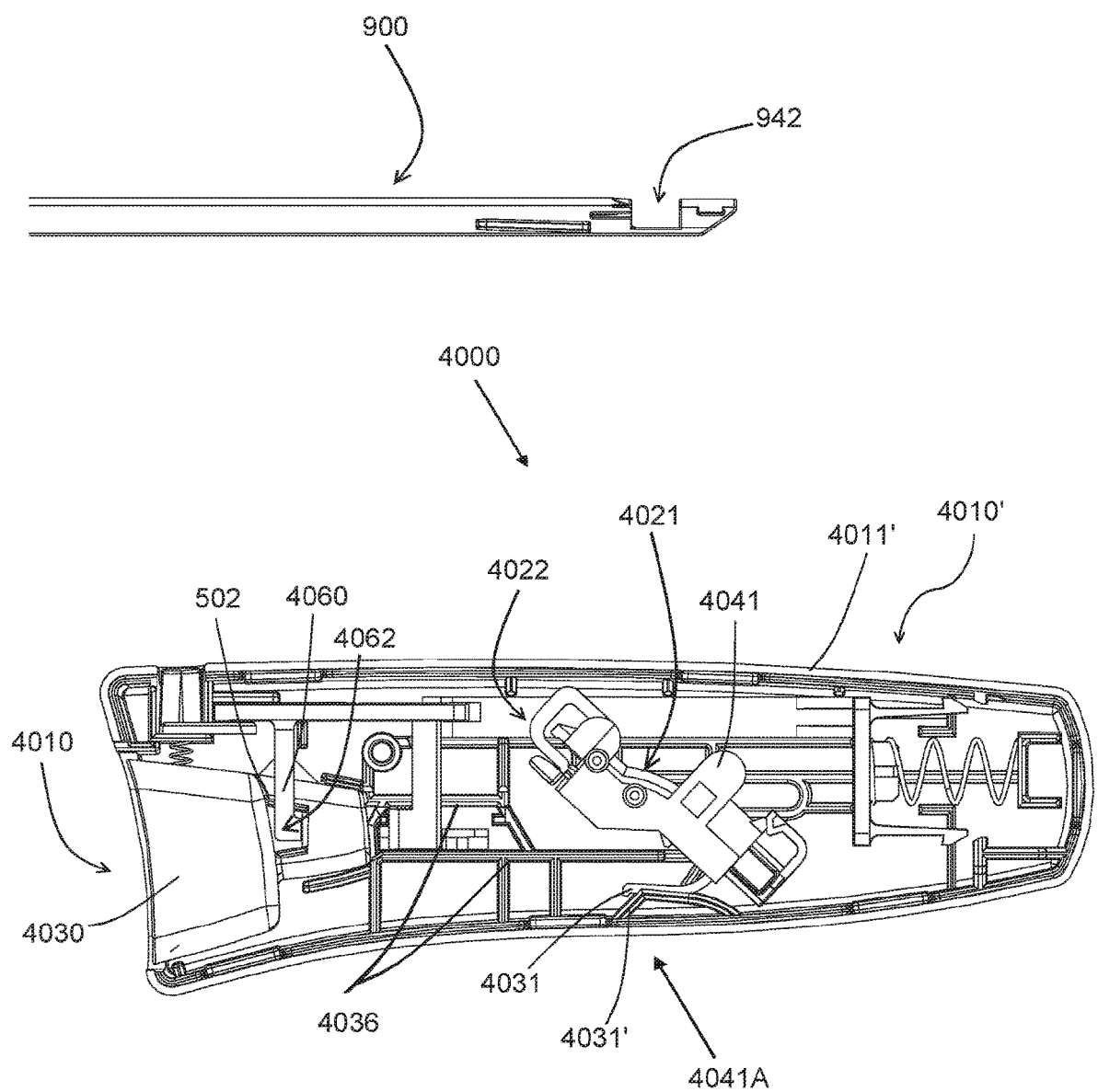

The cartridge 4000 as shown in FIG. 13B defines a path for insertion of the suturing instrument 900 within the cartridge 4000 and to facilitate removal of the suturing instrument 900 therefrom. In one such example, the path comprises a linear path and may be partially defined by the chamber 4010. The cartridge 4000 additionally comprises a magazine 4021 which defines a seat 4022 for releasably holding a portion of a suture. The magazine 4021 comprises a rocker 4041 as shown in FIG. 13B. Rocker 4041 is similar to the rocker 1041 illustrated in Example 4; significantly, however, unlike embodiments described previously hereinabove, the embodiment of the cartridge shown in FIG. 33B lacks a base and the rocker 4041 is held directly within the cartridge housing 4010' and is directly coupled to the housing 4010'. In addition, cartridge 4000 includes a translation mechanism 4085 for moving rocker 4041 and seat 4022 in a controlled and constrained manner. In the context of the present disclosure, a translation mechanism is a feature or component that allows for movement, including but not limited to linear or rotational movement. The translation mechanism 4085 allows for the seat 4022 to move out of the path of the suturing instrument 900 for withdrawal of the suturing instrument 900 from the cartridge 4000. In addition, the translation mechanism 4085 enables movement of the rocker 4041 to move the seat 4022 into alignment with the suturing instrument 900 upon advancement of the suturing instrument 900 within the cartridge 4000. The suturing instrument 900 may be of the type described previously herein above with reference to FIGS. 1C-1E, where the instrument comprises a proximal portion 910, and a distal portion 920 coupled thereto with a tissue receiving gap 942 defined there-between for receiving a tissue to be sutured. When used with such a suturing instrument, the translation mechanism 4085 enables movement of seat 4022 into and out of the tissue receiving gap 942 to allow for alignment of the seat with the suturing instrument and withdrawal of the suturing instrument, respectively.

Figure 13C:
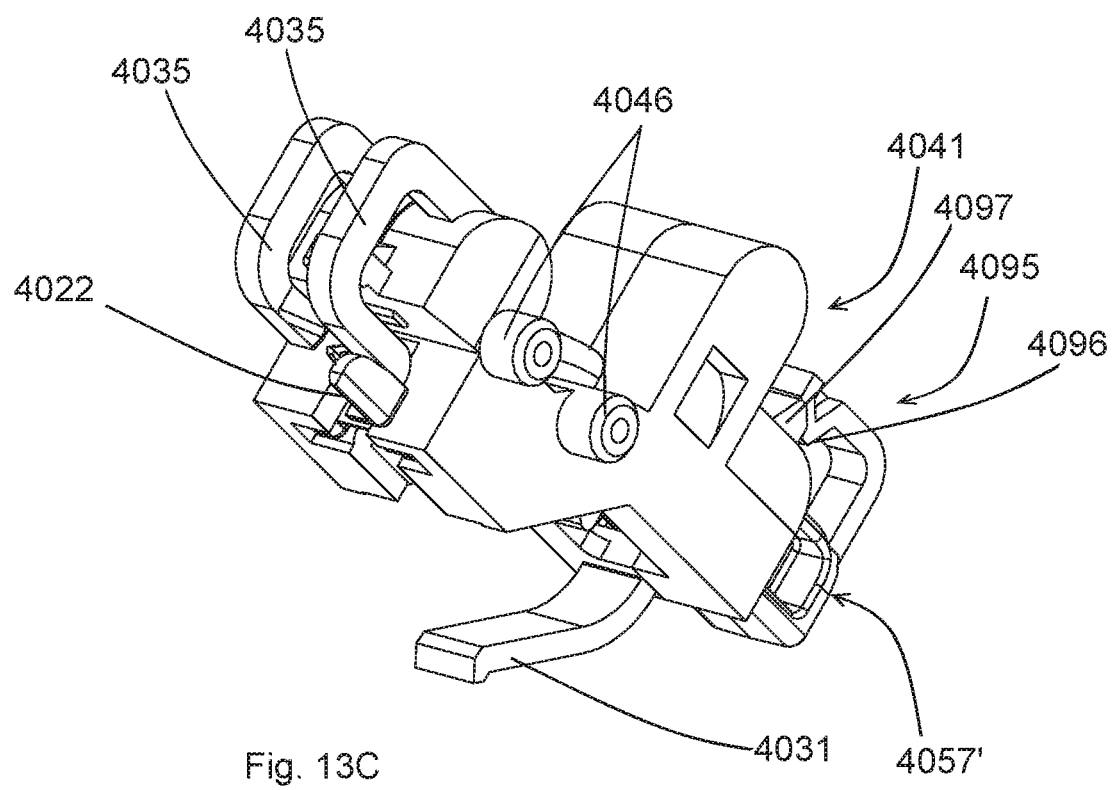
Figure 13D:
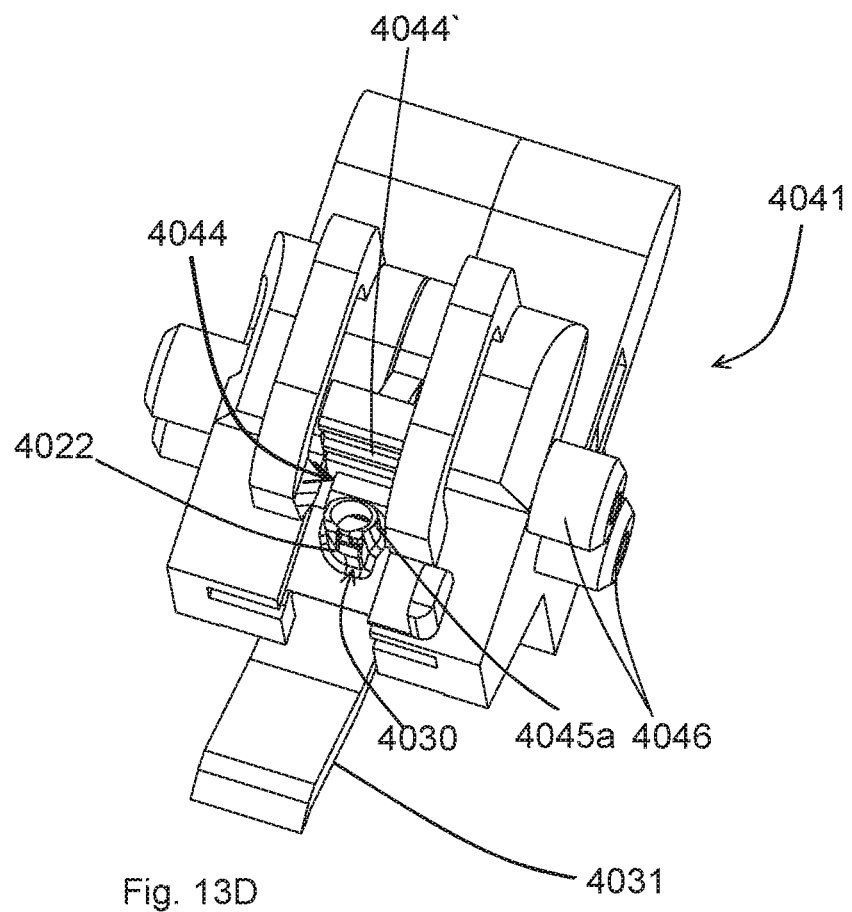
Figure 13E:
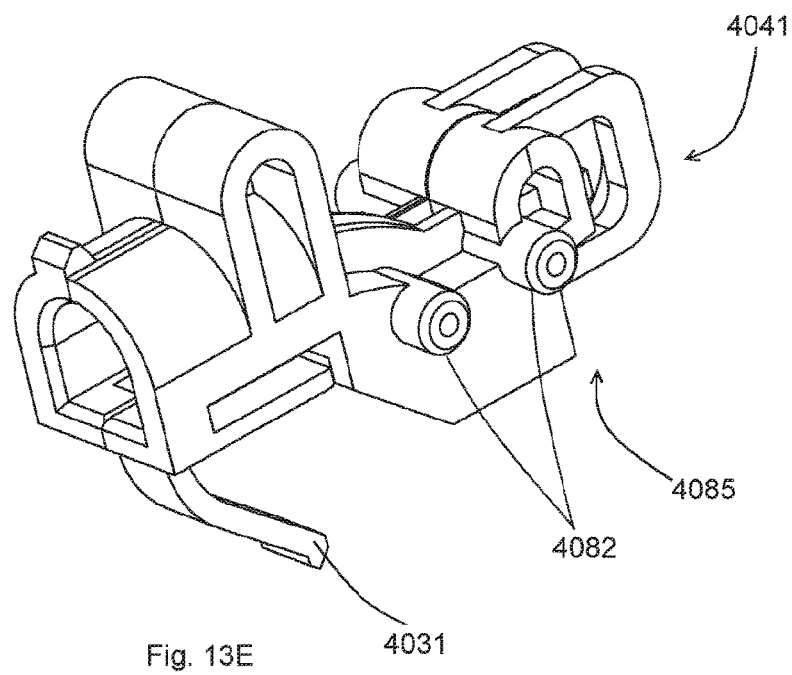
Figure 18E:
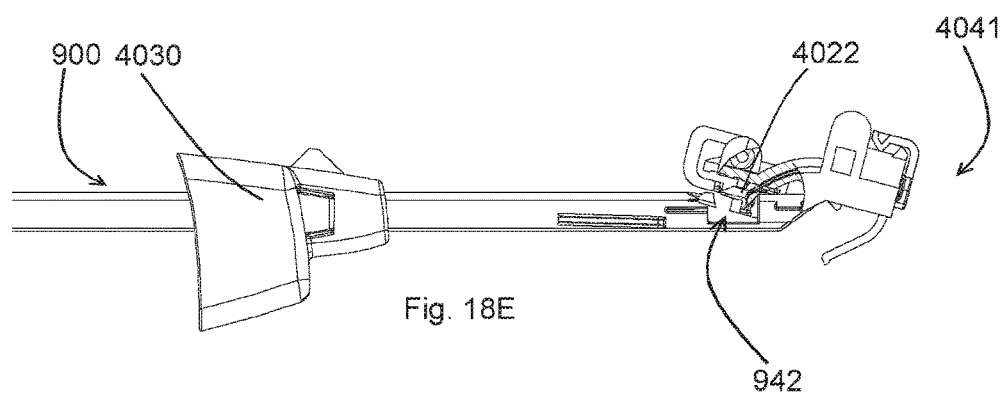
FIG. 18Ai)-18F illustrate a cartridge and method of use thereof in accordance with an embodiment of the present invention.
Figure 18F:
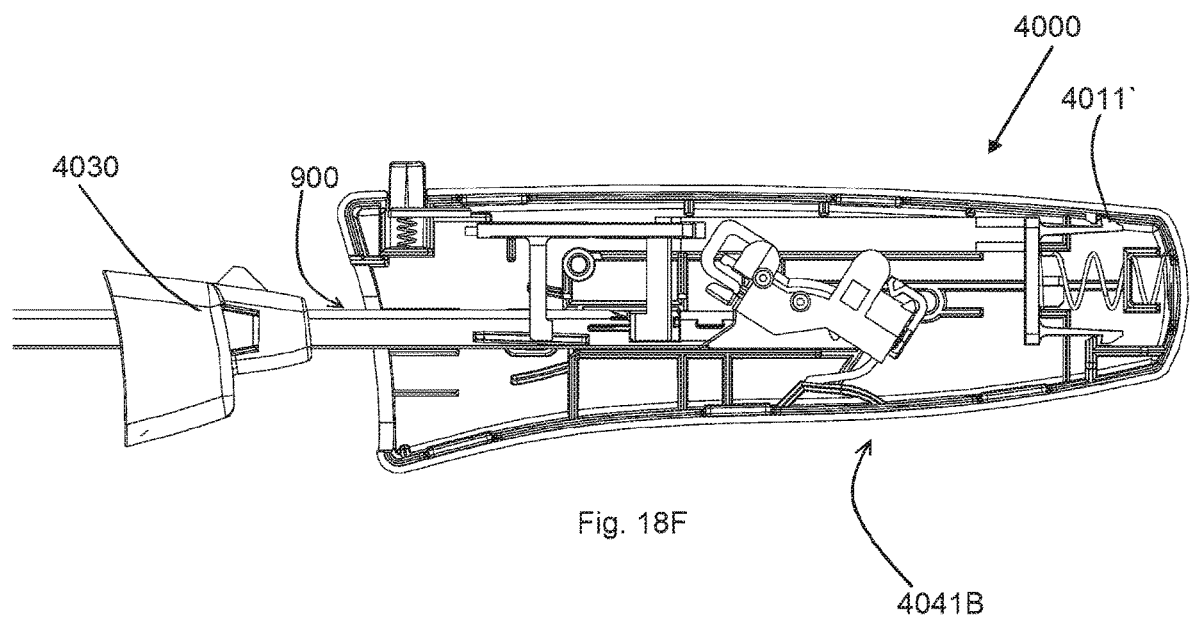

In the particular example shown, as further illustrated in FIGS. 13C-13F, the translation mechanism 4085 comprises a rotational mechanism. Alternatively, in other embodiments, for example as shown previously in FIGS. 4A-4C, the translation mechanism may comprise a spring biased mechanism operable for linear movement. In one example of a rotational translation mechanism, the rotational translation mechanism includes an arcuate track 4080 defined by the cartridge housing 4010', and one or more laterally extending pins 4082 defined by the rocker 4041 that are receivable within the track 4080. More specifically, in such an embodiment, the housing sleeve 4011' of the cartridge housing 4010' includes a groove or track 4080 formed by ribs 4081, that defines a curved path, i.e. a path where at least a portion is curved. When assembled, the track 4080 receives rocker pins 4046' and functions to allow the rocker 4041 to rotate in a pivoting manner while remaining constrained by the track 4080 within the housing 4010'. In such an embodiment, the rotational translation mechanism 4045 allows the rocker 4041 to move between a first position 4041A, as shown in FIG. 13B and FIG. 18F, for positioning the seat 4022 out of the path of the suturing instrument, and a second position 4041B, as shown in FIG. 18C (i) and FIG. 18D(ii), for positioning the seat 4022 in alignment with a portion of the suturing instrument 900, such as the instrument proximal portion 910. More specifically, the rocker 4041 is moveable from its first position 4041A shown in FIG. 18Ai), 18Aii) where the seat 4022 positioned out of the path of the suturing instrument 900, into its second position 4041B where the seat is in alignment with the suturing instrument 900 and positioned within the tissue receiving gap 942 as shown in FIG. 18Ci), 18Cii). FIG. 18Bi) and 18Bii) indicate the position of the rocker 4041 in its intermediate position as it moves from its first position 4041A towards its second position 4041B. FIG. 18Aii) and 18Bii) and 18Cii) illustrate the position of the rocker 4041 and the suturing instrument 900 in isolation from the remainder of the cartridge 4000 in order to provide additional clarity. The rocker 4041 further allows the seat 4022 to be moved out of the path of the suturing instrument 900 after the suture portion has been transferred to the suturing instrument 900. More specifically, the rocker 4041 is pivotable from its second position 4041B to its first position 4041A to allow the seat 4022 to be moved out of the tissue receiving gap 942 of the suturing instrument 900 to allow retraction of the suturing instrument 900 as shown in FIGS. 18E and 18F. Referring now to FIGS. 13C-13E, in the illustrated embodiment, rocker 4041 includes a resilient member or flex-arm 4031 that is operable to engage with the cartridge housing 4010', for example with a locking rib 4031' within the housing sleeve 4011'. Resilient member 4031, in cooperation with locking rib 4031', thus functions to maintain rocker 4041 in a desired initial or first position 4041A which facilitates unimpeded advancement of the suturing instrument 900. Movement of the rocker 4041 is otherwise similar to that of rocker 1041 described herein with respect to FIGS. 9A [i]-9B [ii].

Figure 13F:
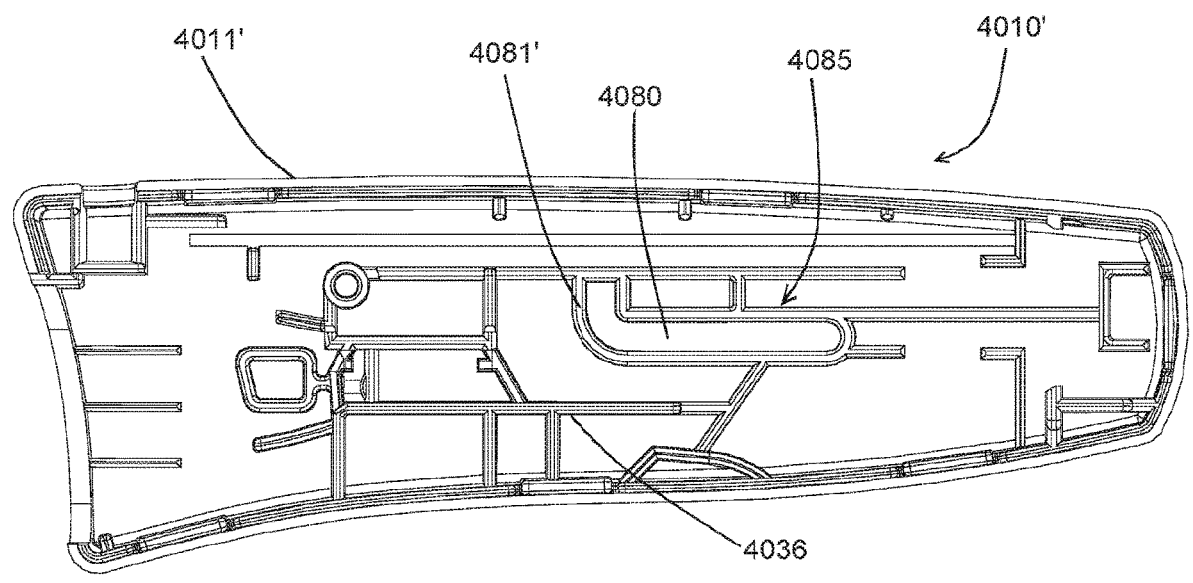
Figure 13G:
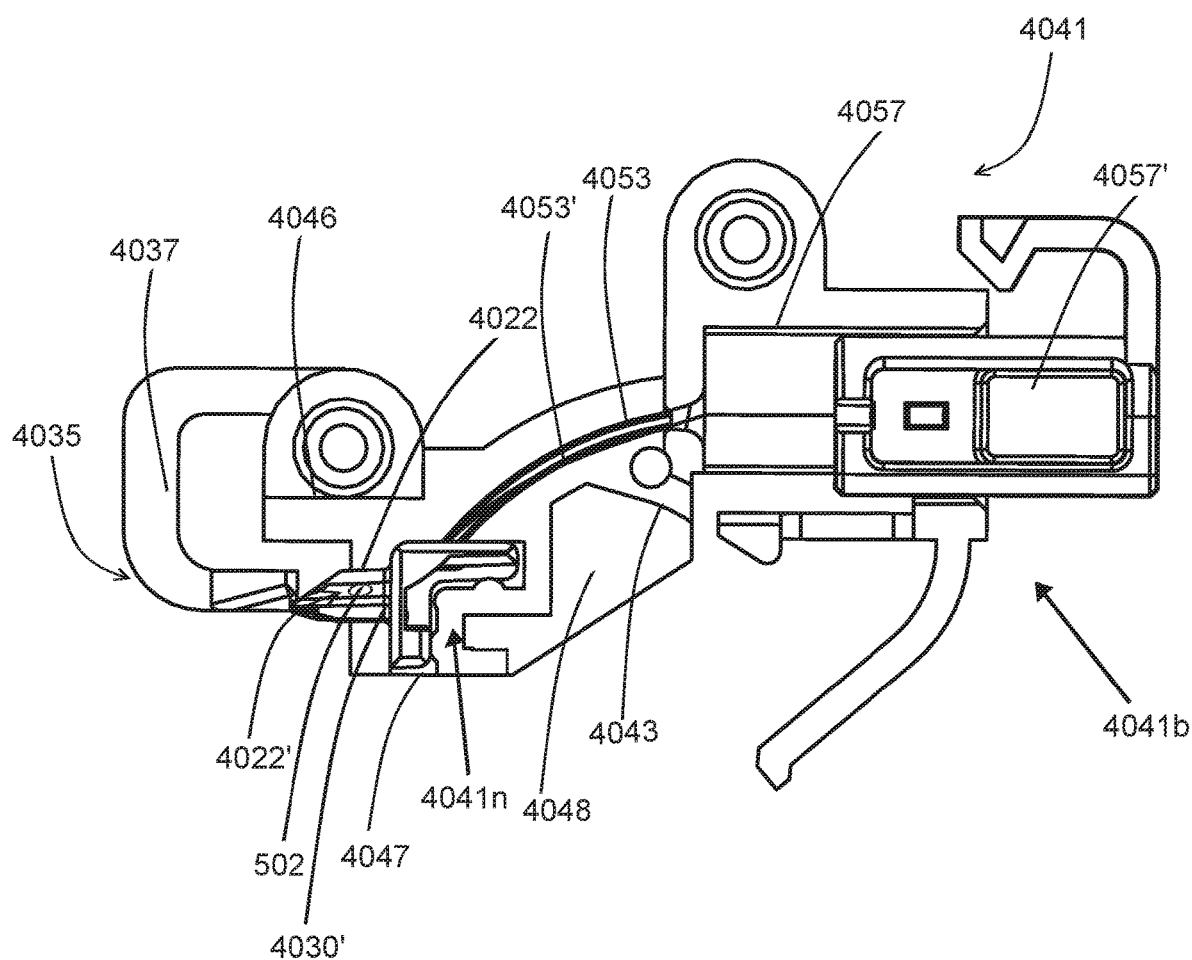

As shown in FIG. 13G, which illustrates a partial cutaway view of the rocker 4041 along a longitudinal axis of the rocker, with a left side portion of the rocker 4041 being visible. The rocker 4041 defines a first or distal bevel face 4043 facing towards the interior of a rocker groove 4044, and more specifically defines a distal wall of the groove distal portion 4048, similar to bevel face 1043 discussed previously hereinabove with reference to FIG. 9A (i). In some embodiments, the distal portion of suturing instrument 900 is configured to interact with the first bevel face 4043 upon advancement of the suturing instrument 900 within the cartridge 4000 as shown in FIG. 18Ai), 18Aii) which illustrate the rocker 4041 in a partial breakaway view with the rocker 4041 being shown in. This results in pivoting of the rocker 4041 from its first position 4041A illustrated in FIG. 18Ai), 18Aii) into its second position 4041B illustrated in FIG. 18Ci), 18Cii), and consequently results in movement of the seat 4022 into the tissue receiving gap 942, to align the seat 4022 with the proximal portion 910 of the suturing instrument 900. In addition, the rocker 4041 defines a second or proximal bevel face similar to bevel face 1043' shown in the embodiment illustrated in FIG. 10B, which faces towards the interior of the rocker groove 4044, and more specifically defines a proximal wall of the groove distal portion 4048. The second bevel face is formed in a right side portion of the rocker 4041 [not visible in FIG. 13G]. In some embodiments, the distal portion 920 of suturing instrument 900 is configured to interact with the second bevel face upon retraction of the suturing instrument 900 from the cartridge 4000. This results in pivoting of the rocker 4041 and consequent movement of the seat 4022 out of the tissue receiving gap 942 and back into its first position 4041A, whereby the seat is moved out of the path of the suturing instrument 900, as illustrated in FIGS. 18E and 18F.

Referring now to FIG. 13B-13G, general alignment concepts are shown as they relate to the alignment of the rocker 4041 and thus the seat 4022 with respect to the suturing instrument 900. The cartridge 4000 comprises several alignment features to facilitate alignment of the seat 4022 with a portion of the suturing instrument 900 to permit transfer of a suture portion held within the seat 4022 onto the suturing instrument 900. In one particular example, the alignment feature comprises an instrument guiding feature to guide the suturing instrument within the cartridge 4000. In some embodiments, the instrument guiding feature is defined by the magazine 4021 such as the rocker 4041. In one such example, the instrument guiding feature comprises one or resilient members 4035 that extend from the magazine 4021. In one particular example, the one or more resilient members 4035 comprise one or more horizontally aligning side arms 4037 for aligning the suturing instrument horizontally with the seat 4022. The side arms 4037 guide the shaft or instrument proximal portion 910 of the suturing instrument 900 up to seat 4022 such that the seat cavity or recess 4022' defined by the seat 4022, is horizontally or laterally aligned with the instrument proximal portion 910. In the particular example shown in FIG. 13G, the horizontally aligning side arms 4037 extend from the rocker 4041 such that they straddle the suturing instrument 900 along its sides upon insertion of the suturing instrument 900 within the cartridge 4000. Additionally, in some embodiments, as shown for example in FIGS. 13H-13J, the rocker 4041 may comprise the one or more resilient members 4035 that comprise one or more vertically aligning side arms 4039 for aligning the suturing instrument vertically with the seat. In one such example, the one or more side arms 4039 comprise a downwardly extending flex arm for engaging an upper surface of the suturing instrument 900. As such, either or both of the horizontally aligning side arms 4037 and vertically aligning side arms 4039 enable alignment of the suture passing member such as needle 930' and the suture receiving recess 932 defined thereby, with the seat cavity or recess 4022' which is moveable into the tissue receiving gap 942 of the suturing instrument 900 as shown in FIG. 13B.

Figure 13H:
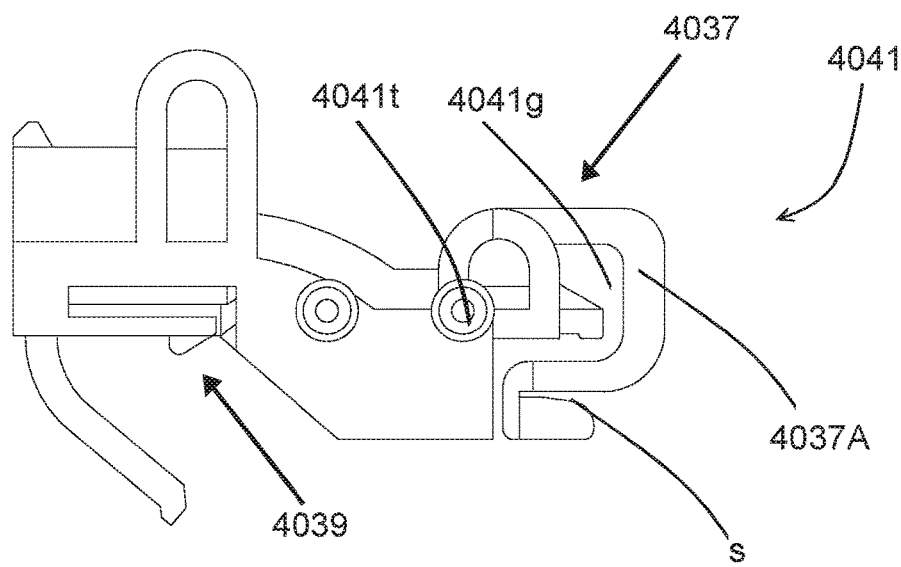
Figure 13I:
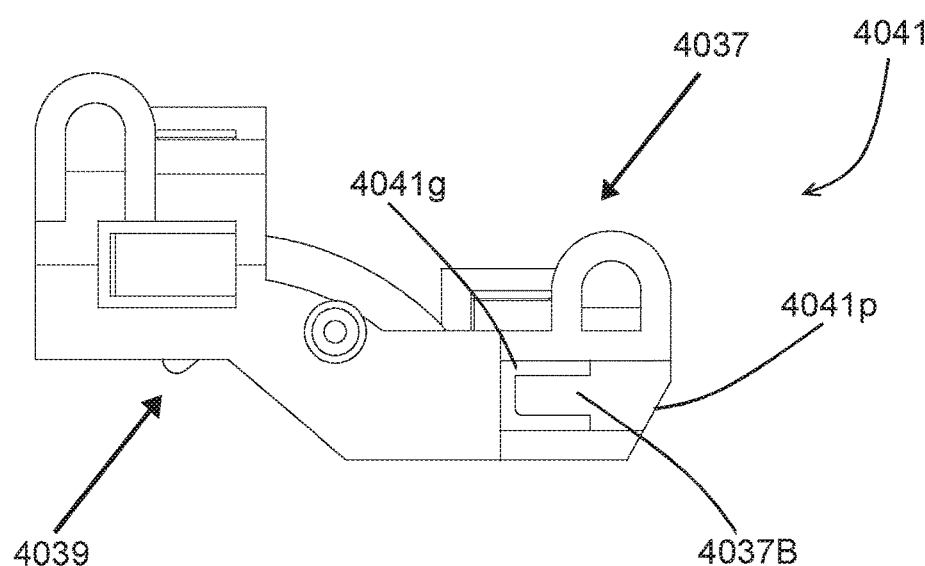
Figure 13J:
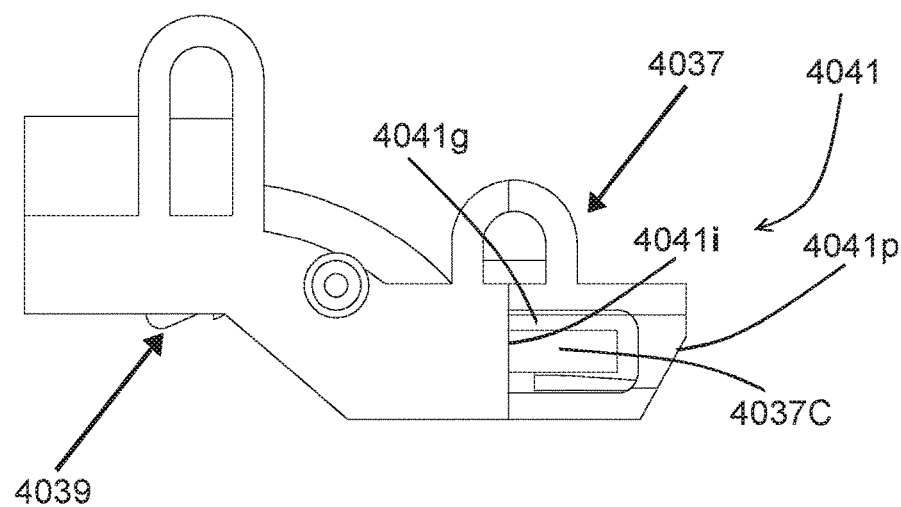

In alternative embodiments, as shown in FIGS. 13H to 13J, the one or more horizontally aligning side arms 4037 may comprise an alternate configuration. In one such example, the side arms 4037A are shown that extend from an upper surface or top portion 4041t of the rocker 4041. In one such example the side arm 4037A defines a slot s for routing and guiding suture to the side of the rocker 4041. In another example, side arms 4037B are provided that extend distally from a front or proximal face 4041p of the rocker 4041, as shown in FIG. 13I. Alternatively, in some embodiments, the one or more side arms 4037C may extend proximally from an intermediate portion 4041i of the rocker 4041 that is positioned distal to the proximal face 4041p of the rocker 4041, as shown in FIG. 13J. Furthermore, as shown in FIGS. 13H to 13J, in some embodiments the one or more side arms 4037A, 4037B and 4037C extend into a space or gap 4041g.

In other embodiments, the instrument guiding feature is defined by the cartridge housing 4010'. In one such example, as shown in FIGS. 13B and 13F, the instrument guiding feature comprises guiding ribs 4036 within the housing sleeve 4011' of cartridge housing 4010'. The suturing instrument 900 is guided and constrained by ribs within the cartridge housing 4010'. The guiding ribs 4036 may be provided such that they accommodate suturing instruments 900 of varying surfaces flatness and may additionally help prevent binding of the suture. The guiding ribs 4036 function to guide the suturing instrument 900 into alignment with the rocker 4041. In some embodiments the cartridge 4000 additionally comprises a suture guiding or routing feature to allow the suture to be routed within the cartridge 4000. In one such example, the suture guiding feature is also defined by the guiding ribs 4036. The guiding ribs 4036 provide clearance for the suture to run from (in some embodiments, a pre-tied knot mounted on) the knot slider 4030 to the rocker 4041.

In other embodiments, as shown in FIG. 13D, additional instrument guiding features are defined by the magazine 4021/rocker 4041. For example, the rocker 4041 defines a locking recess 4044 for receiving a portion of the suturing instrument 900 in press-fit engagement for aligning the seat with the portion of the suturing instrument. The locking recess 4044 is defined by the edge 4044'. Similar to embodiments discussed previously herein above with reference to FIG. 3H to FIG. 3K, the magazine 4021 comprises a projection 4030' defining the seat 4022, as shown in FIG. 13G. In one such example, the projection 4030' comprises one or more reference features 4045a for engaging with an interior of a portion of the suturing instrument 900 for aligning the seat 4022 with the portion of the suturing instrument 900.

Figure 13K:
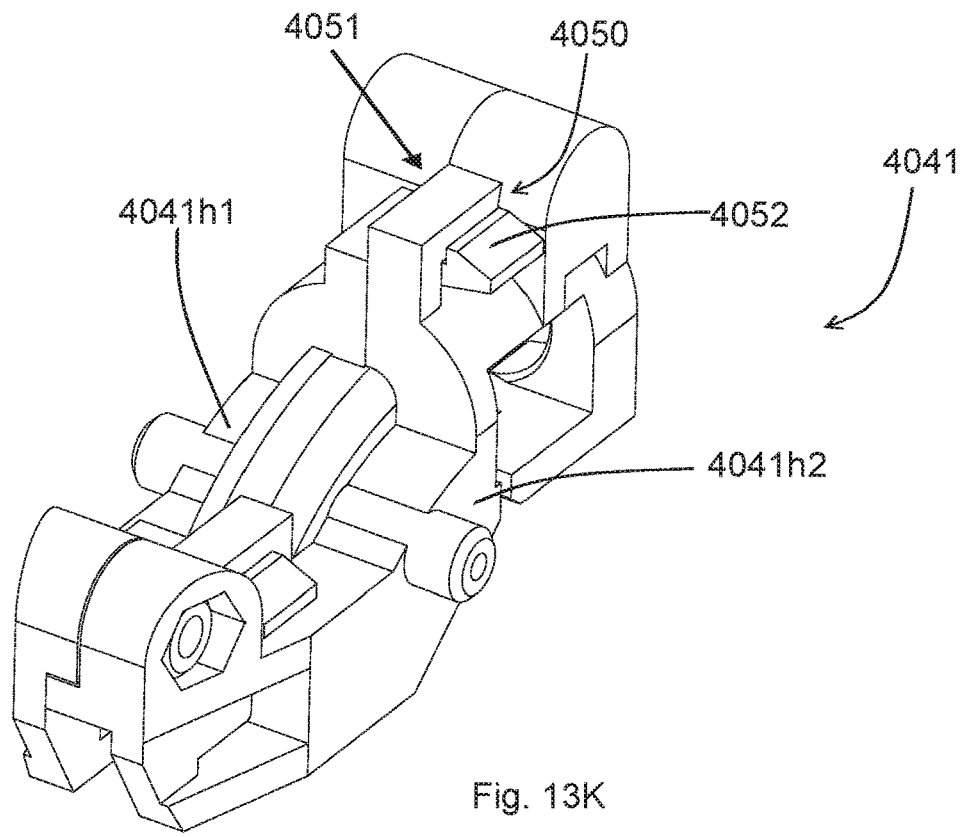
Figure 13L:
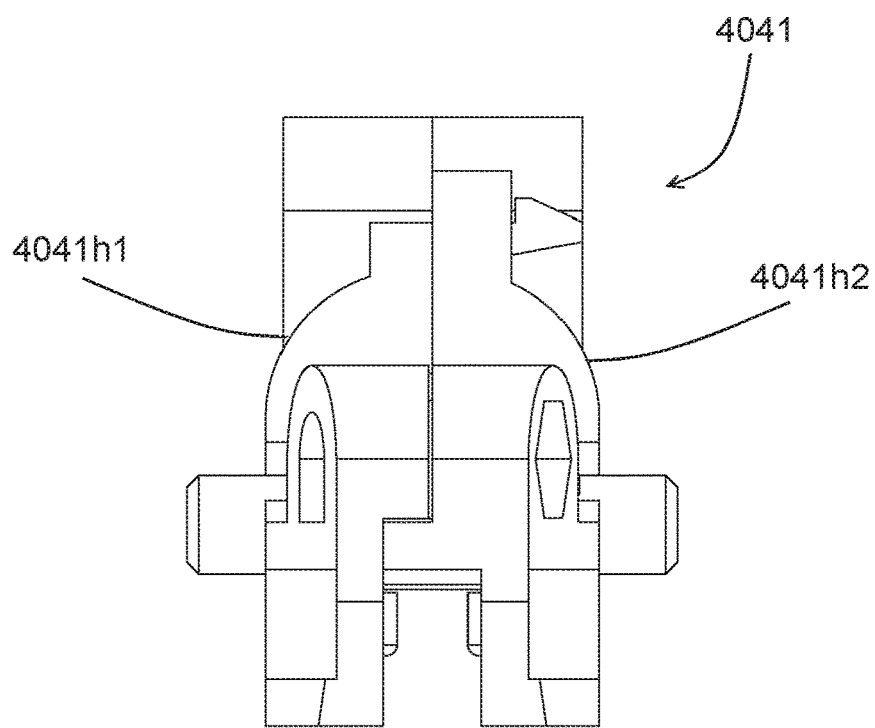

In addition to comprising instrument guiding features, referring again to FIG. 13G, the rocker 4041 additionally defines a channel 4053 in communication with the seat 4022 for allowing movement of a push rod 4053' there-through for advancing a suture end from the seat 4022 into the suturing instrument 900. Furthermore, in some embodiments as shown in FIGS. 13K and 13L, the rocker 4041 comprises lateral halves 4041h1, 4041h2 that are configured to co-operatively engage with one another to form the rocker 4041. In some such embodiments as shown, the lateral halves 4041h1, 4041h2 engage one another via a snap fit or press fit mechanism 4050. As illustrated the snap fit mechanism 4050 comprises a tab 4052 that is receivable within an opening 4051 to be engaged there-with.

Figure 14A:
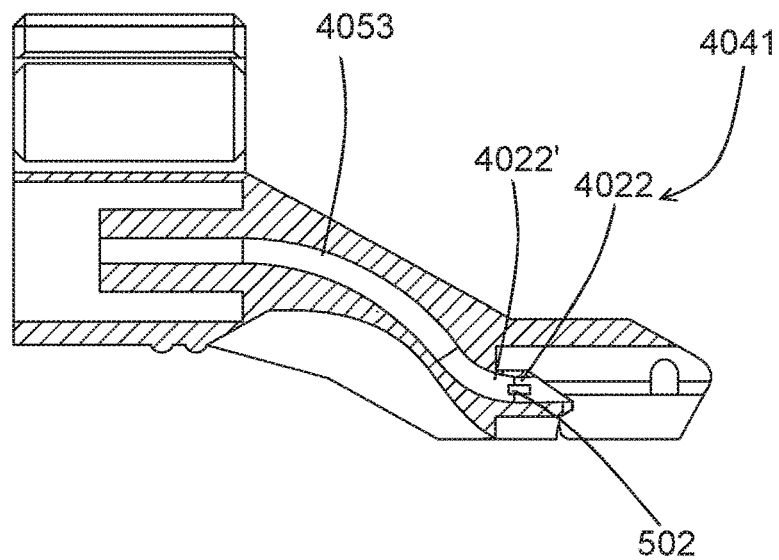
FIGS. 14A-14G illustrate views of a rocker in accordance with alternate embodiments of the present invention.
Figure 14B:
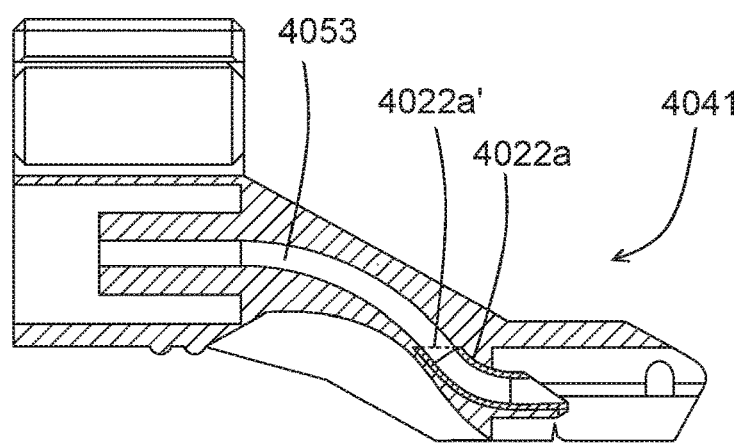
Figure 14C:
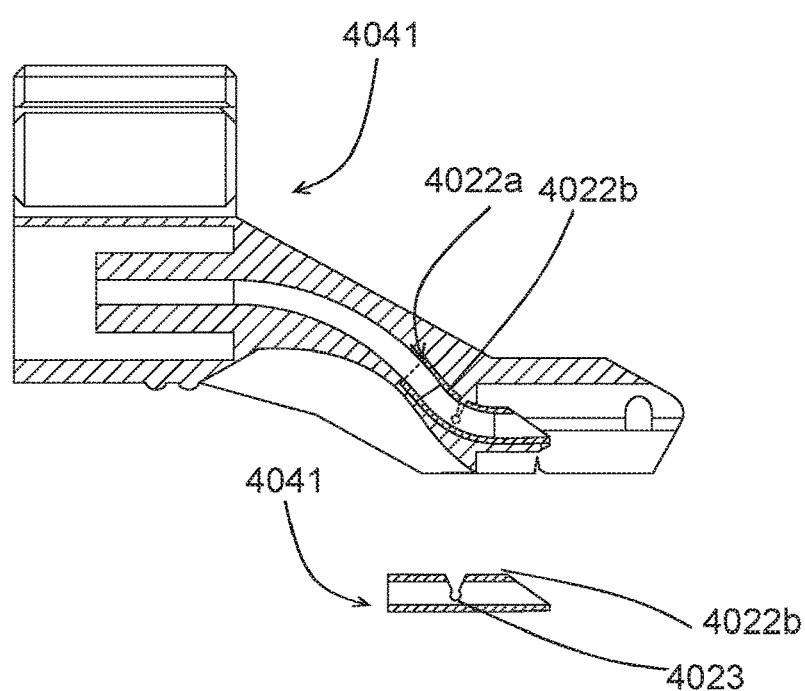
Figure 14D:
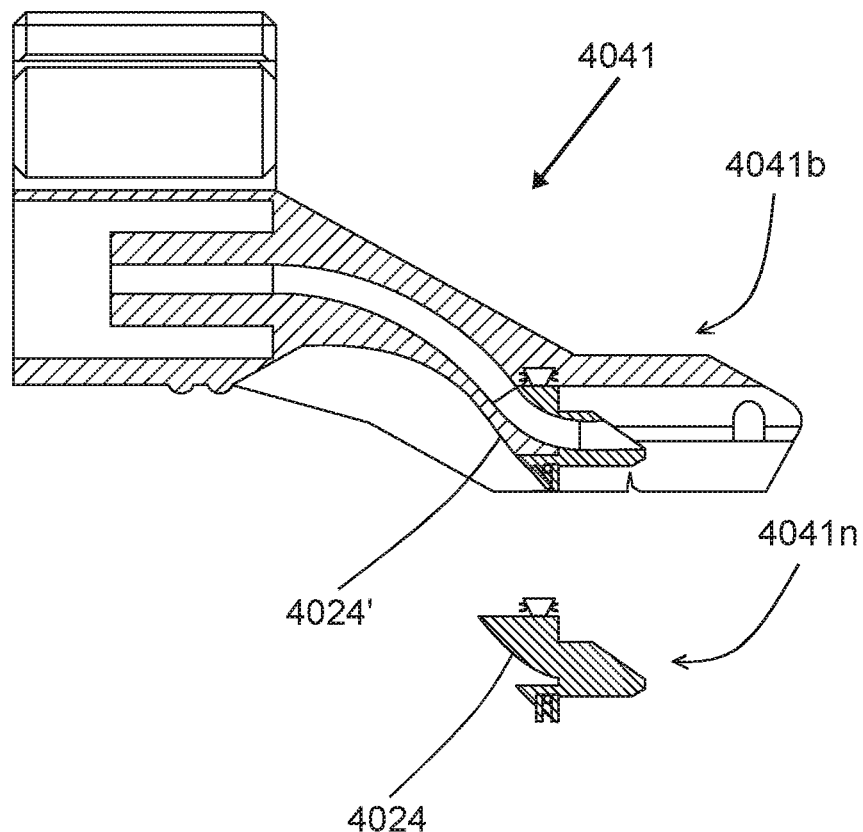

Alternative embodiments of the rocker 4041 are shown in FIGS. 14A-14G. In one particular embodiment as shown in FIG. 14A, the seat 4022 comprises a seat cavity or seat recess 4022' that is defined by the rocker 4041, where the seat cavity or seat recess 4022' is in communication with the wire channel 4053 and extends from the wire channel 4053. In an alternate embodiment, the seat 4022 is defined by a tubular member 4022a, as shown in FIG. 14B, that defines an aperture 4022a' that is in communication with the wire channel 4053. FIG. 14C illustrates a further alternative embodiment, wherein tubular member 4022a comprises a sleeve 4022b that can be inserted within the rocker 4041 to form the seat 4022. The sleeve 4022b defines an opening 4023 in order to provide strain relief to allow it to bend without constricting the inner tube diameter and thus it provides flexibility within the tubular member for ease of insertion and assembly of the seat 4022 within the rocker 4041.

Figure 14E:
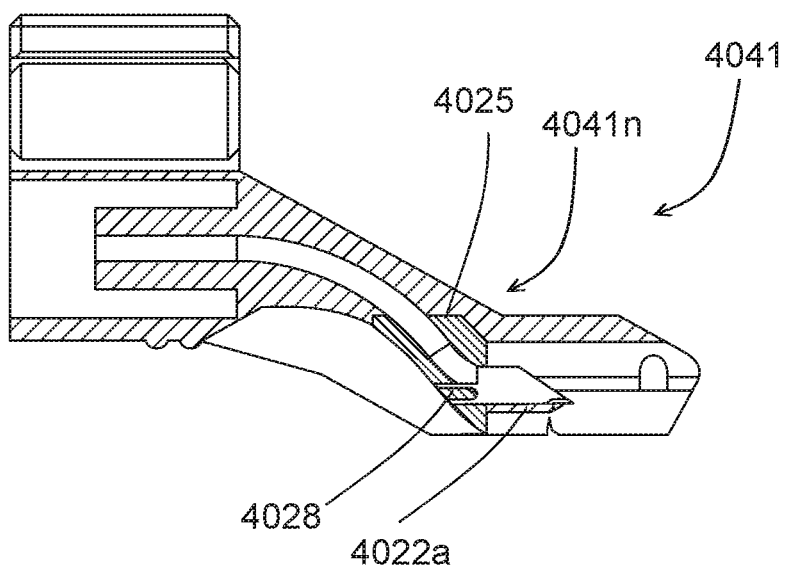
Figure 14F:
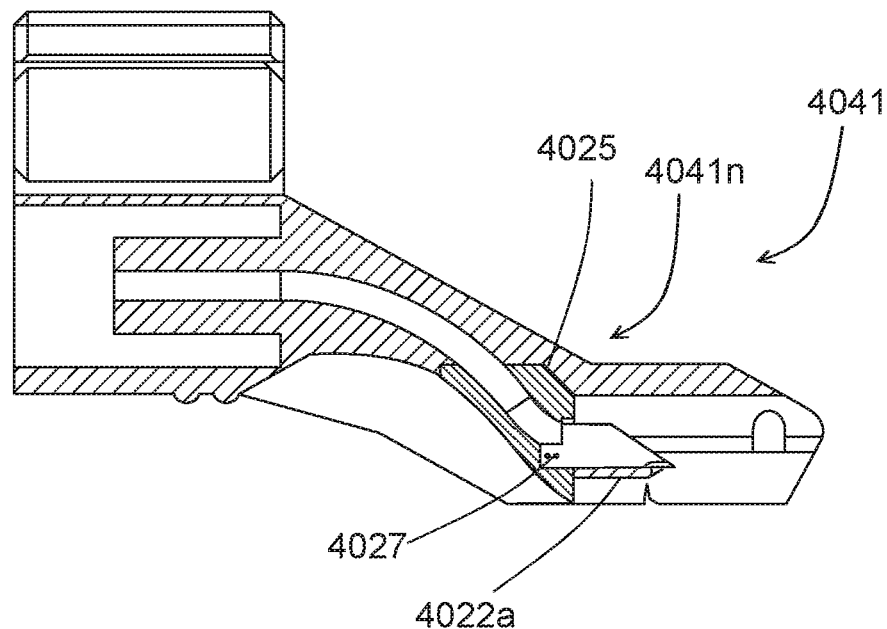
Figure 14G:
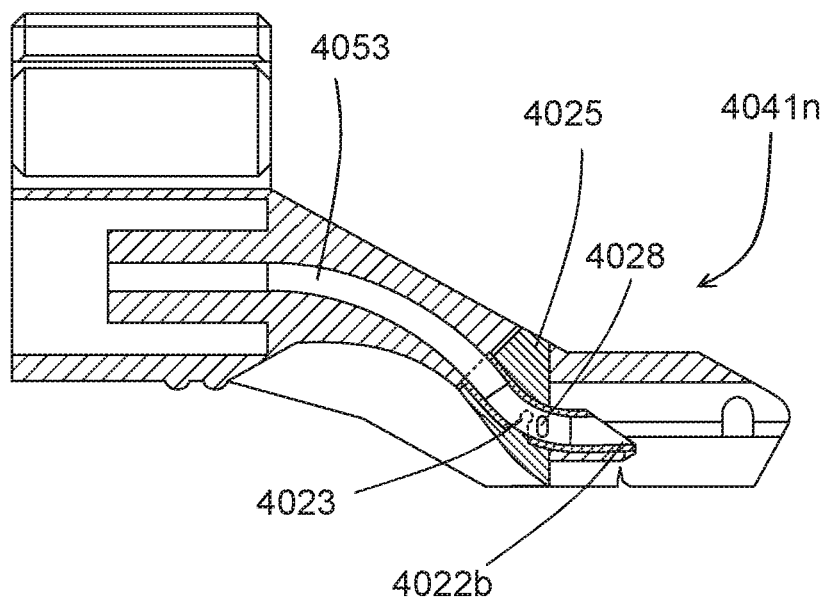

In some embodiments, as shown for example in FIG. 13G, the rocker 4041 comprises a rocker body 4041b and an insert 4041n defining the seat 4022. The insert 4041n defines a wall or median 4047 that allows a portion of the suturing instrument to rest there-against to facilitate alignment, with the instrument distal portion 920 being received in a distal groove portion 4048, the proximal portion 910 being received in a proximal groove portion 4046 and the seat 4022 being positioned within the tissue receiving gap 942, as shown in FIG. 18C(i). In alternate embodiments, as shown for example in FIG. 14D, the insert 4041n defines a rocker recess 4024 for receiving a portion 4024' of the rocker body 4041b therein for securing the insert 4041n within the rocker body 4041b. In some such embodiments, the seat insert 4041n comprises a single unit that is receivable within the rocker 4041. In other embodiments, the insert 4041n further comprises a hub 4025 that is coupled to a tubular member defining the seat 4022 using a coupling mechanism. In one such example, as shown in FIGS. 14E and 14F, the tubular member may comprise a tubular member 4022a similar to the embodiment illustrated in FIG. 14B. In other embodiments, as shown in FIG. 14G, the tubular member may comprise a sleeve 4022b of the type shown in FIG. 14C that is coupled to the hub 4025, with the sleeve 4022b comprising a cut-out or notch/opening 4023 to provide feature for the glue to adhere to, whereas the opening within sleeve 4022b that opens into the channel 4053 provides clearance for a push rod to enter the sleeve 4022b.

In some embodiments, the seat 4022 and the hub 4025 each comprise a polymer. In one specific example, the polymer comprises Acrylonitrile butadiene styrene (ABS). In some such embodiments, the coupling mechanism for coupling the hub and the tubular member comprises a polymer weld. Alternatively, the seat 4022 and the hub 4025 may each comprise a metal such as stainless steel, wherein the coupling mechanism may comprise a metal weld such as a laser weld for example as illustrated in FIG. 14F. In other embodiments, the coupling mechanism may comprise an adhesive 4028 such as glue, as shown in FIGS. 14E and 14G. In some embodiments, for example in any of the embodiments shown in FIGS. 14A-14G, the wire channel 4053 (not labeled in all figures) in conjunction with the seat cavity 4022' comprises a substantially s-shaped configuration.

In further embodiments of the present invention, additional features are provided in a cartridge 4000 for facilitating loading of suture onto a suturing instrument 900. For example, as shown in FIG. 15Ai) to 15Ciii), the cartridge 4000 additionally comprises an instrument retention mechanism 4070 that is configured to permit advancement of a suturing instrument 900 into the cartridge 4000 and to prevent premature retraction or withdrawal there-from until the suture portion is loaded onto the suturing instrument 900. In some embodiments, the instrument retention mechanism 4070 comprises a lock such as a biased locking element 4072' that is moveable away from or out of the path of the advancing suturing instrument 900 to allow substantially unimpeded advancement of the suturing instrument 900 within the cartridge 4000. FIG. 15Ai) through 15Aiii) illustrate the locking element 4072' in its initial position prior to advancement of the instrument within the cartridge. FIG. 15Bi) through 15Biii) illustrate the locking element 4072' moved out of the path of the instrument as the instrument is advanced. In one such example, the biased locking element 4072' comprises a resilient member that flexes, bends or otherwise moves out of the way of the advancing suturing instrument 900 to allow the distal portion 920 of the suturing instrument 900 to advance past the biased locking element 4072'. In some embodiments, for example as illustrated in FIG. 15Ci) through 15Ciii), once the distal tip 920 and the tissue receiving gap 942 advance past the biased locking element 4072', the biased locking element 4072' is configured to engage the proximal portion 910 of the suturing instrument 900, specifically a window or groove 955 of the suturing instrument 900 to thereby substantially prevent, obstruct or limit retraction of the suturing instrument 900 prior to loading of suture onto the suturing instrument 900.

In some such embodiments, a lock release mechanism is provided in order to disengage the lock. For example, a lock release mechanism is provided that may be manually operable to disengage the biased locking element 4072' from the window or groove 955. In other embodiments, a lock release mechanism is provided that is configured to automatically disengage the lock upon transfer or loading of the suture portion onto the suturing instrument 900. In some such embodiments, for example as shown in FIG. 15Ai), the lock release mechanism comprises a spring biased component such as a release arm 4076 that is coupled to a biasing mechanism 4090. The biasing mechanism 4090 is operable to move the release arm 4076 upon transfer of the suture portion to disengage locking element 4072' from the suturing instrument 900.

Figure 16A:
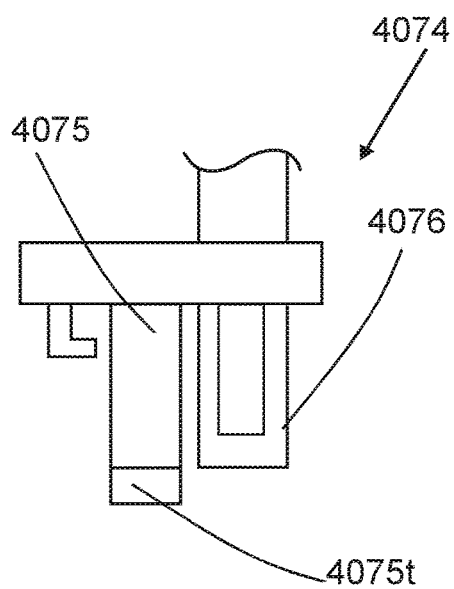
FIGS. 16A-16D illustrate a cartridge comprising an instrument retention mechanism in accordance with an alternate embodiment of the present invention.
Figure 16B:
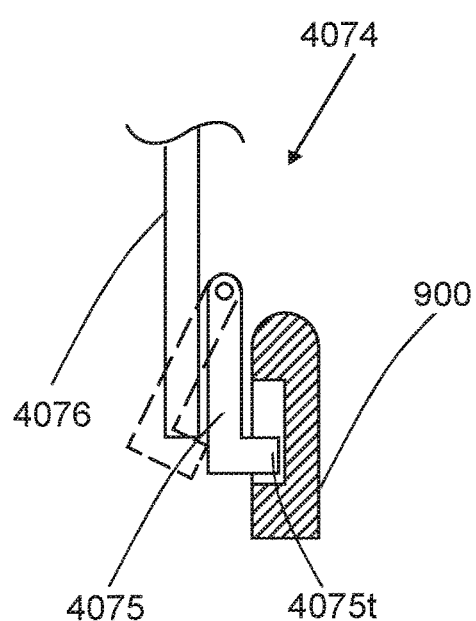
Figure 16C:
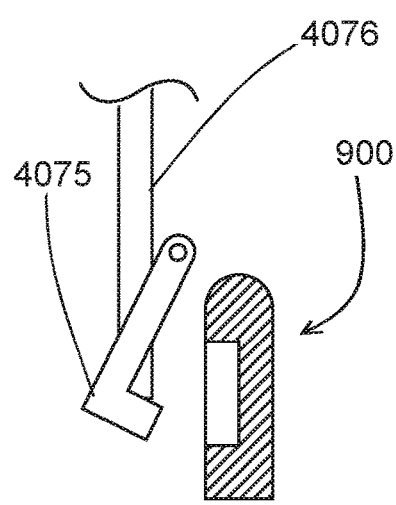
Figure 16D:
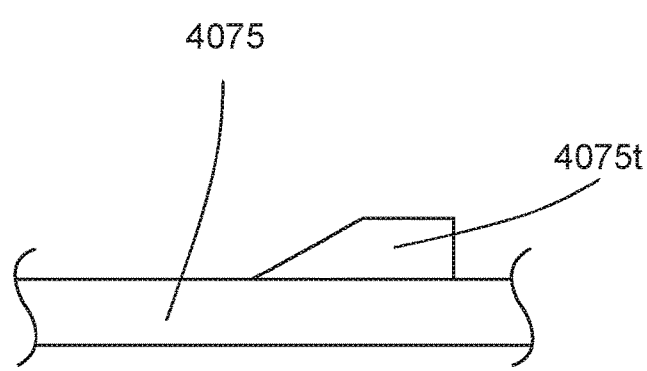

In a specific example shown in FIGS. 16A-16D, a biased locking element is provided that comprises a rotational locking mechanism 4074, wherein the rotational locking mechanism 4074 comprises a rotatable swing arm 4075, terminating in a tab 4075t. In one such example, the rotatable swing arm 4075 is biased via a torsion spring. In the illustrated embodiment, the swing arm 4075 is moveable out of the way or path (as illustrated in the dashed outline provided in FIG. 16B) of the suturing instrument 900 in order to allow advancement of the suturing instrument 900 within the cartridge. In some such embodiments, tab 4075*t* defines a beveled surface. In use, once the distal portion and the tissue receiving gap of the suturing instrument 900 are positioned distal of the tab 4075*t*, the swing arm 4075 is moved into the path of the suturing instrument 900 such that tab 4075*t* engages with the window or groove 955. A release arm 4076 is moveable adjacent the swing arm 4075 to prevent rotation thereof for maintaining the tab within the groove or window 955. As such, the swing arm 4075 functions to lock the suturing instrument 900 within the cartridge to prevent retraction or withdrawal of the suturing instrument 900 prior to loading of the suture onto the suturing instrument 900. As shown in FIG. 16C, the release arm 4076 is then translatable or moveable away from the swing arm 4075 to allow rotation thereof to permit disengagement of the tab from the suturing instrument 900 to permit retraction and removal of the suturing instrument 900 from the cartridge. Alternatively, the lock may comprise a resilient member biased for engaging with the suturing instrument 900 and the release arm may be operable to allow disengagement of the resilient member from the suturing instrument.

In a further alternative as shown in FIGS. 17A-17C(ii), the lock comprises a resilient member 4079 such as a resilient arm for engaging with the suturing instrument 900 for example with the window or groove 955 of the suturing instrument 900. Furthermore, a lock release mechanism 4077 is provided for disengaging the member 4079 upon transfer of the suture portion onto the suturing instrument 900. The lock release mechanism 4077 comprises a spring biased block 4079' that in its initial position 4079'A (FIG. 17A) supports the resilient member 4079 and prevents its movement in the proximal direction. As the instrument 900 is advanced distally through the cartridge, the resilient member 4079 flexes to allow the distal portion 920 of the suturing instrument 900 to advance, as shown in FIG. 17A, and resilient member 4079 is thereafter engageable with the window 955 of the suturing instrument 900 to prevent retraction of the suturing instrument 900, as shown in FIG. 17B (i), 17B (ii). The block 4079' remains in its initial or locked position 4079' A substantially adjacent the resilient member 4079 to prevent bending of the resilient member 4079 in the proximal direction to prevent retraction of the suturing instrument 900 prior to loading of suture onto the suturing instrument 900. Once a suture portion has been loaded onto the suturing instrument 900, the spring biased block 4079', forming the lock release mechanism 4077, moves into its second or unlocked position 4079'B, as shown in FIG. 17C(i), 17*c*(ii), where it no longer interferes with the movement of the resilient member 4079 allowing it to flex proximally, thereby permitting retraction of the suturing instrument 900.

In some embodiments of the present invention, the cartridge includes a delay mechanism to delay transfer of the suture from the cartridge onto the suturing instrument until after the seat, defined by the rocker, is aligned with the suturing instrument 900. More specifically, the delay mechanism prevents actuation of the suture insertion mechanism to transfer the suture from the seat to the instrument prior to alignment of the seat with the suture passing member held within the proximal portion of the suturing instrument.

As outlined previously hereinabove, in some embodiments of the present invention, the distal portion 920 of suturing instrument 900 is configured to interact with a bevel face of the rocker such as the first bevel face 4043 of rocker 4041 upon advancement of the suturing instrument 900 within the cartridge 4000 as shown, for example, in FIG. 18Ai), 18Aii). The rocker 4041 in FIG. 188Ai)-18Bii) is shown in a partial breakaway view with the front half of the rocker 4041 being removed. This results in pivoting of the rocker 4041 from its first position 4041A, illustrated in FIG. 18Ai), 18Aii), into its second position 4041B illustrated in FIG. 18Ci), 18Cii), resulting in movement of the seat 4022 into the tissue receiving gap 942 to align the seat 4022 with the proximal portion 910 of the suturing instrument 900 (specifically with a suture passing member such as needle 930'). An intermediate position of the rocker 4041 is illustrated in FIG. 18Bi), 18Bii) during movement of the rocker 4041 from the first position 4041A towards its second position 4041B.

Upon movement of the seat 4022 into the tissue receiving gap 942, the suturing instrument 900 is advanced distally in order to allow for the needle 930' to be positioned or docked adjacent the seat 4022, for example in abutting contact with the seat 4022 as shown in FIG. 18Cii). Thus, the difference between the cartridge 4000 as shown in FIG. 18Ci) and 18Cii) is that in FIG. 18Ci) the needle 930' and the seat 4022 are at the point at which they are aligned but not yet docked, whereas in FIG. 18Cii) the suturing instrument 900 has been advanced further to allow the needle 930' to dock with the seat 4022. In some embodiments, the suture transfer or insertion mechanism is delayed until such alignment occurs, and is then actuatable to transfer or load the suture portion from the seat 4022 onto the suturing instrument 900. In some such embodiments, the delay mechanism for delaying actuation of the suture insertion mechanism comprises a delay interlock 4095 mounted on the suture insertion mechanism which, in the illustrated example, comprises a push rod hub 4057' coupled to a push rod 4053, as shown in FIGS. 13C and 13D. In one specific embodiment, the delay interlock 4095 comprises a resilient member 4096 coupled to or integral with the push rod hub 4057', the resilient member 4096 (such as a push rod hub flex arm) being configured to co-operatively engage a protrusion 4097 coupled to the rocker 4041 ((Also shown in FIG. 13C and FIG. 18C(ii)), whereby the protrusion 4097 can be understood to be indirectly coupled to the seat 4022). As shown in FIG. 18Cii), the resilient member 4096 is positioned distal to the protrusion 4097 in a first, or unactuated, state of the suture insertion mechanism. Once the seat 4022 is aligned with the needle 930' and in abutting contact with the needle 930', as shown in FIG. 18D(i), the suturing instrument 900 may be advanced distally within the cartridge 4000, causing the push rod hub 4057' to contact a spring hub 4100 and to thereby apply a force to hub 4100 (and, consequently, to spring 4103) as the instrument 900 is further advanced. Once sufficient force is applied by the push rod hub 4057', as shown in FIG. 18D(ii), spring hub 4100 is pushed distally and protrusion 4097 is advanced beyond resilient member 4096, such that resilient member 4096 is positioned proximal to the protrusion 4097. The suture insertion mechanism is now in its second or actuated state resulting in the push rod hub 4057' moving within the push rod hub cavity 4057 shown in FIG. 13.G due to the biasing force of spring 4103 against hub 4100. Movement of the push rod hub 4057' then results in translation of the push rod 4053' coupled thereto to advance the suture portion, such as a suture end 502 comprising compressed suture, from the seat 4022 into or onto the needle 930'. Thus, in such embodiments, actuation of the suture insertion mechanism, and consequent transfer of the suture, is delayed until the delay interlock is positioned appropriately, which occurs following alignment of the seat with the needle 930'.

Some embodiments of the present invention additionally comprise one or more features to provide the user with an indication that the suture portion, such as the suture end 502 [shown, for example, in FIG. 13G] has been transferred from the seat 4022 onto the suturing instrument 900. In some such embodiments, the cartridge 4000 comprises an indicator for indicating transfer of the suture onto the suturing instrument 900. The indicator may comprise one or more of a tactile indicator, a visual indicator or an audible indicator. In one such example, the indicator comprises a tactile indicator comprising a force release mechanism 4200 as shown in FIGS. 18D(i) and 18D(ii). In the illustrated embodiment, a force release mechanism 4200 comprises a spring biased mechanism defined by the spring hub 4100 which itself comprises outwardly extending hub flex arms 4102 as well as a spring 4103. The force release mechanism 4200 provides an indication of a change in a force, which may be felt by the user, between the unactuated state of the suture insertion mechanism and the actuated state of the suture insertion mechanism as discussed hereinabove. More specifically, the force release mechanism 4200 is configured such that the user is able to feel a change in force once the push rod hub 4057' moves from its initial unactuated position shown in FIG. 18D(i) towards its actuated position as shown in FIG. 18D(ii) for transferring the suture portion from the seat 4022 into the needle 930'.

In some embodiments, after transfer of the suture portion to the suturing instrument, the suturing instrument 900 is operable to be advanced distally. As illustrated in FIGS. 18D(i) and 18D(ii), further advancement causes the outwardly extending hub flex arms 4102 of the spring hub 4100 advance beyond ledges or ribs 4102' defined by the cartridge housing 4010' causing the spring 4103 to compress. The movement of the hub flex arms 4102 beyond the ledges 4102', combined with the concurrent compression of the spring 4103, results in a force differential that is felt by the user handling the instrument 900, as there is a reduction in resistance force upon further advancement of the suturing instrument 900. This reduction in force provided by the force release mechanism provides the user with a tactile feel indicating that the suture portion has been transferred onto the suturing instrument 900. Furthermore, in some examples the force release mechanism 4200 additionally provides an audible indication as the hub flex arms 4102 ride over the ledges 4102', whereby the force release mechanism additionally defines a snap release mechanism. In the illustrated embodiment, the tactile and/or audible indicators are not activated immediately upon transfer of the suture portion; rather, the indication is delayed until the instrument is further advanced within the cartridge. In such embodiments, the cartridge 4000 comprises a delay mechanism to delay activation of the indicator (for example for a predetermined time period) following loading of the suture portion from the cartridge onto the suturing instrument 900. This provides a safety and security feature in terms of ensuring that the suture has been loaded prior to an indication being provided to the user to indicate transfer of the suture portion. In other words the indication provides a safety factor to account for dimensional and force variabitlity.

In additional embodiments of the present invention, a visual indicator is provided, comprising a button 4106 including a spring biased mechanism 4106'. In the illustrated embodiment, the spring biased mechanism is configured to cause the button 4106 to be released, allowing it to move from its initial position 4106A [FIG. 18C (ii)] to its second position 4106B [FIG. 18D(ii)], upon transfer of the suture portion onto the suturing instrument 900, thereby providing a visual indication of the suture transfer. In some embodiments, the visual indicator 4106 cooperates with the force release mechanism 4200, whereby visual indicator 4106 is released into its second position 4106B upon movement of the force release mechanism 4200. For example, as illustrated in FIGS. 18D(i) and 18D(ii), distal movement of the force release mechanism 4200 causes horizontal bars 4107' and 4107 coupled to the spring hub 4100 to move longitudinally, thereby releasing a bar 4108 coupled to the button 4106 and freeing the button 4106 to move upwards to its second position 4106B. Thus, in the illustrated embodiment, the indicator is automatically activated upon loading of the suture portion from the cartridge onto the suturing instrument. In one such example, the indicator button 4106 additionally provides an audible indication to the user as the bar 4108 is released from engagement with horizontal bar 4107'. In some such embodiments, the indicator button 4106 may form the primary mechanism for providing an audible indication.

Once the indictor is activated the suturing instrument may then be removed from the cartridge housing as shown in FIGS. 18E and 18F. As discussed previously hereinabove, the rocker 4041 enables unimpeded retraction of the suturing instrument by being made to pivot out of the way of the suturing instrument 900 to return to its initial position 4041A. The seat 4022 is moveable out of the tissue receiving gap 942 of the suturing instrument 900.

Referring still to the embodiment disclosed in FIGS. 18E and 18F, a cartridge 4000 is provided that additionally allows for loading a pre-tied knot onto a suturing instrument 900, for example by allowing loading, mounting or transfer of a knot deployment mechanism or knot slider 4030 onto the suturing instrument 900. In some such embodiments, as the suturing instrument 900 is retracted from the cartridge 4000 after loading of the suture portion onto the suturing instrument 900, the cartridge additionally provides for a knot deployment mechanism or knot slider 4030 (that for example has a pre-tied knot mounted there-about) to be mounted onto the suturing instrument 900 to enable retraction of the knot deployment mechanism or knot slider 4030 along with suturing instrument 900. In one such example as shown in FIG. 13B, the knot deployment mechanism or knot slider 4030 is detachably coupled to the cartridge housing sleeve 4011' by a knot slider release mechanism 4060. In one such example, the knot slider release mechanism comprises a resilient member, for example a snap arm 4062, as shown, where the resilient member is configured to release the knot slider 4030 from the housing sleeve 4011' of the cartridge housing 4010' upon insertion of a suturing instrument 900 there-through. In one such example, the knot slider 4030 and the cartridge housing sleeve 4011' together form the cartridge housing 4010'. The snap arm 4062 provides flexibility and allows the knot slider 4030 to pivot up and down and bend left and right as the suturing instrument 900 is advanced through an opening or chamber within the knot slider 4030 and is guided into ribs defined by the cartridge housing sleeve 4011' to be guided into the rocker 4041. In one such example the knot slider 4030 is releasable from the snap arm 4062 upon advancement of the suturing instrument 900 within the cartridge. For example, as shown in FIG. 18C (i), the knot slider 4030 is releasable from the snap arm 4062 upon alignment of the seat 4022 within the tissue receiving gap 942 of the suturing instrument 900. As such, the knot slider 4030 is decoupled from the housing sleeve 4011' and remains mounted on the suturing instrument to enable the knot slider 4030 to be retracted along with the suturing instrument 900.

Figure 19A:
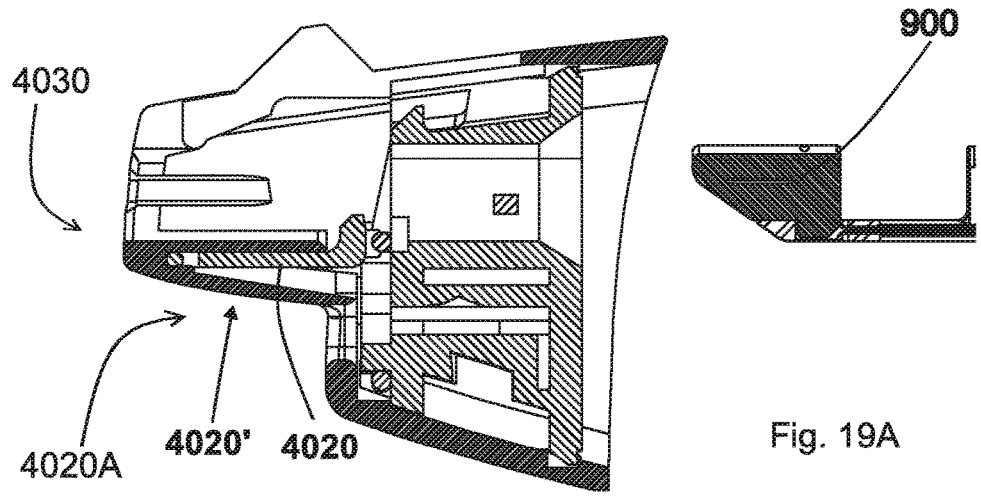
FIGS. 19A-19C illustrate an alternate embodiment of a cartridge knot slider comprising a feature to prevent upside-down (reverse-oriented) insertion of the suturing instrument, in accordance with an embodiment of the present invention.
Figure 19B:
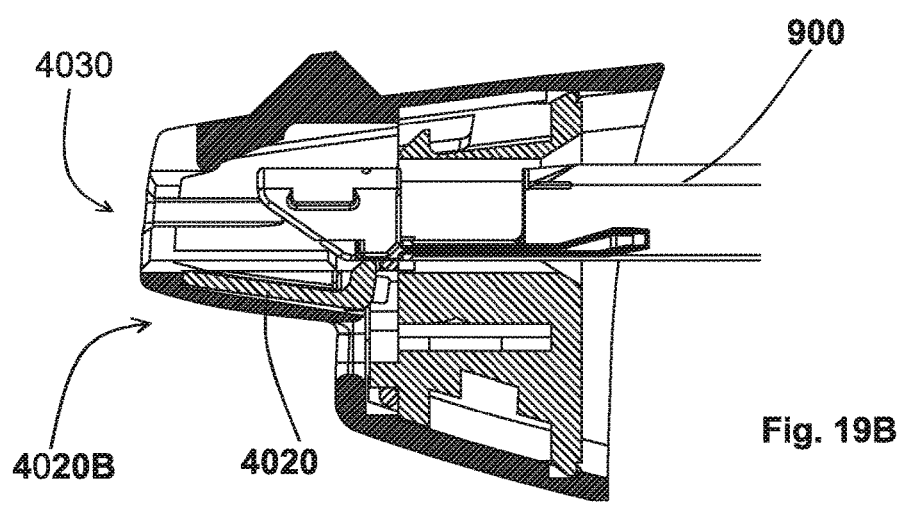
Figure 19C:
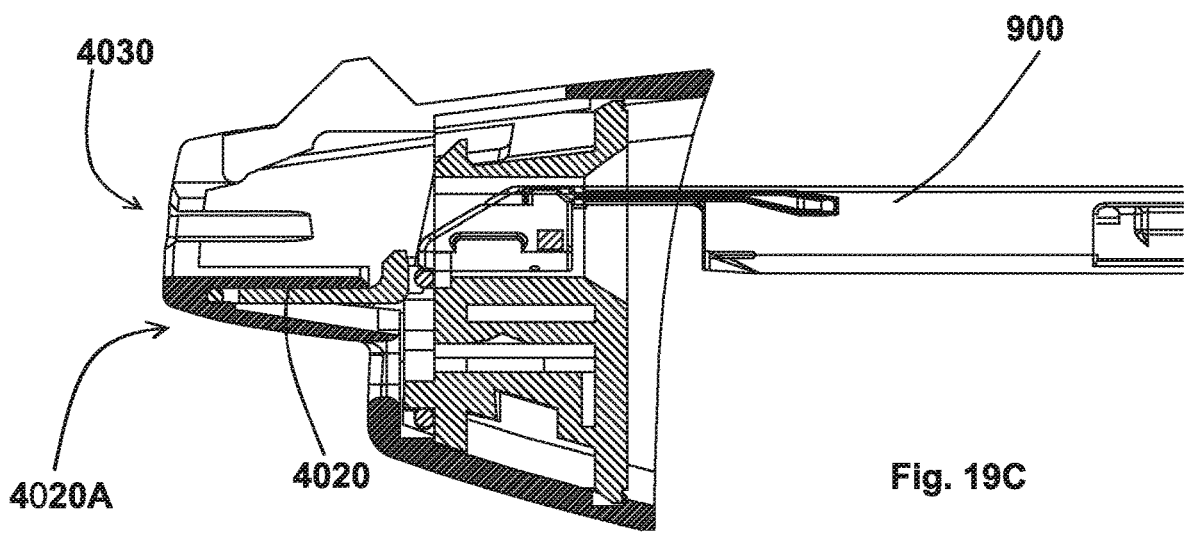

In some embodiments of the present invention, for example as shown in FIGS. 19A to 19B, the knot deployment mechanism or knot slider 4030 additionally comprises a feature for reducing the risk of insertion of the suturing instrument 900 by the user in an upside-down, or inverted, configuration. In some such embodiments, the knot slider 4030 comprises an instrument obstructing feature such as an interlock 4020' comprising an arm 4020 having a closed configuration 4020A and an open configuration 4020B. The interlock arm 4020 is configured to be initially in the closed configuration 4020A for preventing advancement of an inverted suturing instrument 900 into the cartridge [such as cartridge 4000 disclosed herein above]. As illustrated in FIG. 19C, as the suturing instrument 900 is advanced in its inverted configuration into the cartridge 4000 through the knot slider 4030, the interlock 4020' such as the interlock arm 4020 remains in its closed configuration 4020A preventing further advancement of the suturing instrument 900 within the cartridge 4000. More specifically, the interlock 4020' is configured to engage with the flat face 921 of the suturing instrument 900. The flat face 921 of the suturing instrument does not cooperate with the interlock arm 4020 in a manner which allows the interlock arm 4020 to move into its second or open position 4020B. As such, the interlock arm 4020 remains in its closed configuration 4020A impeding advancement of the inverted suturing instrument 900.

Figure 21C:
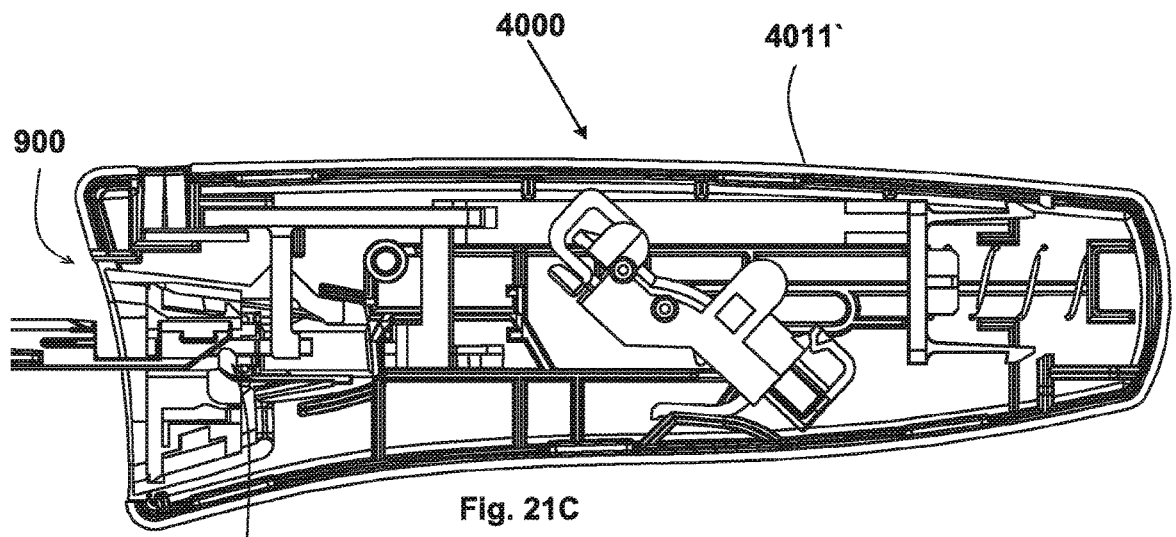
FIGS. 21C-21E illustrate alternate embodiments of an interlock for preventing upside-down (reverse-oriented) insertion of the suturing instrument, in accordance with various embodiments of the present invention.
Figure 21D:
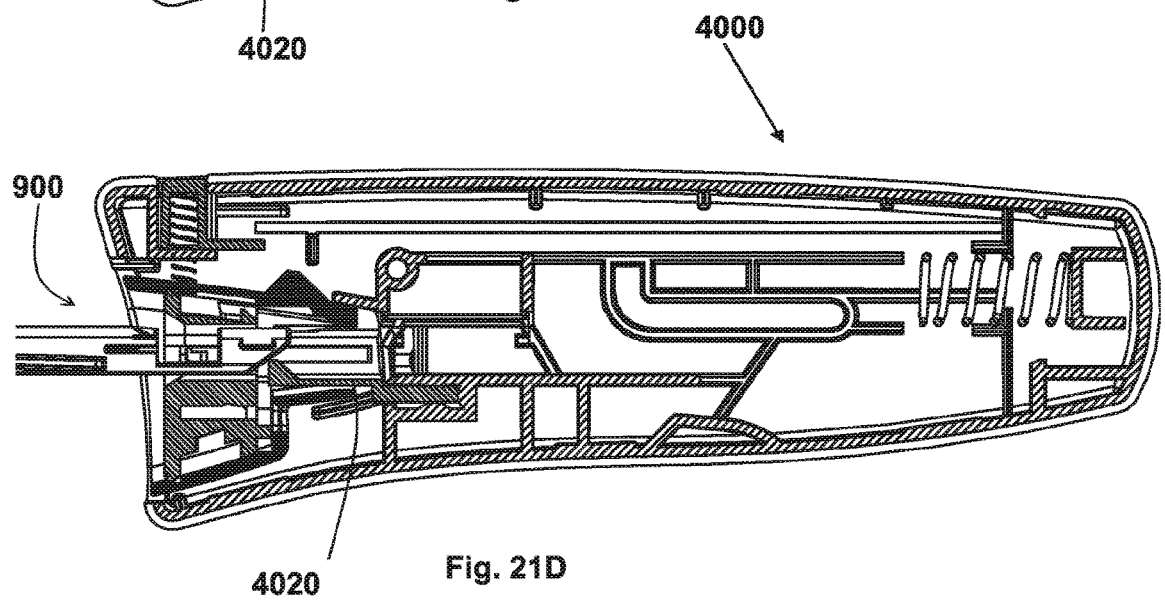
Figure 21E:
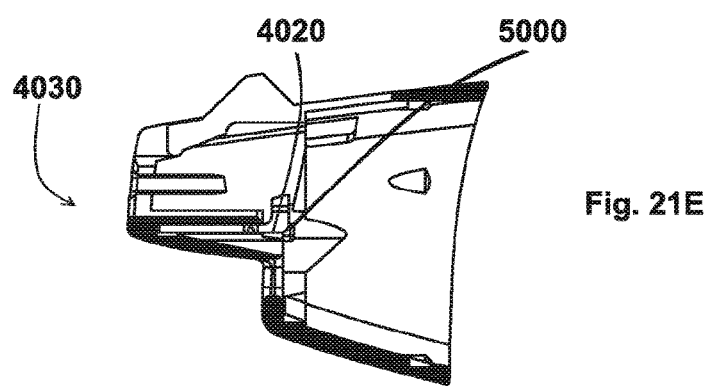

Furthermore, the interlock 4020' such as the interlock arm 4020 is operable to permit advancement of the suturing instrument 900 when it is advanced in its regular or nominal configuration with the instrument 900 being positioned in the right-side up configuration, as shown in FIG. 19A. As shown in FIG. 19B, as the suturing instrument 900 is advanced further through the knot slider 4030, the distal portion 910 of the suturing instrument 900 engages with the interlock arm 4020, thereby moving it into its open configuration 4020B allowing further advancement of the suturing instrument 900 within the cartridge 4000. More specifically, the interlock arm 4020 is configured to engage with the bevel face 923 of the suturing instrument 900 to cause the interlock arm 4020 to move into the open configuration 4020B. In some embodiments, the obstructing feature, such as an interlock 4020', is defined by the knot slider 4030. In alternate embodiments, a cartridge 4000 is provided where the interlock 4020' is defined by and forms a part of the cartridge housing sleeve 4011' instead of the knot slider 4030 [e.g. as shown in FIGS. 21C and 21D]. In one such example as shown in FIG. 21C the interlock arm 4020' is formed integrally with the housing sleeve 4011'. Alternatively, the interlock arm 4020' may be detachably coupled to the housing sleeve 4011' via a press-fit engagement therewith, for example as shown in FIG. 21D. In some embodiments of the present invention, for example as shown in FIGS. 19A-19C, the interlock arm 4020 comprises a pivoting connection forming a pivot arm. In some such embodiments, the pivot arm is held in frictional engagement with a portion of the knot slider 4030, such as the external knot slider 4010y of the cartridge housing 4010'. The pivot arm is operable to maintain closed configuration 4020A by, for example, a component 5000, as shown in FIG. 21E. In some examples, the component may comprise an elastomeric gasket such as an O-ring.

In other embodiments as shown in FIG. 21A (i)-21B (ii) the obstructing feature defines an obstruction feature resilient member, i.e. an alternative embodiment to an interlock arm 4020. FIGS. 21A(i) and 21A(ii) illustrate the alternate interlock arm in its initial closed position 4020A, whereas FIG. 21B(i), 21B(ii) illustrate the alternate interlock arm 4020 in its second or open position 4020B. In the illustrated embodiment, the interlock 4020' such as interlock arm 4020 is configured to co-operate with a lock 4040 within the cartridge 4000 which hold the interlock arm 4020 in its open configuration 4020B to allow the interlock arm 4020 to remain in the open configuration 4020B. This may reducing friction that may resulting from the interlock arm 4020 pressing against the suturing instrument 900, when the knot slider 4030 slides along the suturing instrument 900 during the procedure. In some such embodiments, the lock 4040 comprises a friction-fit mechanism comprising resilient friction tabs 4040'. The lock 4040 comprising resilient tabs 4040' is further illustrated in FIGS. 20A and 20B which shows an interlock 4020' comprising a button 4020". The button 4020" is moveable from its first closed configuration 4020"A shown in FIG. 20A, to its second open configuration 4020"B, shown In FIG. 20B, upon advancement of the suturing instrument 900 in its nominal or right side up configuration, within the cartridge. The button 4020" is then held in its second open position 4020"B by the resilient tabs 4040'. In some embodiments, the button 4020" may be spring-biased.

Figure 22A:
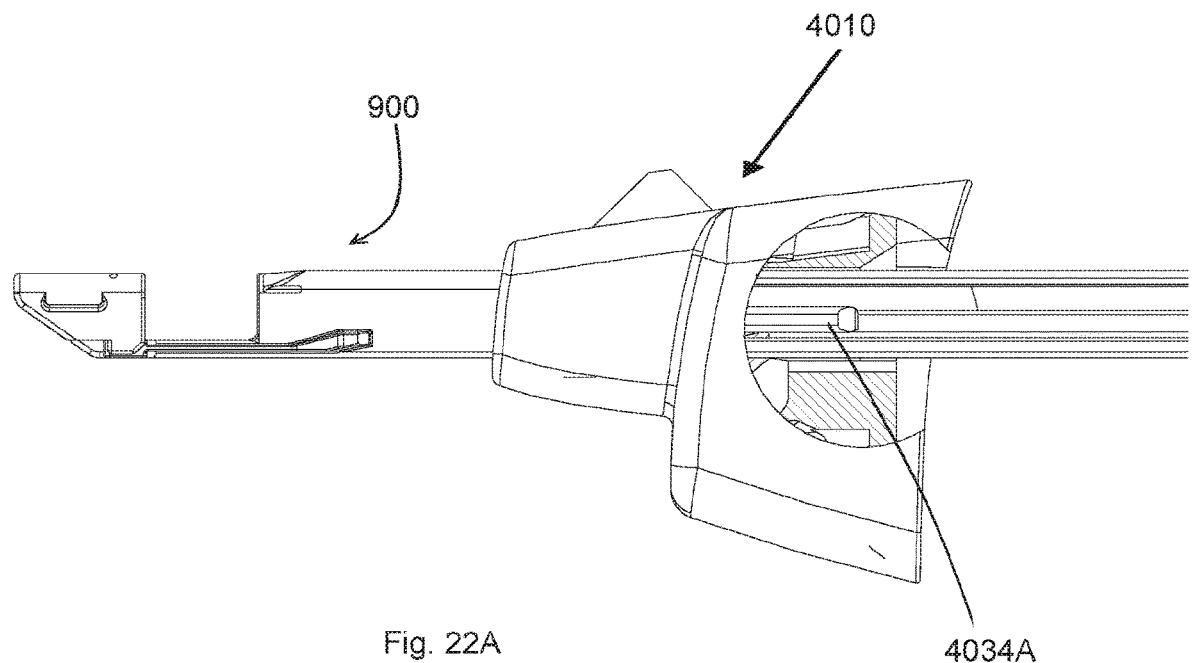
FIGS. 22A-22E illustrate various views of a knot slider comprising an attachment mechanism for slidably engaging with the suturing instrument.
Figure 22B:
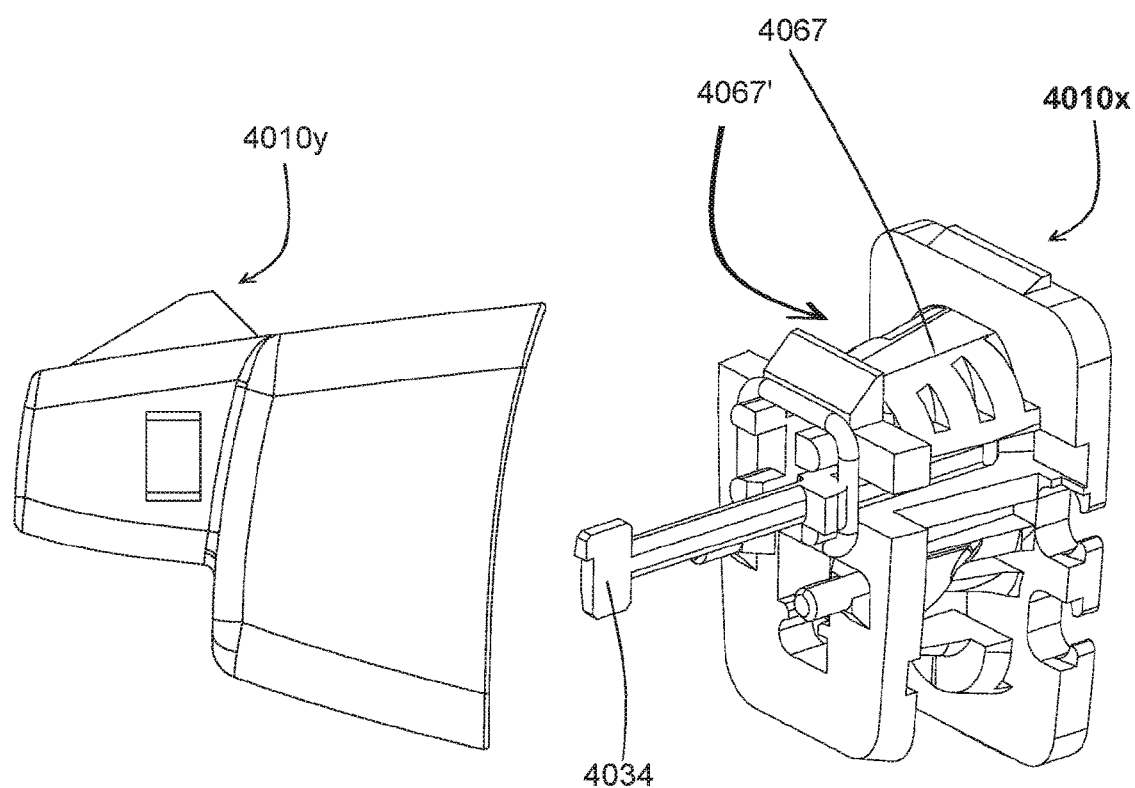
Figure 22C:
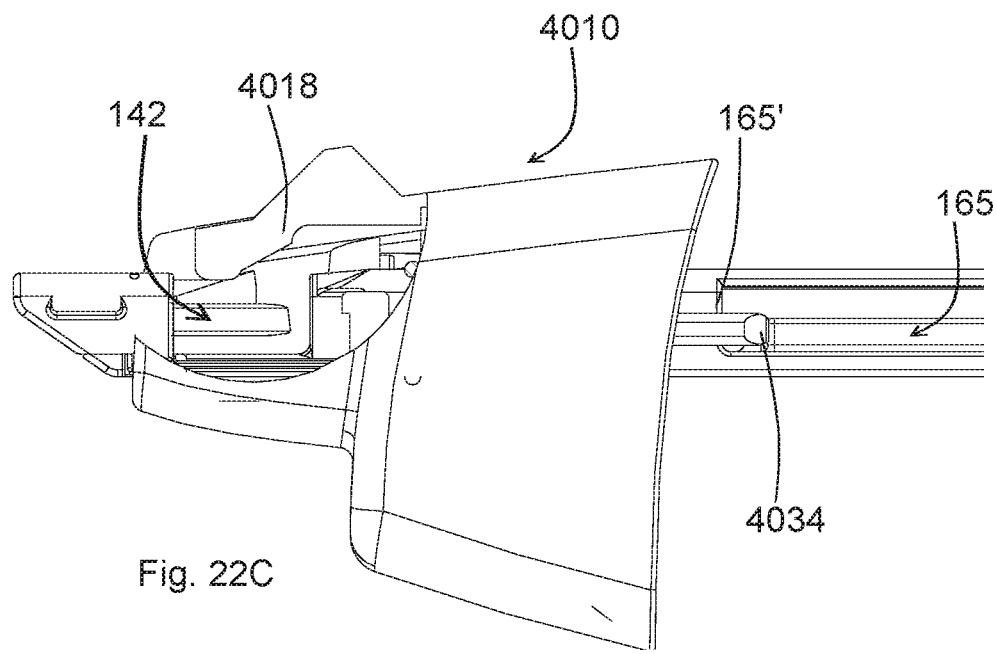
Figure 22D:
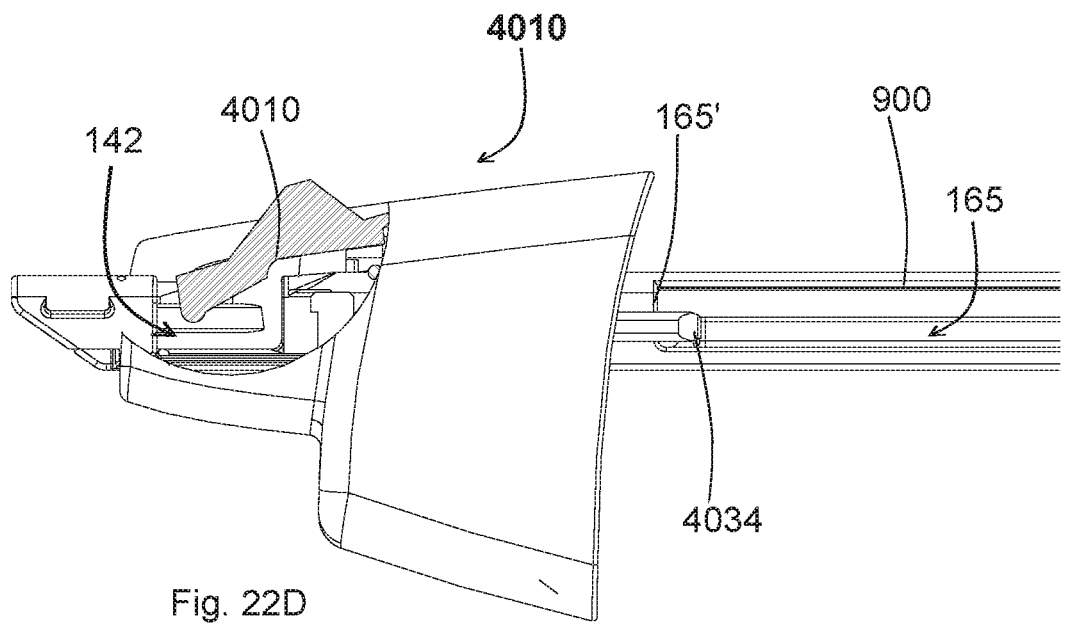
Figure 22E:
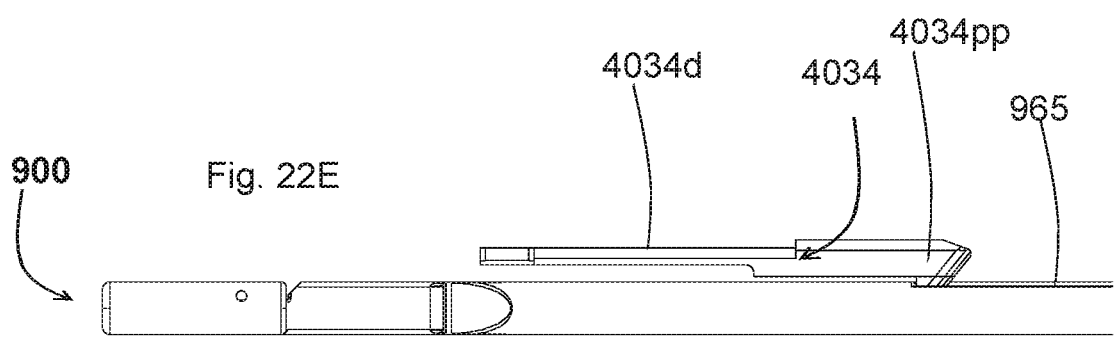

In some embodiments, the knot slider 4030, once mounted on the suturing instrument 900, is operable to be releasably coupled to a handle of the suturing instrument. Knot slider 4030 is further releasable therefrom to slide distally along the instrument proximal portion 910 during use to enable the pre-tied knot mounted about the knot slider 4030 to be deployed therefrom. In some embodiments, the knot slider 4030 comprises an attachment mechanism for slidably engaging with the suturing instrument 900. In one specific example, as shown in FIG. 22A, the attachment mechanism comprises a tail hook or knot slider arm 4034 is slidable along a portion of the suturing instrument 900 such as the window 965 of the suturing instrument 900. In one such example, the knot slider arm 4034 is received within a groove within an inner slider 4030x (that is held within the outer slider 4030y) and slidable therein to be extendable therefrom. The knot slider arm 4034 is initially in its retracted configuration 4034A as shown in FIG. 22A, where it is held within the knot slider 4030. The knot slider arm 4034 is slidable to move into its extended position 4034B and extends out from the knot slider 4030, as shown in FIG. 22C, and engages with a distal wall 965' of the window 965 to stop the knot slider 4030 such that it is positioned over the tissue receiving gap 942. In some such embodiments, the knot slider 4030 comprises a cover arm 4038 and slidable knot slider arm 4034 engages the distal wall 965' to allow the cover arm 4038 be positioned over the tissue receiving gap 942 to allow the cover arm 4038 to deflect inwards to deploy the pre-tied knot distal to the suturing instrument 900, as illustrated in FIG. 22D. In some examples as shown in FIG. 22E, a distal portion 4034d of the tail kook is relatively thinner than a proximal portion 4034p of the knot slider arm 4034 so that it minimizes the risk of the knot slider arm 4034 interfering with the suturing instrument 900 upon advancement of the suturing instrument 900 within the knot slider 4030. In some such embodiments, the proximal portion 4034p is wider than the distal portion 4034d to facilitate engagement of the knot slider arm 4034 with the suturing instrument 900. In some such embodiments, the inner slider FIG. 22B of the knot slider 4030 comprises a suture housing 4067' for storing suture. In one such example the suture housing comprises tubing that is wound about a portion of the knot slider such as a slider central post 4067. The central post 4067 defines a groove 4067' for holding the suture tube. In some such embodiments the tubing comprises PTFE (Polytetrafluoroethylene) such as TEFLON®.

Figure 22F:
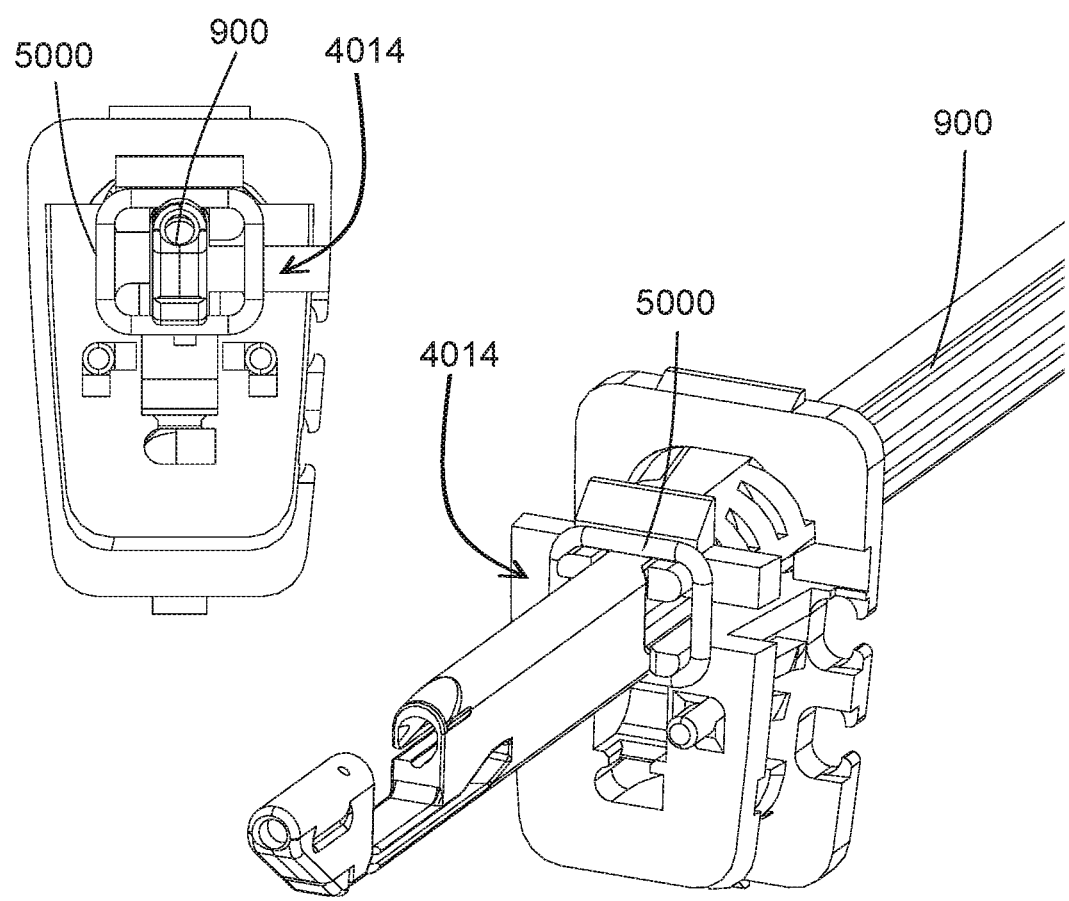
FIG. 22F illustrates a view of a knot slider comprising a feature to facilitate sliding of the knot slider on the suturing instrument.

In some such embodiments, as shown in FIG. 22F as outlined previously herein-above, the knot slider 4030 defines a channel 4014 for receiving the suturing instrument 900 therein. In some such embodiments, the inner slider 4030x of the knot slider 4030 comprises a suspension spring such as a circumferential O-ring mounted about the channel 4014 in order to facilitate movement of the knot slider 4030 along the suturing instrument 900. In a specific example, the O-ring comprises silicone. The O-ring provides shock absorption along the top and bottom of the suturing instrument 900 and facilitates sliding of the knot slider 4030 by decreasing the overall sliding force by allowing the suturing instrument 900 to be in sliding contact with the O-ring. As such the O-ring allows for easier deployment force and reduces the force of sliding and further allows the movement of the knot slider 4030 to be more tolerant and less sensitive to bumps.

Example 5 thus includes various alternatives to features described above and/or additional features not previously mentioned including but not limited to: movement of the magazine, for example the rocker, alignment of the seat and/or rocker, reversibility-prevention features when suture has not been loaded, coupling of the rocker to the push-rod hub, indicator for indicating loading or transfer of suture onto the suturing instrument, interlock to prevent insertion of the suturing instrument in an incompatible orientation and features related to the knot slider.

EXAMPLE 6

Figure 23D:
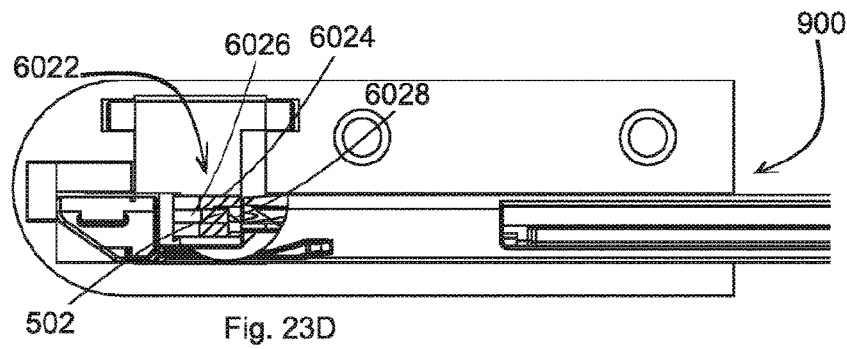
Figure 23E:
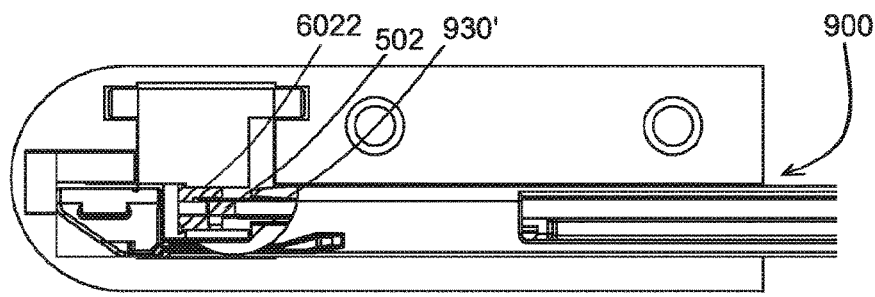
Figure 23F:
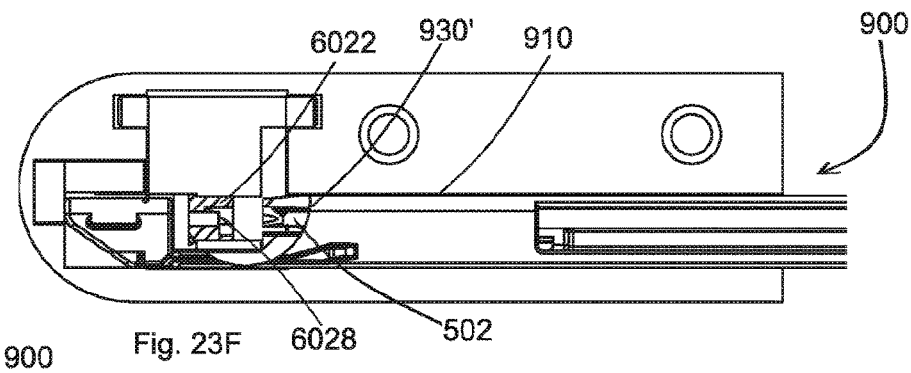

In additional embodiments of the present invention, as shown for example in FIG. 23A, a cartridge 6000 is provided having a housing 6010' for loading suture onto a suturing instrument 900 comprising a suture passing member such as needle for example that is held within the device proximal portion 910. The cartridge 6000 comprises a magazine 6041 defining a seat 6022 for holding an end of the suture. The seat 6022 is structured and configured to allow a suture passing member such as a needle to be advanced over the suture end to capture the suture end. In the illustrated embodiment as shown in FIGS. 23B(i) and 23B(ii), the magazine 6041 is moveable from the first position 6041A into its second position 6041B as shown in FIGS. 23C(i) and 23C(ii) in order to align the seat 6022 within the tissue receiving gap 942 of the suturing instrument 900. The seat 6022 is moveable into alignment with the suture passing member held within the device proximal portion 910. In the specific example shown, the seat 6022 is laterally moveable with the magazine 6041 being pivotable to move the seat 6022 into alignment with the suture passing member. As such the magazine 6041 defines an alignment feature for aligning the seat 6022 with the suture passing member upon insertion of a suturing instrument within the cartridge 6000. In the specific example shown, as the suturing instrument is advanced within the cartridge 6000, the distal tip 920 of the suturing instrument 900 moves a seat interlock 6044 which for example comprises a pin which prevents movement of the seat 6022 prior to insertion of the suturing instrument 900 within the cartridge 6000 [FIG. 23B(i), FIG. 23B(ii)]. More specifically, as the suturing instrument 900 is advanced, the distal portion 920 of the suturing instrument moves the seat interlock 6044 distally which releases the magazine 6041 causing it to pivot into its second position 6041B [FIG. 23C(i), FIG. 23C(ii)]. As such the seat interlock 6044 is configured to be automatically disengaged upon advancement of the suturing instrument 900 within the cartridge 6000 to allow the seat 6022 to be automatically brought into alignment with the suture passing member 930' upon disengagement of the seat interlock 6044. In some such embodiments as shown in FIG. 23D, the seat 6022 comprises a seat block 6024 defines a seat cavity 6022' for holding the suture end 502 in frictional engagement therein, as shown in FIG. 23D. The seat comprises a seat post 6026 adjacent the seat cavity 6022' for retaining the suture end 502 upon advancement of the suturing instrument within the cartridge. The seat block 6024 is operable to be moved away from the suture passing member such as the needle 930' upon advancement of the needle 930' for example upon partial actuation of the trigger of the suturing instrument 900, to allow capture of the suture end by the needle 930', as shown in FIG. 23E. The seat post 6026 functions to keep the suture end 502 in place by preventing the suture end 502 to be moved distally as the seat block 6024 is moved as shown in FIG. 23E.

Figure 23G:
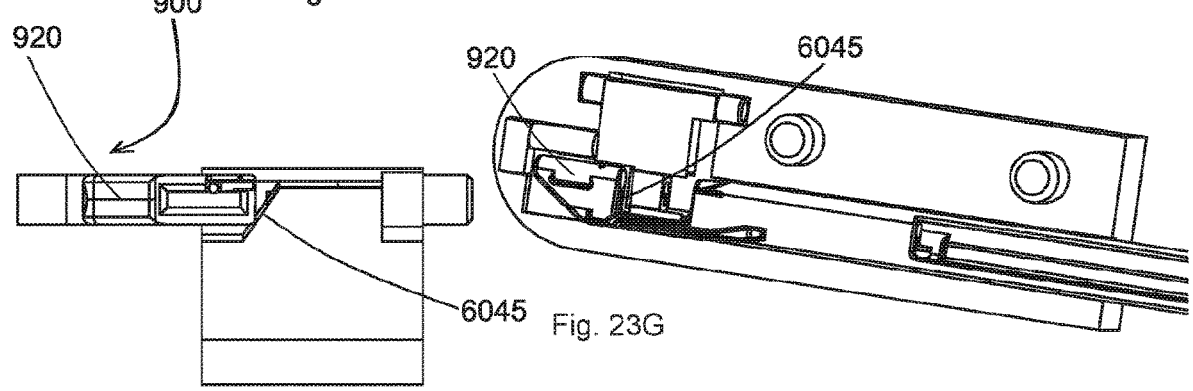

In some such embodiments, the seat 6022 defines a recess 6028 adjacent the seat cavity 6022' for receiving the suture passing member 930', as shown in FIG. 23D. In some such examples the recess 6028 defines a bevel face configured for abutment with a bevel face of the suture passing member such as needle 930'. As the needle 930' is then retracted the suture end 502 held therein is moved along with the needle 930' into the device proximal portion 910. As shown in FIG. 23G, the suturing instrument 900 is then retracted with the distal portion 920 of the suturing instrument 900 interacting with a bevel 6045 of the magazine causing it to move into its first position 6041A allowing the suturing instrument 900 to be retracted. In some such embodiments, the cartridge may comprise an alignment mechanism described in FIGS. 12A-12F.

In some embodiments, one or more of the seat 6022 and the cartridge housing comprise a medical grade polymer such as ABS. Alternatively the cartridge comprises a medical grade metal. In one example the seat 6022 comprises a metal such as stainless steel.

In alternative embodiments of the present invention, as shown in FIG. 24A(i), 24A(ii), the cartridge 700o comprises a pivoting magazine 7021 that comprises two arms 7041, 7042 with one of the arms 7042 defining the seat 7022. As the instrument is inserted within the cartridge 7000 as shown in FIG. 24A(i)—it pushes arm 7041 out of the way to swing arm 7042 within the tissue receiving gap of the suturing instrument 900 to align the seat 7022 with the suturing instrument 900, as shown in FIG. 24A(ii). Similarly, FIGS. 24B(i) and 24B(ii) illustrate a cartridge 7000 with a pivoting magazine 7021. With reference to FIG. 24B(iii), the cartridge 7000 additionally comprises an outer sleeve 7000' that is moveable distally such that bevel 7001 pushes the seat 7022 to pivot it within the tissue receiving gap 942. Once the outer sleeve 7000' is pulled proximally the bevel 7002 engages arm 7041 to pivot the magazine 7021 to move the seat 7022 out of the tissue receiving gap 942. In additional alternatives, as shown in FIG. 24C(i), (ii), a cartridge 8000 is provided that comprises a cam 8041 that is moveable to move a seat 8022 within the tissue receiving gap 942.

As such Example 6 includes various alternatives to features described above and/or additional features not previously mentioned including but not limited to: movement of the magazine, alignment of the seat and/or magazine, specifically mechanisms to enable movement of the magazine to align the seat within the tissue receiving gap of the suturing instrument, and additionally one or more embodiments of a cartridge that are configured to allow a suture passing member of a suturing instrument to capture an end of the suture.

In order to load suture into a surgical suturing instrument or suture passer, in accordance with some embodiments of the present invention as outlined hereinabove regarding Examples 3 and 4, two events or functions typically occur: (1) alignment of the suture portion held within the cartridge with a suture receiving feature within the surgical suturing instrument or the suture passer and (2) insertion or transfer of the suture portion into the suture receiving feature within the suturing instrument or suture passer.

In some embodiments of the present invention, a cartridge configuration is provided that is fully automated—requiring a single "pump-action" user step while completing all mechanical events to load the suture into the suturing instrument. In one such example, a user step to actuate the suture passer trigger to load the suture may not be required.

In addition, the suture cartridge device includes a pre-tied knot and integrated features to store the Suture limbs, which may reduce the required user attention to manage the Suture and may help eliminate the complex knot-tying step required by existing devices. In some such embodiments, a cartridge configuration is provided that contains a detachable knot slider containing a pre-tied knot and storage of the suture.

In some embodiments the cartridge has a side slot for securing the Suture out of the way of the suture passer shaft when it is inserted into the cartridge.

In some such embodiments, the cartridge may be constructed of Medical Grade plastic/metal components such as ABS for the cartridge base, seat, suture lock, interlocks and other mechanical components. In some embodiments, stainless steel may be utilized for the seat, silicone in O-rings for holding the Suture. In some embodiments the suture contained in the cartridge may comprise polyethylene.

Furthermore, embodiments of the present invention as outlined herein allow the suture end to be positioned or constrained in the following degrees for alignment to occur in order to allow the suture to be loaded onto the suturing instrument. The suture portion is positioned such that it position is maintained along the X axis (lateral direction), Y-axis (vertical or up and down directions), Z axis (linear or longitudinal direction) as well along the Y-rotational axis and the Z rotational axis. Further details of the alignment mechanism are provided herein below.

In some embodiments of the present invention, in order to align the suture with a suture receiving feature of the suture passer (such as suture receiving passage within suture passing member a magazine defining a seat is provided that is operable to be mechanically interlocked with the suture passer such that when the suture cartridge is inserted over the suture passer and pressed, the magazine and thus the seat is configured to rotate down, aligning the suture portion within the seat with the suture passer. In some such embodiments the magazine defining the seat, grabs onto the suture passer to align the suture portion in the X-axis and Y-axis and constrain X-rotation and Y-rotation of the Suture. Furthermore, the seat mates with and is pushed up to the suture passer to align the suture in the Z-axis.

In some embodiments, as outlined in examples 3 and 4, the magazine comprises a feature to hold/lock the suture to the side and align it with the suture slot in the suture passer shaft. In some embodiments as outlined above in examples 3 and 4, a cartridge base interlock is provided in the form of a button that the user presses to allow the cartridge base to move. Furthermore, some embodiments provide a a suture lock using which the suture is manually unlocked by the user at a specified time In some embodiments as described herein above with reference to examples 3 and 4, embodiments of the present invention provide an alignment mechanism that comprises a magazine defining a seat that automatically pivots into place from the top to align the suture with the suture passer. The magazine is mechanically interlocked with the suture passer such that when the cartridge containing the magazine that defines the seat, is inserted onto the suture passer, the geometry of the suture passer presses a bevel on the magazine and causes the magazine and thus the seat defined thereby, to pivot into place. In one such example the seat is a part of a rocker as outlined in further detail herein above as discussed in examples 3 and 4.

In some embodiments aligning of the seat using a pivoting rocker is beneficial when the suture passer has complex features around the site at which the suture is loaded (or otherwise) limiting the alignment of the seat to be purely linear. As well, the rocker is beneficial when an automatic (without desire of user interaction to align the seat) mechanism is desired. This is because it may generally be easier to move a pivoting part through a desired displacement on an arc than a sliding part through a desired displacement along an axis. (this is due to reduced friction/binding and increased mechanical advantaged gained in a pivoting system)

In some embodiments the seat is configured such that it is defined by a tubular member (seat defining member or projection) that extends out from the body of the magazine such as the rocker and is receivable into the hole on the suture passer and up against the feature in the suture passer (such as the suture passing member such as the needle) into which the suture is loaded. The projection that extends into the hole in the suture passer has an interference fit with the inner walls of the hole to align the seat/suture within a repeatable tolerance zone relative to the feature on the suture passer that receives the suture. Having this interference fit may reduce the tolerance stack-up of misalignment.

In some embodiments the magazine is configured such that the magazine and thus the seat defined thereby aligns perfectly with the corresponding features on the suture passer such that the mechanism cannot possibly ever jam because the geometry does not allow that to happen.

In some embodiments, the magazine is configured such that it has an interference fit with reference features on the suture passer to positively align the seat defining member or projection within a repeatable tolerance zone relative to the hole that contains the suture passing member such as the needle on the suture passer. Having this interference fit may reduce the tolerance stack-up of misalignment.

In some embodiments of the present invention, an alternative seat is provided, the seat containing a cavity that has an interference fit with the outer diameter of the needle. As described previously, the needle is then held in the "out" position during shipping with a lock such as cam lock that hooks the needle, or a trigger lock that hold the trigger slightly depressed. In a manual version, the user is required to press the trigger to cause the needle to move out and into the seat cavity before the suture is pulled. In some such embodiments, having the "Needle-out" configuration may have a reduced tolerance stackup of misalignment compared to the "Needle-In" configuration.

In further embodiments of the present invention, as an alternative to a top-pivoting magazine, some embodiments of the present invention may provide a seat that pivots inwardly from the side. Alternatively, a seat may be provided that slides from the side(s) or from the top. Furthermore, instead of an automatic alignment seat, a magazine may be provided that is pushed into place by the user at a specified time to push the seat into place. Furthermore, in some embodiments where the magazine comprises a rocker as described above, a button may be pressed to enable the rocker to rotate.

In some embodiments of the present invention, the alignment feature comprises a moveable seat as outlined above. In some such embodiments the seat is moveable relative to the base. In other embodiments the seat is moveable relative to the chamber defined by the housing of the cartridge. In such embodiments, the seat may be automatically moveable (upon advancement of the suturing instrument within the cartridge).

In alternative embodiments a fully automatic mechanism is provided for aligning and transferring suture. In other embodiments, a more simplified mechanical design may be provided that reduces the number of steps that the user is required perform in order to load the suture. In some embodiments, the mechanical design provides one or more steps that the user is required to perform to load the suture.

In alternative embodiments, with reference to example 4, a push rod interlock may be provided in the form of a button that the user presses in order to allow the push rod to move to push the suture end into the suturing instrument.

In some embodiments as described herein above with reference to example 4, the embodiment provides for automatic decoupling of the knot slider. In alternative embodiments, the Knot Slider may be manually decoupled from the Cartridge Base by the user at a specified time. In some such embodiments a visual indicator window may be provided that shows the user when the Lobster has been loaded and when the suture Knot Slider can be released. In some embodiments, with reference now to example 3, a similar mechanism in the form of a visual indicator window may be provided that shows the user when the Lobster has been loaded and when the suture lock may be released.

In some embodiments of the present invention a cartridge is provided that provides an additional means for providing an indication for when the suture has been loaded into the suture passing member. In some such embodiments, an interlock in the seat, i.e. a seat interlock may be provided which senses when the suture has left the seat. Alternatively the cartridge may provide clear or see-through components so the user can physically see when the Suture has been loaded. Furthermore, in still a further alternative, optical sensors may be provided that detect when the suture has been loaded.

In still some additional embodiments, with reference to example 4, instead of a sliding tail hook on the knot slider a fixed tail hook may be provided.

Referring again to various examples provided hereinabove, including but not limited to examples 2, 3 and 4, embodiments of the present invention provide a cartridge for loading a suture onto a suturing instrument, the cartridge defining a path for insertion thereto and withdrawal therefrom of the suturing instrument, the cartridge comprising:a seat for releasably holding a portion of a suture; and a translation mechanism for moving the seat out of a path of a suturing instrument inserted into the cartridge to allow for withdrawal of the suturing instrument from the cartridge. Thus, such embodiments provide a cartridge operable to move the seat out of the way of the suturing instrument following loading of the suture so that the suturing instrument can be withdrawn. In some such embodiments, the seat is moveable to align with a portion of the suturing instrument to allow for loading of the suture, such that the seat is moveable between: a first state whereby it is not obstructing a path of the suturing instrument to permit insertion of the suturing instrument into the cartridge; a second state in which the seat is moved into alignment with a portion of the suturing instrument, such as a tissue receiving gap described above, to allow for loading the suture portion onto the suturing instrument; and a third state whereby the seat is moved out of the path of the suturing instrument to permit substantially unobstructed withdrawal of the suturing instrument from the cartridge.

As described hereinabove, some embodiment of a cartridge include a magazine comprising the seat. In some such embodiments, movement of the magazine, and thereby the seat, between the various states may be accomplished via a rotational mechanism (such as in examples 9 and 10 where the magazine comprises a rocker) or the movement may be accomplished via a linear mechanism such as a spring biased mechanism, for example as illustrated in Example 2 above.

In accordance with a broad embodiment of the present invention a method is provided for loading a suture onto a surgical suturing instrument, the suture comprising suture loops and terminating in a suture end. The method involves mounting the suture loops onto a surgical suturing instrument positioned through the suture loops. The suture end is aligned with the suture receiving passage of the suture passing member and suture end is transferred to the suture receiving passage of the suture passing member. The step of aligning the suture end may involve restraining the suturing instrument with respect to the suture end. The suture end may be aligned by moving the suture end with respect to the suturing passing member. In some examples, the step of aligning the suture end may comprise moving the suture passing member with respect to the suture end. In some embodiments the method of loading the suture onto the suturing instrument is performed using a suture loading apparatus such as a cartridge. The cartridge may be used to both mount suture loops onto the surgical instrument and to align the suture end with the suture receiving passage of the suture passing member In a general embodiment of the present invention, a method is provided for suturing within an inter-vertebral disc. The method involves using a cartridge to load suture onto a suturing instrument, and then using the surgical suturing instrument to deliver the suture into the inter-vertebral disc. In some embodiments, the cartridge is used to load suture at the point of use, for example by a physician just prior to using the suturing instrument within a patient. In a specific example of the method, the suturing instrument is used to pass or insert suture into a region of tissue surrounding a defect within the inter-vertebral disc and approximating the defect using the suture. In an instant of this example, approximating the defect involves forming a loop of suture around the defect using the suture to provide a 360 degree approximation of the defect. After the suture is used to approximate the defect a means is provided to secure the suture within the inter-vertebral disc such as knot. In some embodiments, the knot comprises a pre-tied knot and is deployed after the step of approximating the defect. In a particular example the cartridge provides a pre-tied knot.

In some embodiments the method of loading the suture onto the suturing instrument is performed using a suture loading apparatus such as a cartridge. More specifically with reference now to FIGS. 1A-1F, a cartridge 100 is provided for loading suture 500 onto the suturing instrument 900. The suture 500 comprises suture loops or pre-tied knot 502 that opens into a service loop 501 comprising a tug loop 507 that terminates in the suture end 504 held within the seat 122. Referring now to FIG. 1F, the distal tip 920 of suturing instrument 900 is inserted the housing 10' through the channel 14 within the chamber 10, such that it is positioned through the suture loops or pre-tied knot 502 mounted on the housing 10'. The distal tip 920 of the suturing instrument 900 is then advanced distally through and past the channel 14 so that the housing 10' is now mounted onto the proximal portion or shaft 910 of the suturing instrument. Since the base 120 is flexibly coupled via flexible tube 152 to the housing 10', this allows the cartridge base 120 to be positioned to the side and out of the way (away from the longitudinal axis of the suturing instrument 900) to permit the suturing instrument 900 to be advanced. The flexible tube 152 bends to allow the cartridge base 120 to be kept off to the side from the path of the surgical suturing instrument 900 as it is advanced through the housing 10'. The suturing instrument 900 is positioned such that the distal tip 920 and the neck portion 940 as well as the tissue receiving gap 942, are positioned distal to the housing 10'.

The cartridge base 120 is then moved back towards the longitudinal axis of the suturing instrument 900 to be clipped into the surgical suturing instrument 900. In the example illustrated in FIG. 1A-1F, the restraint 25 comprises a locking recess 125 that corresponds to the shape of the suturing instrument 900. Specifically it is a recess that is shaped to accommodate the neck portion 940, and a segment of the proximal and distal portions 910, 920 of the suturing instrument 900. Referring again to FIG. 1F, the cartridge base 120 is then snapped to the suturing instrument 900. The suturing instrument 900 is received within the locking recess 125 such that the base 120 press-fits around it. The locking recess 125 functions to restrain the suturing instrument to help align the seat 122 and thus the suture end 504 held within the with the seat 122 with the suture receiving passage 932 of the suturing instrument 900.

As outlined previously, the cartridge base 120 additionally comprises an alignment recess 130 adjacent the seat 122 to further assist in aligning the seat 122 with the suture receiving passage 932 of the suturing instrument 900. The alignment recess 130 is dimensioned to receive the suture passing member 930 such as needle 930'. Once the movement of the suturing instrument 900 is constrained or restricted by the locking recess 125, the needle 930' is advanced (for example by actuating a trigger) within the alignment recess 130 such that the needle 930' is positioned adjacent the seat 122.

As mentioned previously, the suture is routed through the base slot 128 that is in communication with the seat 122, as shown in FIG. 1B. Once the suturing instrument 900 is inserted within the locking recess 125 (in the position shown in FIG. 1F), the base slot 128 is aligned with the longitudinal opening 928 within the instrument proximal portion 910 and with the slit 938 within the needle 930'. The suture tug loop 507 that exits the cartridge 100 is then pulled (proximally) by tugging on it for to draw the suture end 504 from the seat 122 and into the aligned suture receiving passage 932 of the suture passing member 930 to position the suture end 504 therein. As the tug loop 507 is pulled, the suture retention pin 165 holds a portion of the tug loop 507 to prevent the service loop 501 from being pulled out of the suture spool 160. The suture retaining component 165 may then be removed, releasing the suture 500. In one specific example where the trigger is actuated to advance the needle 930' within the recess, the trigger may be released at this point. Once, suture end 504 is loaded onto the suturing instrument 900, the cartridge housing 10' is then advanced proximally along the instrument proximal portion or shaft 910, for example till the handle of the suturing instrument 900 and coupled there. Once the housing 10' is advanced proximally the flexible tube 152 is detached from the housing 10', decoupling the base 120 from the housing' 10'. The cartridge base 120 can be removed from the suturing instrument by unsnapping the cartridge base 120 from the surgical suturing instrument 900. More specifically, the suturing instrument 900 is decoupled from the locking recess 125 of the base 120.

The suturing instrument 900 is then used to pass suture 500 through a region of tissue for example within an intervertebral disc of a patient's body to apply suture thereto, for example to close a defect within the inter-vertebral disc. As the suture 500 is passed through the inter-vertebral disc, the suturing instrument 900 is then pulled such that the suture 500 held within suture storage such as suture spool 160 is payed out. The tension within the suture 500 then decouples the housing 10' from the instrument proximal portion or shaft 910, allowing the housing 10' to slide distally along the suturing instrument 900 and deploy the pre-tied knot 502 within the inter-vertebral disc to secure the suture 500 passed through the disc.

The cartridge base 220 may be removed from the surgical instrument and discarded.

In accordance with an alternate embodiment of the present invention, a method is provided for loading suture 500 onto the suturing instrument 900 using a cartridge 400, as shown in FIGS. 2A-2C. The cartridge comprises a housing 10' (for example of the type previously described) that is detachably coupled to the base 420. The cartridge is loaded onto the suturing instrument 900 by advancing the instrument 900 through the housing 10' and then through the instrument receiving recess 425' within the cartridge base 420 with the spring mounted magazine 421 (or interlock 421') being initially positioned in its first or initial position 421A, as shown in FIG. 4B. In some embodiments, the cartridge 400 axially receives (or in other words permits axial advancement of) a portion of a suturing instrument 900 relative to the base in order to load the suture onto the suturing instrument 900. In other words, the cartridge 400 permits loading suture onto the surgical instrument 900 by allowing the surgical instrument 900 to be received axially through the cartridge 400. For example the suturing instrument 900 may be advanced distally through the cartridge 400 or the cartridge 400 may be moved proximally along the suturing instrument). In one example, the method provides for front end loading of the suturing instrument 900' using the cartridge 400.

In a particular example, as the instrument 900 is advanced distally through the cartridge base 420, a tapered section of the distal tip 920 engages a slant or incline 923 of the interlock 421' automatically moving the magazine 421 (and thus the seat 422) downwards and into the tissue receiving gap 942 of the suturing instrument 900 to align the seat 422 (and the suture end 504 held therein) with the suture receiving passage 932, as illustrated in FIG. 2C. The spring mounted magazine 421 (or interlock 421') is now positioned in its second position 421B. The movement of the magazine 421 into the tissue receiving gap 942, and the distal advancement of the suturing instrument 900 through the magazine 421, further functions as a restraining feature to lock or restrain the suturing instrument 900 with respect to the cartridge 400. In some embodiments the suturing instrument 900 is slid into the cartridge 400 until it stops.

Furthermore, as the magazine 421 moves downwards during distal advancement of the suturing instrument 900, the projection 430 moves into the shaft 910, such that bevel 434 of the projection 430 abuts against the needle bevel 934. This helps align the seat 422 (and suture end 504 held releasably within the seat channel 424) with the suture receiving passage 932 of the suturing instrument 900. Thus, the magazine 321 (FIG. 2C) is automatically moved into its second position to align the seat 422 with the suture passing member 930 upon relative movement between the cartridge base 420 and the instrument 900. In some embodiments, the housing 10' may be advanced proximally along the shaft 910 until it abuts against the instrument handle, decoupling the base 420 from the housing 910'. The base 420 can then be removed from the suturing instrument 900. In some embodiments, the base 420 can be automatically detached as the instrument 900 is withdrawn proximally and magazine 421 moves into its initial position 421A. The pre-tied knot 502 on the housing 10' may be deployed in the manner described previously for cartridge embodiments 100, 200.

Generally embodiments of the present invention as outlined herein above provide a cartridge 1000 that permits axial loading of a suturing instrument 900 for example of the type described previously herein with reference to FIGS. 3A-3O. The suturing instrument 900 particularly provides a challenge as the instrument 900 defines an instrument distal portion 920 and an instrument proximal portion 910 defining a tissue receiving gap 942 there-between, where the suture passing member 930 that is to be loaded with suture is held within the instrument proximal portion 910.

Thus, in order to permit axial loading of the suturing instrument 900, the cartridge 1000 provides a means for aligning the suture with the suture passing member 930 by allowing the suture to remain out of the way of the advancing suturing instrument 900 to enable advancement of the instrument distal portion 920 without hindrance. Thus, the suture is kept out of the way of the suturing instrument 900 until the instrument distal portion 920 has advanced past the suture, allowing the suture to then be moved into the tissue receiving gap 942 thereafter to align the suture with the suture passing member 930 to transfer the suture therein.

In accordance with an embodiment of the present invention, with reference now to FIG. 4A, a method of use of the cartridge 1000 is disclosed for facilitating loading of suture 500 onto a surgical suturing instrument 900, for example at the point of use. In some embodiments a pivoting seat 1022 such as that defined by the rocker 1041 facilitates axial loading by enabling the rocker 1041 to remain out of way of the path of the advancing suturing instrument 900 until the tissue receiving gap 942 is positioned within the rocker cavity 1027'. Once the suturing instrument 900 is in place the cartridge 1000 enables the rocker 1041 to pivot down into the tissue receiving gap 942, such that the seat 1022 is positioned adjacent and aligned with the suture passing member 930 such as a needle 930'.

As shown in FIG. 4A, the method provides for initially positioning the suturing instrument 900 within the cartridge 1000. The suturing instrument 900 is then passed axially through the cartridge 1000 to enable front end loading of the suturing instrument 900. More specifically, With reference to FIGS. 4A and 3C, the suturing instrument 900 is inserted into the opening 1016 within the housing 1010' and is guided by the beveled interior edge 1016' into the channel 1014 of the cartridge housing 1010' and advanced distally As outlined above, channel 1014 extends longitudinally through the housing 1010' and is in communication with the base recess 1025 formed within the base 1020, forming a restraint 25. Thus, as the suturing instrument 900 is advanced through the cartridge 1000, it extends from the channel 1014 into the instrument receiving groove 1025a of the recess 1025 within the base 1020 that is in communication with the channel 1014. The restraint 25 constrains or limits the movement of the suturing instrument 900 in the transverse (i.e. up and down) and lateral directions as well along a longitudinal path defined thereby. The restraint 25 enables the suturing instrument 900 to be advanced in sliding engagement therein to maintain the position to the suturing instrument 900 along a path that is in line with the final position of the seat 1022 to facilitate alignment therewith to enable transfer of suture into a portion of the suturing instrument. The suturing instrument 900 is then advanced further such that the distal portion or end 920 of the suturing instrument 900 exits recess 1025a of the base 1020. More specifically, in the illustrated embodiment as shown in FIG. 4A, as the suturing instrument 900 is advanced it passes through the instrument receiving groove 1025a of the base 1020 [ Shown in FIG. 3E] into the rocker recess 1027 of the base 1020, until it is received within the distal groove portion 1048 of the rocker 1041. As such the suturing instrument 900 is positioned adjacent the suture 500 held within the suture groove 1025b [Also shown in FIG. 3D]. As outlined previously, the suture 500 is held within the cartridge 1000 such that the suture end 504 is held within the seat 1022 from where it exits into the pivot recess or cavity 1027 and is routed along the suture groove 1025b of the base recess 1025.

Referring again to FIG. 4A, the distal portion 920 of the suturing instrument 900 is initially received within the distal groove portion 1048 of the rocker groove 1044, with the rocker 1041 being in its initial or first position 1041A. As shown in FIG. 4B, upon advancement of the suturing instrument 900, the distal surface of the distal tip 920 then contacts and engages the bevel surface 1043 of the groove 1044 along the rear wall of the of the distal groove portion 1048 The instrument distal tip engages the bevel face 1043 exerting a force there-against to enable the rocker 1041 to move from its first position into its second position 1041B, as shown in FIGS. 4C (i), 4C(ii) and 4C(iii). More specifically, the distal portion 920 of the suturing instrument 900 is advanced with a sufficient force to enable the rocker 1041 to disengage from a location within the rocker recess 1027 where it is held in place in its initial position 1041A, as shown in FIG. 4A, for example by frictional engagement or a tab.

With reference again to FIG. 4C(i), 4C(ii), 4C(iii), once rocker 1041 is released from engagement, it starts to pivot down. As the rocker 1041 pivots into position the proximal portion 910 of the suturing instrument 900 is received into the proximal groove portion 1046. The pivotal movement of the rocker 1041 enables the suturing instrument 900 to be loaded axially by allowing the distal end 920 to advance past the seat 1022 of the rocker 1041 before the rocker 1041 pivots down into the tissue receiving gap 942 such that the seat 1022 is now positioned within the tissue receiving gap 942 of the suturing instrument 900. As shown in FIG. 4D, the surgical suturing instrument 900 is then continued to be advanced into the base 1020, until the suture passing member 930 such as the needle 930' is in abutting contact with the seat 1022. Once the needle 930' abuts the projection 1030, it halts the movement of the suturing instrument 900 with respect to and within the cartridge 1000. More specifically, as shown in FIG. 4D and earlier with reference to FIG. 3M, the bevel face 934 of the needle 930' is in abutting contact with bevel face 1034 of the projection 1030 that defines the seat 1022 such the needle slot 938 and the shaft slot 928 [behind the needle 930' and the projection 1030 that forms the seat 1022] are in line with and adjacent the seat slot 1028. The shaft slot 928 and the needle slot 938 are visible in FIGS. 1D and 1E, discussed earlier.

In some embodiments of the present invention, in order to align the suture 404 with a suture receiving feature of the suturing instrument 900 (such as suture receiving passage 932 within suture passing member 930) a magazine in the form of a rocker 1041 is provided that is operable to be mechanically interlocked with the suturing instrument such that when the suture cartridge is inserted over the suturing instrument and pressed, the rocker 1041 is configured to rotate down, aligning the suture end 504 with the suturing instrument. In some such embodiments the rocker 1041 grabs onto the suturing instrument 900 to align the suture end 504 in the X-axis (laterally) and Y-axis (transverse/vertical or up and down directions and constrains the rotation the suture end in the X and Y rotational directions. Furthermore, the rocker 1041 mates with and is pushed proximally up to the suturing instrument 900 to align the Suture in the Z-axis (linear or longitudinal directions).

Figure 6A:
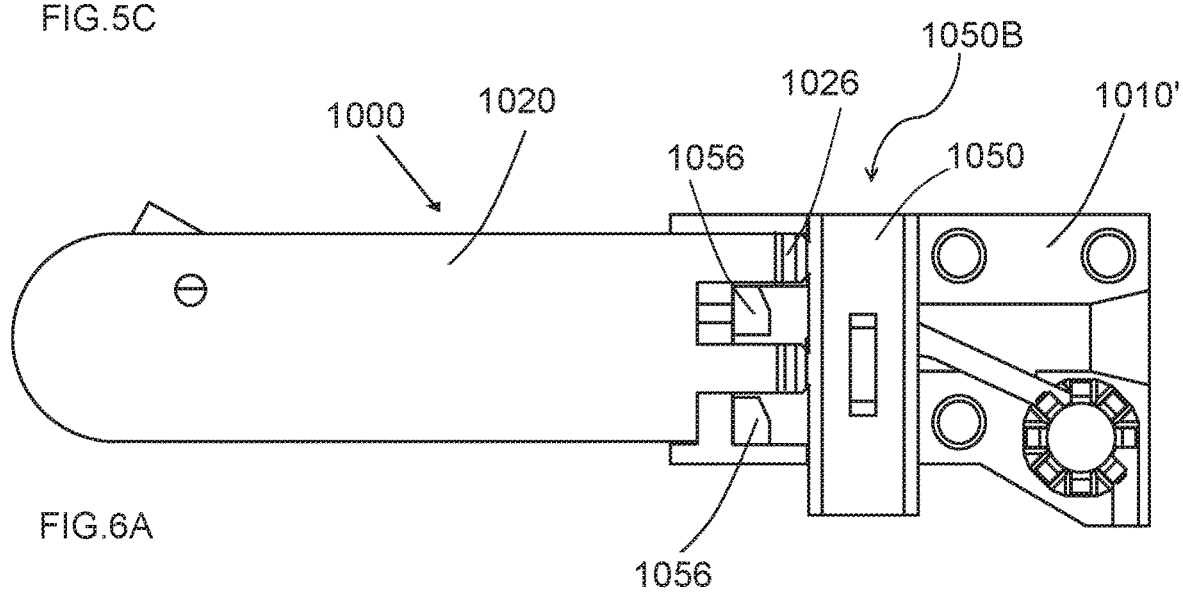
FIGS. 6A-6B illustrate views of an interlock mechanism of a cartridge in accordance with an embodiment of the present invention.
Figure 6B:
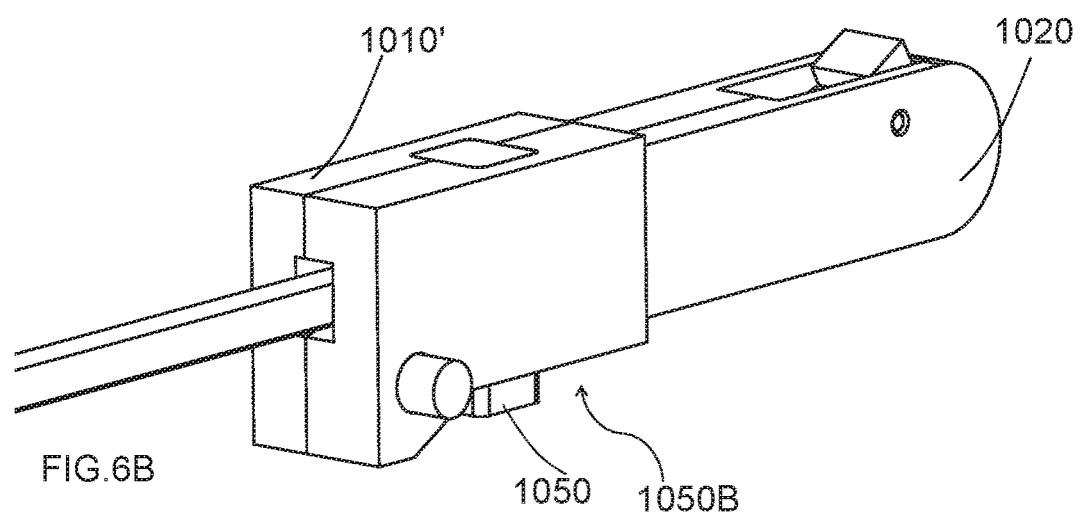

As outlined previously up until this point the interlock 1050 remains in its initial locked position 1050A which ensures that the base 1020 remains coupled to the housing 1010' as shown in FIGS. 5A and 5C As further illustrated in FIG. 5B, in this position the interlock arms 1056 are positioned axially adjacent the locking arms 1026 of the base and prevent the movement of the base 1020 relative to the housing 1010'. As such the locking arms 1026 of the base 1020 are in engagement with the interlock arms 1056. However, one the seat 1022 and thus the suture end 504 has been aligned with the needle 930' the cartridge 1000 enables direct transfer of the suture end 504 into the needle 930' using the housing 1010'. In other words the seat 1022 is in alignment with and adjacent the bevel face 934 of the needle 930' the suture end held in a force fit inside the seat 1022 can then be transferred into the needle 930' (FIGS. 3M and 4D). As shown in FIGS. 6A and 6B, the interlock 1050 is then moved from its locked position 1050A to its unlocked position 1050B to disengage the housing 1010' [which defines a suture transferring component 1011 as discussed previously herein] from the base to transfer the suture onto the suturing instrument 900. More specifically, the housing 1010' and as such the suture transferring component 1011 defined thereby, is detached from the base 1020 allowing the housing 1010' to be pulled back such that the suture end 504 is transferred into the needle 930', as shown in FIG. 7A. The detached base 1020 may be removed thereafter as shown. As such the cartridge 1000 of the present embodiment allows suture to be independently transferred from the cartridge 1000 into the suture passing instrument 900. In additional embodiments, where suture loops that form a partially pre-tied knot may be mounted about the housing 1010', the housing 1010' additionally provides for loading a partially pre-tied knot on the suturing instrument 900.

Figure 7F:
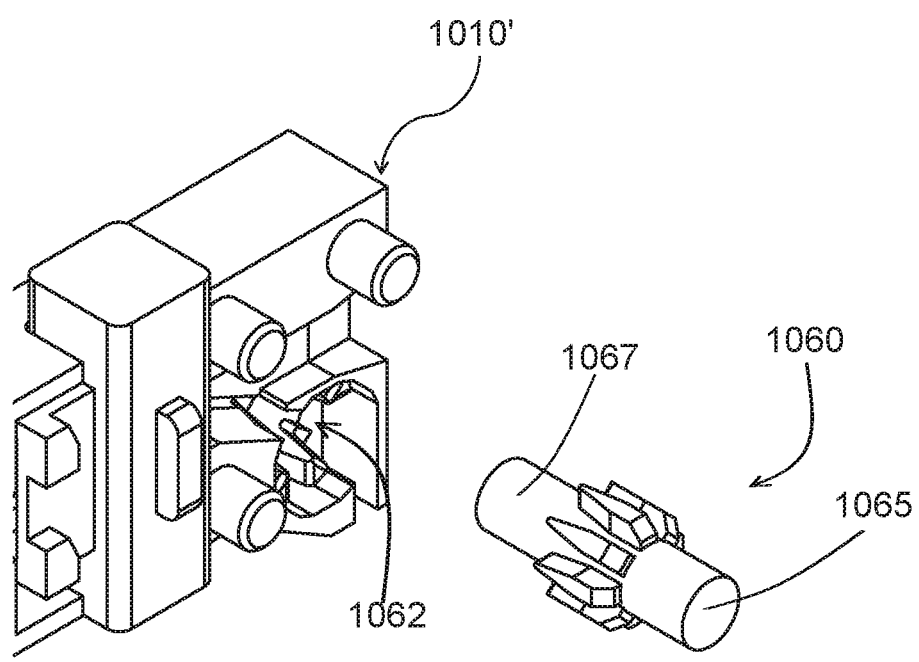

In some embodiments once the suture end 504 has been loaded into the needle the housing 1010' may then be removed. In other embodiments where the housing provides a partially pre-tied knot and/or carries excess suture therein for example in a spool, the housing 1010' may remain mounted on the instrument proximal portion 910 to retain the partially pre-tied knot and or excess suture on the suturing instrument 900. In the embodiment illustrated in FIGS. 7A-7E, the suture lock 1060 may be disengaged to allow the housing 1010' and as such the suture transferring component 1011 defined thereby to be disengaged with the suturing instrument 900 after the suture end 504 has been loaded onto the suturing instrument 900. With reference now to FIGS. 7A-7B, 7E which illustrate the lock in its initial locked configuration 1060A. As discussed previously, herein in the initial locked configuration 1060A, the suture 500 is routed through the suture lock engaging component 1062 of the housing 1010', and the suture lock 1060 is press fit in the suture lock engaging component 1062 thereby pressing the suture 500 between the teeth 1064 of the suture lock 1060 and corresponding teeth 1064' of the suture lock engaging component 1062, and as such the suture 500 is coupled to the housing 1010'. In order to release the lock 1060, the lock is the moved into its second position 1060B as shown in FIGS. 7D and 7F, moving the teeth 1064, 1064' out of engagement with one another and releasing the suture held therein. The housing 1010' and thus the suture transferring component 1011, may then be removed from the suturing instrument 900.

Thus, embodiments of the present invention provide a cartridge 1000 that provides a means to load suture into a suture passing instrument of the type as described herein (such as suturing instrument 900) having an instrument proximal portion 910 and an instrument distal end 920 defining a tissue receiving gap 942 there-between. The current embodiment additionally facilitates automatic alignment of suture 500 (for example end 504 of the suture 500) by allowing the rocker 1041 to pivot into the tissue receiving gap upon engagement with the instrument distal end 920 as it is being advanced into the cartridge 1000.

As such in terms of general overview of the embodiment described herein above in Example 3, in order to facilitate insertion of the suture portion held within the cartridge, alignment of the suture portion must have occurred and three basic mechanical events are configured to take place (i) an applied force on the Suture relative to the Suture Passer in one direction [for example proximally]. (ii) Relative motion between Suture and Suture Passer in the same direction (iii) Relative motion between Suture and Seat in the opposite direction.

In some such embodiments, a suture cartridge is provided that that exerts a force on the end of the suture to load it into the surgical suturing instrument or the suture Passer. All mechanical events achieved by the suture cartridge device are obtained in a single "pump" action performed by the user and in some embodiments may not require actuation of the suture passer (suturing instrument) trigger. {In some such embodiments the single "pump" action may be likened to that of a shotgun loading action.

As such in some embodiments of the present invention, a suture cartridge is provided that uses a pulling force on the end of the suture to load it into the suture passer as outlined in example 3 herein above. In some embodiments, the pull method may be used to insert suture into a suture passer that would allow space for a generally straight-line pull of the suture in the direction of loading. In some situations the pull method may be used when it is required that the suture stay managed/in tension throughout the loading procedure.

In some embodiments, the seat locks onto a limb. The mechanical events to insert the suture occur in the following ways: (1) to apply the force to the end of the suture, the strand of suture is pulled in the middle by a means of grasping the strand with the Suture Lock. (2) To achieve relative motion between the suture and suture passer, the suture passer is fixed with respect to the suture, such that when the applied pulling force is exerted onto the Suture, the suture passer stays still and the suture moves towards and into the suture passer. (3_to achieve relative motion between the suture and seat (in the Suture Cartridge), the seat is also fixed with respect to the Suture, such that when the applied pulling force is exerted onto the Suture, the seat stays still and the suture moves away from and out of the seat.

In some embodiments, a pull insertion mechanism is provided that has a suture lock which is a piece that can move independently from the cartridge base and the suture passer that holds the suture proximally to the seat and is moved away from the seat, thus pulling the suture and creating the required force and relative motion.

In some embodiments, the suture lock automatically decouples from the cartridge base once the seat has fully aligned the suture (suture portion) with the suture passer. This is done by way of an interlock that prevents the Suture lock from moving relative to the cartridge base until the full alignment step has occurred (i.e. prevents the suture from being pulled before it is fully aligned).

In some embodiments, the pull insertion mechanism comprises a suture Lock that automatically unlocks from the suture once the suture (e.g. suture end) has been successfully loaded into the suture passer. As such unlocking of the suture allows the suture passer to then pass the suture freely. In some examples, the unlocking is performed by way of an interlock which prevents unlocking to occur until the point at which the suture is successfully loaded into the suture passer. In one such example, the suture lock interlock may be force/displacement based using a spring to ensure that a given amount of force is exerted on the suture to obtain a given displacement of the suture lock. In some embodiments, the force may be calibrated to be much greater than the maximum theoretical/empirically derived force required to successfully load the Suture. Once this force is achieved, a certain displacement may also be achieved causing the interlock to unlock the suture.

In some such embodiments, a pre-tied knot is provided on a knot slider which is integrated with a suture lock and houses the suture strands. The knot Slider remains on the suture passer after the suture cartridge is actuated to load the suture into the suture passer and functions to release the suture knot to the surgical site once the suture passer is used.

In accordance with an embodiment of the present invention, with reference now to FIG. 9A[i]-10D[ii], a method of use of the cartridge 2000 is disclosed for facilitating loading of suture 500 onto a surgical suturing instrument 900, for example at the point of use. In some embodiments a pivoting seat 1022 such as that defined by the rocker 1041 facilitates axial loading by enabling the rocker 1041 to remain out of way of the path of the advancing suturing instrument 900 until the tissue receiving gap 942 is positioned substantially within the rocker cavity 1027'. Once the suturing instrument 900 is in place the cartridge 1000 enables the rocker 1041 to pivot down into the tissue receiving gap 942, such that the seat 1022 is positioned adjacent and aligned with the suture passing member 930 such as a needle 930'. The cartridge 2000 additionally provides a suture transferring component 2011 for transferring the suture end 504 from the seat 1022 into the suture receiving recess 932 of the suturing instrument 900. The cartridge 2000 additionally provides a knot slider 2030 that permits loading of a pre-tied knot 502 onto the suturing instrument 900.

In some embodiments], the method provides for initially positioning the suturing instrument 900 within the cartridge 2000. The method is described in reference to the advancement of the suturing instrument 900 within the cartridge 2000. However, in some such embodiments the cartridge 2000 is loaded onto the suturing instrument 900 via a proximal movement of the cartridge 2000 over the suturing instrument 900. As such the suturing instrument 900 the cartridge 2000 are moveable relative to one another.

With reference now to FIG. 9A[i], the cartridge 300 is loaded proximally over the suturing instrument 900, with the suturing instrument 900 being passed axially through the cartridge 3000 to enable front end loading of the suturing instrument 900. More specifically, the suturing instrument 900 is inserted through the chamber 1010 of the housing 1010' defined by the knot slider 2030. The suturing instrument is guided by the beveled interior edge 2016' of the opening 2016 into the channel 2014 of the knot slider (FIG. 8D and FIG. 9A [iii]), and as such mounting the knot slider 2030 and the pre-tied knot mounted onto the suturing instrument. As the suturing instrument 900 is advanced further it is received within the instrument receiving groove 2025a of the base recess 2025 within the base 2020. The base recess 2025 and the channel 1014, function as the restraint 25 to constraint or limit the movement of the suturing instrument 900 in the transverse (i.e. up and down) and lateral directions as well along a longitudinal path defined thereby. The restraint 25 enables the suturing instrument 900 to be advanced in sliding engagement therein to maintain the position to the suturing instrument 900 along a path that is in line with the final position of the seat 1022 to facilitate alignment therewith to enable transfer of suture into a portion of the suturing instrument. The instrument receiving groove 2025a guides the suturing instrument into the rocker recess 1027. As outlined previously, the suture 500 is held within the cartridge 2000 such that the suture end 504 is held within the seat 1022 from where it exits into the pivot recess or cavity 1027 and is routed along the suture groove 1025b of the base recess 1025. As such the suturing instrument 900 is positioned adjacent the suture 500 held within the suture groove 1025b, also shown in (FIGS. 8F[i], 8F[ii]).

Referring again to FIG. 9A[i],[ii], the distal portion 920 of the suturing instrument 900 is initially received within the distal groove portion 1048 of the rocker groove 1044, with the rocker 1041 being in its initial or first position 1041A. Upon advancement the instrument distal tip 920 contacts and engages the bevel surface 1043 along the rear wall of the of the distal groove portion 1048 exerting a force thereagainst to move the rocker 1041 to rom its first position 1041A into its second position 1041B, as shown in FIGS. 9B[i],[ii]. More specifically, the distal portion 920 of the suturing instrument 900 is advanced with a sufficient force to enable the rocker 1041 to disengage from the friction tab 2029 within the rocker recess 1027 where it is held in place in its initial position 1041A, as shown in FIG. 9A[i].

With reference again to FIGS. 9B [i], 9B [ii], once rocker 1041 is released from engagement within the rocker recess 1027, it starts to pivot down into the rocker cavity 1027'. As the rocker 1041 pivots into position the proximal portion 910 of the suturing instrument 900 is received into the proximal groove portion 1046. The pivotal movement of the rocker 1041 enables the suturing instrument 900 to be loaded axially by allowing the distal end 920 to advance past the seat 1022 of the rocker 1041 before the rocker 1041 pivots down into the rocker cavity 1027' that corresponds to the tissue receiving gap 942 such that the seat 1022 is now positioned within the tissue receiving gap 942 of the suturing instrument 900.

In some embodiments of the present invention, in order to align the suture 504 with a suture receiving feature of the suturing instrument 900 (such as suture receiving passage 932 within suture passing member 930) a magazine in the form of a rocker 1041 is provided that is operable to be mechanically interlocked with the suturing instrument such that when the suture cartridge is inserted over the suturing instrument and pressed, the rocker 1041 is configured to rotate down, aligning the suture end 504 with the suturing instrument. In some such embodiments the rocker 1041 grabs onto the suturing instrument 900 to align the suture end 504 in the X-axis (laterally) and Y-axis (transverse/ vertical or up and down directions and constrains the rotation the suture end in the X and Y rotational directions. Furthermore, the rocker 1041 mates with and is pushed proximally up to the suturing instrument 900 to align the suture in the Z-axis (linear or longitudinal directions).

As shown in FIG. 9B[i],[ii], the surgical suturing instrument 900 is then continued to be advanced into the base 2020, upto/until the suture passing member 930 such as the needle 930' is in abutting contact with the seat 1022. Once the needle 930' abuts the projection 1030, it halts the movement of the suturing instrument 900 with respect to and within the cartridge 1000. More specifically, as shown in FIG. 4D and earlier with reference to FIG. 3M, the bevel face 934 of the needle 930' is in abutting contact with bevel face 1034 of the projection 1030 that defines the seat 1022 such the needle slot 938 and the shaft slot 928 [behind the needle 930' and the projection 1030 that forms the seat 1022] are in line with and adjacent the seat slot 1028. The shaft slot 928 and the needle slot 938 are visible in FIGS. 1D and 1E, discussed earlier.

As outlined previously up until this point the interlock 2050 remains in its initial locked position 1050A which ensures that the base 1020 remains coupled to the housing 1010' as shown in FIGS. 9A[i],9A[ii]. As further illustrated in FIGS. 9C[i], 9C[ii], in this position the interlock arm 2056 is positioned axially adjacent and distal to the base 2020. The interlock arm prevents the movement of the base 2020 relative to the housing 2010'. However, as the seat 1022 moves into the rocker cavity 1027' of the rocker recess 1027 (and thus the suture end 504 has been aligned with the needle 930') the rocker bar 2055 moves the interlock tab 2054 adjacent the base wall 2054' to be positioned out of way of the interlock 2050. As shown in FIGS. 9D[i], 9D[ii], the interlock 2050 is then moved from its locked position 2050A to its unlocked position 2050B to disengage the base 2020 from the housing 1010' [which defines a suture transferring component 1011 as discussed previously herein]. This allows the base 2020 and the knot slider 2030 attached thereto to slide distally as the housing sleeve 1011' is pulled proximally (FIGS. 9E[i],9E[ii]). In the illustrated example, the interlock 2050 is moved by the user.

Upon relative movement of the suture transferring component 1011 proximally relative to the base 2020, the base 2020 moves distally and presses against the push sleeve hub 2012 that moves distally within the sleeve cavity 2012'. As the push sleeve hub 2012 is biased towards the base 2020 via a spring mechanism [that comprises two springs 2013], it functions to push the push rod hub 2057 upon translation of the suture transferring component 2011 with respect to the base 2020. The push rod hub 2057 translates proximally within push rod cavity 2057' (FIGS. 9Bii, 9E[ii]) causing the longitudinally extending wire 2053' to translate proximally within the wire channel 2053 in communication with the seat 1022 to push the suture end 504 held within the seat 1022 into the suture receiving passage 932 of the suturing instrument 900.

Figure 9F:
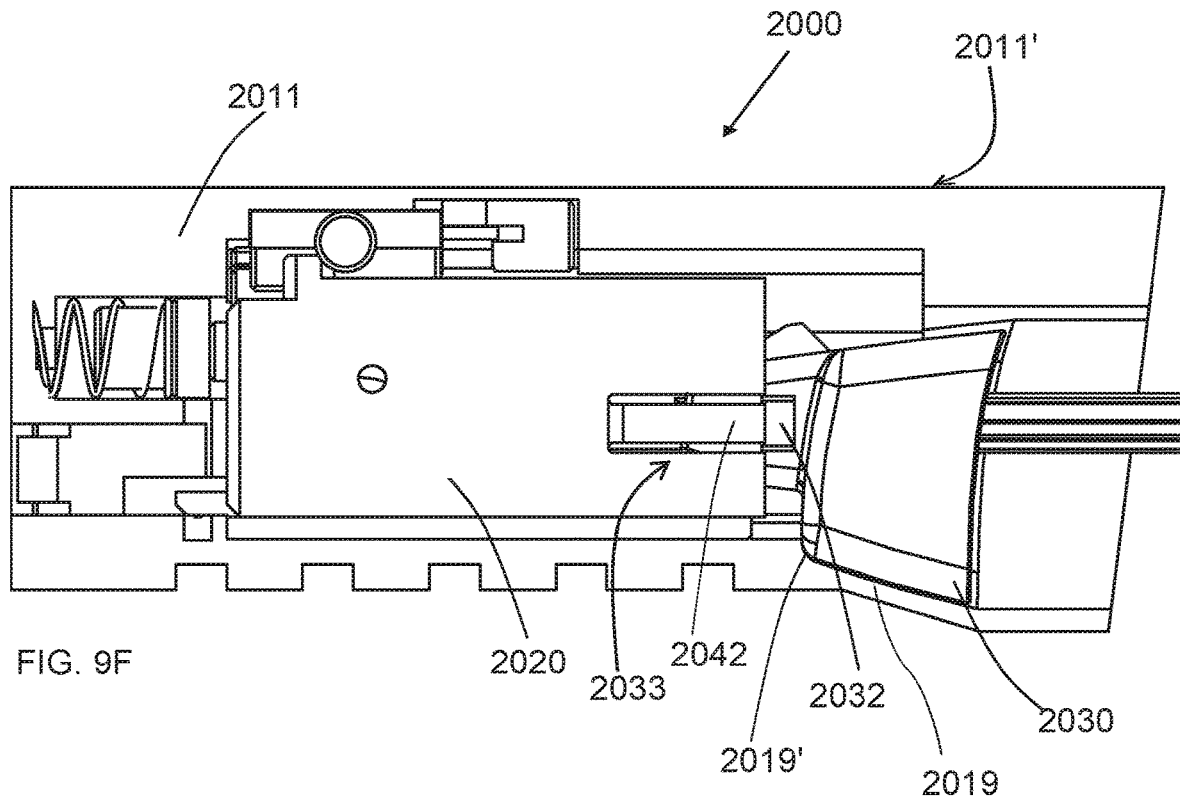

As the base 2020 is advanced distally, the knot slider 2030 is moveable with base 2020 the knot slider 2030 is moveable distally along the knot slider recess 2018 within the housing sleeve 2011' upon distal movement of the base 2020 within the housing sleeve 2011'. However, the wall of the housing sleeve 1011' adjacent the tapered inner wall 2019 [FIG. 8B] of the knot slider recess 2018 functions as a stop to prevent further distal movement of the knot slider 2030 to disengage snap arms 2042 of the base 2020 from the snap grooves of the knot slider 2030, as shown in FIG. 9F. As such the knot slider release interlock 2033 is disengaged releasing the knot slider 2030. In additional embodiments, where suture loops that form a partially pre-tied knot may be mounted about the housing 1010', the housing 1010' additionally provides for loading a partially pre-tied knot on the suturing instrument 900.

Figure 11B:
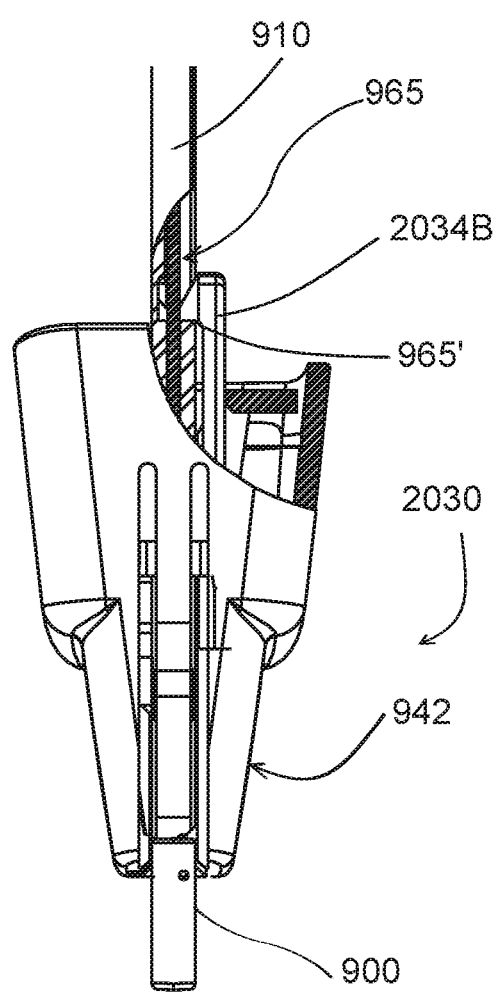
Figure 11C:
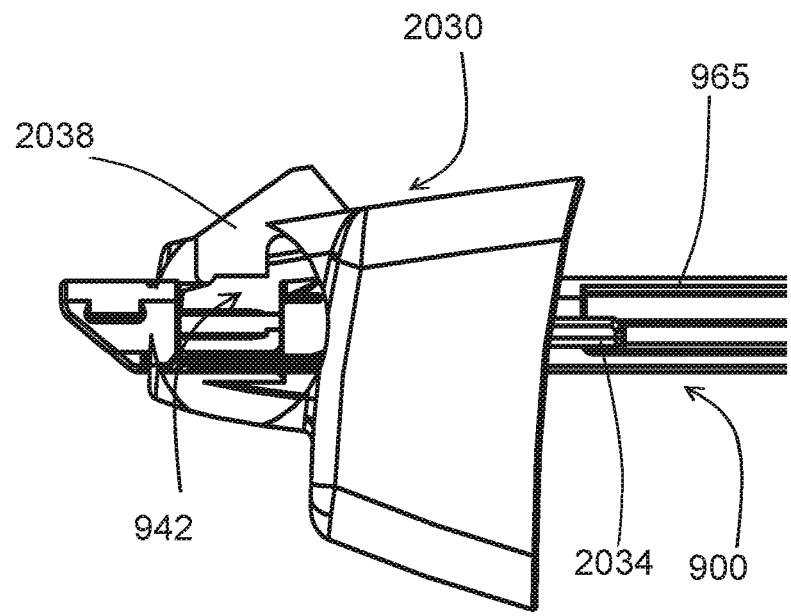
Figure 11D:
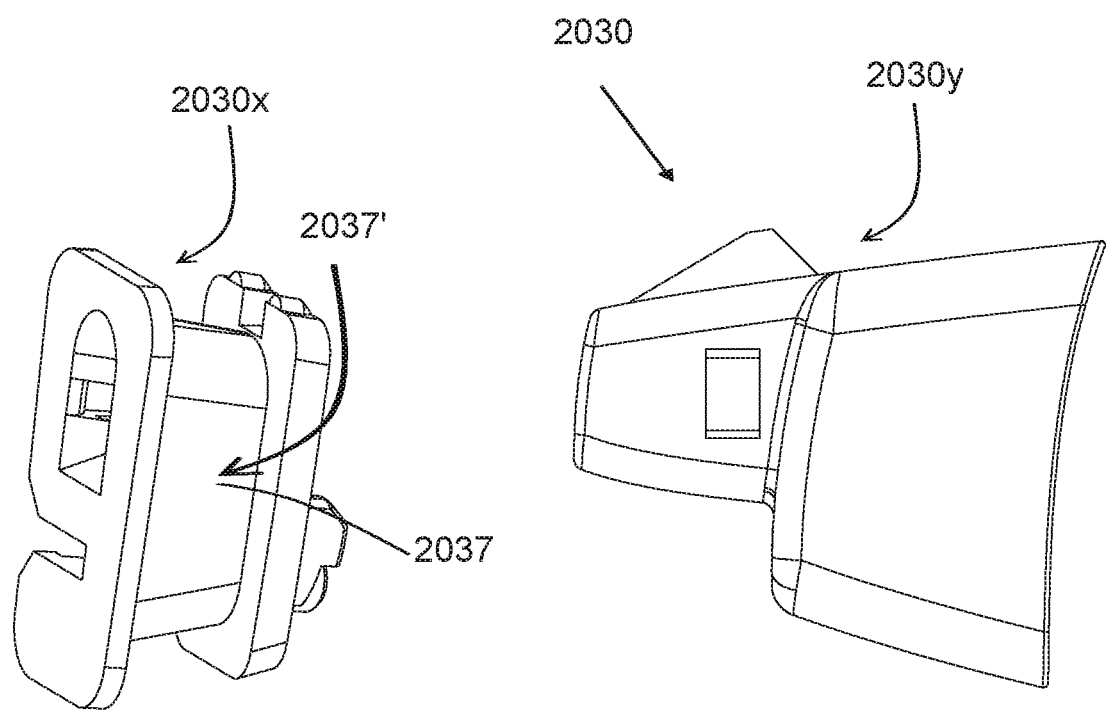

In some embodiments the suture is contained within tubing [for example inside a polytetrafluoroethylene (PTFE) tube] mounted on the inside the knot slider 2030 [FIG. 11D], the cartridge additionally provides for loading or mounting the suture limbs within the knot slider 2030 on the suturing instrument 900 along with the partially pre-tied knot.

Figure 10A:
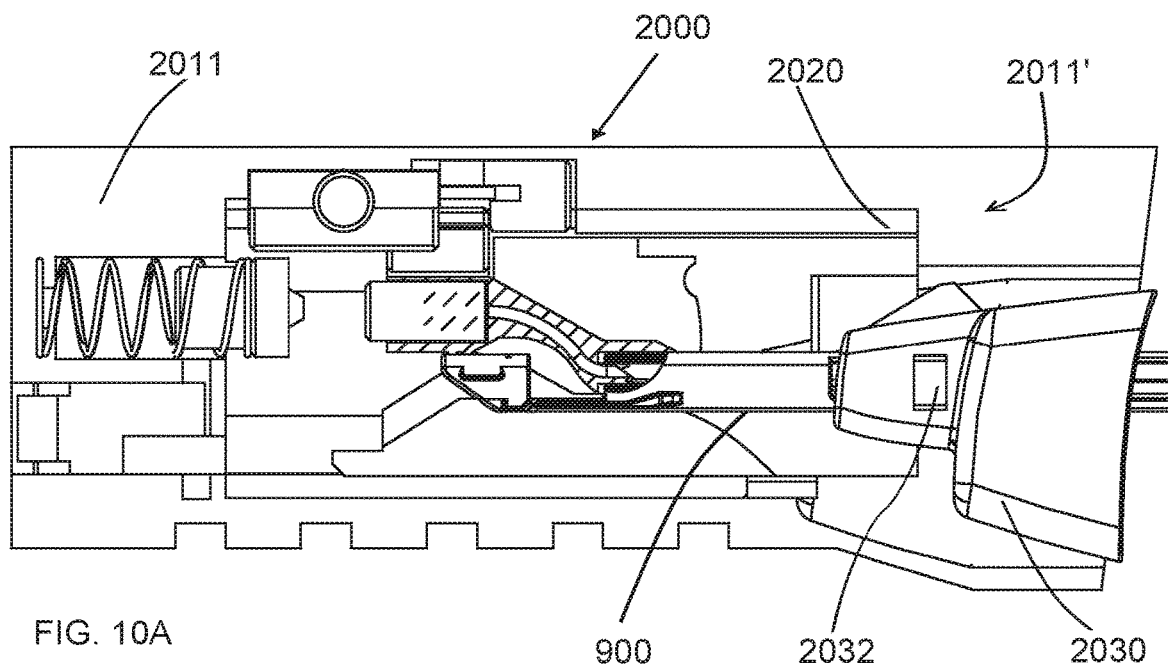
Figure 10B:
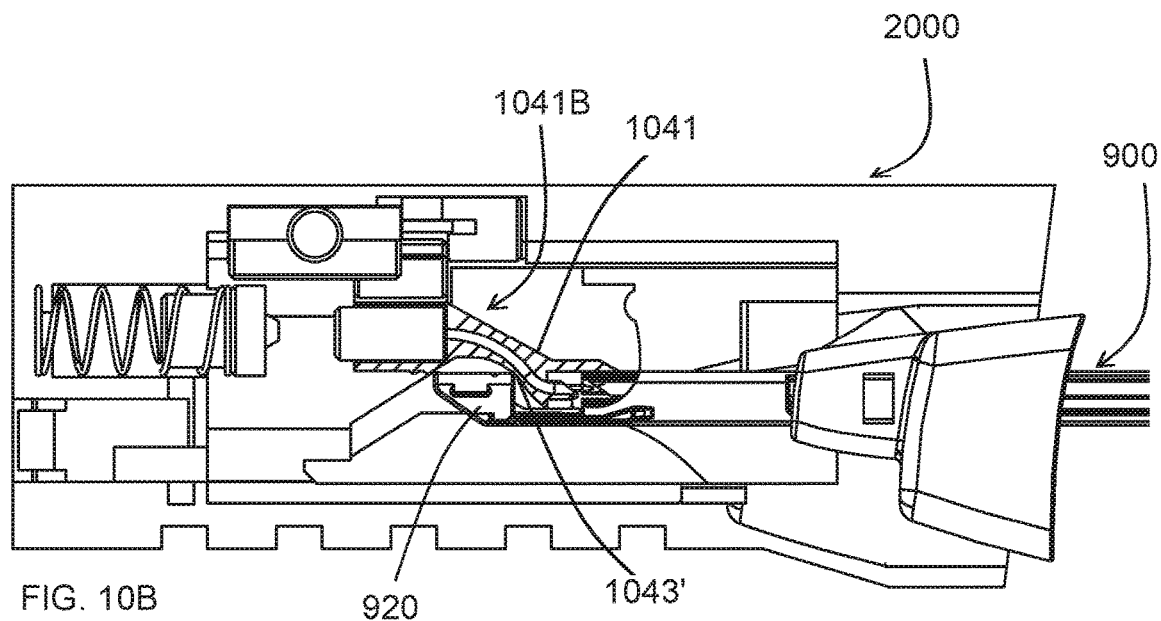
Figure 10C:
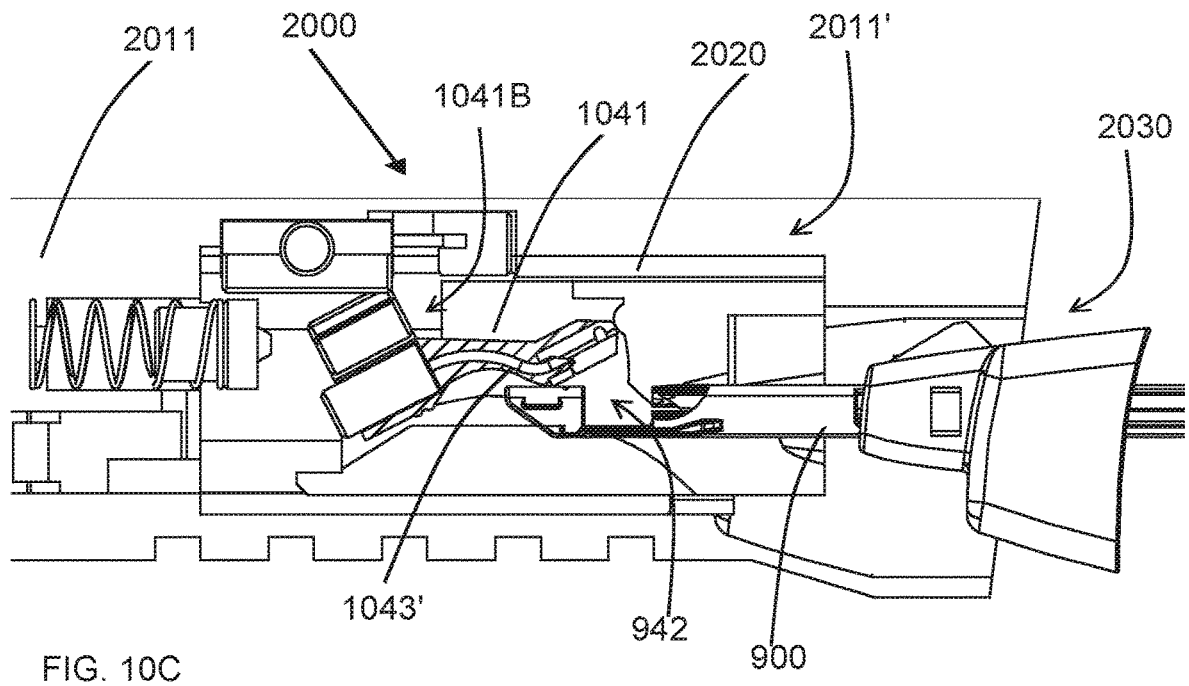

In some embodiments once the suture end 504 has been loaded into the needle the housing 1010' the cartridge 2000 may then be removed and may be pulled proximally. As such in some embodiments the cartridge 2000 is loaded onto the suturing instrument 900 and removed thereafter using a pumping action. The relative movement of the suturing instrument with respect to the cartridge 2000 is in a proximal direction. As the suturing instrument 900 is pulled proximally the knot slider 2030 remains mounted thereon and is removed with the suturing instrument 900 (as shown in FIG. 10A). As the suturing instrument 900 is retracted the distal head 920 interacts with the bevel face 1043' of the rocker 1041 (FIG. 10B). This enables the rocker 1041 to move out from the tissue receiving gap 942 allowing the suturing instrument 900 to be removed, without hindrance as shown in FIG. 10C.

The knot slider arm 2034 is slidable along the instrument window or groove 965 in said inner position 2034A. The knot slider arm 2034 may remain in its initial position 2034A as it is slid proximally along the instrument proximal portion or shaft 910, for example to be attached with a handle portion 960 of the instrument 900 [shown in FIG. 11A]. Once the instrument 900 has been used to pass suture the tissue the instrument 900 may be used thereafter to deploy the pre-tied knot 502. As the instrument 900 is pulled back proximally after suturing the knot slider 2030 disengages from the handle portion of the suturing instrument and slides distally along the shaft proximal portion of the suturing instrument 900. As shown in FIG. 11B, as the knot slider slides distally along the shaft 910 it engages with a front wall 965' of the shaft groove 965, causing the knot slider arm 2034 to move out from the slider groove 2036 into said external position 2034B to enable positioning of said knot slider 2030 over the tissue receiving gap 942 [FIG. 11C] such that a cover arm 2038 of the knot slider is positioned over the tissue receiving gap 942. This enables deployment of the pre-tied 502 from the knot slider 2030 while maintaining engagement of the knot slider 2030 with the suturing instrument 900 and as such prevents the pre-tied knot from falling in or getting caught in the tissue receiving gap 942.

Thus, embodiments of the present invention additionally provide a cartridge 2000 that provides a means to load suture into a suture passing instrument 900 of the type as described herein having an instrument proximal portion 910 and an instrument distal end 920 defining a tissue receiving gap 942 there-between. The current embodiment additionally facilitates automatic alignment of suture 500 (for example end 504 of the suture 500) by allowing the rocker 1041 to pivot into the tissue receiving gap upon engagement with the instrument distal end 920 as it is being advanced into the cartridge 1000. Furthermore, cartridge 2000 provides a suture transferring component 2011 to transfer suture into the suture passing member and additionally provides a knot slider 2030 to mount a pre-tied knot 502 onto the suturing instrument 900.

As such in terms of general overview of the embodiment described herein above in example 4, in order to facilitate insertion of the suture portion held within the cartridge, alignment of the suture portion must have occurred and three basic mechanical events are configured to take place (i) an applied force on the Suture relative to the Suture Passer in one direction [for example proximally]. (ii) Relative motion between Suture and Suture Passer in the same direction (iii) Relative motion between Suture and Seat in the opposite direction.

In some such embodiments, a suture cartridge is provided that that exerts a force on the end of the suture to load it into the surgical suturing instrument or the suture Passer. All mechanical events achieved by the suture cartridge device are obtained in a single "pump" action performed by the user and in some embodiments may not require actuation of the suture passer (suturing instrument) trigger. {In some such embodiments the single "pump" action may be likened to that of a shotgun loading action.

In some such embodiments, a suture cartridge is provided that uses a pushing force on the end of the suture to load it into the suture passer as outlined in example 4 herein above. In one such example the cartridge applies a direct pushing force to the suture to load it onto the suture passer.

In some embodiments, the cartridge comprises a push rod which is a part of the cartridge independent from the seat and suture passer. It is a piece that exists inside the seat and upon actuation presses against the end of the suture to push it forwards in the seat.

In some embodiments, the mechanical events to insert the suture occur in the following ways: (i) to apply the force to the end of the suture a flexible, moveable push rod exists in an S-shaped lumen that exists in the seat. The push rod has a tip that contacts the suture. (ii) To achieve relative motion between the suture and suture passer, the suture passer is fixed with respect to the Suture, such that when the applied pushing force is exerted onto the suture, the suture passer stays still and the suture moves towards and into the suture passer. (iii) to achieve relative motion between the suture and seat (in the suture cartridge), the seat is also fixed with respect to the push rod and suture, such that when the applied pushing force is exerted onto the suture, the seat stays still and the suture moves away from and out of the seat.

In some embodiments, once insertion of the suture has been achieved, a part of the cartridge that contains the suture limbs (the knot slider) detaches from the cartridge and remains attached to the suture passer. In some embodiments the push method can be used when a high loading force is required.

In some embodiments, the cartridge mechanism comprises a push rod that is a piece that can move independently from the cartridge base, seat and suture passer and it is a piece that exists inside the seat and upon actuation presses against the end of the suture to push it forwards in the Seat.

In some embodiments, the push insertion mechanism is configured such that the push rod pushes the suture once the seat has fully aligned the Suture with the suture passer. This may be done by way of a series of interlocks that prevent the push rod from moving relative to the seat until the full alignment step has occurred (i.e. prevents the suture from being pushed before it is fully aligned). Interlocks: 1: Rocker Interlock to prevent the rocker from moving until shaft is inserted [tab or detent 2029 FIG. 8C]. 2: Rocker Geometry: being such that it prevents seat member from contacting shaft during rocker rotation (For example bevel 1043 in FIG. 9A[i] of the rocker and its location and configuration in reference to the seat ensures that the seat does not contact the shaft as the instrument is advanced). 3: Push Rod Interlock: to prevent the push rod from moving before the seat is aligned with the needle. 5: Push Spring: in some embodiments the push rod is actuated with a spring (as outlined above in example 4) to ensure that a given amount of force was being exerted on the suture for a given displacement of the push rod. This force would be calibrated to be much greater than the maximum theoretical/empirically derived force required to successfully load the Suture. Once this force was achieved, a certain displacement would also be achieved and the interlock would unlock the Suture.

In some embodiments, as outlined previously herein above the cartridge is configured for containing a pre-tied knot on a knot slider which also houses the suture strands. The Knot Slider [for e.g. 2030 as described above) automatically detaches from the cartridge Base and remains on the suture passer after the suture cartridge is actuated. The knot slider functions to release the suture knot to the surgical site once the suture passer is used.

In some embodiments interlock may be provided. For example: Knot slider release interlock (for example knot slider release interlock 2033 as described above) which prevents the knot slider form releasing until the suture has been loaded into the needle. In some embodiments, there may be an additional suture retention interlock that prevents the suture limb from moving until the shaft is removed from the cartridge.

Suture Storage: As outlined previously with reference to FIG. 11D, the cartridge in some embodiments stores the suture limbs within the Knot Slider inside a (polytetrafluoroethylene) PTFE tube. Furthermore, as outlined in example 4, the cartridge comprises knot slider retention features on shaft. In some embodiments the cartridge has a Knot Slider that contains a tail hook that retains the knot slider on the suture passer shaft at the end of the procedure. As outlined previously, the tail hook is enclosed within the knot slider and once the knot slider slides to the end of the shaft, the tail hook slides out of the knot slider and hooks onto the shaft.

Thus, as described herein above, various embodiments of a cartridge, and methods of use thereof, are disclosed. These embodiments provide a cartridge for loading suture at the point-of-use onto a surgical suturing instrument such as a suture passing instrument or suture passer, where the suturing instrument includes a suture passing member onto/into which the suture is to be loaded, and where the application requires/benefits from a pre-tied knot. In some embodiments a suture loading cartridge is provided with a feature for securing a pre-tied knot with the ability to deploy the pre-tied knot onto the suture passer (for example by passing the suturing instrument through a chamber of the cartridge that has the knot tied about it), as well as a second feature for aligning a suture end with the suture passing member of the suture passer to facilitate loading of the suture onto/into the suture passing member. In some embodiments the second feature for aligning the suture may be movable with respect to the first feature (so that the suture passer can be inserted into the cartridge through the pre-tied knot after which a suture end loaded into the cartridge can be brought into alignment with the suture passing member).

In one broad aspect, embodiments of the present invention provide a cartridge for loading a suture onto a suturing instrument, the cartridge defining a path for insertion thereto and withdrawal therefrom of the suturing instrument, the cartridge comprising: a seat for releasably holding a portion of a suture; and a translation mechanism for moving the seat out of a path of a suturing instrument inserted into the cartridge to allow for withdrawal of the suturing instrument from the cartridge.

In another broad aspect, embodiments of the present invention provide a cartridge for loading a suture onto a suturing instrument, the cartridge comprising: a seat for releasably holding a portion of a suture; and an alignment feature for facilitating alignment of the seat with a suturing instrument to permit transfer of the suture portion from the seat onto the suturing instrument.

In still an additional broad aspect, embodiments of the present invention provide A cartridge for loading suture onto a suturing instrument, the cartridge comprising: a seat for holding a portion of the suture; and an instrument retention mechanism configured to allow advancement of a suturing instrument into the cartridge and to prevent premature retraction therefrom.

In a further broad aspect embodiments of the present invention comprise a cartridge for loading a suture onto a suturing instrument, the cartridge comprising: a seat for releasably holding a portion of a suture to enable transfer of the suture onto the suturing instrument; and an indicator for indicating transfer of the suture portion onto the suturing instrument.

In still an additional embodiment, a cartridge is provided for loading suture onto a suturing instrument, the cartridge comprising: a seat for holding a portion of a suture; and an obstructing feature having a closed configuration and an open configuration, the obstructing feature being configured to be initially in the closed configuration for preventing advancement of an inverted suturing instrument into the cartridge, and to be moveable into the open configuration upon insertion of the suturing instrument into the cartridge in a nominal orientation.

In still another broad aspect, embodiments of the present invention provide a cartridge for loading suture onto a suturing instrument, the cartridge comprising: a seat for releasably holding a portion of the suture; an alignment feature for aligning the seat with a portion of the suturing instrument; a suture insertion mechanism that is actuatable to insert the suture portion from the seat onto the suturing instrument; and a delay interlock to prevent actuation of the suture insertion mechanism prior to alignment of the seat with the portion of the suturing instrument.

In still another broad aspect, embodiments of the present invention provide a cartridge for In still a further broad aspect, embodiments of the present invention provide a cartridge for loading a pre-tied knot onto a suturing instrument, the cartridge comprising: a cartridge housing; a knot slider for carrying a pre-tied knot thereabout; and a knot slider release mechanism for detachably coupling the knot slider to the cartridge housing.

In an additional broad aspect, embodiments of the present invention provide a cartridge for a cartridge for loading suture onto a suturing instrument comprising a suture passing member, the cartridge comprising a seat for holding an end of the suture, the seat being structured and configured to allow a suture passing member to be advanced over the suture end to capture the suture end.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A cartridge for loading a suture onto a suture passing instrument, the cartridge comprising:
   a cartridge housing and a magazine retained within the housing, the magazine comprising a rocker defining a seat for releasably holding a portion of the suture, the rocker configured to rotate from a first position to a second position; and
   an alignment feature for facilitating alignment of the seat with the suture passing instrument inserted into the cartridge to permit transfer of the suture portion from the seat onto a suture passing member of the suture passing instrument.

2. The cartridge of claim 1, further comprising a suture transfer mechanism that is actuatable to insert the suture portion from the seat onto the suture passing instrument of the suture passing instrument.

3. The cartridge of claim 2, wherein the suture transfer mechanism comprises an automatic suture transfer mechanism for transferring the suture portion from the seat onto the suture passing instrument upon alignment of the seat with the suture passing instrument.

4. The cartridge of claim 2, wherein the suture transfer mechanism comprises a push suture transfer mechanism that is actuated automatically upon alignment of the suture passing instrument within the cartridge to push the suture portion from the seat into the suture passing instrument in a single linear motion of the cartridge with respect to the suture passing instrument upon reception of the suture passing instrument within the cartridge.

5. The cartridge of claim 2, further comprising a delay interlock to prevent actuation of the suture transfer mechanism prior to alignment of the seat with a portion of the suture passing instrument.

6. The cartridge of claim 2, wherein the suture transfer mechanism comprises a pull suture transfer mechanism that is actuated upon alignment of the suture passing instrument within the cartridge to pull the suture portion from the seat into the suture passing instrument.

7. The cartridge of claim 1, wherein the rocker is further configured to linearly translate from the first position to the second position.

8. The cartridge of claim 1, wherein the alignment feature comprises a restraint.

9. The cartridge of claim 8, wherein the restraint comprises an alignment recess.

10. The cartridge of claim 9, wherein the alignment recess comprises an instrument receiving recess.

11. The cartridge of claim 1, wherein the alignment feature comprises an instrument guiding feature to guide the suture passing instrument within the cartridge.

12. The cartridge of claim 11, wherein the instrument guiding feature is defined by the cartridge housing.

13. The cartridge of claim 11, wherein the instrument guiding feature is defined by the magazine.

14. A cartridge for loading a suture onto a suturing instrument, the cartridge comprising:
   a housing;
   a seat coupled to the housing for releasably holding a portion of the suture, the seat being configured to allow relative movement between the seat and the housing for aligning the suture portion with the suturing instrument;
   an alignment feature for aligning the seat with a portion of the suturing instrument;
   a suture transfer mechanism that is actuatable to insert the suture portion from the seat onto a suture passing member of the suturing instrument; and
   a magazine retained within the housing, the magazine comprising a rocker defining the seat;
   wherein the alignment feature comprises an instrument guiding feature to guide the suturing instrument within the cartridge,
   and the instrument guiding feature comprises one or more resilient members that extend from the magazine and wherein the one or more resilient members comprise one or more side arms for aligning the suturing instrument with the seat.

15. The cartridge of claim 14, wherein the one or more side arms extend laterally for straddling the suturing instrument upon insertion of the suturing instrument within the cartridge.

* * * * *